(12) United States Patent
Turberg et al.

(10) Patent No.: US 12,384,769 B2
(45) Date of Patent: Aug. 12, 2025

(54) HETEROARYL-SUBSTITUTED AMINOALKYL AZOLE COMPOUNDS AS PESTICIDES

(71) Applicant: Elanco Animal Health GmbH, Monheim am Rhein (DE)

(72) Inventors: Andreas Turberg, Haan (DE); Iring Heisler, Duesseldorf (DE); Joachim Telser, Wuppertal (DE); Alexander Arlt, Cologne (DE); Peter Jeschke, Bergisch Gladbach (DE); Hans-Georg Schwarz, Dorsten (DE); Martin Fuesslein, Duesseldorf (DE); Yolanda Cancho Grande, Leverkusen (DE); Kerstin Ilg, Cologne (DE); Ulrich Ebbinghaus-Kintscher, Dortmund (DE); Peter Loesel, Leverkusen (DE); Marc Linka, Duesseldorf (DE); Arunas Jonas Damijonaitis, Leverkusen (DE); Ingo Limberg, Wuppertal (DE)

(73) Assignee: Elanco Animal Health GmbH, Monheim am Rhein (DE)

( * ) Notice: Subject to any disclaimer, the term of this patent is extended or adjusted under 35 U.S.C. 154(b) by 866 days.

(21) Appl. No.: 17/603,548

(22) PCT Filed: Apr. 8, 2020

(86) PCT No.: PCT/EP2020/060069
§ 371 (c)(1),
(2) Date: Oct. 13, 2021

(87) PCT Pub. No.: WO2020/212235
PCT Pub. Date: Oct. 22, 2020

(65) Prior Publication Data
US 2023/0046680 A1     Feb. 16, 2023

(30) Foreign Application Priority Data

Apr. 15, 2019   (EP) .................................... 19169209

(51) Int. Cl.
| | |
|---|---|
| *C07D 413/14* | (2006.01) |
| *A01N 43/653* | (2006.01) |
| *A01N 43/76* | (2006.01) |
| *A01N 43/78* | (2006.01) |
| *A01N 43/90* | (2006.01) |
| *C07D 403/14* | (2006.01) |
| *C07D 417/14* | (2006.01) |
| *C07D 471/04* | (2006.01) |

(52) U.S. Cl.
CPC ......... *C07D 413/14* (2013.01); *A01N 43/653* (2013.01); *A01N 43/76* (2013.01); *A01N 43/78* (2013.01); *A01N 43/90* (2013.01); *C07D 403/14* (2013.01); *C07D 417/14* (2013.01); *C07D 471/04* (2013.01)

(58) Field of Classification Search
CPC .. C07D 413/14; C07D 403/14; C07D 417/14; C07D 471/04; A01N 43/653; A01N 43/76; A01N 43/90
See application file for complete search history.

(56) References Cited

U.S. PATENT DOCUMENTS

| | | |
|---|---|---|
| 2010/0099692 A1 | 4/2010 | Natsuhara et al. |
| 2010/0137314 A1 | 6/2010 | Natsuhara et al. |
| 2018/0186778 A1 | 7/2018 | Tosatti et al. |
| 2019/0256501 A1 | 8/2019 | Tosatti et al. |
| 2019/0354814 A1 | 11/2019 | Schobel et al. |
| 2020/0066415 A1 | 2/2020 | Hettig et al. |
| 2020/0404919 A1 | 12/2020 | Schwarz et al. |

(Continued)

FOREIGN PATENT DOCUMENTS

| | | |
|---|---|---|
| CN | 107428732 A | 12/2017 |
| CN | 108477173 A | 9/2018 |
| EP | 3369320 A1 | 9/2018 |

(Continued)

OTHER PUBLICATIONS

Yuzlenko et al., "Potent Adenosine A1 and A2a Receptors Antagonists: Recent Developments," Current Medicinal Chemistry, Dec. 1, 2006, pp. 3609-3625, vol. 13, No. 30, Bentham, NL.

(Continued)

*Primary Examiner* — D Margaret M Seaman

(74) *Attorney, Agent, or Firm* — McBee Moore & Vanik, IP, LLC

(57) ABSTRACT

The present invention relates to novel heteroaryl-substituted aminoalkyl azole compounds of the general formula (I), in which the structural elements Y, $Q^1$, $Q^2$, $R^1$, $R^2$, $R^3$ and $R^4$ have the meaning given in the description, to formulations and compositions comprising such compounds and for their use in the control of animal pests including arthropods and insects in plant protection and to their use for control of ectoparasites on animals.

16 Claims, No Drawings

(56) References Cited

U.S. PATENT DOCUMENTS

| | | | |
|---|---|---|---|
| 2021/0147387 A1 | 5/2021 | Arlt et al. | |
| 2021/0155608 A1 | 5/2021 | Arlt et al. | |

FOREIGN PATENT DOCUMENTS

| | | | |
|---|---|---|---|
| EP | 3456716 A1 | 3/2019 | |
| JP | 2008280342 A | 11/2008 | |
| JP | 2008280343 A | 11/2008 | |
| JP | 2018517716 A | 7/2018 | |
| SU | 446506 A1 | 10/1974 | |
| TW | 202203248 A | 1/2022 | |
| WO | 2006002422 A2 | 1/2006 | |
| WO | 2013078126 A1 | 5/2013 | |
| WO | 2013130660 A1 | 9/2013 | |
| WO | 2014053450 A1 | 4/2014 | |
| WO | 2014117090 A1 | 7/2014 | |
| WO | 2016128298 A1 | 8/2016 | |
| WO | 2017192385 A1 | 11/2017 | |
| WO | 2019170626 A1 | 9/2019 | |
| WO | 2019/197549 | * | 10/2019 |
| WO | 2019197468 A1 | 10/2019 | |
| WO | 2019201835 A1 | 10/2019 | |
| WO | 2019202077 A1 | 10/2019 | |
| WO | 2019206799 A1 | 10/2019 | |
| WO | 2019215198 A1 | 11/2019 | |
| WO | 2020002563 A1 | 1/2020 | |
| WO | 2021013719 A1 | 1/2021 | |
| WO | 2021013720 A1 | 1/2021 | |
| WO | 2021068179 A1 | 4/2021 | |
| WO | 2021069567 A1 | 4/2021 | |
| WO | 2021069569 A1 | 4/2021 | |
| WO | 2021099303 A1 | 5/2021 | |
| WO | 2021105091 A1 | 6/2021 | |

OTHER PUBLICATIONS

Ishikawa et al., "Cyclic Guanidines, XIII. Synthesis of 2-Amino-4-phenyl-3, 4-dihydrothieno [2, 3-d] pyrimidine Derivatives," Chemical and Pharmaceutical Bulletin, Pharmaceutical Society of Japan, Mar. 31, 1980, pp. 3172-3177, vol. 28, No. 11, Japan.

Clark R F et al., "Novel inhibitors of bacterial protein synthesis: structure-activity relationships for 1, 8-naphthyridine derivatives incorporating position 3 and 4 variants," Bioorganic & Medicinal Chemistry Letters, Jun. 21, 2004, pp. 3299-3302, vol. 14, No. 12, Pergamon, Amsterdam, NL.

FUELOEPOVA Veronika et al., "Solid-Phase Synthesis of Trisubstituted 2, 5-Dihydrobenzo [f] [1,2,5] thiadiazepine 1, 1-Dioxide Derivatives," ACS Combinational Science, American Chemical Society, Aug. 11, 2014, pp. 412-420, vol. 16, No. 8, United States.

Brahmachari U N et al., "Studies in Quinoline Compounds. Part I," Journal of the Indian Chemical Society, Industrial and Newsedi, Indian Chemical Society, Jan. 1, 1930, pp. 527-530, Calcutta, IN.

International Search Report of International Patent Application No. PCT/EP2020/060069 dated May 29, 2020.

CAS Registry [Online], Compound RN: 1925255-88-4, 1925255-88-4, 1925125-49-0, 1925032-86-5, 1925032-83-2, etc.,Columbus, Ohio, US, Jun. 5, 2016, 16 pages.

Database Registry , Mar. 12, 2019 , RN 2283546-80-3, RN 2273097-02-0, RN 2261010-13-1, RN 2249005-29-4, RN 2175124-33-9, RN 2161732-01-8, RN 2159779-81-2, RN 2156741-36-3, RN 2156734-14-2, RN 2156731-52-9, Retrieved from STN international [online] ;retrieved on Dec. 5, 2024.

Chemical Plant Protection, edited by Professor G. S. Gruzdev, third edition (revised), Moscow, Agropromizdat, 1987, p. 27, p. 386-389.

Govorushko S.M. "Mammals and birds—agricultural pests: global situation" Agricultural biology, No. 6, 2014, pp. 15-25.

G. Dyson, P. May, "Chemistry of Synthetic Medicinal Substances", transl. from English. Moscow: "Mir", 1964, pp. 12-19.

RN 2273097-02-0 Registry Ed Entered STN: Feb. 26, 2019; RN 2000189-77-3 Registry Ed Entered STN: Sep. 26, 2016; RN 1925033-19-7 Registry Ed Entered STN: Jun. 5, 2016; RN 1922785-37-2 Registry Ed Entered STN: Jun. 1, 2016; RN 1869285-13-1 Registry Ed Entered STN: Feb. 18, 2016; RN 1707097-45-7 Registry Ed Entered STN: May 18, 2015; RN 1524754-23-1 Registry Ed Entered STN: Jan. 20, 2014; RN 1513373-21-1 Registry Ed Entered STN: Jan. 7, 2014; RN 1502484-21-0 Registry Ed Entered STN: Dec. 24, 2013; RN.

* cited by examiner

HETEROARYL-SUBSTITUTED AMINOALKYL AZOLE COMPOUNDS AS PESTICIDES

CROSS-REFERENCE TO RELATED APPLICATIONS

This application is the National Stage entry of International Application No. PCT/EP2020/060069, filed 8 Apr. 2020, which claims priority to European Patent Application No. 19169209.4, filed 15 Apr. 2019.

BACKGROUND

Field

The present invention relates to novel heteroaryl-substituted aminoalkyl azole compounds, to formulations and compositions comprising such compounds and to their use in the control of animal pests including arthropods and insects in plant protection and to their use for control of ectoparasites on animals.

Description of Related Art

Certain heteroaryl-triazole and heteroaryl-tetrazole compounds are disclosed for the use in controlling ectoparasites on animals in WO 2017/192385.

Use on crop pests has been described in WO 2019/170626 and in WO 2019/215198. Further literature on heteroarylazole compounds comprises WO 2019/197468, WO 2019/201835, WO 2019/202077, WO 2019/206799 and WO 2020/002563.

Modern plant protection products and veterinary ectoparasiticides have to meet many demands, for example in relation to efficacy, persistence, spectrum and resistance breaking properties. Questions of toxicity, the combinability with other active compounds or formulation auxiliaries play a role, as well as the question of the expense that the synthesis of an active compound requires. Furthermore, resistances may occur. For all these reasons, the search for novel crop protection compositions or veterinary ectoparasiticides cannot be considered to be complete, and there is a constant need for novel compounds having properties which, compared to the known compounds, are improved at least in respect of individual aspects.

SUMMARY

It was an object of the present invention to provide compounds which widen the spectrum of the pesticides in various aspects.

The present invention therefore provides compounds of the general formula (I)

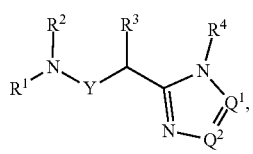

(I)

in which (Configuration 1-1):
$Q^1$ and $Q^2$ are independently $CR^5$ or N, provided at least one of $Q^1$ and $Q^2$ is N;

Y is a direct bond or optionally substituted $CH_2$;
$R^1$ is hydrogen; in each case optionally substituted $C_1$-$C_6$alkyl, $C_3$-$C_6$cycloalkyl$C_1$-$C_6$alkyl, $C_2$-$C_6$alkenyl, $C_2$-$C_6$alkynyl;
or phenyl-$C_1$-$C_6$alkyl, in which phenyl is optionally substituted with one to five substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, and in each case optionally substituted $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl;
$R^2$ is a heteroaromatic bicyclic system containing 9-10 ring members including 1-4 heteroatoms selected from the group consisting of N, O, and S and optionally substituted with 0-4 substituents X, and 0-2 substituents Z and 0-1 substitutents $Z^1$;
X is selected from the group consisting of hydrogen, halogen, hydroxy, —CN, —COOH, —CONH$_2$, —NO$_2$, —NH$_2$, —SF$_5$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)SO$_2$$C_1$-$C_4$alkyl, —N(SO$_2$$C_1$-$C_4$alkyl)$_2$, —CO$_2$$C_1$-$C_4$alkyl, —CONH($C_1$-$C_4$alkyl), —CONH($C_3$-$C_6$cycloalkyl), —CONH-phenyl, —CON($C_1$-$C_4$alkyl)$_2$, —CON($C_1$-$C_4$alkyl)($C_3$-$C_6$cycloalkyl), —CON($C_1$-$C_4$alkyl)-phenyl, —C(=NO$C_1$-$C_4$alkyl)H, —C(=NO$C_1$-$C_4$alkyl)-$C_1$-$C_4$alkyl, tri($C_1$-$C_4$alkyl)silyl;
and 3-6 membered heterocyclyl containing 1-2 heteroatoms selected from the group consisting of N, O, and S and optionally substituted with up to 4 substituents selected independently from the group consisting of fluorine, chlorine, bromine and $C_1$-$C_3$alkyl;
Z is selected from the group consisting of hydrogen, halogen, hydroxy, —CN, —COOH, —CONH$_2$, —NO$_2$, —NH$_2$, —SF$_5$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)SO$_2$$C_1$-$C_4$alkyl, —N(SO$_2$$C_1$-$C_4$alkyl)$_2$, —CO$_2$$C_1$-$C_4$alkyl, —CONH($C_1$-$C_4$alkyl), —CONH($C_3$-$C_6$cycloalkyl), —CONH-phenyl, —CON($C_1$-$C_4$alkyl)$_2$, —CON($C_1$-$C_4$alkyl)($C_3$-$C_6$cycloalkyl), —CON($C_1$-$C_4$alkyl)-phenyl, —C(=NO$C_1$-$C_4$alkyl)H, —C(=NO$C_1$-$C_4$alkyl)-$C_1$-$C_4$alkyl, tri($C_1$-$C_4$alkyl)silyl;
and 3-6 membered heterocyclyl containing 1-2 heteroatoms selected from the group consisting of N, O, and S and optionally substituted with up to 4 substituents selected independently from the group consisting of fluorine, chlorine, bromine and $C_1$-$C_3$alkyl;

$Z^1$ is hydrogen, or in each case optionally substituted $C_1$-$C_6$alkyl, $C_3$-$C_6$cycloalkyl, $C_2$-$C_3$haloalkyl, or $C_1$-$C_4$alkoxy;

$R^3$ is hydrogen or optionally substituted $C_1$-$C_6$alkyl;

$R^4$ is pyridine, pyrimidine, pyrazine, pyridazine or 5-membered heteroaryl wherein the pyridine, pyrimidine, pyrazine, pyridazine or 5-membered heteroaryl is optionally substituted with one to three substituents selected from the group consisting of halogen, hydroxy, —CN, —COOH, —CONH$_2$, —NO$_2$, —NH$_2$, —SF$_5$, and in each case optionally substituted $C_1$-$C_6$alkyl, $C_3$-$C_6$cycloalkyl, $C_1$-$C_3$haloalkyl, $C_3$-$C_6$halocycloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkyl sulfinyl, $C_1$-$C_3$halo alkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)SO$_2$$C_1$-$C_4$alkyl, —N(SO$_2$$C_1$-$C_4$alkyl)$_2$, —CO$_2$$C_1$-$C_4$alkyl, —CONH($C_1$-$C_4$alkyl), —CONH($C_3$-$C_6$cycloalkyl), —CONH-phenyl, —CONHSO$_2$($C_1$-$C_4$alkyl), —CON($C_1$-$C_4$alkyl)$_2$, —CON($C_1$-$C_4$alkyl)($C_3$-$C_6$cycloalkyl), —CON($C_1$-$C_4$alkyl)-phenyl, —CON($C_1$-$C_4$alkyl)SO$_2$($C_1$-$C_4$alkyl), —C(=NO$C_1$-$C_4$alkyl)H, —C(=NO$C_1$-$C_4$alkyl)-$C_1$-$C_4$alkyl;

and 3-6 membered heterocyclyl containing 1-2 heteroatoms selected from the group consisting of N, O, and S and optionally substituted with up to 4 substituents selected independently from the group consisting of fluorine, chlorine, bromine and $C_1$-$C_3$alkyl;

$R^5$ is hydrogen, halogen, CN, or in each case optionally substituted $C_1$-$C_3$alkyl, $C_1$-$C_3$haloalkyl, $C_3$-$C_4$cycloalkyl, $C_3$-$C_4$halocycloalkyl, $C_1$-$C_3$alkoxy, $C_1$-$C_3$haloalkoxy, —C(O)—$C_1$-$C_3$alkoxy, —CH—($C_1$-$C_3$alkoxy)$_2$, —CO$_2$$C_1$-$C_4$alkyl, —CONH($C_1$-$C_4$alkyl), —CON($C_1$-$C_4$alkyl)$_2$, —NHCO—$C_1$-$C_4$alkyl, —N($C_1$-$C_4$alkyl)CO—$C_1$-$C_4$alkyl, —C(=NO$C_1$-$C_4$alkyl)H, or —C(=NO$C_1$-$C_4$alkyl)-$C_1$-$C_4$alkyl.

DETAILED DESCRIPTION OF A PREFERRED EMBODIMENT

According to a further embodiment the present invention provides compounds of the formula (I)

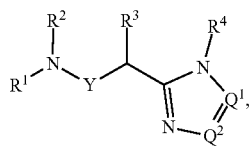

(I)

in which (Configuration 1-2):

$Q^1$ and $Q^2$ are independently $CR^5$ or N, provided at least one of $Q^1$ and $Q^2$ is N;

Y is a direct bond or optionally substituted CH$_2$;

$R^1$ is hydrogen; in each case optionally substituted $C_1$-$C_6$alkyl, $C_3$-$C_6$cycloalkyl$C_1$-$C_6$alkyl, $C_6$alkenyl, $C_2$-$C_6$alkynyl;

or phenyl-$C_1$-$C_6$alkyl, in which phenyl is optionally substituted with one to five substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, and in each case optionally substituted $C_1$-$C_6$alkyl, $C_3$-$C_6$cycloalkyl, $C_3$-$C_6$cycloalkyl-$C_1$-$C_6$alkyl, $C_1$-$C_3$halo alkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl;

$R^2$ is a heteroaromatic bicyclic system containing 9-10 ring members including 1-4 heteroatoms selected from the group consisting of N, O, and S and optionally substituted with 0-4 substituents X, and 0-2 substituents Z and 0-1 substitutents $Z^1$;

X is selected from the group consisting of
hydrogen, halogen, hydroxy, —CN, —COOH, —CONH$_2$, —NO$_2$, —NH$_2$, —SF$_5$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_3$-$C_6$cycloalkoxy, $C_1$-$C_3$alkylthio, $C_1$-$C_3$alkylsulfinyl, $C_1$-$C_3$alkyl sulfonyl, $C_3$-$C_6$cycloalkylthio, $C_3$-$C_6$cycloalkyl sulfinyl, $C_3$-$C_6$cycloalkyl sulfonyl, $C_1$-$C_3$haloalkylthio, $C_1$-$C_3$haloalkylsulfinyl, $C_1$-$C_3$halo alkylsulfonyl, phenylsulfanyl, phenylsulfinyl, phenylsulfonyl, heterocyclylsulfanyl, heterocyclylsulfinyl, heterocyclylsulfonyl, heteroarylsulfanyl, heteroarylsulfinyl, heteroarylsulfonyl, S—$C_1$-$C_6$alkylsulfinimidoyl, S—$C_3$-$C_6$cycloalkylsulfinimidoyl, S-phenylsulfinimidoyl, S-heterocyclylsulfinimidoyl, S-heteroarylsulfinimidoyl, S—$C_1$-$C_6$alkylsulfonimidoyl, S—$C_3$-$C_6$cycloalkylsulfonimidoyl, S-phenylsulfonimidoyl, S-heterocyclylsulfonimidoyl, S-heteroarylsulfonimidoyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)SO$_2$$C_1$-$C_4$alkyl, —N(SO$_2$$C_1$-$C_4$alkyl)$_2$, —CO$_2$$C_1$-$C_4$alkyl, —CONH($C_1$-$C_4$alkyl), —CONH($C_3$-$C_6$cycloalkyl), —CONH-phenyl, —CON($C_1$-$C_4$alkyl)$_2$, —CON($C_1$-$C_4$alkyl)($C_3$-$C_6$cycloalkyl), —CON($C_1$-$C_4$alkyl)-phenyl, —SO$_2$NH($C_1$-$C_6$alkyl), —SO$_2$N($C_1$-$C_6$alkyl)$_2$, —SO$_2$N($C_1$-$C_6$alkyl)($C_3$-$C_6$cycloalkyl), —SO$_2$NH($C_3$-$C_6$cycloalkyl), —SO$_2$N($C_3$-$C_6$cycloalkyl)$_2$, —SO$_2$NH(heterocyclyl), —SO$_2$N($C_1$-$C_4$alkyl)(heterocyclyl), —SO$_2$N($C_3$-$C_6$cycloalkyl)(heterocyclyl), —C(=NO$C_1$-$C_4$alkyl)H, —C(=NO$C_1$-$C_4$alkyl)-$C_1$-$C_4$alkyl, tri($C_1$-$C_4$alkyl)silyl;

and 3-6 membered heterocyclyl containing 1-2 heteroatoms selected from the group consisting of N, O, and S and optionally substituted with up to 4 substituents selected independently from the group consisting of fluorine, chlorine, bromine and $C_1$-$C_3$alkyl;

Z is selected from the group consisting of
hydrogen, halogen, hydroxy, —CN, —COOH, —CONH$_2$, —NO$_2$, —NH$_2$, —SF$_5$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, phenylsulfanyl, phenylsulfinyl, phenylsulfonyl, $C_1$-$C_3$haloalkylthio, $C_1$-$C_3$halo alkylsulfinyl, $C_1$-$C_3$halo alkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)SO$_2$-$C_4$alkyl, —N(SO$_2$$C_1$-$C_4$alkyl)$_2$, —CO$_2$$C_1$-$C_4$alkyl, —CONH($C_1$-$C_4$alkyl), —CONH($C_3$-$C_6$cycloalkyl), —CONH-phenyl, —CON($C_1$-$C_4$alkyl)$_2$, —CON($C_1$-$C_4$alkyl)($C_3$-$C_6$cycloalkyl), —CON($C_1$-$C_4$alkyl)-phenyl, —C(=NO$C_1$-$C_4$alkyl)H, —C(=NO$C_1$-$C_4$alkyl)-$C_1$-$C_4$alkyl, tri($C_1$-$C_4$alkyl)silyl;

and 3-6 membered heterocyclyl containing 1-2 hetero atoms selected from the group consisting of N, O, and S and optionally substituted with up to 4 substituents selected independently from the group consisting of fluorine, chlorine, bromine and $C_1$-$C_3$alkyl;

$Z^1$ is hydrogen, or in each case optionally substituted $C_1$-$C_6$alkyl, $C_3$-$C_6$cycloalkyl, $C_2$-$C_3$haloalkyl, or $C_1$-$C_4$alkoxy;

$R^3$ is hydrogen or optionally substituted $C_1$-$C_6$alkyl;

$R^4$ is pyridine, pyrimidine, pyrazine, pyridazine or 5-membered heteroaryl wherein the pyridine, pyrimidine, pyrazine, pyridazine or 5-membered heteroaryl is optionally substituted with one to three substituents selected from the group consisting of halogen, hydroxy, —CN, —COOH, —CO$_2$—$C_1$-$C_6$alkyl, —SO$_2$NH$_2$, —CONH$_2$, —CSNH$_2$, —NO$_2$, —NH$_2$, —SF$_5$;

and in each case optionally substituted $C_1$-$C_6$alkyl, $C_3$-$C_6$cycloalkyl, $C_1$-$C_6$haloalkyl, $C_3$-$C_6$halocycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_3$-$C_6$cycloalkylsulfanyl, $C_3$-$C_6$cycloalkylsulfinyl, $C_3$-$C_6$cycloalkylsulfonyl, $C_2$-$C_4$alkenylsulfanyl, $C_2$-$C_4$alkenylsulfinyl, $C_2$-$C_4$alkenylsulfonyl, $C_2$-$C_4$alkinylsulfanyl, $C_2$-$C_4$alkinylsulfinyl, $C_2$-$C_4$alkinylsulfonyl, phenylsulfanyl, phenylsulfinyl, phenylsulfonyl, S—$C_1$-$C_6$alkylsulfinimidoyl, S—$C_3$-$C_6$cycloalkyl sulfinimidoyl, S—$C_2$-$C_6$alkenylsulfinimidoyl, S—$C_2$-$C_6$alkinylsulfinimidoyl, S-phenylsulfinimidoyl, S—$C_1$-$C_6$alkylsulfonimidoyl, S—$C_3$-$C_6$cycloalkylsulfonimidoyl, S—$C_2$-$C_6$alkenylsulfonimidoyl, S—$C_2$-$C_6$alkinylsulfonimidoyl, S-phenylsulfonimidoyl, —NH($C_1$-$C_6$alkyl), —N($C_1$-$C_6$alkyl)$_2$, —NHCO—$C_1$-$C_6$alkyl, —N($C_1$-$C_6$alkyl)CO—$C_1$-$C_6$alkyl, —N($C_3$-$C_6$cycloalkyl)CO—$C_1$-$C_6$alkyl, —NHCO—$C_3$-$C_6$cycloalkyl, —N($C_1$-$C_6$ alkyl)CO—($C_3$-$C_6$cycloalkyl), —N($C_3$-$C_6$cycloalkyl)CO—($C_3$-$C_6$cycloalkyl), —N($C_1$-$C_6$alkyl)CO-phenyl, —N($C_3$-$C_6$cycloalkyl)CO-phenyl, —NHCO-phenyl, —N(CO—$C_1$-$C_6$alkyl)$_2$, —N(CO—$C_3$-$C_6$cycloalkyl)$_2$, —N(CO-phenyl)$_2$, —N(CO—$C_3$-$C_6$cycloalkyl)(CO—$C_1$-$C_6$alkyl), —N(CO—$C_3$-$C_6$cycloalkyl)(CO-phenyl), —N(CO—$C_1$-$C_6$alkyl)(CO-phenyl), —CONH($C_1$-$C_6$alkyl), —CON($C_1$-$C_6$alkyl)$_2$, —CONH($C_3$-$C_6$cycloalkyl), —CON($C_1$-$C_6$alkyl)($C_3$-$C_6$cycloalkyl), —CONH($C_3$-$C_6$cycloalkyl alkyl), CON($C_1$-$C_6$alkyl)($C_3$-$C_6$cycloalkylalkyl), —CON($C_3$-$C_6$cycloalkyl)$_2$, —CONH—SO$_2$—$C_1$-$C_6$alkyl, —CONH—SO$_2$-phenyl, —CONH—SO$_2$—($C_3$-$C_6$cycloalkyl), —CON($C_1$-$C_6$alkyl)-SO$_2$—$C_1$-$C_6$alkyl, —CON($C_1$-$C_6$alkyl)-SO$_2$-phenyl, —CON($C_1$-$C_6$alkyl)-SO$_2$—($C_3$-$C_6$cycloalkyl), —CONH-phenyl, —CON($C_1$-$C_6$alkyl)phenyl, —CON($C_3$-$C_6$cycloalkyl)phenyl, —N(SO$_2$$C_1$-$C_6$alkyl)$_2$, —N(SO$_2$$C_1$-$C_6$halo alkyl)$_2$, —N(SO$_2$$C_3$-$C_6$cycloalkyl)$_2$, —N(SO$_2$$C_1$-$C_6$alkyl)SO$_2$-phenyl, —N(SO$_2$$C_3$-$C_6$cycloalkyl)SO$_2$-phenyl, —NHSO$_2$—$C_1$-$C_6$alkyl, —NHSO$_2$—$C_1$-$C_6$haloalkyl, —N($C_1$-$C_6$alkyl)SO$_2$—$C_1$-$C_6$alkyl, —N($C_3$-$C_6$cycloalkyl)SO$_2$—$C_1$-$C_6$alkyl, —NHSO$_2$-phenyl, —N($C_1$-$C_6$alkyl)SO$_2$-phenyl, —N($C_3$-$C_6$cycloalkyl)SO$_2$-phenyl, —NHSO$_2$—$C_3$-$C_6$cycloalkyl, —N($C_1$-$C_6$alkyl)SO$_2$—($C_3$-$C_6$cycloalkyl), —N($C_3$-$C_6$cycloalkyl)SO$_2$—($C_3$-$C_6$cycloalkyl), —SO$_2$NH($C_1$-$C_6$alkyl), —SO$_2$N($C_1$-$C_6$alkyl)$_2$, —SO$_2$N($C_1$-$C_6$alkyl)($C_3$-$C_6$cycloalkyl), —SO$_2$NH($C_3$-$C_6$cycloalkyl), —SO$_2$N($C_3$-$C_6$cycloalkyl)$_2$, —SO$_2$NH(phenyl), —SO$_2$N($C_1$-$C_6$ alkyl) (phenyl), —SO$_2$N($C_1$-$C_4$cycloalkyl)(phenyl), —C(=NO$C_1$-$C_6$alkyl)H and —C(=NO$C_1$-$C_6$alkyl)-$C_1$-$C_6$alkyl;

and 3-6 membered heterocyclyl containing 1-2 heteroatoms selected from the group consisting of N, O, and S and optionally substituted with up to 4 substituents selected independently from the group consisting of fluorine, chlorine, bromine and $C_1$-$C_3$alkyl;

or one of the substituents may optionally be selected from the following substructures S1-S24, in which the bond to the pyridine, pyrimidine, pyrazine, pyridazine or 5-membered heteroaryl is marked with a # and $Z^4$ is CO or SO$_2$ and $Y^4$ is independently selected from CO or SO$_2$:

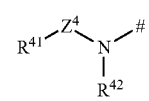

S1

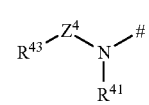

S2

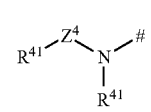

S3

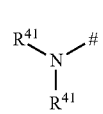

S4

S5

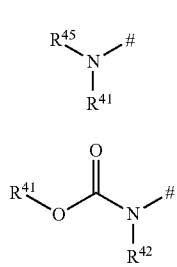

S6

S7

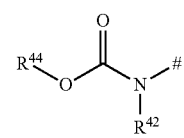

-continued

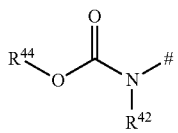
S8

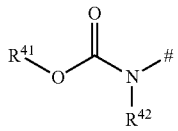
S9

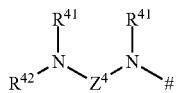
S10

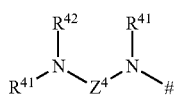
S11

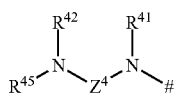
S12

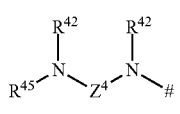
S13

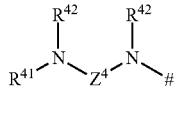
S14

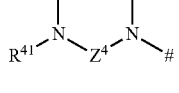
S15

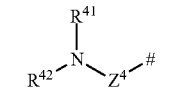
S16

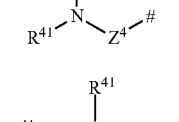
S17

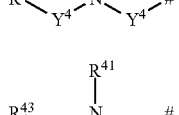
S18

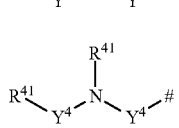
S19

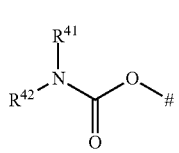
S20

S21

-continued

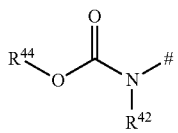
S22

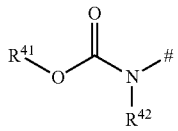
S23

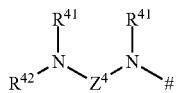
S24

$R^{41}$ is a heterocyclic ring which is selected from the group consisting of 3- to 10-membered saturated or partially unsaturated heterocyclyl, 5-membered heteroaryl, 6-membered heteroaryl, 9-membered heteroaryl and 10-membered heteroaryl, each of which is optionally substituted by one to three substituents independently selected from the group consisting of halogen, =O (oxo), =S (thiono), hydroxy, —CN, —COOH, —SO$_2$NH$_2$, —CONH$_2$, —CSNH$_2$, —NO$_2$, —SF$_5$, —NH$_2$;

and in each case optionally substituted —CO$_2$—C$_1$-C$_6$alkyl, C$_1$-C$_6$alkyl, C$_3$-C$_6$cycloalkyl, C$_3$-C$_6$cycloalkyl-C$_1$-C$_6$alkyl, C$_1$-C$_6$haloalkyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_3$-C$_6$cycloalkylsulfanyl, C$_3$-C$_6$cycloalkyl sulfinyl, C$_3$-C$_6$cycloalkylsulfonyl, C$_1$-C$_6$haloalkylthio, C$_1$-C$_6$haloalkylsulfinyl, C$_1$-C$_6$haloalkylsulfonyl, C$_2$-C$_4$alkenylsulfanyl, C$_2$-C$_4$alkenylsulfinyl, C$_2$-C$_4$alkenylsulfonyl, C$_2$-C$_4$alkinylsulfanyl, C$_2$-C$_4$alkinylsulfinyl, C$_2$-C$_4$alkinylsulfonyl, phenylsulfanyl, phenylsulfinyl, phenylsulfonyl, S—C$_1$-C$_6$alkylsulfinimidoyl, S—C$_3$-C$_6$cycloalkylsulfinimidoyl, S—C$_2$-C$_6$alkenylsulfinimidoyl, S—C$_2$-C$_6$alkinylsulfinimidoyl, S-phenylsulfinimidoyl, S—C$_1$-C$_6$alkylsulfonimidoyl, S—C$_3$-C$_6$cycloalkylsulfonimidoyl, S—C$_2$-C$_6$alkenylsulfonimidoyl, S—C$_2$-C$_6$alkinylsulfonimidoyl, S-phenylsulfonimidoyl, —NH(C$_1$-C$_6$alkyl), —N(C$_1$-C$_6$alkyl)$_2$, —NHCO—C$_1$-C$_6$alkyl, —N(C$_1$-C$_6$alkyl)CO—C$_1$-C$_6$alkyl, —N(C$_3$-C$_6$cycloalkyl)CO—C$_1$-C$_6$alkyl, —NHCO—C$_3$-C$_6$cycloalkyl, —N(C$_1$-C$_6$alkyl)CO—(C$_3$-C$_6$cycloalkyl), —N(C$_3$-C$_6$cycloalkyl)CO—(C$_3$-C$_6$cycloalkyl), —N(C$_1$-C$_6$alkyl)CO-phenyl, —N(C$_3$-C$_6$cycloalkyl)CO-phenyl, —NHCO-phenyl, —N(CO—C$_1$-C$_6$alkyl)$_2$, —N(CO—C$_3$-C$_6$cycloalkyl)$_2$, —N(CO-phenyl)$_2$, —N(CO—C$_3$-C$_6$cycloalkyl)(CO—C$_1$-C$_6$alkyl), —N(CO—C$_3$-C$_6$cycloalkyl)(CO-phenyl), —N(CO—C$_1$-C$_6$alkyl)(CO-phenyl), —CONH(C$_1$-C$_6$alkyl), —CON(C$_1$-C$_6$alkyl)$_2$, —CONH(C$_3$-C$_6$cycloalkyl), —CON(C$_1$-C$_6$alkyl)(C$_3$-C$_6$cycloalkyl), —CON(C$_3$-C$_6$cycloalkyl)$_2$, —CONH—SO$_2$—C$_1$-C$_6$alkyl, —CONH—SO$_2$-phenyl, —CONH—SO$_2$—(C$_3$-C$_6$cycloalkyl), —CON(C$_1$-C$_6$alkyl)-SO$_2$—C$_1$-C$_6$alkyl, —CON(C$_1$-C$_6$alkyl)-SO$_2$-phenyl, —CON(C$_1$-C$_6$alkyl)-SO$_2$—(C$_3$-C$_6$cycloalkyl), —CONH-phenyl, —CON(C$_1$-C$_6$alkyl)phenyl, —CON(C$_3$-

$C_6$cycloalkyl)phenyl, —N(SO$_2$C$_1$-C$_6$alkyl)$_2$, —N(SO$_2$C$_1$-C$_6$haloalkyl)$_2$, —N(SO$_2$C$_3$-C$_6$cycloalkyl)$_2$, —N(SO$_2$C$_1$-C$_6$alkyl)SO$_2$-phenyl, —N(SO$_2$C$_3$-C$_6$cycloalkyl)SO$_2$-phenyl, —NHSO$_2$—C$_1$-C$_6$alkyl, —NHSO$_2$—C$_1$-C$_6$halo alkyl, —N(C$_1$-C$_6$alkyl)SO$_2$—C$_1$-C$_6$alkyl, —N(C$_3$-C$_6$cycloalkyl)SO$_2$—C$_1$-C$_6$alkyl, —NHSO$_2$-phenyl, —N(C$_1$-C$_6$alkyl)SO$_2$-phenyl, —N(C$_3$-C$_6$cycloalkyl)SO$_2$-phenyl, —NHSO$_2$—C$_3$-C$_6$cycloalkyl, —N(C$_1$-C$_6$alkyl)SO$_2$—(C$_3$-C$_6$cycloalkyl), —N(C$_3$-C$_6$cycloalkyl)SO$_2$—(C$_3$-C$_6$cycloalkyl), —SO$_2$NH(C$_1$-C$_6$alkyl), —SO$_2$N(C$_1$-C$_6$alkyl)$_2$, —SO$_2$N(C$_1$-C$_6$alkyl)(C$_3$-C$_6$cycloalkyl), —SO$_2$NH(C$_3$-C$_6$cycloalkyl), —SO$_2$N(C$_3$-C$_6$cycloalkyl)$_2$, —SO$_2$NH(phenyl), —SO$_2$N(C$_1$-C$_6$alkyl)(phenyl), —SO$_2$N(C$_1$-C$_4$cycloalkyl)(phenyl), —NHCS—C$_1$-C$_6$alkyl, —N(C$_1$-C$_6$alkyl)CS—C$_1$-C$_6$alkyl, —N(C$_3$-C$_6$cycloalkyl)CS—C$_1$-C$_6$alkyl, —NHCS—C$_3$-C$_6$cycloalkyl, —N(C$_1$-C$_6$alkyl)CS—(C$_3$-C$_6$cycloalkyl), —N(C$_3$-C$_6$cycloalkyl)CS—(C$_3$-C$_6$cycloalkyl), —N(C$_1$-C$_6$alkyl)CS-phenyl, —N(C$_3$-C$_6$cycloalkyl)CS-phenyl, —NHCS-phenyl, —CSNH(C$_1$-C$_6$alkyl), —CSN(C$_1$-C$_6$alkyl)$_2$, —CSNH(C$_3$-C$_6$cycloalkyl), —CSN(C$_1$-C$_6$alkyl)(C$_3$-C$_6$cycloalkyl), —CSN(C$_3$-C$_6$cycloalkyl)$_2$, —CSNH-phenyl, —CSN(C$_1$-C$_6$alkyl)phenyl, —CSN(C$_3$-C$_6$cycloalkyl)phenyl, —C(=NOC$_1$-C$_6$alkyl)H, —C(=NOC$_1$-C$_6$alkyl)-C$_1$-C$_6$alkyl, phenyl and 5- to 6-membered heteroaryl;

$R^{42}$ is hydrogen, hydroxy;
  or in each case optionally substituted C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_6$alkyl, phenyl-C$_1$-C$_6$alkyl, naphthyl-C$_1$-C$_6$alkyl, C$_1$-C$_6$alkoxy-, C$_1$-C$_6$haloalkoxy;
  or phenyl, wherein the phenyl is optionally substituted by one to three substituents independently selected from the group consisting of halogen, —CN, and in each case optionally substituted C$_1$-C$_6$alkyl, C$_3$-C$_6$cycloalkyl, C$_1$-C$_6$haloalkyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_3$-C$_6$cycloalkylthio, C$_3$-C$_6$cycloalkylsulfinyl, C$_3$-C$_6$cycloalkylsulfonyl, C$_1$-C$_6$haloalkylthio, C$_1$-C$_6$haloalkylsulfinyl, and C$_1$-C$_6$haloalkylsulfonyl;

$R^{43}$ is in each case optionally substituted C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_6$alkyl, phenyl-C$_1$-C$_6$alkyl, naphthyl-C$_1$-C$_6$alkyl, C$_1$-C$_6$alkoxy-, C$_1$-C$_6$haloalkoxy;
  or phenyl, wherein the phenyl is optionally substituted by one to three substituents independently selected from the group consisting of halogen, —CN, and in each case optionally substituted C$_1$-C$_6$alkyl, C$_3$-C$_6$cycloalkyl, C$_1$-C$_6$haloalkyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_3$-C$_6$cycloalkylthio, C$_3$-C$_6$cycloalkylsulfinyl, C$_3$-C$_6$cycloalkylsulfonyl, C$_1$-C$_6$haloalkylthio, C$_1$-C$_6$haloalkylsulfinyl, and C$_1$-C$_6$haloalkylsulfonyl;

$R^{44}$ is in each case optionally substituted C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_6$alkyl, phenyl-C$_1$-C$_6$alkyl, naphthyl-C$_1$-C$_6$alkyl;

$R^{45}$ is hydrogen or in each case optionally substituted C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_6$alkyl, phenyl-C$_1$-C$_6$alkyl, naphthyl-C$_1$-C$_6$alkyl;

or $R^{41}$ and $R^{42}$ together with the nitrogen atom to which they are attached, represent a monocyclic or polycyclic optionally substituted 3- to 12-membered saturated or partially unsaturated heterocyclyl which may contain further heteroatoms;

$R^5$ is —NH$_2$, hydrogen, halogen, —CN, or in each case optionally substituted C$_1$-C$_3$alkyl, C$_1$-C$_3$haloalkyl, C$_3$-C$_4$cycloalkyl, C$_3$-C$_4$halocycloalkyl, C$_1$-C$_3$alkoxy, C$_1$-C$_3$haloalkoxy, —CH—(C$_1$-C$_3$alkoxy)$_2$, —CO$_2$C$_1$-C$_4$alkyl, —CONH(C$_1$-C$_4$alkyl), —CON(C$_1$-C$_4$alkyl)$_2$, —NHCO—C$_1$-C$_4$alkyl, —N(C$_1$-C$_4$alkyl)CO—C$_1$-C$_4$alkyl, —NHCO—C$_3$-C$_6$cycloalkyl, —N(C$_1$-C$_4$alkyl)CO—C$_3$-C$_6$cycloalkyl, —N(C$_3$-C$_6$cycloalkyl)CO—C$_3$-C$_6$cycloalkyl, —C(=NOC$_1$-C$_4$alkyl)H, or —C(=NOC$_1$-C$_4$alkyl)-C$_1$-C$_4$alkyl.

The compounds of the formula (I) likewise encompass any diastereomers or enantiomers and E/Z isomers which exist, and also salts and N-oxides of compounds of the formula (I), and the use thereof for control of animal pests.

Preferred radical definitions for the formulae specified above and hereinafter are given below.

Preference (Configuration 2-1) is given to the compounds of the formula (I) in which $Q^1$ and $Q^2$ are independently CR$^5$ or N, provided at least one of $Q^1$ and $Q^2$ is N;

Y is a direct bond;

$R^1$ is hydrogen; in each case optionally substituted C$_1$-C$_6$alkyl, C$_3$-C$_6$cycloalkylC$_1$-C$_6$alkyl, C$_2$-C$_6$alkenyl, C$_2$-C$_6$alkynyl;
  or phenyl-C$_1$-C$_6$alkyl, in which phenyl is optionally substituted with one to five substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, and in each case optionally substituted C$_1$-C$_6$alkyl, C$_3$-C$_6$cycloalkyl, C$_3$-C$_6$cycloalkyl-C$_1$-C$_6$alkyl, C$_1$-C$_3$halo alkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkyl sulfonyl, C$_1$-C$_3$haloalkylthio, C$_1$-C$_3$haloalkylsulfinyl, C$_1$-C$_3$haloalkylsulfonyl;

$R^2$ is selected from one of the following bicyclic heterocycles T1-T70, in which the bond to the N atom is marked with a #;

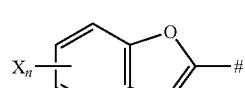

T1

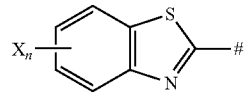

T2

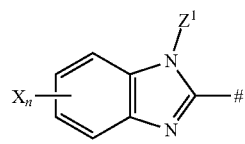

T3

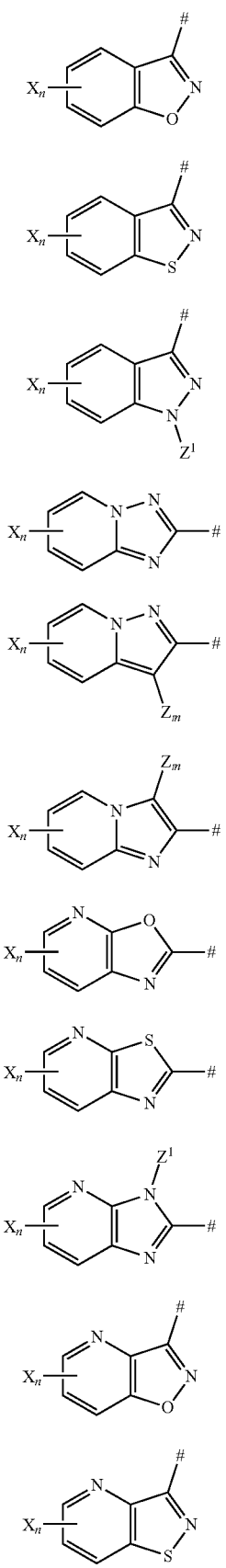
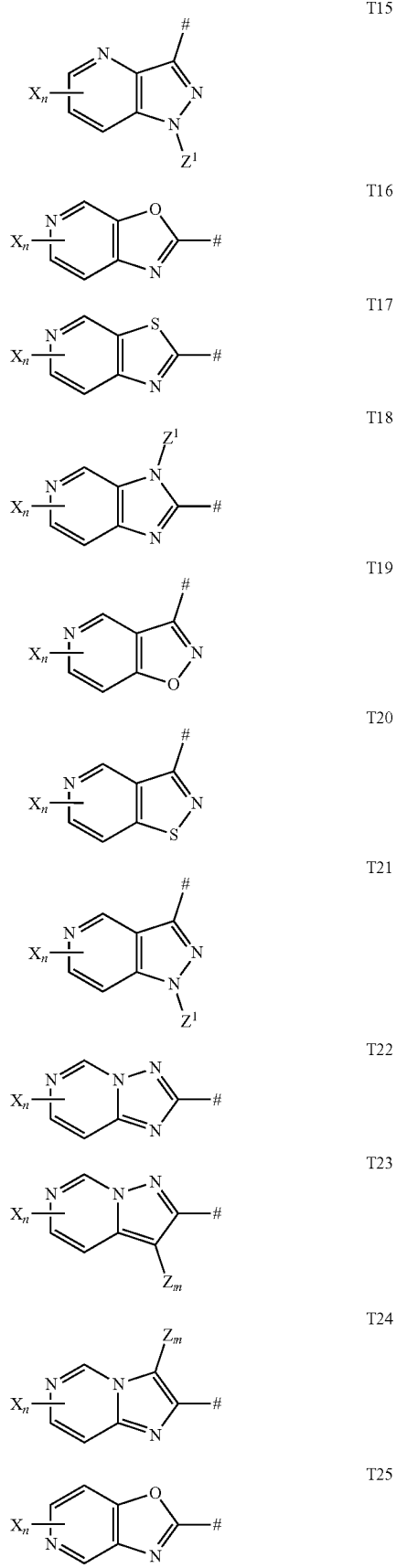

-continued
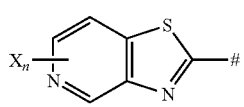
T26
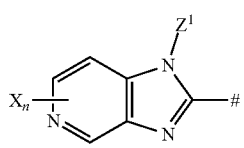
T27
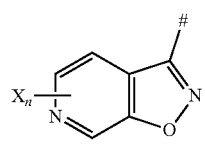
T28
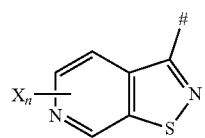
T29
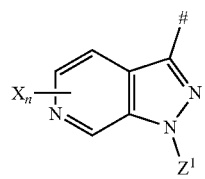
T30
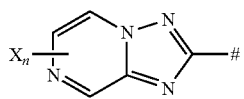
T31
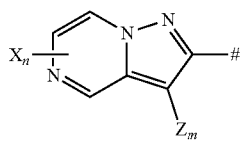
T32
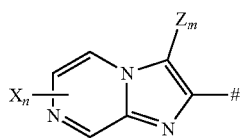
T33
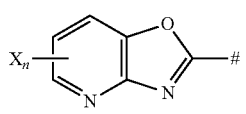
T34
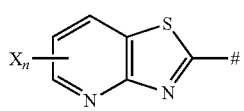
T35
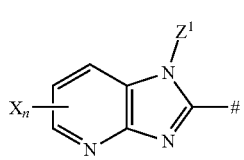
T36
-continued
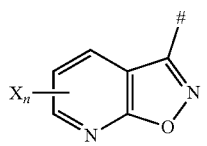
T37
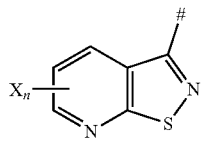
T38
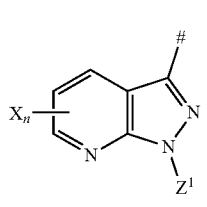
T39
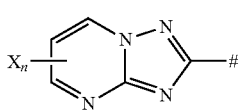
T40
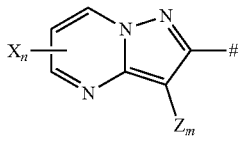
T41
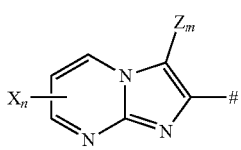
T42
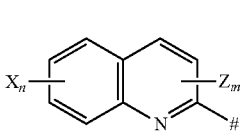
T43
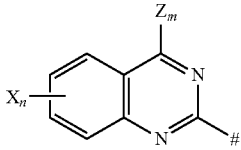
T44
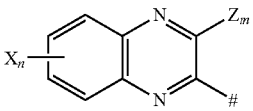
T45
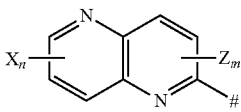
T46
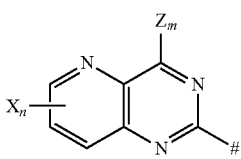
T47

-continued
T48 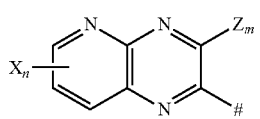
T49 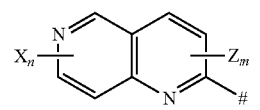
T50 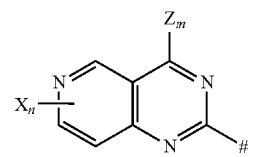
T51 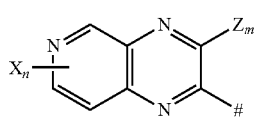
T52 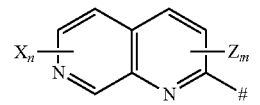
T53 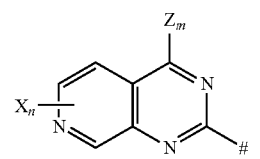
T54 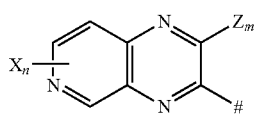
T55 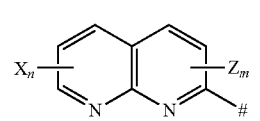
T56 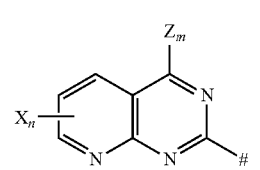
T57 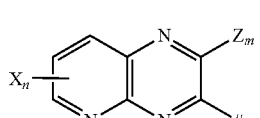
T58 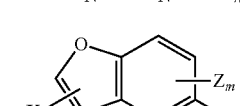
T59 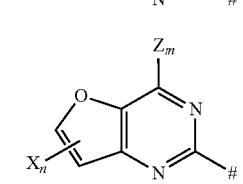
-continued
T60 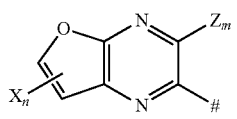
T61 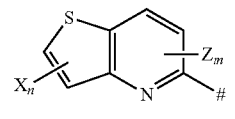
T62 
T63 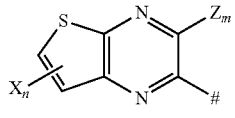
T64 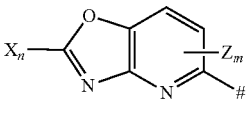
T65 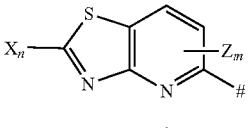
T66 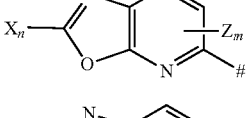
T67 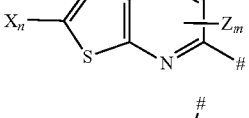
T68 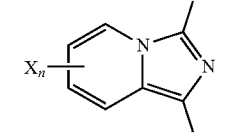
T69 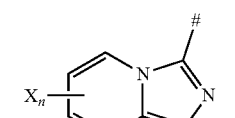
T70 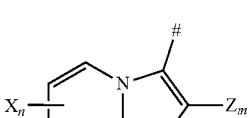
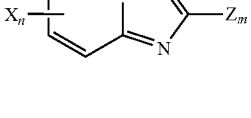
wherein
n is an integer from 0 to 4;
m is an integer from 0 to 2;
X is selected from the group consisting of hydrogen, halogen, hydroxy, —CN, —COOH, —CONH$_2$, —NO$_2$, —NH$_2$, and in each case optionally substituted C₁-C₆alkyl, C₃-C₆cycloalkyl, C₁-C₃haloalkyl, C₁-C₄alkoxy, C₁-C₃haloalkoxy, C₁-C₃alkylthio, C₁-C₃alkylsulfinyl, C₁-C₃alkylsulfonyl, C₁-C₃haloalkylthio, C₁-C₃haloalkylsulfinyl, C₁-C₃haloalkylsulfonyl, —NH(C₁-C₄alkyl), —N(C₁-C₄alkyl)₂, —NHCO—C₁-C₄alkyl, NHCO—C₃-C₆cycloalkyl, —NHSO₂(C₁-C₄alkyl), —N(C₁-C₄alkyl)CO—C₁-C₄alkyl, —N(C₁-C₄alkyl)CO—C₃-C₆cyclolkyl, —N(C₁-C₄alkyl)SO₂C₁-C₄alkyl, —N(SO₂C₁-C₄alkyl)₂, —CO₂C₁-C₄alkyl, —CONH(C₁-C₄alkyl), —CONH(C₃-C₆cycloalkyl), —CONH-phenyl, —CONHSO₂(C₁-C₄alkyl), —CON(C₁-C₄alkyl)₂, —CON(C₁-C₄alkyl) (C₃-C₆cycloalkyl), —CON(C₁-C₄alkyl)-phenyl, —CON(C₁-C₄alkyl) SO₂(C₁-C₄alkyl), —C(=NOC₁-C₄alkyl)H, —C(=NOC₁-C₄alkyl)-C₁-C₄alkyl;

and 4-6 membered heterocyclyl containing 1-2 heteroatoms selected from the group consisting of N and O and optionally substituted with 1-2 substituents selected from the group consisting of methyl and ethyl;

Z is selected from the group consisting of hydrogen, halogen, hydroxy, —CN, —COOH, —CONH₂, —NO₂, —NH₂, and in each case optionally substituted C₁-C₆alkyl, C₃-C₆cycloalkyl, C₁-C₃haloalkyl, C₁-C₄alkoxy, C₁-C₃haloalkoxy, C₁-C₃alkylthio, C₁-C₃alkylsulfinyl, C₁-C₃alkylsulfonyl, C₁-C₃haloalkylthio, C₁-C₃haloalkylsulfinyl, C₁-C₃haloalkylsulfonyl, —NH(C₁-C₄alkyl), —N(C₁-C₄alkyl)₂, —NHCO—C₁-C₄alkyl, NHCO—C₃-C₆cycloalkyl, —NHSO₂(C₁-C₄alkyl), —N(C₁-C₄alkyl)CO—C₁-C₄alkyl, —N(C₁-C₄alkyl)CO—C₃-C₆cyclolkyl, —N(C₁-C₄alkyl)SO₂C₁-C₄alkyl, —N(SO₂C₁-C₄alkyl)₂, —CO₂C₁-C₄alkyl, —CONH(C₁-C₄alkyl), —CONH(C₃-C₆cycloalkyl), —CONH-phenyl, —CONHSO₂(C₁-C₄alkyl), —CON(C₁-C₄alkyl)₂, —CON(C₁-C₄alkyl) (C₃-C₆cycloalkyl), —CON(C₁-C₄alkyl)-phenyl, —CON(C₁-C₄alkyl)SO₂(C₁-C₄alkyl), —C(=NOC₁-C₄alkyl)H, —C(=NOC₁-C₄alkyl)-C₁-C₄alkyl;

Z¹ is hydrogen, or in each case optionally substituted C₁-C₆alkyl, C₃-C₆cycloalkyl, or C₂-C₃haloalkyl;

R³ is hydrogen or optionally substituted C₁-C₆alkyl;

R⁴ is pyridine, pyrimidine, pyrazine, pyridazine or 5-membered heteroaryl, wherein the pyridine, pyrimidine, pyrazine, pyridazine or 5-membered heteroaryl is optionally substituted with one to three substituents selected from the group consisting of halogen, hydroxy, —CN, —COOH, —CONH₂, —NO₂, —NH₂, —SF₅, and in each case optionally substituted C₁-C₆alkyl, C₃-C₆cycloalkyl, C₁-C₃haloalkyl, C₃-C₆halocycloalkyl, C₁-C₄alkoxy, C₁-C₃haloalkoxy, C₁-C₃alkylthio, C₁-C₃alkylsulfinyl, C₁-C₃alkylsulfonyl, C₁-C₃haloalkylthio, C₁-C₃haloalkylsulfinyl, C₁-C₃haloalkylsulfonyl, —NH(C₁-C₄alkyl), —N(C₁-C₄alkyl)₂, —NHCO—C₁-C₄alkyl, NHCO—C₃-C₆cycloalkyl, —NHSO₂(C₁-C₄alkyl), —N(C₁-C₄alkyl)CO—C₁-C₄alkyl, —N(C₁-C₄alkyl)CO—C₃-C₆cyclolkyl, —N(C₁-C₄alkyl) SO₂C₁-C₄alkyl, —N(SO₂C₁-C₄alkyl)₂, —CO₂C₁-C₄alkyl, —CONH(C₁-C₄alkyl), —CONH(C₃-C₆cycloalkyl), —CONH-phenyl, —CONHSO₂(C₁-C₄alkyl), —CON(C₁-C₄alkyl)₂, —CON(C₁-C₄alkyl) (C₃-C₆cycloalkyl), —CON(C₁-C₄alkyl)-phenyl, —CON(C₁-C₄alkyl)SO₂(C₁-C₄alkyl), —C(=NOC₁-C₄alkyl)H, —C(=NOC₁-C₄alkyl)-C₁-C₄alkyl;

and 3-6 membered heterocyclyl containing 1-2 heteroatoms selected from the group consisting of N, O and S and optionally substituted with up to 4 substituents selected independently from the group consisting of fluorine, chlorine, bromine and C₁-C₃alkyl;

R⁵ is hydrogen, halogen, CN, or in each case optionally substituted C₁-C₃alkyl, C₁-C₃haloalkyl, C₃-C₄cycloalkyl, C₃-C₄halocycloalkyl, C₁-C₃alkoxy, C₁-C₃haloalkoxy, —C(O)—C₁-C₃alkoxy, —CH—(C₁-C₃alkoxy)₂, —CO₂C₁-C₄alkyl, —CONH(C₁-C₄alkyl), —CON(C₁-C₄alkyl)₂, —NHCO—C₁-C₄alkyl, —N(C₁-C₄alkyl)CO—C₁-C₄alkyl, —C(=NOC₁-C₄alkyl)H, or —C(=NOC₁-C₄alkyl)-C₁-C₄alkyl.

According to a further embodiment preference (Configuration 2-2) is given to the compounds of the formula (I), in which Q¹ and Q² are independently CR⁵ or N, provided at least one of Q¹ and Q² is N;

Y is a direct bond;

R¹ is hydrogen; in each case optionally substituted C₁-C₆alkyl, C₃-C₆cycloalkylC₁-C₆alkyl, C₂-C₆alkenyl, C₂-C₆alkynyl;

or phenyl-C₁-C₆alkyl, in which phenyl is optionally substituted with one to five substituents, each independently selected from the group consisting of halogen, hydroxy, —CN, —COOH, —CONH₂, —CSNH₂, —NO₂, —Si(CH₃)₃, —SF₅, —NH₂, and in each case optionally substituted C₁-C₆alkyl, C₃-C₆cycloalkyl, C₃-C₆cycloalkyl-C₁-C₆alkyl, C₁-C₃halo alkyl, C₁-C₄alkoxy, C₁-C₃haloalkoxy, C₁-C₃alkylthio, C₁-C₃alkylsulfinyl, C₁-C₃alkylsulfonyl, C₁-C₃haloalkylthio, C₁-C₃haloalkylsulfinyl, C₁-C₃haloalkylsulfonyl;

R² is selected from one of the following bicyclic heterocycles T1-T70, in which the bond to the N atom is marked with a #;

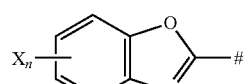
T1

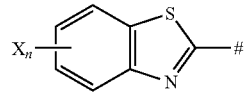
T2

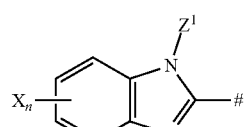
T3

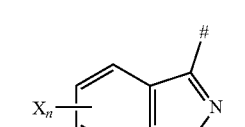
T4

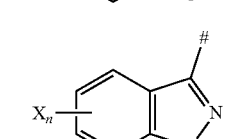
T5

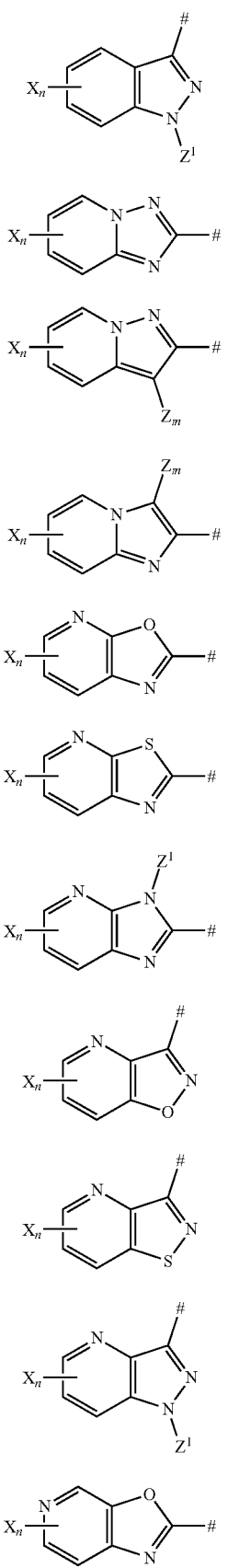
T6
T7
T8
T9
T10
T11
T12
T13
T14
T15
T16
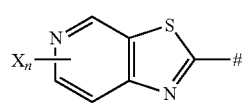
T17
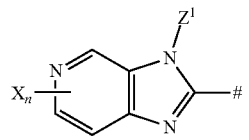
T18
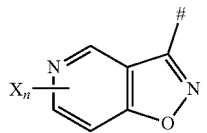
T19
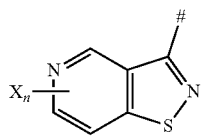
T20
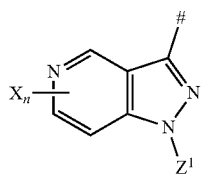
T21
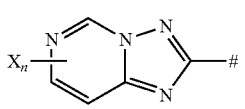
T22
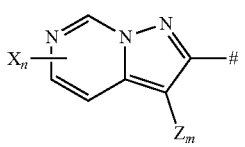
T23
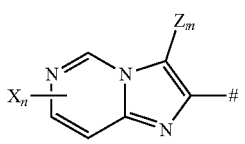
T24
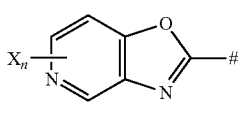
T25
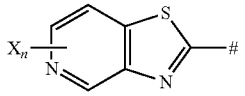
T26
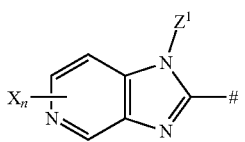
T27

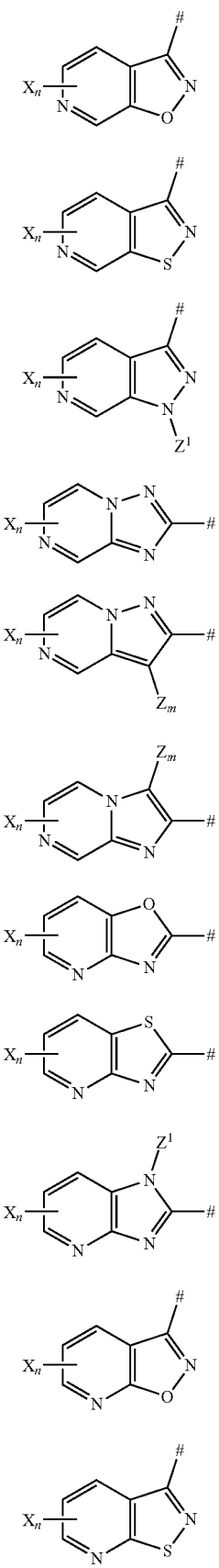
T28
T29
T30
T31
T32
T33
T34
T35
T36
T37
T38
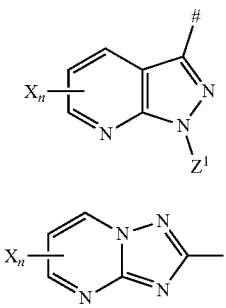
T39
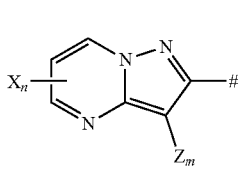
T40
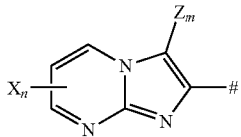
T41
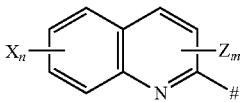
T42
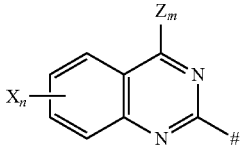
T43
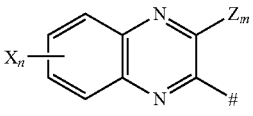
T44
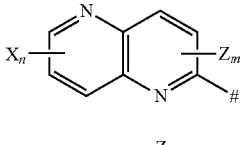
T45
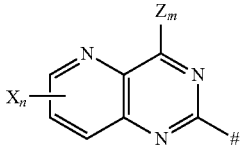
T46
T47
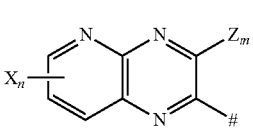
T48
T49

-continued

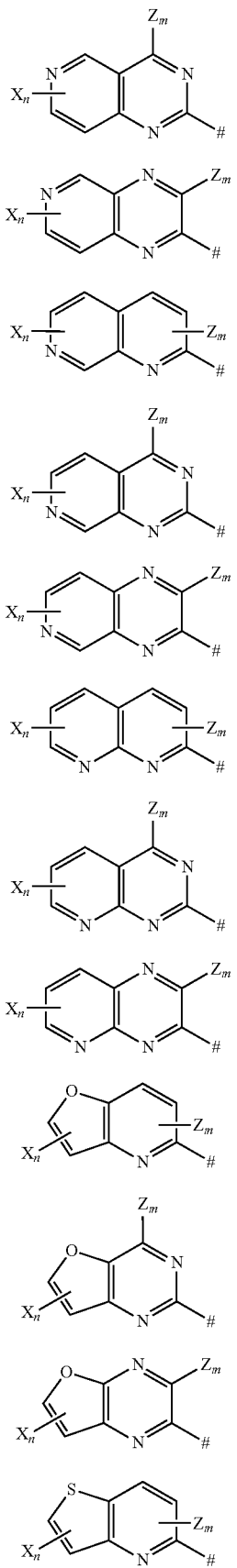

T50

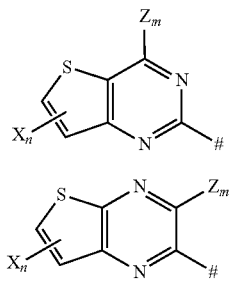
T62

T51

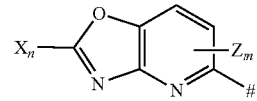
T63

T52

T64

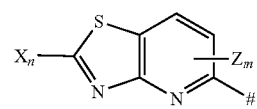
T65

T53

T66

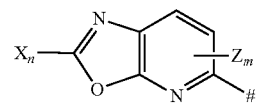
T67

T54

T55

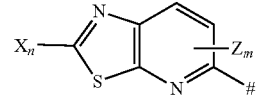
T68

T56

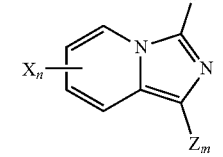
T69

T57

T58

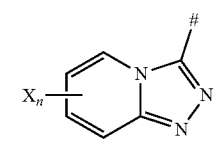
T70

T59 wherein
n is an integer from 0 to 4;
m is an integer from 0 to 2;
X is selected from the group consisting of hydrogen, halogen, hydroxy, —CN, —COOH, —CONH$_2$, —NO$_2$, —NH$_2$, and in each case optionally substituted C$_1$-C$_6$alkyl, C$_3$-C$_6$cycloalkyl, C$_1$-C$_3$haloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, C$_3$-C$_6$cycloalkylthio, C$_3$-C$_6$cycloalkylsulfinyl, C$_3$-C$_6$cycloalkylsulfonyl, C$_1$-C$_3$haloalkylthio, C$_1$-C$_3$haloalkylsulfinyl, C$_1$-C$_3$halo alkyl sulfonyl, phenylsulfanyl, phenylsulfinyl, phenylsulfonyl, —NH(C$_1$-C$_4$alkyl), —N(C$_1$-C$_4$alkyl)$_2$, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)

T60

T61

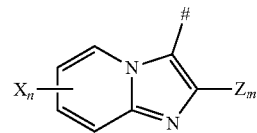

CO—$C_3$-$C_6$cyclolkyl, —N($C_1$-$C_4$alkyl)$SO_2C_1$-$C_4$alkyl, —N($SO_2C_1$-$C_4$alkyl)$_2$, —$CO_2C_1$-$C_4$alkyl, —CONH($C_1$-$C_4$alkyl), —CONH($C_3$-$C_6$cycloalkyl), —CONH-phenyl, —CONH$SO_2$($C_1$-$C_4$alkyl), —CON($C_1$-$C_4$alkyl)$_2$, —CON($C_1$-$C_4$alkyl)($C_3$-$C_6$cycloalkyl), —CON($C_1$-$C_4$alkyl)-phenyl, —CON($C_1$-$C_4$alkyl)$SO_2$($C_1$-$C_4$alkyl), —C(=NO$C_1$-$C_4$alkyl)H, —C(=NO$C_1$-$C_4$alkyl)-$C_1$-$C_4$alkyl;

and 4-6 membered heterocyclyl containing 1-2 heteroatoms selected from the group consisting of N and O and optionally substituted with 1-2 substituents selected from the group consisting of methyl and ethyl;

Z is selected from the group consisting of hydrogen, halogen, hydroxy, —CN, —COOH, —$CONH_2$, —$NO_2$, —$NH_2$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —$NHSO_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)$SO_2C_1$-$C_4$alkyl, —N($SO_2C_1$-$C_4$alkyl)$_2$, —$CO_2C_1$-$C_4$alkyl, —CONH($C_1$-$C_4$alkyl), —CONH($C_3$-$C_6$cycloalkyl), —CONH-phenyl, —CONH$SO_2$($C_1$-$C_4$alkyl), —CON($C_1$-$C_4$alkyl)$_2$, —CON($C_1$-$C_4$alkyl)($C_3$-$C_6$cycloalkyl), —CON($C_1$-$C_4$alkyl)-phenyl, —CON($C_1$-$C_4$alkyl)$SO_2$($C_1$-$C_4$alkyl), —C(=NO$C_1$-$C_4$alkyl)H, —C(=NO$C_1$-$C_4$alkyl)-$C_1$-$C_4$alkyl;

$Z^1$ is hydrogen, or in each case optionally substituted $C_1$-$C_6$alkyl, $C_3$-$C_6$cycloalkyl, or $C_2$-$C_3$haloalkyl;

$R^3$ is hydrogen or optionally substituted $C_1$-$C_6$alkyl;

$R^4$ is pyridine, pyrimidine, pyrazine, pyridazine or 5-membered heteroaryl, wherein the pyridine, pyrimidine, pyrazine, pyridazine or 5-membered heteroaryl is optionally substituted with one to three substituents selected from the group consisting of halogen, hydroxy, —CN, —COOH, —$CONH_2$, —$SO_2NH_2$, —$NO_2$, —$NH_2$, —$SF_5$, and in each case optionally substituted $C_1$-$C_6$alkyl, $C_3$-$C_6$cycloalkyl, $C_1$-$C_3$haloalkyl, $C_3$-$C_6$halocycloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkyl sulfonyl, $C_1$-$C_3$haloalkylthio, $C_1$-$C_3$haloalkylsulfinyl, $C_1$-$C_3$haloalkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —$NHSO_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)$SO_2C_1$-$C_4$alkyl, —N($SO_2C_1$-$C_4$alkyl)$_2$, —$CO_2C_1$-$C_4$alkyl, —CONH($C_1$-$C_4$alkyl), —CONH($C_3$-$C_6$cycloalkyl), —CONH-phenyl, —CONH$SO_2$($C_1$-$C_4$alkyl), —CON($C_1$-$C_4$alkyl)$_2$, —CON($C_1$-$C_4$alkyl) ($C_3$-$C_6$cycloalkyl), —CONH($C_3$-$C_6$cycloalkyl alkyl), —CON($C_1$-$C_6$alkyl)($C_3$-$C_6$cycloalkyl alkyl), —CON($C_1$-$C_4$alkyl)-phenyl, —CON($C_1$-$C_4$alkyl)$SO_2$($C_1$-$C_4$alkyl), —C(=NO$C_1$-$C_4$alkyl)H, —C(=NO$C_1$-$C_4$alkyl)-$C_1$-$C_4$alkyl;

and 3-6 membered heterocyclyl containing 1-2 heteroatoms selected from the group consisting of N, O and S and optionally substituted with up to 4 substituents selected independently from the group consisting of fluorine, chlorine, bromine and $C_1$-$C_3$alkyl;

or one of the substituents may optionally be selected from the following substructures S1-S24, in which the bond to the pyridine, pyrimidine, pyrazine, pyridazine or 5-membered heteroaryl is marked with a # and $Z^4$ is CO or $SO_2$ and $Y^4$ is independently selected from CO or $SO_2$:

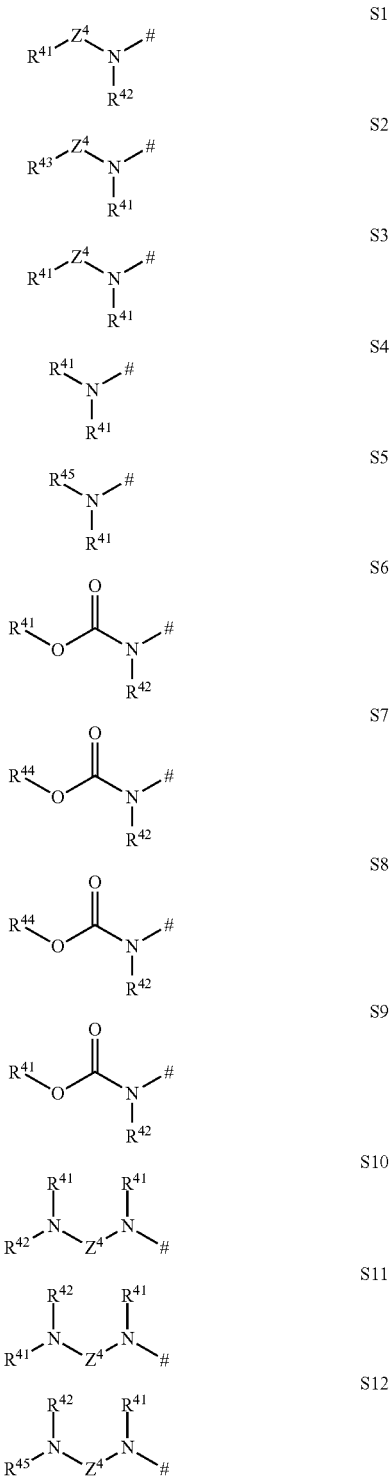

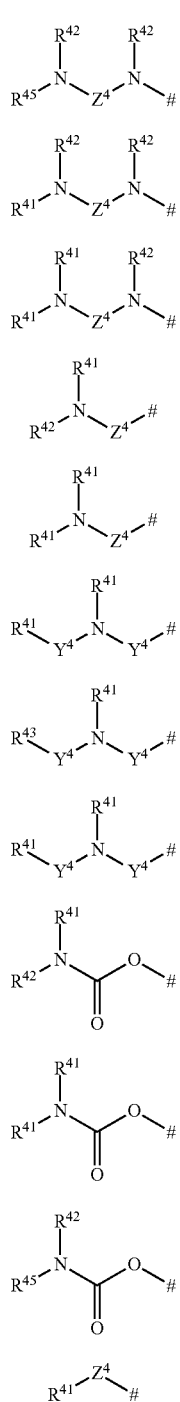

S13
S14
S15
S16
S17
S18
S19
S20
S21
S22
S23
S24

$R^{41}$ is a heterocyclic ring which is selected from the group consisting of 4- to 10-membered saturated or partially unsaturated heterocyclyl, 5-membered heteroaryl and 6-membered heteroaryl, each of which is optionally substituted by one to three substituents independently selected from the group consisting of halogen, =O (oxo), =S (thiono), hydroxy, —CN, —COOH, —SO$_2$NH$_2$, —CONH$_2$, —CSNH$_2$, —NO$_2$, —SF$_5$, —NH$_2$;

and —CO$_2$—C$_1$-C$_4$alkyl, C$_1$-C$_4$alkyl, C$_3$-C$_6$cycloalkyl, C$_3$-C$_6$cycloalkyl-C$_1$-C$_4$alkyl, C$_1$-C$_4$halo alkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_3$-C$_6$cycloalkylsulfanyl, C$_3$-C$_6$cycloalkylsulfinyl, C$_3$-C$_6$cycloalkyl sulfonyl, C$_1$-C$_4$halo alkylthio, C$_1$-C$_4$haloalkylsulfinyl, C$_1$-C$_4$halo alkylsulfonyl, —NH(C$_1$-C$_4$alkyl), —N(C$_1$-C$_4$alkyl)$_2$, —NHCO—C$_1$-C$_4$alkyl, —N(C$_1$-C$_4$alkyl)CO—C$_1$-C$_4$alkyl, —N(C$_3$-C$_6$cycloalkyl)CO—C$_1$-C$_4$alkyl, —NHCO—C$_3$-C$_6$cycloalkyl, —N(C$_1$-C$_4$alkyl)CO—(C$_3$-C$_6$cycloalkyl), —N(C$_3$-C$_6$cycloalkyl)CO—(C$_3$-C$_6$cycloalkyl), —N(CO—C$_1$-C$_4$alkyl)$_2$, —N(CO—C$_3$-C$_6$cycloalkyl)$_2$, —N(CO—C$_3$-C$_6$cycloalkyl)(CO—C$_1$-C$_4$alkyl), —CONH(C$_1$-C$_4$alkyl), —CON(C$_1$-C$_4$alkyl)$_2$, —CONH(C$_3$-C$_6$cycloalkyl), —CON(C$_1$-C$_4$ alkyl)(C$_3$-C$_6$cycloalkyl), —CON(C$_3$-C$_6$cycloalkyl)$_2$, —CONH—SO$_2$—C$_1$-C$_4$alkyl, —CONH—SO$_2$—(C$_3$-C$_6$cycloalkyl), —CON(C$_1$-C$_4$alkyl)-SO$_2$—C$_1$-C$_4$alkyl, —CON(C$_1$-C$_4$alkyl)-SO$_2$—(C$_3$-C$_6$cycloalkyl), —N(SO$_2$C$_1$-C$_4$alkyl)$_2$, —N(SO$_2$C$_1$-C$_4$halo alkyl)$_2$, —N(SO$_2$C$_3$-C$_6$cycloalkyl)$_2$, —NHSO$_2$—C$_1$-C$_4$alkyl, —NHSO$_2$—C$_1$-C$_4$halo alkyl, —N(C$_1$-C$_4$alkyl)SO$_2$—C$_1$-C$_4$alkyl, —N(C$_3$-C$_6$cycloalkyl)SO$_2$—C$_1$-C$_4$alkyl, —NHSO$_2$—C$_3$-C$_6$cycloalkyl, —N(C$_1$-C$_4$ alkyl)SO$_2$—(C$_3$-C$_6$cycloalkyl), —N(C$_3$-C$_6$cycloalkyl)SO$_2$—(C$_3$-C$_6$cycloalkyl), —SO$_2$NH(C$_1$-C$_4$alkyl), —SO$_2$N(C$_1$-C$_4$alkyl)$_2$, —SO$_2$N(C$_1$-C$_4$alkyl)(C$_3$-C$_6$cycloalkyl), —SO$_2$NH(C$_3$-C$_6$cycloalkyl), —SO$_2$N(C$_3$-C$_6$cycloalkyl)$_2$, —C(=NOC$_1$-C$_4$alkyl)H, —C(=NOC$_1$-C$_4$alkyl)-C$_1$-C$_4$alkyl;

$R^{42}$ is hydrogen, hydroxy;

and C$_1$-C$_4$alkyl, C$_1$-C$_4$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_4$alkyl, phenyl-C$_1$-C$_4$alkyl, naphthyl-C$_1$-C$_4$alkyl, C$_1$-C$_4$alkoxy-, C$_1$-C$_4$haloalkoxy;

$R^{43}$ is C$_1$-C$_4$alkyl, C$_1$-C$_4$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_4$alkyl, phenyl-C$_1$-C$_4$alkyl, naphthyl-C$_1$-C$_4$alkyl, C$_1$-C$_4$alkoxy-, C$_1$-C$_4$haloalkoxy;

$R^{44}$ is C$_1$-C$_4$alkyl, C$_1$-C$_4$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_4$alkyl, phenyl-C$_1$-C$_4$alkyl, naphthyl-C$_1$-C$_4$alkyl;

$R^{45}$ is hydrogen and C$_1$-C$_4$alkyl, C$_1$-C$_4$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_4$alkyl, phenyl-C$_1$-C$_4$alkyl, naphthyl-C$_1$-C$_4$ alkyl;

or $R^{41}$ and $R^{42}$ together with the nitrogen atom to which they are attached, represent a monocyclic, spirocyclic or bridged polycyclic 4- to 12-membered saturated or partially unsaturated heterocyclyl which may contain up to two further heteroatoms selected from the group of oxygen, nitrogen and sulfur and which is optionally substituted with one to three substituents selected from the group consisting of halogen, =O (oxo), =S (thiono), hydroxy, —CN, —COOH, —SO$_2$NH$_2$, —CONH$_2$, —CSNH$_2$, —NO$_2$, —SF$_5$, and —NH$_2$;

and in each case optionally substituted —CO$_2$—C$_1$-C$_4$alkyl, C$_1$-C$_4$alkyl, C$_3$-C$_6$cycloalkyl, C$_1$-C$_4$haloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_3$-C$_6$cycloalkylsulfanyl, C$_3$-C$_6$cycloalkylsulfinyl, C$_3$-C$_6$cycloalkylsulfonyl, $C_1$-$C_4$haloalkylthio, $C_1$-$C_4$haloalkylsulfinyl, $C_1$-$C_4$halo alkyl sulfonyl, —$NHSO_2$—$C_1$-$C_4$alkyl, —$NHCO_2$—$C_1$-$C_4$alkyl, —$OCONH$—$C_1$-$C_4$alkyl, —$NH(C_1$-$C_4$alkyl), —$N(C_1$-$C_4$alkyl)_2$, —$NHCO$—$C_1$-$C_4$alkyl, —$N(C_1$-$C_4$alkyl)CO$—$C_1$-$C_4$alkyl, —$NHCO$—$C_1$-$C_4$cycloalkyl, —$N(C_1$-$C_4$alkyl)$CO$—$C_3$-$C_6$cycloalkyl, —$CO_2C_1$-$C_4$alkyl, —$CONH(C_1$-$C_4$alkyl), —$CONH(C_3$-$C_6$cycloalkyl), —$CON(C_1$-$C_4$alkyl)_2$, —$SO_2NH(C_1$-$C_4$alkyl)$;

$R^5$ is hydrogen, halogen, CN, or in each case optionally substituted $C_1$-$C_3$alkyl, $C_1$-$C_3$haloalkyl, $C_3$-$C_4$cycloalkyl, $C_3$-$C_4$halocycloalkyl, $C_1$-$C_3$alkoxy, $C_1$-$C_3$haloalkoxy, —$CH$—$(C_1$-$C_3$alkoxy$)_2$, —$CO_2C_1$-$C_4$alkyl, —$CONH(C_1$-$C_4$alkyl), —$CON(C_1$-$C_4$alkyl)_2$, —$NHCO$—$C_1$-$C_4$alkyl, —$N(C_1$-$C_4$alkyl)CO$—$C_1$-$C_4$alkyl, —$C(=NOC_1$-$C_4$alkyl$)H$, or —$C(=NOC_1$-$C_4$alkyl)$-$C_1$-$C_4$alkyl.

Further preferred (Configuration 3-1) are the compounds of the formula (I) in which $Q^1$ is N;

$Q^2$ is $CR^5$;

Y is a direct bond;

$R^1$ is hydrogen; $C_1$-$C_6$alkyl, optionally substituted with a substituent selected from the group of —CN, methoxy, ethoxy, methylthio and methylsulfonyl; or $C_1$-$C_6$haloalkyl; $C_3$-$C_6$cycloalkyl$C_1$-$C_6$alkyl; $C_2$-$C_6$alkenyl; $C_2$-$C_6$alkynyl; or $C_2$-$C_6$haloalkenyl;

$R^2$ is selected from one of the following bicyclic heterocycles T1-T21, T23-T30, T32-T39, T41, T42, T68-T70, in which the bond to the N atom is marked with a #;

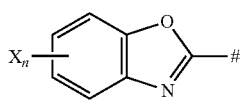
T1

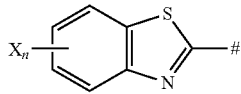
T2

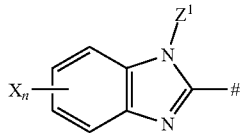
T3

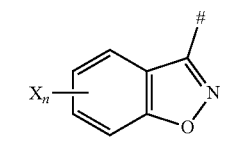
T4

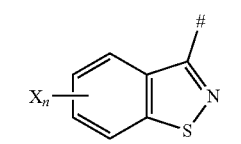
T5

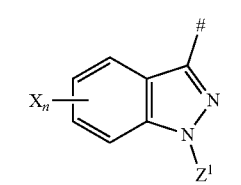
T6

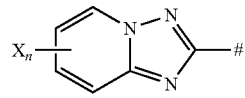
T7

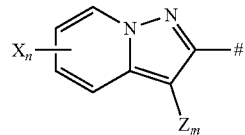
T8

T9

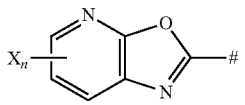
T10

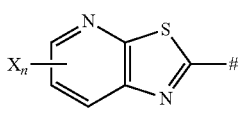
T11

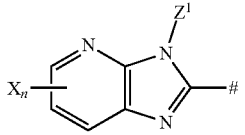
T12

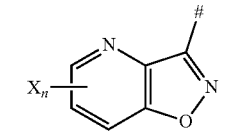
T13

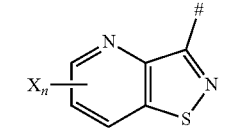
T14

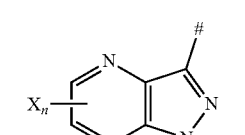
T15

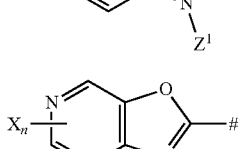
T16

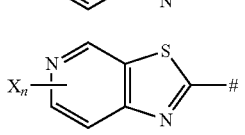
T17

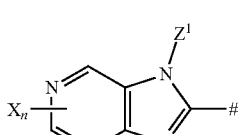
T18

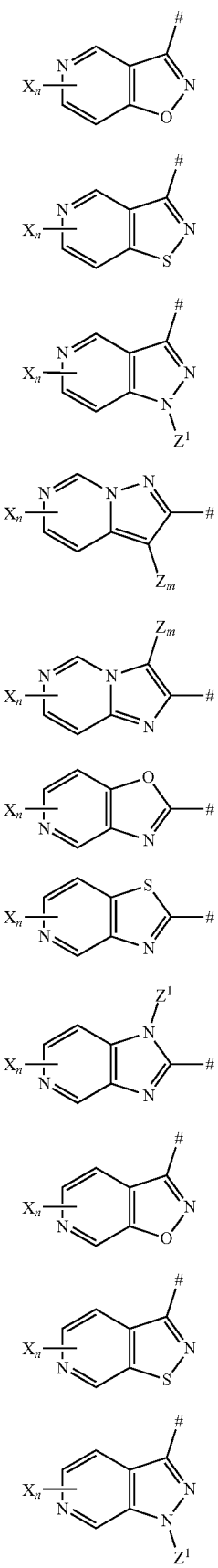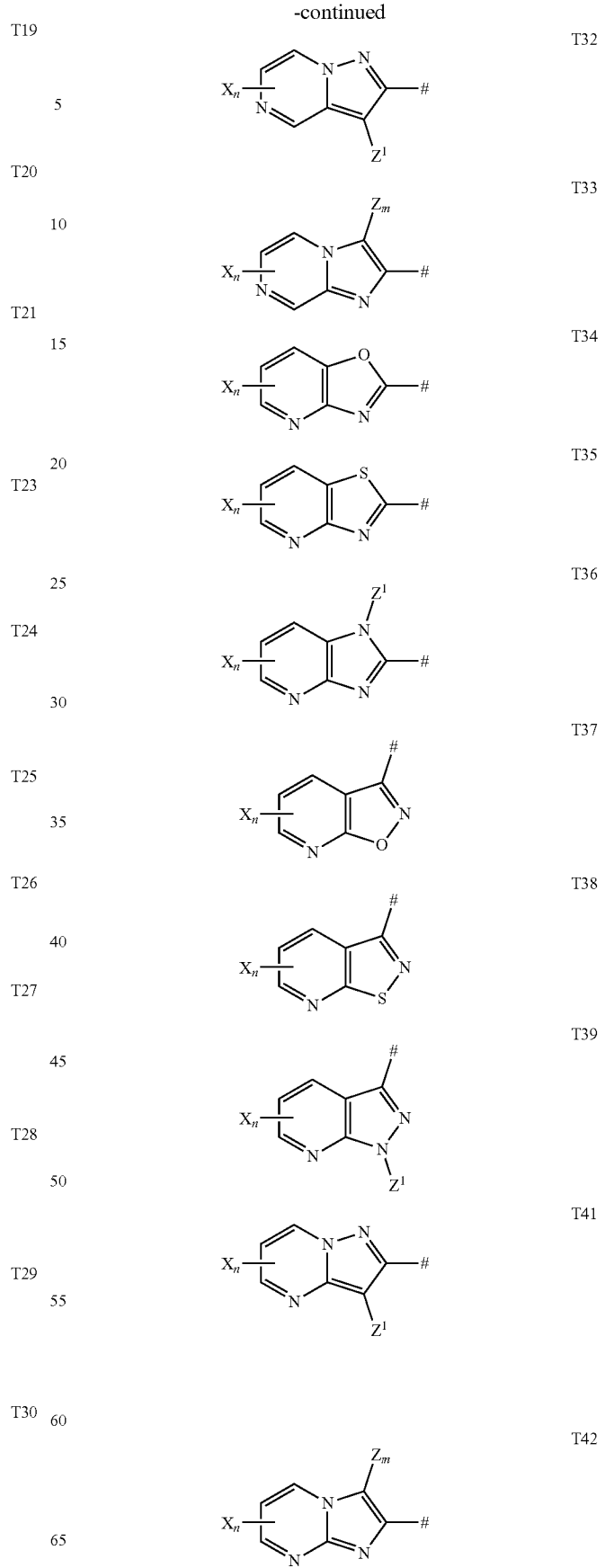

-continued

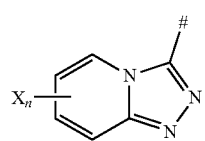
T68

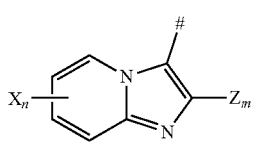
T69

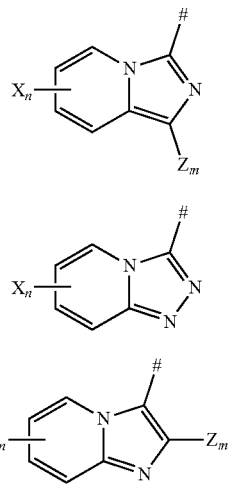
T70 wherein
n is an integer from 0 to 4;
m is an integer from 0 to 2;
X is selected from the group consisting of hydrogen, halogen, hydroxy, —CN, —COOH, —CONH$_2$, —NO$_2$, —NH$_2$, and in each case optionally substituted C$_1$-C$_6$alkyl, C$_3$-C$_6$cycloalkyl, C$_1$-C$_3$haloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, —NH(C$_1$-C$_4$alkyl), —N(C$_1$-C$_4$alkyl)$_2$, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)CO—C$_3$-C$_6$cyclolkyl, —N(C$_1$-C$_4$alkyl)SO$_2$C$_1$-C$_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CONHSO$_2$(C$_1$-C$_4$alkyl), —CON(C$_1$-C$_4$alkyl)$_2$, —CON(C$_1$-C$_4$alkyl)(C$_3$-C$_6$cycloalkyl), —CON(C$_1$-C$_4$alkyl)-phenyl, —CON(C$_1$-C$_4$alkyl)SO$_2$(C$_1$-C$_4$alkyl), —C(=NOC$_1$-C$_4$alkyl)H, —C(=NOC$_1$-C$_4$alkyl)-C$_1$-C$_4$alkyl;

and 4-6 membered heterocyclyl containing 1-2 oxygen atoms and optionally substituted with 1-2 substituents selected from the group consisting of methyl and ethyl;

Z is selected from the group consisting of hydrogen, halogen, hydroxy, —CN, —COOH, —CONH$_2$, —NO$_2$, —NH$_2$, and in each case optionally substituted C$_1$-C$_6$alkyl, C$_3$-C$_6$cycloalkyl, C$_1$-C$_3$haloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, —NH(C$_1$-C$_4$alkyl), —N(C$_1$-C$_4$alkyl)$_2$, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)CO—C$_3$-C$_6$cyclolkyl, —N(C$_1$-C$_4$alkyl)SO$_2$C$_1$-C$_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CONHSO$_2$(C$_1$-C$_4$alkyl), —CON(C$_1$-C$_4$alkyl)$_2$, —CON(C$_1$-C$_4$alkyl) (C$_3$-C$_6$cycloalkyl), —CON(C$_1$-C$_4$alkyl)-phenyl, —CON(C$_1$-C$_4$alkyl)SO$_2$(C$_1$-C$_4$alkyl), —C(=NOC$_1$-C$_4$alkyl)H, —C(=NOC$_1$-C$_4$alkyl)-C$_1$-C$_4$alkyl;

Z$^1$ is selected from the group consisting of hydrogen and C$_1$-C$_6$alkyl;

R$^3$ is hydrogen or C$_1$-C$_6$alkyl;

R$^4$ is pyridine, pyrimidine, pyrazine, pyridazine or 5-membered heteroaryl, wherein the pyridine, pyrimidine, pyrazine, pyridazine or 5-membered heteroaryl is optionally substituted with one to three substituents selected from the group consisting of halogen, hydroxy, —CN, —COOH, —CONH$_2$, —NO$_2$, —NH$_2$, —SF$_5$, and in each case optionally substituted C$_1$-C$_6$alkyl, C$_3$-C$_6$cycloalkyl, C$_1$-C$_3$haloalkyl, C$_3$-C$_6$halocycloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkyl sulfinyl, C$_1$-C$_3$haloalkylsulfonyl, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)CO—C$_3$-C$_6$cyclolkyl, —N(C$_1$-C$_4$alkyl)SO$_2$C$_1$-C$_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CONHSO$_2$(C$_1$-C$_4$alkyl), —CON(C$_1$-C$_4$alkyl)$_2$, —CON(C$_1$-C$_4$alkyl) (C$_3$-C$_6$cycloalkyl), —CON(C$_1$-C$_4$alkyl)-phenyl, —CON(C$_1$-C$_4$alkyl)SO$_2$(C$_1$-C$_4$alkyl);

and 3-6 membered heterocyclyl containing 1-2 heteroatoms selected from the group consisting of N, O, and S and optionally substituted with up to 4 substituents selected independently from the group consisting of fluorine, chlorine, bromine, methyl and ethyl;

R$^5$ is hydrogen, halogen, CN, or in each case optionally substituted C$_1$-C$_3$alkyl, C$_1$-C$_3$haloalkyl, C$_3$-C$_4$cycloalkyl, C$_3$-C$_4$halocycloalkyl, C$_1$-C$_3$alkoxy, or C$_1$-C$_3$haloalkoxy.

According to a further embodiment further preferred (Configuration 3-2) are the compounds of the formula (I) in which Q$^1$ is N;
Q$^2$ is CR$^5$;
Y is a direct bond;
R$^1$ is hydrogen; C$_1$-C$_6$alkyl, optionally substituted with a substituent selected from the group of —CN, methoxy, ethoxy, methylthio and methylsulfonyl; or C$_1$-C$_6$haloalkyl; C$_3$-C$_6$cycloalkylC$_1$-C$_6$alkyl; C$_2$-C$_6$alkenyl; C$_2$-C$_6$alkynyl; or C$_2$-C$_6$haloalkenyl;
R$^2$ is selected from one of the following bicyclic heterocycles T1-T21, T23-T30, T32-T39, T41, T42, T68-T70, in which the bond to the N atom is marked with a #;

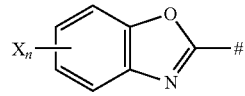
T1

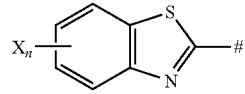
T2

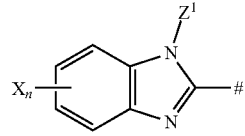
T3

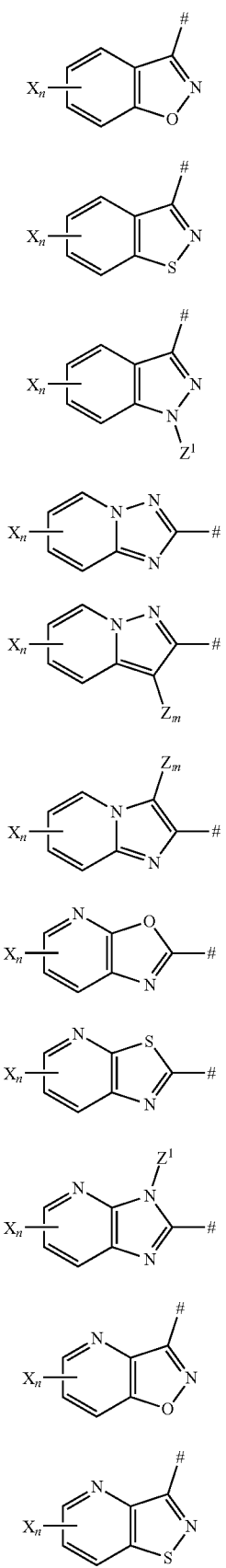
T4
T5
T6
T7
T8
T9
T10
T11
T12
T13
T14
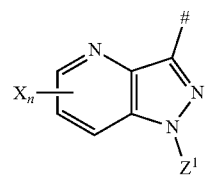
T15
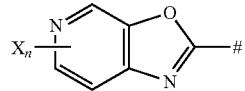
T16
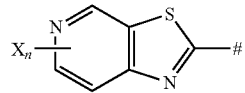
T17
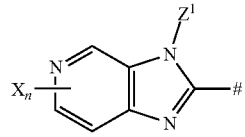
T18
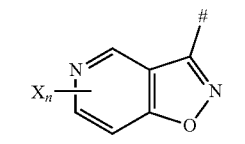
T19
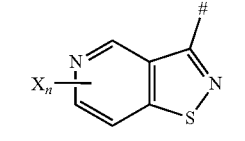
T20
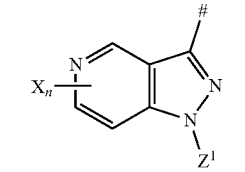
T21
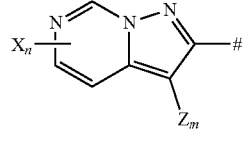
T23
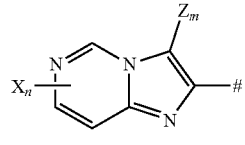
T24
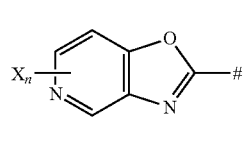
T25
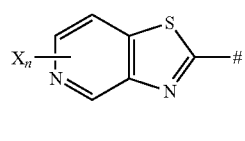
T26

T27 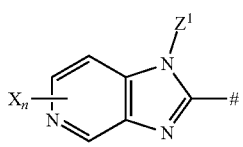

T28 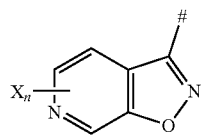

T29 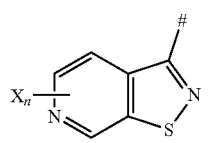

T30 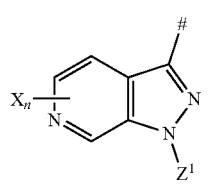

T32 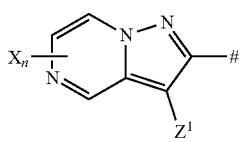

T33 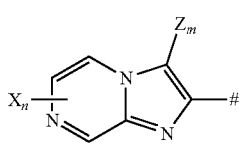

T34 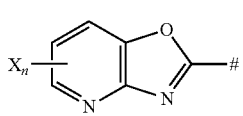

T35 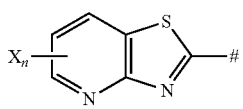

T36 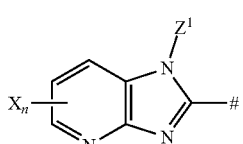

T37 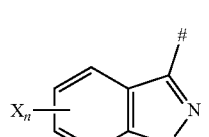

T38 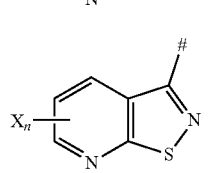

T39 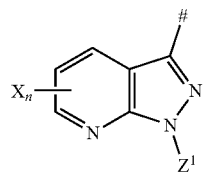

T41 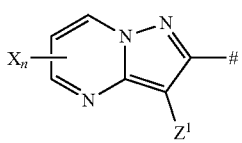

T42 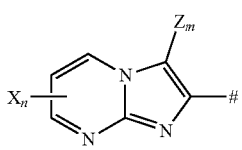

T68 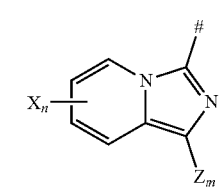

T69 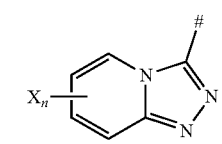

T70 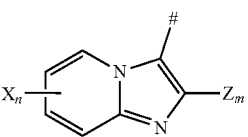

wherein n is an integer from 0 to 4;

m is an integer from 0 to 2;

X is selected from the group consisting of hydrogen, halogen, hydroxy, —CN, —COOH, —CONH$_2$, —NO$_2$, —NH$_2$, —SF$_5$ and in each case optionally substituted C$_1$-C$_6$alkyl, C$_3$-C$_6$cycloalkyl, C$_1$-C$_3$haloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, cycloalkylthio, cycloalkylsulfinyl, cycloalkylsulfonyl, C$_1$-C$_3$haloalkylthio, C$_1$-C$_3$haloalkylsulfinyl, C$_1$-C$_3$haloalkylsulfonyl, phenylsulfonyl, —NH(C$_1$-C$_4$alkyl), —N(C$_1$-C$_4$alkyl)$_2$, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)CO—C$_3$-C$_6$cyclolkyl, —N(C$_1$-C$_4$alkyl)SO$_2$C$_1$-C$_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CONHSO$_2$(C$_1$-C$_4$alkyl), —CON(C$_1$-C$_4$alkyl)$_2$, —CON(C$_1$-C$_4$alkyl)(C$_3$-C$_6$cycloalkyl), —CON(C$_1$-C$_4$alkyl)-phenyl, —CON(C$_1$-C$_4$alkyl)SO$_2$(C$_1$-C$_4$alkyl), —C(=NOC$_1$-C$_4$alkyl)H, —C(=NOC$_1$-C$_4$alkyl)-C$_1$-C$_4$alkyl;

and 4-6 membered heterocyclyl containing 1-2 oxygen atoms and optionally substituted with 1-2 substituents selected from the group consisting of methyl and ethyl;

Z is selected from the group consisting of hydrogen, halogen, hydroxy, —CN, —COOH, —CONH$_2$, —NO$_2$, —NH$_2$, and in each case optionally substituted C$_1$-C$_6$alkyl, C$_3$-C$_6$cycloalkyl, C$_1$-C$_3$haloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, —NH(C$_1$-C$_4$alkyl), —N(C$_1$-C$_4$alkyl)$_2$, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)CO—C$_3$-C$_6$cyclolkyl, —N(C$_1$-C$_4$alkyl)SO$_2$C$_1$-C$_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CONHSO$_2$(C$_1$-C$_4$alkyl), —CON(C$_1$-C$_4$alkyl)$_2$, —CON(C$_1$-C$_4$alkyl)(C$_3$-C$_6$cycloalkyl), —CON(C$_1$-C$_4$alkyl)-phenyl, —CON(C$_1$-C$_4$alkyl)SO$_2$(C$_1$-C$_4$alkyl), —C(=NOC$_1$-C$_4$alkyl)H, —C(=NOC$_1$-C$_4$alkyl)-C$_1$-C$_4$alkyl;

Z$^1$ is selected from the group consisting of hydrogen and C$_1$-C$_6$alkyl;

R$^3$ is hydrogen or C$_1$-C$_6$alkyl;

R$^4$ is pyridine, pyrimidine, pyrazine, pyridazine or 5-membered heteroaryl, wherein the pyridine, pyrimidine, pyrazine, pyridazine or 5-membered heteroaryl is optionally substituted with one to three substituents selected from the group consisting of halogen, hydroxy, —CN, —COOH, —CONH$_2$, —SO$_2$NH$_2$, —NO$_2$, —NH$_2$, —SF$_5$, and in each case optionally substituted C$_1$-C$_6$alkyl, C$_3$-C$_6$cycloalkyl, C$_1$-C$_3$haloalkyl, C$_3$-C$_6$halocycloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)CO—C$_3$-C$_6$cyclolkyl, —N(C$_1$-C$_4$alkyl)SO$_2$C$_1$-C$_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CONHSO$_2$(C$_1$-C$_4$alkyl), —CON(C$_1$-C$_4$alkyl)$_2$, —CON(C$_1$-C$_4$alkyl)(C$_3$-C$_6$cycloalkyl), —CONH(C$_3$-C$_6$cycloalkylalkyl), —CON(C$_1$-C$_6$alkyl)(C$_3$-C$_6$cycloalkylalkyl), —CON(C$_1$-C$_4$alkyl)-phenyl, —CON(C$_1$-C$_4$alkyl)SO$_2$—(C$_1$-C$_4$alkyl);

and 3-6 membered heterocyclyl containing 1-2 heteroatoms selected from the group consisting of N, O, and S and optionally substituted with up to 4 substituents selected independently from the group consisting of fluorine, chlorine, bromine, methyl and ethyl;

or one of the substituents may optionally be selected from the following substructures 51, S2, S3, S4, S5, S16 and S17, in which the bond to the pyridine, pyrimidine, pyrazine, pyridazine or 5-membered heteroaryl is marked with a # and Z$^4$ is CO:

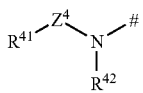
S1

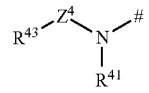
S2

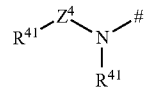
S3

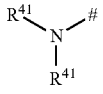
S4

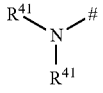
S5

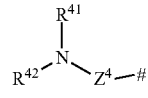
S16

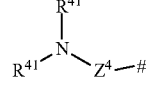
S17

R$^{41}$ is a heterocyclic ring which is selected from the group consisting of 4- to 8-membered saturated or partially unsaturated heterocyclyl, 5-membered heteroaryl and 6-membered heteroaryl, each of which is optionally substituted by one to two substituents independently selected from the group consisting of halogen, =O (oxo), =S (thiono), hydroxy, —CN, —COOH, —SO$_2$NH$_2$, —CONH$_2$, —CSNH$_2$, —NO$_2$, —SF$_5$, —NH$_2$;

and —CO$_2$—C$_1$-C$_3$alkyl, C$_1$-C$_3$alkyl, C$_3$-C$_4$cycloalkyl, C$_1$-C$_3$halo alkyl, C$_1$-C$_3$alkoxy, C$_1$-C$_3$halo alkoxy, C$_1$-C$_3$alkylthio, C$_1$-C$_3$alkylsulfinyl, C$_1$-C$_3$alkylsulfonyl, C$_3$-C$_4$cycloalkyl sulfanyl, C$_3$-C$_4$cycloalkylsulfinyl, C$_3$-C$_4$cycloalkyl sulfonyl, C$_1$-C$_3$haloalkylthio, C$_1$-C$_3$haloalkylsulfinyl, C$_1$-C$_3$halo alkylsulfonyl, —NH(C$_1$-C$_3$ alkyl), —N(C$_1$-C$_3$ alkyl)$_2$, —NHCO—C$_1$-C$_3$ alkyl, —N(C$_1$-C$_3$ alkyl)CO—C$_1$-C$_3$ alkyl, —N(C$_3$-C$_4$cycloalkyl)CO—C$_1$-C$_3$ alkyl, —NHCO—C$_3$-C$_4$cycloalkyl, —N(C$_1$-C$_3$ alkyl)CO—(C$_3$-C$_4$cycloalkyl), —N(C$_3$-C$_4$cycloalkyl)CO—(C$_3$-C$_4$cycloalkyl), —CONH(C$_1$-C$_3$alkyl), —CON(C$_1$-C$_3$ alkyl)$_2$, —CONH(C$_3$-C$_4$cycloalkyl), —CON(C$_1$-C$_3$ alkyl)(C$_3$-C$_4$cycloalkyl), —CON(C$_3$-C$_4$cycloalkyl)$_2$, —NHSO$_2$—C$_1$-C$_3$ alkyl, —NHSO$_2$—C$_1$-C$_3$halo alkyl, —N(C$_1$-C$_3$alkyl)SO$_2$—C$_1$-C$_3$alkyl, —N(C$_3$-C$_4$cycloalkyl)SO$_2$—C$_1$-C$_3$alkyl, —NHSO$_2$—C$_3$-C$_4$cycloalkyl, —N(C$_1$-C$_3$ alkyl)SO$_2$—(C$_3$-C$_4$cycloalkyl), —N(C$_3$-C$_4$cycloalkyl)SO$_2$—(C$_3$-C$_4$cycloalkyl), —SO$_2$NH(C$_1$-C$_3$ alkyl), —SO$_2$N(C$_1$-C$_3$ alkyl)$_2$, —SO$_2$N(C$_1$-C$_3$ alkyl)(C$_3$-C$_4$cycloalkyl), —SO$_2$NH(C$_3$-C$_4$cycloalkyl), —SO$_2$N(C$_3$-C$_4$cycloalkyl)$_2$;

R$^{42}$ is hydrogen, hydroxy;

and C$_1$-C$_3$alkyl, C$_1$-C$_3$haloalkyl, C$_2$-C$_4$alkenyl, C$_2$-C$_4$haloalkenyl, C$_2$-C$_4$alkynyl, C$_3$-C$_4$cycloalkyl, C$_3$-C$_4$cycloalkyl-C$_1$-C$_2$alkyl, phenyl-C$_1$-C$_2$alky, C$_1$-C$_3$alkoxy;

$R^{43}$ is $C_1$-$C_3$alkyl, $C_1$-$C_3$haloalkyl, $C_2$-$C_4$alkenyl, $C_2$-$C_4$haloalkenyl, $C_2$-$C_4$alkynyl, $C_3$-$C_4$cycloalkyl, $C_3$-$C_4$cycloalkyl-$C_1$-$C_2$alkyl, phenyl-$C_1$-$C_2$alkyl, $C_1$-$C_3$alkoxy;

$R^{44}$ is $C_1$-$C_3$alkyl, $C_1$-$C_3$haloalkyl, $C_2$-$C_4$alkenyl, $C_2$-$C_4$haloalkenyl, $C_2$-$C_4$alkynyl, $C_3$-$C_4$cycloalkyl, $C_3$-$C_4$cycloalkyl-$C_1$-$C_2$alkyl, phenyl-$C_1$-$C_2$alkyl;

$R^{45}$ is hydrogen and $C_1$-$C_3$alkyl, $C_1$-$C_3$haloalkyl, $C_2$-$C_4$alkenyl, $C_2$-$C_4$haloalkenyl, $C_2$-$C_4$alkynyl, $C_3$-$C_4$cycloalkyl, $C_3$-$C_4$cycloalkyl-$C_1$-$C_2$alkyl, phenyl-$C_1$-$C_2$alkyl;

or $R^{41}$ and $R^{42}$ together with the nitrogen atom to which they are attached, represent a monocyclic, spirocyclic or bridged polycyclic 4- to 8-membered saturated heterocyclyl which may contain up to one further heteroatom selected from the group of oxygen, nitrogen and sulfur and which is optionally substituted with one to three substituents selected from the group consisting of halogen, =O (oxo), =S (thiono), hydroxy, and —CN; and —$CO_2$—$C_1$-$C_3$ alkyl, $C_1$-$C_3$ alkyl, $C_3$-$C_4$cycloalkyl, $C_1$-$C_3$haloalkyl, $C_1$-$C_3$ alkoxy, $C_1$-$C_3$haloalkoxy, $C_1$-$C_3$ alkylthio, $C_1$-$C_3$ alkylsulfinyl, $C_1$-$C_3$ alkylsulfonyl, $C_3$-$C_4$cycloalkylsulfanyl, $C_3$-$C_4$cycloalkylsulfinyl, $C_3$-$C_4$cycloalkylsulfonyl, $C_1$-$C_3$haloalkylthio, $C_1$-$C_3$haloalkylsulfinyl, $C_1$-$C_3$haloalkylsulfonyl, —NHCO—$C_1$-$C_3$ alkyl, —N($C_1$-$C_3$ alkyl)CO—$C_1$-$C_3$ alkyl, —NHCO—$C_1$-$C_3$cycloalkyl, —N($C_1$-$C_3$ alkyl)CO—$C_3$-$C_4$cycloalkyl, —$CO_2C_1$-$C_3$ alkyl, —CONH($C_1$-$C_3$ alkyl), —CONH($C_3$-$C_4$cycloalkyl), and —CON($C_1$-$C_3$ alkyl)$_2$;

$R^5$ is hydrogen, halogen, CN, or in each case optionally substituted $C_1$-$C_3$alkyl, $C_1$-$C_3$haloalkyl, $C_3$-$C_4$cycloalkyl, $C_3$-$C_4$halocycloalkyl, $C_1$-$C_3$alkoxy, or $C_1$-$C_3$haloalkoxy.

Particularly preferred (Configuration 4-1) are the compounds of the formula (I) in which $Q^1$ is N;
$Q^2$ is $CR^5$;
Y is a direct bond;
$R^1$ is hydrogen, methyl, ethyl, n-propyl, isopropyl, cyanomethyl, methoxymethyl, ethoxymethyl, methoxyethyl, ethoxyethyl, methylthioethyl, methylsulfonylethyl, 2,2-difluoroethyl, 2,2,2-trifluoroethyl, cyclopropylmethyl, cyclobutylmethyl, 2-propen-1-yl, 3-methyl-but-2-en-1-yl, 3,3-difluoro-prop-2-en-1-yl, 3,3-dichloro-prop-2-en-1-yl or 2-propyn-1-yl;
$R^2$ is selected from one of the following bicyclic heterocycles T1, T2, T3, T7 or T8, in which the bond to the N atom is marked with a #;

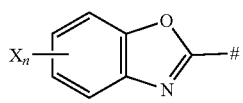

T1

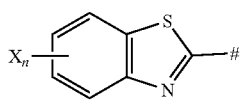

T2

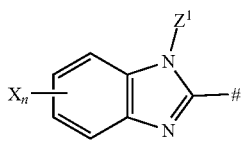

T3

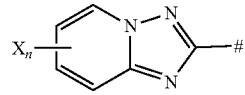

T7

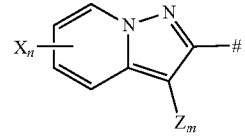

T8 wherein
n is an integer from 0 to 2; and
m is an integer from 0 to 1; and
X is selected from the group consisting of hydrogen, fluorine, chlorine, bromine, iodine, —CN, —$NO_2$, methyl, ethyl, isopropyl, difluoromethyl, trifluoromethyl, pentafluoroethyl, cyclopropyl, cyclobutyl, oxacyclobutyl, cyclopentyl, oxacyclopent-2-yl, methoxy, difluoromethoxy, trifluoromethoxy, methylthio, methylsulfinyl, methylsulfonyl, difluoromethylthio, difluoromethylsulfinyl, difluoromethylsulfonyl, trifluoromethylthio, trifluoromethylsulfinyl, and trifluoromethylsulfonyl; and Z is selected from the group consisting of hydrogen, fluorine, chlorine, bromine, methyl, ethyl and cyclopropyl;

$Z^1$ is selected from the group consisting of hydrogen and methyl;

$R^3$ is methyl;

$R^4$ is pyridine or pyrimidine, wherein the pyridine or pyrimidine is optionally substituted with one to three substituents selected from the group consisting of fluorine, chlorine, bromine, iodine, CN, —$NO_2$, methyl, ethyl, difluoromethyl, trifluoromethyl, pentafluoroethyl, cyclopropyl, methoxy, difluoromethoxy, trifluoromethoxy, methylthio, methylsulfinyl, methylsulfonyl, difluoromethylthio, difluoromethylsulfinyl, difluoromethylsulfonyl, trifluoromethylthio, trifluoromethylsulfinyl, and trifluoromethylsulfonyl;

$R^5$ is hydrogen, methyl, ethyl, n-propyl, isopropyl, cyclopropyl, trifluoromethyl or difluoromethyl.

According to a further embodiment particularly preferred (Configuration 4-2) are the compounds of the formula (I) in which $Q^1$ is N;
$Q^2$ is $CR^5$;
Y is a direct bond;
$R^1$ is hydrogen, methyl, ethyl, n-propyl, isopropyl, cyanomethyl, methoxymethyl, ethoxymethyl, methoxyethyl, ethoxyethyl, methylthioethyl, methylsulfonylethyl, 2,2-difluoroethyl, 2,2,2-trifluoroethyl, cyclopropylmethyl, cyclobutylmethyl, 2-propen-1-yl, 3-methyl-but-2-en-1-yl, 3,3-difluoro-prop-2-en-1-yl, 3,3-dichloro-prop-2-en-1-yl or 2-propyn-1-yl;
$R^2$ is selected from one of the following bicyclic heterocycles T1, T2, T3, T7 or T8, in which the bond to the N atom is marked with a #;

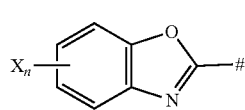

T1

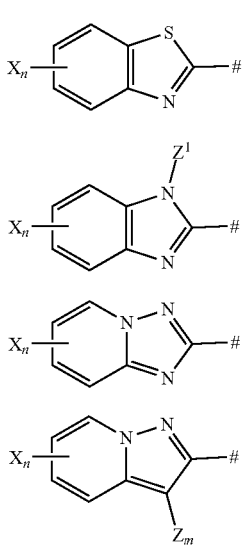

wherein
n is an integer from 0 to 2; and
m is an integer from 0 to 1; and
X is selected from the group consisting of hydrogen, fluorine, chlorine, bromine, iodine, —CN, —NO$_2$, —SF$_5$, methyl, ethyl, isopropyl, tert-butyl, difluoromethyl, trifluoromethyl, pentafluoroethyl, cyclopropyl, cyclobutyl, oxacyclobutyl, cyclopentyl, oxacyclopent-2-yl, methoxy, difluoromethoxy, trifluoromethoxy, methylthio, methylsulfinyl, methylsulfonyl, ethylthio, ethylsulfinyl, ethylsulfonyl, difluoromethylthio, difluoromethylsulfinyl, difluoromethylsulfonyl, trifluoromethylthio, trifluoromethylsulfinyl, and trifluoromethylsulfonyl; cyclopropylthio, cyclopropylsulfinyl, cylopropylsulfonyl, phenylsulfanyl, phenylsulfinyl, phenylsulfonyl, and
Z is selected from the group consisting of hydrogen, fluorine, chlorine, bromine, methyl, ethyl and cyclopropyl;
Z$^1$ is selected from the group consisting of hydrogen and methyl;
R$^3$ is hydrogen or methyl;
R$^4$ is thiazol, pyridine, pyrazine, pyridazine or pyrimidine, wherein the thiazol, pyridine, pyrazine, pyridazine or pyrimidine is optionally substituted with one to three substituents selected from the group consisting of fluorine, chlorine, bromine, iodine, —CN, —NO$_2$, —CONH$_2$, —SO$_2$NH$_2$, methyl, ethyl, difluoromethyl, trifluoromethyl, pentafluoroethyl, cyclopropyl, methoxy, difluoromethoxy, trifluoromethoxy, methylthio, methylsulfinyl, methylsulfonyl, difluoromethylthio, difluoromethylsulfinyl, difluoromethylsulfonyl, trifluoromethylthio, trifluoromethylsulfinyl, trifluoromethylsulfonyl, morpholinylcarbonyl, dimethylmorpholinylcarbonyl, piperidinylcarbonyl, pyrrolidinylcarbonyl, azetidinylcarbonyl, azepanylcarbonyl, oxazepanylcarbonyl, N-methylcarbamoyl, N-ethylcarbamoyl, N,N-dimethylcarbamoyl, N,N-diethylcarbamoyl, N-cyclopropylmethyl, N-methylcarbamoyl, morpholinylsulfonyl, dimethylmorpholinylsulfonyl, piperidinylsulfonyl, pyrrolidinylsulfonyl, azetidinylsulfonyl, azepanylsulfonyl, and oxazepanylsulfonyl; oxetanyl, tetrahydrofuranyl, pyranyl R$^5$ is hydrogen, methyl, ethyl, n-propyl, isopropyl, cyclopropyl, trifluoromethyl, methoxy, ethoxy, propoxy, trifluoromethoxy, cyclopropoxy or difluoromethyl.

Very particularly preferred (Configuration 5-1) are the compounds of the formula (I) in which
Q$^1$ is N;
Q$^2$ is CR$^5$;
Y is a direct bond;
R$^1$ is hydrogen;
R$^2$ is selected from one of the following bicyclic heterocycles T1 or T2, in which the bond to the N atom is marked with a #

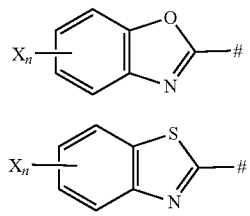

wherein
n is an integer of 0-2; and
X is independently selected from the group consisting of hydrogen, chlorine, bromine, trifluoromethyl, and methyl;
R$^3$ is methyl;
R$^4$ is pyrimidin-2-yl, 5-chloro-pyridin-2-yl, 5-cyano-pyridin-2-yl, 5-(trifluoromethyl)-pyridin-2-yl, or 3-chloro-5-(trifluoromethyl)-pyridin-2-yl;
R$^5$ is hydrogen or methyl.

According to a further embodiment very particularly preferred (Configuration 5-2) are the compounds of the formula (I) in which
Q$^1$ is N;
Q$^2$ is CR$^5$;
Y is a direct bond;
R$^1$ is hydrogen;
R$^2$ is selected from one of the following bicyclic heterocycles T1, T2 and T7 in which the bond to the N atom is marked with a # wherein
n is an integer of 0-2; and
X is independently selected from the group consisting of hydrogen, chlorine, bromine, —CN, —SF$_5$, trifluoromethyl, trifluoromethoxy, difluoromethoxy, methyl, isopropyl, tert-butyl, cyclopropyl, methylthio, ethylthio, cyclopropylthio and phenylsulfonyl;

$R^3$ is methyl;

$R^4$ is thiazol, pyridine, pyrazine, pyridazine or pyrimidine, wherein the thiazol, pyridine, pyrazine, pyridazine or pyrimidine is unsubstituted or is substituted with one or two substituents selected from the group consisting of fluorine, chlorine, bromine, —CN, —$NH_2$, —$CONH_2$, —$SO_2NH_2$, methyl, trifluoromethyl, methoxy, ethoxy, morpholin-4-ylcarbonyl, dimethylmorpholin-4-ylcarbonyl, pyrrolidine-1-ylcarbonyl, N-ethylcarbamoyl, N,N-diethylcarbamoyl, (N-cyclopropylmethyl,N-methyl)carbamoyl and oxetanyl or said thiazol, pyridine, pyrazine, pyridazine or pyrimidine optionally carries a second substituent selected from fluorine, chlorine and bromine;

$R^5$ is hydrogen, methyl, methoxy or cyclopropyl.

In a further preferred embodiment, the invention relates to compounds of the formula (I')

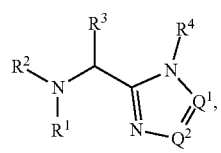

in which the structural elements $Q^1$, $Q^2$, $R^1$, $R^2$, $R^3$, $R^4$ and $R^5$ have the meaning given in Configuration (1-1) or in Configuration (2-1) or in Configuration (3-1) or in Configuration (4-1) or in Configuration (5-1).

According to another preferred embodiment, the invention relates to compounds of Formula (I') in which the structural elements $Q^1$, $Q^2$, $R^1$, $R^2$, $R^3$, $R^4$ and $R^5$ have the meaning given in Configuration (1-2) or in or in Configuration (2-2) or in Configuration (3-2) or in Configuration (4-2) or in Configuration (5-2).

In further preferred embodiments of the compounds of the formula (I'), $Q^1$ represents N or $CR^5$ and $Q^2$ represents N and all further structural elements $R^1$, $R^2$, $R^3$, $R^4$ and $R^5$ have the meaning described above in Configuration (1-1) or in Configuration (2-1) or in Configuration (3-1) or in Configuration (4-1) or in Configuration (5-1).

In other further preferred embodiments of the compounds of the formula (I'), $Q^1$ represents N and $Q^2$ represents $CR^5$ and all further structural elements $R^1$, $R^2$, $R^3$, $R^4$ and $R^5$ have the meaning described above in Configuration (1-1) or in Configuration (2-1) or in Configuration (3-1) or in Configuration (4-1) or in Configuration (5-1) or according to yet an additional embodiment, all further structural elements $R^1$, $R^2$, $R^3$, $R^4$ and $R^5$ have the meaning described above in Configuration (1-2) or in Configuration (2-2) or in Configuration (3-2) or in Configuration (4-2) or in Configuration (5-2)

Among these, particular preference is given to the configurations shown below:

| Compounds of the formula | with $Q^1$ as per | with $Q^2$ as per | all other structural elements as per |
|---|---|---|---|
| I' | N | $CR^5$ | Configuration (1-1) |
| I' | N | $CR^5$ | Configuration (2-1) |
| I' | N | $CR^5$ | Configuration (3-1) |
| I' | N | $CR^5$ | Configuration (4-1) |
| I' | N | $CR^5$ | Configuration (5-1) |
| I' | $CR^5$ | N | Configuration (1-1) |
| I' | $CR^5$ | N | Configuration (2-1) |
| I' | $CR^5$ | N | Configuration (3-1) |
| I' | $CR^5$ | N | Configuration (4-1) |
| I' | $CR^5$ | N | Configuration (5-1) |
| I' | N | N | Configuration (1-1) |
| I' | N | N | Configuration (2-1) |
| I' | N | N | Configuration (3-1) |
| I' | N | N | Configuration (4-1) |
| I' | N | N | Configuration (5-1) | or, according to a further embodiment:

| I' | N | $CR^5$ | Configuration (1-2) |
|---|---|---|---|
| I' | N | $CR^5$ | Configuration (2-2) |
| I' | N | $CR^5$ | Configuration (3-2) |
| I' | N | $CR^5$ | Configuration (4-2) |
| I' | N | $CR^5$ | Configuration (5-2) |
| I' | $CR^5$ | N | Configuration (1-2) |
| I' | $CR^5$ | N | Configuration (2-2) |
| I' | $CR^5$ | N | Configuration (3-2) |
| I' | $CR^5$ | N | Configuration (4-2) |
| I' | $CR^5$ | N | Configuration (5-2) |
| I' | N | N | Configuration (1-2) |
| I' | N | N | Configuration (2-2) |
| I' | N | N | Configuration (3-2) |
| I' | N | N | Configuration (4-2) |
| I' | N | N | Configuration (5-2) |

In another preferred embodiment, the invention covers compounds of formula I''

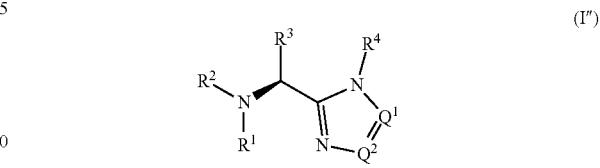

in which the structural elements $Q^1$, $Q^2$, $R^1$, $R^2$, $R^3$, $R^4$ and $R^5$ have the meaning given in Configuration (1-1) or in Configuration (2-1) or in Configuration (3-1) or in Configuration (4-1) or in Configuration (5-1) or, according to another embodiment $Q^1$, $Q^2$, $R^1$, $R^2$, $R^3$, $R^4$ and $R^5$ have the meaning given in Configuration (1-2) or in Configuration (2-2) or in Configuration (3-2) or in Configuration (4-2) or in Configuration (5-2).

In further preferred embodiments of the compounds of the formula (I''), $Q^1$ represents N or $CR^5$ and $Q^2$ represents N and all further structural elements $R^1$, $R^2$, $R^3$, $R^4$ and $R^5$ have the meaning described above in Configuration (1-1) or in Configuration (2-1) or in Configuration (3-1) or in Configuration (4-1) or in Configuration (5-1) or, according to another embodiment $R^1$, $R^2$, $R^3$, $R^4$ and $R^5$ have the meaning given in Configuration (1-2) or in Configuration (2-2) or in Configuration (3-2) or in Configuration (4-2) or in Configuration (5-2).

In other further preferred embodiments of the compounds of the formula (I''), $Q^1$ represents N and $Q^2$ represents $CR^5$ and all further structural elements $R^1$, $R^2$, $R^3$, $R^4$ and $R^5$ have the meaning described above in Configuration (1-1) or in Configuration (2-1) or in Configuration (3-1) or in Configuration (4-1) or in Configuration (5-1) or, according to another embodiment $R^1$, $R^2$, $R^3$, $R^4$ and $R^5$ have the meaning given in Configuration (1-2) or in Configuration (2-2) or in Configuration (3-2) or in Configuration (4-2) or in Configuration (5-2).

Among these, particular preference is given to the configurations shown below:

| Compounds of the formula | with Q¹ as per | with Q² as per | all other structural elements as per |
|---|---|---|---|
| I″ | N | CR⁵ | Configuration (1-1) |
| I″ | N | CR⁵ | Configuration (2-1) |
| I″ | N | CR⁵ | Configuration (3-1) |
| I″ | N | CR⁵ | Configuration (4-1) |
| I″ | N | CR⁵ | Configuration (5-1) |
| I″ | CR⁵ | N | Configuration (1-1) |
| I″ | CR⁵ | N | Configuration (2-1) |
| I″ | CR⁵ | N | Configuration (3-1) |
| I″ | CR⁵ | N | Configuration (4-1) |
| I″ | CR⁵ | N | Configuration (5-1) |
| I″ | N | N | Configuration (1-1) |
| I″ | N | N | Configuration (2-1) |
| I″ | N | N | Configuration (3-1) |
| I″ | N | N | Configuration (4-1) |
| I″ | N | N | Configuration (5-1) | or, according to a further embodiment:

| | | | |
|---|---|---|---|
| I″ | N | CR⁵ | Configuration (1-2) |
| I″ | N | CR⁵ | Configuration (2-2) |
| I″ | N | CR⁵ | Configuration (3-2) |
| I″ | N | CR⁵ | Configuration (4-2) |
| I″ | N | CR⁵ | Configuration (5-2) |
| I″ | CR⁵ | N | Configuration (1-2) |
| I″ | CR⁵ | N | Configuration (2-2) |
| I″ | CR⁵ | N | Configuration (3-2) |
| I″ | CR⁵ | N | Configuration (4-2) |
| I″ | CR⁵ | N | Configuration (5-2) |
| I″ | N | N | Configuration (1-2) |
| I″ | N | N | Configuration (2-2) |
| I″ | N | N | Configuration (3-2) |
| I″ | N | N | Configuration (4-2) |
| I″ | N | N | Configuration (5-2) |

In accordance with a further aspect, the present invention covers intermediate compounds which are useful for the preparation of the compounds of general formula (I), supra.

Particularly, the invention covers the intermediate compounds of general formula (k):

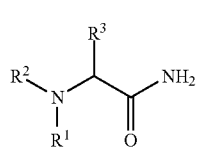

(k)

in which the structural elements R¹, R² and R³ have the meaning given in Configuration (1-1) or in Configuration (2-1) or in Configuration (3-1) or in Configuration (4-1) or in Configuration (5-1); or, according to a further embodiment, the structural elements R¹, R² and R³ have the meaning given in Configuration (1-2) or in Configuration (2-2) or in Configuration (3-2) or in Configuration (4-2) or in Configuration (5-2)

Particularly, the invention covers the intermediate compounds of general formula (k):

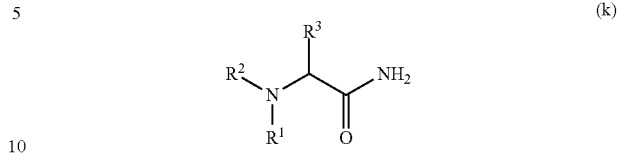

(k)

in which:
R¹ is hydrogen;
R² is selected from one of the following bicyclic heterocycles T1 or T2, in which the bond to the N atom is marked with a #

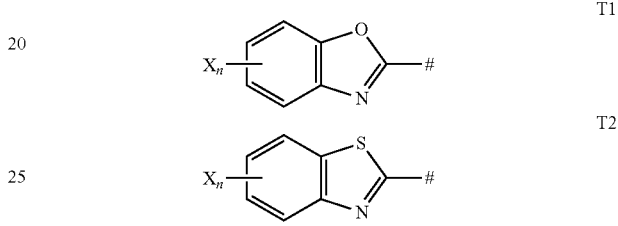

wherein
n is an integer of 0-2; and
X is independently selected from the group consisting of hydrogen, chlorine, bromine, trifluoromethyl, and methyl;
R³ is methyl or trifluoromethyl.

According to a further embodiment the invention covers in particular the intermediate compounds of general formula (k), wherein
R¹ is hydrogen;
R² is selected from one of the following bicyclic heterocycles T1, T2 and T7 in which the bond to the N atom is marked with a #

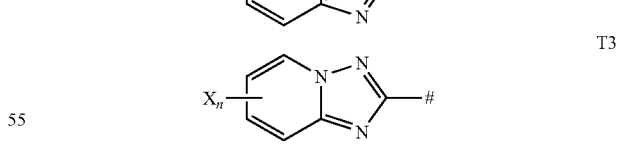

wherein
n is an integer of 0-2; and
X is independently selected from the group consisting of hydrogen, chlorine, bromine, cyano, SF₅, trifluoromethyl, trifluoromethoxy, difluoromethoxy, methyl, isopropyl, tert-butyl, cyclopropyl, methylthio, ethylthio, cyclopropylthio and phenylsulfonyl;
R³ is hydrogen or methyl;
The compounds of the formula (I) may possibly also, depending on the nature of the substituents, be in the form of stereoisomers, i.e. in the form of geometric and/or optical isomers or isomer mixtures of varying composition. This invention provides both the pure stereoisomers and any desired mixtures of these isomers, even though it is generally only compounds of the formula (I) that are discussed here.

However, preference is given in accordance with the invention to using the optically active, stereoisomeric forms of the compounds of the formula (I) and salts thereof.

The invention therefore relates both to the pure enantiomers and diastereomers and to mixtures thereof for controlling animal pests, including arthropods and particularly insects.

If appropriate, the compounds of the formula (I) may be present in various polymorphic forms or as a mixture of various polymorphic forms. Both the pure polymorphs and the polymorph mixtures are provided by the invention and can be used in accordance with the invention.

According to further aspects the invention relates to:

I. Formulations, comprising at least one compound of the formula (I), (I') or (I") as described herein.
II. Formulation according to aspect I which is an agrochemical formulations.
III. Formulation according to aspect I, which is a veterinary formulation.
IV. Formulation according to aspect I to III, further comprising at least one extender and/or at least one surface-active substance.
V. Formulation according to aspects I to IV, characterized in that the compound of the formula (I), (I') or (I") is in a mixture with at least one further active compound.
VI. Method for controlling pests, especially animal pests, characterized in that a compound of the formula (I), (I') or (I") as described herein or a formulation according to any of aspects I to V is allowed to act on the pests and/or their habitat, wherein methods for treatment of the animal body by surgery or therapy and diagnostic methods practised on the animal body are excluded.
VII. Method according to aspect VI, characterized in that the pest is an animal pest and comprises an insect, an arachnid or a nematode, or in that the pest is an insect, an arachnid or a nematode.
VIII. Use of a compound of the formula (I), (I') or (I") as described herein or of a formulation according to any of aspects I to V for controlling animal pests, wherein methods for treatment of the animal body by surgery or therapy and diagnostic methods practised on the animal body are excluded.
IX. Use according to aspect VIII, characterized in that the animal pest comprises an insect, an arachnid or a nematode, or in that the animal pest is an insect, an arachnid or a nematode.
X. Use according to aspect VIII or IX in crop protection.
XI. Use according to aspect VIII or IX in the field of animal health.
XII. Use according to aspect VIII or IX in vector control.
XIII. Compounds of formula (I), (I') or (I") as described herein, which are for use as medicaments.
XIV. Veterinary formulation according to aspect III to V which optionally comprises at least one further component selected from pharmaceutically acceptable auxiliaries, excipients, solvents and/or at least one additional pharmaceutically active agent.
XV. Veterinary formulation according to aspect III to V or XIV, comprising at least one additional pharmaceutically active agent.
XVI. Veterinary formulation according to any of the aspects III to V, XIV or XV which are in the form of an injectable formulation.
XVII. Veterinary formulation according to any of the aspects III to V, XIV or XV, which are in the form of a formulation for oral administration.
XVIII. Compounds of the formula (I), (I') or (I") as described herein or veterinary formulations according to aspects III to V or XIV to XVII for treating animals.
XIX. Compounds or veterinary formulation according to aspect XVIII, wherein the animals to be treated are selected from companion animals.
XX. Compounds or veterinary formulation according to aspect XIX, wherein the companion animals are selected from cats and dogs.
XXI. Use of the compounds of the formula (I), (I') or (I") as described herein or veterinary formulations according to aspects III to V or XIV to XVII for controlling ectoparasites.
XXII. Use according to aspect XXI, wherein the ectoparasites are selected from insects and arachnids.
XXIII. Use according to aspect XXII, wherein the insects and arachnids are selected from the group consisting of lice, mosquitoes, flies, fleas, ticks and mites.
XXIV. Compounds of the formula (I), (I') or (I") as described herein or veterinary formulations according to aspects III to V or XIV to XVII for preparing pharmaceutical compositions for controlling parasites on animals.

Definitions

The person skilled in the art is aware that, if not stated explicitly, the expressions "a" or "an" as used in the present application may, depending on the situation, mean "one (1)", "one (1) or more" or "at least one (1)".

For all the structures described herein, such as ring systems and groups, adjacent atoms must not be —O—O— or —O—S—.

Structures having a variable number of possible carbon atoms (C atoms) may be referred to in the present application as $C_{lower\ limit\ of\ carbon\ atoms}$—$C_{upper\ limit\ of\ carbon\ atoms}$ structures ($C_{LL}$-$C_{UL}$ structures), in order thus to be stipulated more specifically. Example: an alkyl group may consist of 3 to 10 carbon atoms and in that case corresponds to $C_3$-$C_{10}$alkyl. Ring structures composed of carbon atoms and heteroatoms may be referred to as "LL- to UL-membered" structures. One example of a 6-membered ring structure is toluene (a 6-membered ring structure substituted by a methyl group).

If a collective term for a substituent, for example $C_{LL}$-$C_{UL}$alkyl, is at the end of a composite substituent, for example $C_{LL}$-$C_{UL}$cycloalkyl-$C_{LL}$-$C_{UL}$alkyl, the constituent at the start of the composite substituent, for example the $C_{LL}$-$C_{UL}$cycloalkyl, may be mono- or polysubstituted identically or differently and independently by the latter substituent, for example $C_{LL}$-$C_{UL}$alkyl. All the collective terms used in this application for chemical groups, cyclic systems and cyclic groups can be stipulated more specifically through the addition "$C_{LL}$-$C_{UL}$" or "LL- to UL-membered".

In the definitions of the symbols given in the above formulae, collective terms which are generally representative of the following substituents were used:

Halogen relates to elements of the 7th main group, preferably fluorine, chlorine, bromine and iodine, more preferably fluorine, chlorine and bromine, and even more preferably fluorine and chlorine.

Examples of heteroatom are N, O, S, P, B, Si. Preferably, the term "heteroatom" relates to N, S and O.

According to the invention, "alkyl"—on its own or as part of a chemical group—represents straight-chain or branched hydrocarbons preferably having 1 to 6 carbon atoms, for example methyl, ethyl, n-propyl, isopropyl, n-butyl, isobutyl, s-butyl, t-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylpropyl, 1,3-dimethylbutyl, 1,4-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preference is also given to alkyls having 1 to 4 carbon atoms such as, inter alia, methyl, ethyl, ethyl, n-propyl, isopropyl, n-butyl, isobutyl, s-butyl or t-butyl. The inventive alkyls may be substituted by one or more identical or different radicals.

According to the invention, "alkenyl"—on its own or as part of a chemical group—represents straight-chain or branched hydrocarbons preferably having 2 to 6 carbon atoms and at least one double bond, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preference is also given to alkenyls having 2 to 4 carbon atoms such as, inter alia, 2-propenyl, 2-butenyl or 1-methyl-2-propenyl. The inventive alkenyls may be substituted by one or more identical or different radicals.

According to the invention, "alkynyl"—on its own or as part of a chemical group—represents straight-chain or branched hydrocarbons preferably having 2 to 6 carbon atoms and at least one triple bond, for example 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-3-butynyl, 1,2-dimethyl-3-butynyl, 2,2-dimethyl-3-butynyl, 1-ethyl-3-butynyl, 2-ethyl-3-butynyl, 1-ethyl-1-methyl-2-propynyl and 2,5-hexadiynyl. Preference is also given to alkynyls having 2 to 4 carbon atoms such as, inter alia, ethynyl, 2-propynyl or 2-butynyl-2-propenyl. The inventive alkynyls may be substituted by one or more identical or different radicals.

According to the invention, "cycloalkyl"—on its own or as part of a chemical group—represents mono-, bi- or tricyclic hydrocarbons preferably having 3 to 10 carbons, for example cyclopropyl, cyclobutyl, cyclopentyl, cyclohexyl, cycloheptyl, cyclooctyl, bicyclo[2.2.1]heptyl, bicyclo[2.2.2]octyl or adamantyl. Preference is also given to cycloalkyls having 3, 4, 5, 6 or 7 carbon atoms such as, inter alia, cyclopropyl or cyclobutyl. The inventive cycloalkyls may be substituted by one or more identical or different radicals.

According to the invention, "alkylcycloalkyl" represents mono-, bi- or tricyclic alkylcycloalkyl preferably having 4 to 10 or 4 to 7 carbon atoms, for example methylcyclopropyl, ethylcyclopropyl, isopropylcyclobutyl, 3-methylcyclopentyl and 4-methylcyclohexyl. Preference is also given to alkylcycloalkyls having 4, 5 or 7 carbon atoms such as, inter alia, ethylcyclopropyl or 4-methylcyclohexyl. The inventive alkylcycloalkyls may be substituted by one or more identical or different radicals.

According to the invention, "cycloalkylalkyl" represents mono-, bi- or tricyclic cycloalkylalkyl preferably having 4 to 10 or 4 to 7 carbon atoms, for example cyclopropylmethyl, cyclobutylmethyl, cyclopentylmethyl, cyclohexylmethyl and cyclopentylethyl. Preference is also given to cycloalkylalkyls having 4, 5 or 7 carbon atoms such as, inter alia, cyclopropylmethyl or cyclobutylmethyl. The inventive cycloalkylalkyls may be substituted by one or more identical or different radicals.

According to the invention, "hydroxyalkyl" represents a straight-chain or branched alcohol preferably having 1 to 6 carbon atoms, for example methanol, ethanol, n-propanol, isopropanol, n-butanol, isobutanol, s-butanol and t-butanol. Preference is also given to hydroxyalkyl groups having 1 to 4 carbon atoms. The inventive hydroxyalkyl groups may be substituted by one or more identical or different radicals.

According to the invention, "alkoxy" represents a straight-chain or branched O-alkyl preferably having 1 to 6 carbon atoms, for example methoxy, ethoxy, n-propoxy, isopropoxy, n-butoxy, isobutoxy, s-butoxy and t-butoxy. Preference is also given to alkoxy groups having 1 to 4 carbon atoms. The inventive alkoxy groups may be substituted by one or more identical or different radicals.

According to the invention, "alkylthio", or "alkylsulfanyl", represents straight-chain or branched S-alkyl preferably having 1 to 6 carbon atoms, for example methylthio, ethylthio, n-propylthio, isopropylthio, n-butylthio, isobutylthio, s-butylthio and t-butylthio. Preference is also given to alkylthio groups having 1 to 4 carbon atoms. The inventive alkylthio groups may be substituted by one or more identical or different radicals.

According to the invention, "alkylsulfinyl" represents straight-chain or branched alkylsulfinyl preferably having 1 to 6 carbon atoms, for example methylsulfinyl, ethylsulfinyl, n-propylsulfinyl, isopropylsulfinyl, n-butylsulfinyl, isobutylsulfinyl, s-butylsulfinyl and t-butylsulfinyl. Preference is also given to alkylsulfinyl groups having 1 to 4 carbon atoms. The inventive alkylsulfinyl groups may be substituted by one or more identical or different radicals.

According to the invention, "alkylsulfonyl" represents straight-chain or branched alkylsulfonyl preferably having 1 to 6 carbon atoms, for example methylsulfonyl, ethylsulfonyl, n-propylsulfonyl, isopropylsulfonyl, n-butylsulfonyl, isobutylsulfonyl, s-butylsulfonyl and t-butylsulfonyl. Preference is also given to alkylsulfonyl groups having 1 to 4 carbon atoms. The inventive alkylsulfonyl groups may be substituted by one or more identical or different radicals.

According to the invention, "alkylcarbonyl" represents straight-chain or branched alkyl-C(=O) preferably having 2 to 7 carbon atoms such as methylcarbonyl, ethylcarbonyl, n-propylcarbonyl, isopropylcarbonyl, s-butylcarbonyl and t-butylcarbonyl. Preference is also given to alkylcarbonyls having 1 to 4 carbon atoms. The inventive alkylcarbonyls may be substituted by one or more identical or different radicals.

According to the invention, "alkoxycarbonyl"—alone or as a constituent of a chemical group—represents straight-chain or branched alkoxycarbonyl, preferably having 1 to 6 carbon atoms or having 1 to 4 carbon atoms in the alkoxy moiety, for example methoxycarbonyl, ethoxycarbonyl, n-propoxycarbonyl, isopropoxycarbonyl, s-butoxycarbonyl and t-butoxycarbonyl. The inventive alkoxycarbonyl groups may be substituted by one or more identical or different radicals.

According to the invention, "alkylaminocarbonyl" represents straight-chain or branched alkylaminocarbonyl having preferably 1 to 6 carbon atoms or 1 to 4 carbon atoms in the alkyl moiety, for example methylaminocarbonyl, ethylaminocarbonyl, n-propylaminocarbonyl, isopropylaminocarbonyl, s-butylaminocarbonyl and t-butylaminocarbonyl. The inventive alkylaminocarbonyl groups may be substituted by one or more identical or different radicals.

According to the invention, "N,N-dialkylaminocarbonyl" represents straight-chain or branched N,N-dialkylaminocarbonyl having preferably 1 to 6 carbon atoms or 1 to 4 carbon atoms in the alkyl moiety, for example N,N-dimethylaminocarbonyl, N,N-diethylaminocarbonyl, N,N-di(n-propylamino)carbonyl, N,N-di(isopropylamino)carbonyl and N,N-di-(s-butylamino)carbonyl. The inventive N,N-dialkylaminocarbonyl groups may be substituted by one or more identical or different radicals.

According to the invention, "aryl" represents a mono-, bi- or polycyclic aromatic system having preferably 6 to 14, especially 6 to 10, ring carbon atoms, for example phenyl, naphthyl, anthryl, phenanthrenyl, preferably phenyl. In addition, aryl also represents polycyclic systems such as tetrahydronaphthyl, indenyl, indanyl, fluorenyl, biphenyl, where the bonding site is on the aromatic system. The inventive aryl groups may be substituted by one or more identical or different radicals.

Examples of substituted aryls are the arylalkyls, which may likewise be substituted by one or more identical or different radicals in the $C_1$-$C_4$alkyl and/or $C_6$-$C_{14}$aryl moiety. Examples of such arylalkyls include benzyl and phenyl-1-ethyl.

According to the invention, "heterocycle", "heterocyclic ring" or "heterocyclic ring system" represents a carbocyclic ring system having at least one ring in which at least one carbon atom is replaced by a heteroatom, preferably by a heteroatom from the group consisting of N, O, S, P, B, Si, Se, and which is saturated, unsaturated or heteroaromatic and may be unsubstituted or substituted, where the bonding site is on a ring atom. Unless defined differently, the heterocyclic ring contains preferably 3 to 9 ring atoms, especially 3 to 6 ring atoms, and one or more, preferably 1 to 4, especially 1, 2 or 3, heteroatoms in the heterocyclic ring, preferably from the group consisting of N, O, and S, although no two oxygen atoms should be directly adjacent. The heterocyclic rings usually contain not more than 4 nitrogen atoms and/or not more than 2 oxygen atoms and/or not more than 2 sulphur atoms. When the heterocyclyl radical or the heterocyclic ring is optionally substituted, it may be fused to other carbocyclic or heterocyclic rings. In the case of optionally substituted heterocyclyl, the invention also embraces polycyclic systems, for example 8-azabicyclo[3.2.1]octanyl or 1-azabicyclo[2.2.1]heptyl. In the case of optionally substituted heterocyclyl, the invention also embraces spirocyclic systems, for example 1-oxa-5-azaspiro[2.3]hexyl. Inventive heterocyclyl groups are, for example, piperidinyl, piperazinyl, morpholinyl, thiomorpholinyl, dihydropyranyl, tetrahydropyranyl, dioxanyl, pyrrolinyl, pyrrolidinyl, imidazolinyl, imidazolidinyl, thiazolidinyl, oxazolidinyl, dioxolanyl, dioxolyl, pyrazolidinyl, tetrahydrofuranyl, dihydrofuranyl, oxetanyl, oxiranyl, azetidinyl, aziridinyl, oxazetidinyl, oxaziridinyl, oxazepanyl, oxazinanyl, azepanyl, oxopyrrolidinyl, dioxopyrrolidinyl, oxomorpholinyl, oxopiperazinyl and oxepanyl.

Of particular significance are heteroaryls, i.e. heteroaromatic systems. According to the invention, the term heteroaryl represents heteroaromatic compounds, i.e. completely unsaturated aromatic heterocyclic compounds which fall under the above definition of heterocycles. Preference is given to 5- to 7-membered rings having 1 to 3, preferably 1 or 2, identical or different heteroatoms from the group above. Inventive heteroaryls are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The inventive heteroaryl groups may also be substituted by one or more identical or different radicals.

The term "in each case optionally substituted" means that a group/substituent, such as a alkyl, alkenyl, alkynyl, alkoxy, alkylthio, alkylsulfinyl, alkylsulfonyl, cycloalkyl, aryl, phenyl, benzyl, heterocyclyl and heteroaryl radical, is substituted, meaning, for example, a substituted radical derived from the unsubstituted base structure, where the substituents, for example, one (1) substituent or a plurality of substituents, preferably 1, 2, 3, 4, 5, 6 or 7, are selected from a group consisting of amino, hydroxyl, halogen, nitro, cyano, isocyano, mercapto, isothiocyanato, $C_1$-$C_4$carboxyl, carbonamide, $SF_5$, aminosulphonyl, $C_1$-$C_4$alkyl, $C_1$-$C_4$haloalkyl, $C_3$-$C_4$cycloalkyl, $C_2$-$C_4$alkenyl, $C_5$-$C_6$cycloalkenyl, $C_2$-$C_4$alkynyl, N-mono-$C_1$-$C_4$alkyl amino, NA-di-$C_1$-$C_4$alkylamino, N—$C_1$-$C_4$alkanoyl amino, $C_1$-$C_4$alkoxy, $C_1$-$C_4$haloalkoxy, $C_2$-$C_4$alkenyloxy, $C_2$-$C_4$alkynyloxy, $C_3$-$C_4$cycloalkoxy, $C_5$-$C_6$cycloalkenyloxy, $C_1$-$C_4$alkoxycarbonyl, $C_2$-$C_4$alkenyloxycarbonyl, $C_2$-$C_4$alkynyloxycarbonyl, $C_6$-, $C_{10}$-, $C_{14}$-aryloxycarbonyl, $C_1$-$C_4$alkanoyl, $C_2$-$C_4$alkenylcarbonyl, $C_2$-$C_4$alkynylcarbonyl, $C_6$-, $C_{10}$-, $C_{14}$-arylcarbonyl, $C_1$-$C_4$alkylthio, $C_1$-$C_4$haloalkylthio, $C_3$-$C_4$cycloalkylthio, $C_2$-$C_4$alkenylthio, $C_5$-$C_6$cycloalkenylthio, $C_2$-$C_4$alkynylthio, $C_1$-$C_4$alkylsulfinyl, including both enantiomers of the $C_1$-$C_4$alkylsulfinyl group, $C_1$-$C_4$haloalkylsulfinyl, including both enantiomers of the $C_1$-$C_4$haloalkylsulfinyl group, $C_1$-$C_4$alkylsulfonyl, $C_1$-$C_4$halo alkyl sulfonyl, N-mono-$C_1$-$C_4$alkylaminosulfonyl, N,N-di-$C_1$-$C_4$alkylaminosulfonyl, $C_1$-$C_4$alkylphosphinyl, $C_1$-$C_4$alkylphosphonyl, including both enantiomers of $C_1$-$C_4$alkylphosphinyl and $C_1$-$C_4$alkylphosphonyl, N—$C_1$-$C_4$alkylaminocarbonyl, NA-di-$C_1$-$C_4$alkylaminocarbonyl, N—$C_1$-$C_4$alkanoylaminocarbonyl, N—$C_1$-$C_4$alkanoyl-N—$C_1$-$C_4$alkylaminocarbonyl, $C_6$-, $C_{10}$-, $C_{14}$-aryl, $C_6$-, $C_{10}$-, $C_{14}$-aryloxy, benzyl, benzyloxy, benzylthio, $C_6$-, $C_{10}$-, $C_{14}$-arylthio, $C_6$-, $C_{10}$-, $C_{14}$-arylamino, benzylamino, heterocyclyl and trialkylsilyl, substituents bonded via a double bond, such as $C_1$-$C_4$alkylidene (e.g. methylidene or ethylidene), an oxo group, an imino group and a substituted imino group. When two or more radicals form one or more rings, these may be carbocyclic, heterocyclic, saturated, partly saturated, unsaturated, for example including aromatic rings and with further substitution. The substituents mentioned by way of example ("first substituent level") may, if they contain hydrocarbonaceous components, optionally have further substitution therein ("second substituent level"), for example by one or more of the substituents each independently selected from halogen, hydroxyl, amino, nitro, cyano, isocyano, azido, acylamino, an oxo group and an imino group. The term "(optionally) substituted" group preferably embraces just one or two substituent levels.

The inventive halogen-substituted chemical groups or halogenated groups (for example alkyl or alkoxy) are mono- or polysubstituted by halogen up to the maximum possible number of substituents. Such groups are also referred to as halo groups (for example haloalkyl). In the case of polysubstitution by halogen, the halogen atoms may be the same or different, and may all be bonded to one carbon atom or may be bonded to a plurality of carbon atoms. Halogen is especially fluorine, chlorine, bromine or iodine, preferably fluorine, chlorine or bromine and more preferably fluorine. More particularly, halogen-substituted groups are monohalocycloalkyl such as 1-fluorocyclopropyl, 2-fluorocyclopropyl or 1-fluorocyclobutyl, monohaloalkyl such as 2-chloroethyl, 2-fluoroethyl, 1-chloroethyl, 1-fluoroethyl, chloromethyl, or fluoromethyl; perhaloalkyl such as trichloromethyl or trifluoromethyl or $CF_2CF_3$, polyhaloalkyl such as difluoromethyl, 2-fluoro-2-chloroethyl, dichloromethyl, 1,1,2,2-tetrafluoroethyl or 2,2,2-trifluoroethyl. Further examples of haloalkyls are trichloromethyl, chlorodifluoromethyl, dichlorofluoromethyl, chloromethyl, bromomethyl, 1-fluoroethyl, 2-fluoroethyl, 2,2-difluoroethyl, 2,2,2-trifluoroethyl, 2,2,2-trichloroethyl, 2-chloro-2,2-difluoroethyl, pentafluoroethyl, 3,3,3-trifluoropropyl and pentafluoro-t-butyl. Preference is given to haloalkyls having 1 to 4 carbon atoms and 1 to 9, preferably 1 to 5, identical or different halogen atoms selected from fluorine, chlorine and bromine. Particular preference is given to haloalkyls having 1 or 2 carbon atoms and 1 to 5 identical or different halogen atoms selected from fluorine and chlorine, such as, inter alia, difluoromethyl, trifluoromethyl or 2,2-difluoroethyl. Further examples of halogen-substituted compounds are haloalkoxy such as $OCF_3$, $OCHF_2$, $OCH_2F$, $OCF_2CF_3$, $OCH_2CF_3$, $OCH_2CHF_2$ and $OCH_2CH_2C_1$, haloalkylsulfanyls such as difluoromethylthio, trifluoromethylthio, trichloromethylthio, chlorodifluoromethylthio, 1-fluoroethylthio, 2-fluoroethylthio, 2,2-difluoroethylthio, 1,1,2,2-tetrafluoroethylthio, 2,2,2-trifluoroethylthio or 2-chloro-1,1,2-trifluoroethylthio, haloalkylsulfinyls such as difluoromethylsulfinyl, trifluoromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluoroethylsulfinyl and 2-chloro-1,1,2-trifluoroethylsulfinyl, haloalkylsulfinyls such as difluoromethylsulfinyl, trifluoromethylsulfinyl, trichloromethylsulfinyl, chlorodifluoromethylsulfinyl, 1-fluoroethylsulfinyl, 2-fluoroethylsulfinyl, 2,2-difluoroethylsulfinyl, 1,1,2,2-tetrafluoroethylsulfinyl, 2,2,2-trifluoroethylsulfinyl and 2-chloro-1,1,2-trifluoroethylsulfinyl, haloalkylsulfonyl groups such as difluoromethylsulfonyl, trifluoromethylsulfonyl, trichloromethylsulfonyl, chlorodifluoromethylsulfonyl, 1-fluoroethylsulfonyl, 2-fluoroethylsulfonyl, 2,2-difluoroethylsulfonyl, 1,1,2,2-tetrafluoroethylsulfonyl, 2,2,2-trifluoroethylsulfonyl and 2-chloro-1,1,2-trifluoroethylsulfonyl.

In the case of radicals having carbon atoms, preference is given to those having 1 to 4 carbon atoms, especially 1 or 2 carbon atoms. Preference is generally given to substituents from the group of halogen, e.g. fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given here to the substituents methyl, methoxy, fluorine and chlorine.

Substituted amino such as mono- or disubstituted amino means a radical from the group of the substituted amino radicals which are N-substituted, for example, by one or two identical or different radicals from the group of alkyl, hydroxy, amino, alkoxy, acyl and aryl; preferably N-mono- and N,N-dialkylamino, (for example methylamino, ethylamino, N,N-dimethylamino, N,N-diethylamino, N,N-di-n-propylamino, N,N-diisopropylamino or N,N-dibutylamino), N-mono- or N,N-dialkoxyalkylamino groups (for example N-methoxymethylamino, N-methoxyethylamino, N,N-di(methoxymethyl)amino or N,N-di(methoxyethyl)amino), N-mono- and N,N-diarylamino, such as optionally substituted anilines, acylamino, N,N-diacylamino, N-alkyl-N-arylamino, N-alkyl-N-acylamino and also saturated N-heterocycles; preference is given here to alkyl radicals having 1 to 4 carbon atoms; here, aryl is preferably phenyl or substituted phenyl; for acyl, the definition given further below applies, preferably $(C_1-C_4)$-alkanoyl. The same applies to substituted hydroxylamino or hydrazino.

Substituted amino also includes quaternary ammonium compounds (salts) having four organic substituents on the nitrogen atom.

Optionally substituted phenyl is preferably phenyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, $(C_1-C_4)$alkylthio, $(C_1-C_4)$haloalkylthio, $(C_1-C_4)$alkylsulfinyl $(C_1-C_4)$haloalkylsulfinyl, $(C_1-C_4)$alkylsulfonyl $(C_1-C_4)$haloalkylsulfonyl, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and 4-trichloromethylphenyl, 2,4-, 3,5-, 2,5- and 2,3-dichlorophenyl, o-, m- and p-methoxyphenyl, 4-heptafluorophenyl.

Optionally substituted cycloalkyl is preferably cycloalkyl which is unsubstituted or mono- or polysubstituted, preferably up to trisubstituted, by identical or different radicals from the group of halogen, cyano, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl and $(C_1-C_4)$haloalkoxy, especially by one or two $(C_1-C_4)$alkyl radicals.

Inventive compounds may occur in preferred embodiments. Individual embodiments described herein may be combined with one another. Not included are combinations which contravene the laws of nature and which the person skilled in the art would therefore rule out on the basis of his/her expert knowledge. Ring structures having three or more adjacent oxygen atoms, for example, are excluded.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixture of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded herefrom are methods for the surgical or therapeutic treatment of the human or animal body and diagnostic methods carried out on the human or animal body.

The invention furthermore relates to the use of the compounds of the formula (I) as pesticides, in particular crop protection agents.

In the context of the present application, the term "pesticide" in each case also always comprises the term "crop protection agent".

The compounds of the formula (I), having good plant tolerance, favourable homeotherm toxicity and good environmental compatibility, are suitable for protecting plants and plant organs against biotic and abiotic stressors, for increasing harvest yields, for improving the quality of the harvested material and for controlling animal pests, especially insects, arachnids, helminths, in particular nematodes, and molluscs, which are encountered in agriculture, in horticulture, in animal husbandry, in aquatic cultures, in forests, in gardens and leisure facilities, in the protection of stored products and of materials, and in the hygiene sector.

Within the context of the present patent application, the term "hygiene" is understood to mean any and all measures, procedures and practices which aim to prevent disease, in particular infectious disease, and which serve to protect the health of humans and animals and/or to protect the environment, and/or which maintain cleanliness. In accordance with the invention, this especially includes measures for cleaning, disinfection and sterilisation of, for example, textiles or hard surfaces, especially surfaces of glass, wood, concrete, porcelain, ceramics, plastic or also of metal(s), and for ensuring that these are kept free of hygiene pests and/or their excretions. Preferably excluded from the scope of the invention in this regard are surgical or therapeutic treatment procedures applicable to the human body or to the bodies of animals and diagnostic procedures which are carried out on the human body or on the bodies of animals.

The term "hygiene sector" thus covers all areas, technical fields and industrial applications in which these hygiene measures, procedures and practices are important, in relation for example to hygiene in kitchens, bakeries, airports, bathrooms, swimming pools, department stores, hotels, hospitals, stables, animal husbandries, etc.

The term "hygiene pest" is therefore understood to mean one or more animal pests whose presence in the hygiene sector is problematic, in particular for health reasons. It is therefore a primary objective to avoid or minimize the presence of hygiene pests, and/or exposure to them, in the hygiene sector. This can be achieved in particular through the application of a pesticide that can be used both to prevent infestation and to tackle an infestation which is already present. Preparations which avoid or reduce exposure to pests can also be used. Hygiene pests include, for example, the organisms mentioned below.

The term "hygiene protection" thus covers all actions to maintain and/or improve these hygiene measures, procedures and practices.

The compounds of the formula (I) can preferably be used as pesticides. They are active against normally sensitive and resistant species and against all or some stages of development. The abovementioned pests include:

pests from the phylum of the Arthropoda, in particular from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici*; from the class of the Chilopoda, for example *Geophilus* spp., *Scutigera* spp.;

from the order or the class of the Collembola, for example *Onychiurus armatus; Sminthurus viridis*; from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agrilus* spp., for example *Agrilus planipennis, Agrilus coxalis, Agrilus bilineatus, Agrilus anxius, Agriotes* spp., for example *Agriotes linneatus, Agriotes mancus, Alphitobius diaperinus, Amphimallon solstitialis, Anobium punctatum, Anoplophora* spp., for example *Anoplophora glabripennis, Anthonomus* spp., for example *Anthonomus grandis, Anthrenus* spp., *Apion* spp., *Apogonia* spp., *Atomaria* spp., for example *Atomaria linearis, Attagenus* spp., *Bans caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dendroctonus* spp., for example *Dendroctonus pon-*

*derosae, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Limonius ectypus, Lissorhoptrus oryzophilus, Listronotus (=Hyperodes)* spp., *Lixus* spp., *Luperodes* spp., *Luperomorpha xanthodera, Lyctus* spp., *Megacyllene* spp., for example *Megacyllene robiniae, Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., for example *Scolytus multistriatus, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Dermaptera, for example *Anisolabis maritime, Forficula auricularia, Labidura riparia;* from the order of the Diptera, for example *Aedes* spp., for example *Aedes aegypti, Aedes albopictus, Aedes stictius, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* or *Pegomyia* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda;* from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma pini, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., for example *Dysaphis apiifolia, Dysaphis plantaginea,*

*Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lopholeucaspis japonica, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., for example *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Perkinsiella* spp., *Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pulvinaria* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Aelia* spp., *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Megacopta cribraria, Miridae, Monalonion atratum, Nezara* spp., for example *Nezara viridula, Nysius* spp., *Oebalus* spp., *Pentomidae, Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Camponotus* spp., *Dolichovespula* spp., *Diprion* spp., for example *Diprion similis, Hoplocampa* spp., for example *Hoplocampa cookei, Hoplocampa testudinea, Lasius* spp., *Linepithema* (*Iridiomyrmex*) *humile, Monomorium pharaonis, Paratrechina* spp., *Paravespula* spp., *Plagiolepis* spp., *Sirex* spp., for example *Sirex noctilio, Solenopsis invicta, Tapinoma* spp., *Technomyrmex albipes, Urocerus* spp., *Vespa* spp., for example *Vespa crabro, Wasmannia auropunctata, Xeris* spp.; from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diparopsis* spp., *Diatraea saccharalis, Dioryctria* spp., for example *Dioryctria zimmermani, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholita* spp., for example *Grapholita molesta, Grapholita prunivora, Hedylepta* spp., *Helicoverpa* spp., for example *Helicoverpa* armigera, *Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., *for example Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., for example *Ostrinia nubilalis, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Podesia* spp., for example *Podesia syringae, Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Chaetanaphothrips leeuweni, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., for example *Thrips palmi, Thrips tabaci;* from the order of the Zygentoma (=Thysanura), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, for example from the class of the Bivalvia, for example *Dreissena* spp., and also from the class of the Gastropoda, for example *Anion* spp., for example *Anion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

plant pests from the phylum of the Nematoda, i.e. phytoparasitic nematodes, in particular *Aglenchus* spp., for example *Aglenchus agricola, Anguina* spp., for example *Anguina tritici, Aphelenchoides* spp., *for example Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., *for example Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella xenoplax* (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., *for example Helicotylenchus dihystera, Hemicriconemoides* spp., *Hemicycliophora* spp., *Heterodera* spp., *for example Heterodera avenae, Heterodera glycines, Heterodera schachtii, Hirschmaniella* spp., *Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., for example *Paratrichodorus minor, Paratylenchus* spp., *Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example *Tylenchorhynchus annulatus, Tylenchulus* spp., for example *Tylenchulus semipenetrans, Xiphinema* spp., for example *Xiphinema index.*

The compounds of the formula (I) can optionally, at certain concentrations or application rates, also be used as herbicides, safeners, growth regulators or agents to improve plant properties, as microbicides or gametocides, for example as fungicides, antimycotics, bactericides, viricides (including agents against viroids) or as agents against MLO (*mycoplasma*-like organisms) and RLO (*rickettsia*-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are prepared either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), the esters (including fats and oils) and (poly)ethers, the unsubstituted and substituted amines, amides, lactams (such as N-alkylpyrrolidones) and lactones, the sulphones and sulphoxides (such as dimethyl sulphoxide), the carbonates and the nitriles.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, carbonates such as propylene carbonate, butylene carbonate, diethyl carbonate or dibutyl carbonate, or nitriles such as acetonitrile or propanenitrile.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, carbonates such as propylene carbonate, butylene carbonate, diethyl carbonate or dibutyl carbonate, nitriles such as acetonitrile or propanenitrile, and also water.

In principle, it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam-formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), isethionate derivatives, phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

It is possible to use colorants such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc as further auxiliaries in the formulations and the use forms derived therefrom.

Additional components may be stabilizers, such as low-temperature stabilizers, preservatives, antioxidants, light stabilizers or other agents which improve chemical and/or physical stability. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and thereby increase the mobility of active compounds in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001 and 98% by weight of the compound of the formula (I) or, with particular preference, between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms is usually between 0.00000001 and 95% by weight of the compound of the formula (I), preferably between 0.00001 and 1% by weight, based on the weight of the use form. The compounds are employed in a customary manner appropriate for the use forms.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, such active compound combinations may improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellants and/or plant activators and/or growth regulators and/or fertilizers. Likewise, the compounds of the formula (I) can be used to improve plant properties such as, for example, growth, yield and quality of the harvested material.

In a particular embodiment according to the invention, the compounds of the formula (I) are present in formulations or the use forms prepared from these formulations in a mixture with further compounds, preferably those as described below.

If one of the compounds mentioned below can occur in different tautomeric forms, these forms are also included even if not explicitly mentioned in each case. Further, all named mixing partners can, if their functional groups enable this, optionally form salts with suitable bases or acids.

Insecticides/Acaricides/Nematicides

The active compounds identified here by their common names are known and are described, for example, in the pesticide handbook ("The Pesticide Manual" 16th Ed., British Crop Protection Council 2012) or can be found on the Internet (e.g. http://www.alanwood.net/pesticides). The classification is based on the current IRAC Mode of Action Classification Scheme at the time of filing of this patent application.

(1) Acetylcholinesterase (AChE) inhibitors, preferably carbamates selected from alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb, or organophosphates selected from acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemetonmethyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, preferably cyclodiene-organochlorines selected from chlordane and endosulfan, or phenylpyrazoles (fiproles) selected from ethiprole and fipronil.

(3) Sodium channel modulators, preferably pyrethroids selected from acrinathrin, allethrin, d-cis-trans allethrin, d-trans allethrin, bifenthrin, bioallethrin, bioallethrin s-cyclopentenyl isomer, bioresmethrin, cyproprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, preferably neonicotinoids selected from acetamiprid, clothianidin, dinotefuran, imidacloprid, nitenpyram, thiacloprid and thiamethoxam, or nicotine, or sulfoximines selected from sulfoxaflor, or butenolids selected from flupyradifurone, or mesoionics selected from triflumezopyrim.

(5) Nicotinic acetylcholine receptor (nAChR) allosteric modulators, preferably spinosyns selected from spinetoram and spinosad.

(6) Glutamate-gated chloride channel (GluCl) allosteric modulators, preferably avermectins/milbemycins selected from abamectin, emamectin benzoate, lepimectin and milbemectin.

(7) Juvenile hormone mimics, preferably juvenile hormone analogues selected from hydroprene, kinoprene and methoprene, or fenoxycarb or pyriproxyfen.

(8) Miscellaneous non-specific (multi-site) inhibitors, preferably alkyl halides selected from methyl bromide and other alkyl halides, or chloropicrine or sulphuryl fluoride or borax or tartar emetic or methyl isocyanate generators selected from diazomet and metam.

(9) Chordotonal organ TRPV channel modulators selected from pymetrozine and pyrifluquinazone.

(10) Mite growth inhibitors selected from clofentezine, hexythiazox, diflovidazin and etoxazole.

(11) Microbial disruptors of the insect gut membrane selected from *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and B.t. plant proteins selected from Cry1Ab, Cry1Ac, Cry1Fa, Cry1A.105, Cry2Ab, Vip3A, mCry3A, Cry3Ab, Cry3Bb and Cry34Ab1/35Ab1.

(12) Inhibitors of mitochondrial ATP synthase, preferably ATP disruptors selected from diafenthiuron, or organotin compounds selected from azocyclotin, cyhexatin and fenbutatin oxide, or propargite or tetradifon.

(13) Uncouplers of oxidative phosphorylation via disruption of the proton gradient selected from chlorfenapyr, DNOC and sulfluramid.

(14) Nicotinic acetylcholine receptor channel blockers selected from bensultap, cartap hydrochloride, thiocylam and thiosultap-sodium.

(15) Inhibitors of chitin biosynthesis, type 0, selected from bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1 selected from buprofezin.

(17) Moulting disruptor (in particular for Diptera, i.e. dipterans) selected from cyromazine.

(18) Ecdysone receptor agonists selected from chromafenozide, halofenozide, methoxyfenozide and tebufenozide.

(19) Octopamine receptor agonists selected from amitraz.

(20) Mitochondrial complex III electron transport inhibitors selected from hydramethylnone, acequinocyl and fluacrypyrim.

(21) Mitochondrial complex I electron transport inhibitors, preferably METI acaricides selected from fenazaquin, fenpyroximate, pyrimidifen, pyridaben, tebufenpyrad and tolfenpyrad, or rotenone (Derris).

(22) Voltage-dependent sodium channel blockers selected from indoxacarb and metaflumizone.

(23) Inhibitors of acetyl CoA carboxylase, preferably tetronic and tetramic acid derivatives selected from spirodiclofen, spiromesifen and spirotetramat.

(24) Mitochondrial complex IV electron transport inhibitors, preferably phosphines selected from aluminium phosphide, calcium phosphide, phosphine and zinc phosphide, or cyanides selected from calcium cyanide, potassium cyanide and sodium cyanide.

(25) Mitochondrial complex II electron transport inhibitors, preferably beta-ketonitrile derivatives selected from cyenopyrafen and cyflumetofen, and carboxanilides selected from pyflubumide.

(28) Ryanodine receptor modulators, preferably diamides selected from chlorantraniliprole, cyantraniliprole and flubendiamide.

(29) Chordotonal organ Modulators (with undefined target site) selected from flonicamid.

(30) further active compounds selected from Acynonapyr, Afidopyropen, Afoxolaner, Azadirachtin, Benclothiaz, Benzoximate, Benzpyrimoxan, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, Dimpropyridaz, epsilon-Metofluthrin, epsilon-Momfluthrin, Flometoquin, Fluazaindolizine, Fluensulfone, Flufenerim, Flufenoxystrobin, Flufiprole, Fluhexafon, Fluopyram, Flupyrimin, Fluralaner, Fluxametamide, Fufenozide, Guadipyr, Heptafluthrin, Imidaclothiz, Iprodione, Isocycloseram, kappa-Bifenthrin, kappa-Tefluthrin, Lotilaner, Meperfluthrin, Oxazosulfyl, Paichongding, Pyridalyl, Pyrifluquinazon, Pyriminostrobin, Spirobudiclofen, Spiropidion, Tetramethylfluthrin, Tetraniliprole, Tetrachlorantraniliprole, Tigolaner, Tioxazafen, Thiofluoximate iodomethane; furthermore preparations based on *Bacillus firmus* (I-1582, BioNeem, Votivo), and also the following compounds: 1-{2-fluoro-4-methyl-5-[(2,2,2-trifluoroethyl) sulphinyl]phenyl}-3-(trifluoromethyl)-1H-1,2,4-triazole-5-amine (known from WO2006/043635) (CAS 885026-50-6), {[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4- yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), (3E)-3-[1-[(6-chloro-3-pyridyl)methyl]-2-pyridylidene]-1,1,1-trifluoro-propan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-isoxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl) benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl) sulfinyl]-propanamide, (+)—N-[3-chloro-1-(3-pyridinyl)-1H-pyrazol-4-yl]-N-ethyl-3-[(3,3,3-trifluoropropyl) sulfinyl]-propanamide and (−)—N-[3-chloro-1-(3-pyridinyl)-1H-pyrazol-4-yl]-N-ethyl-3-[(3,3,3-trifluoropropyl) sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl)phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-, 1-[N-4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo [3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2,6-dimethylphenyl)-8-methoxy-1-methyl-2-oxo-1,8-diazaspiro[4.5]dec-3-en-4-yl-carbonic acid ethyl ester (known from WO 2010/066780 A1, WO 2011151146 A1) (CAS 1229023-00-0), 4-[(5S)-5-(3,5-Dichloro-4-fluorophenyl)-4,5-dihydro-5-(trifluoromethyl)-3-isoxazolyl]-N-[(4R)-2-ethyl-3-oxo-4-isoxazolidinyl]-2-methyl-benzamide (bekannt aus WO 2011/067272, WO2013/050302) (CAS 1309959-62-3).

Fungicides

The active ingredients specified herein by their Common Name are known and described, for example, in The Pesticide Manual (16th Ed. British Crop Protection Council) or can be searched in the internet (e.g. www.alanwood.net/pesticides).

All named fungicidal mixing partners of the classes (1) to (15) can, if their functional groups enable this, optionally form salts with suitable bases or acids. All named mixing partners of the classes (1) to (15) can include tautomeric forms, where applicable.

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) Pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)-cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-

(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) Mefentrifluconazole, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel (2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)-oxiran-2-yl]methyl}-2,4-dihydro-3H-1,2,4-triazole-3-thione, (1.059) 5-(4-chlorobenzyl)-2-(chloro-methyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{[3-(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Ipfentrifluconazole.

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1- methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) Fluindapyr, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}-phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) isoflucypram, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoro-methyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide, (2.057) pyrapropoyne.

3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) mandestrobin, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate, (3.030) metyltetraprole, (3.031) florylpicoxamid.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.
6) Compounds capable to induce a host defence, for example (6.001) acibenzolar-S-methyl, (6.002) isotianil, (6.003) probenazole, (6.004) tiadinil.
7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.
8) Inhibitors of the ATP production, for example (8.001) silthiofam.
9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.
10) Inhibitors of the lipid and membrane synthesis, for example (10.001) propamocarb, (10.002) propamocarb hydrochloride, (10.003) tolclofos-methyl.
11) Inhibitors of the melanin biosynthesis, for example (11.001) tricyclazole, (11.002) 2,2,2-trifluoroethyl {3-methyl-1-[(4-methylbenzoyl)amino]butan-2-yl}carbamate.
12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).
13) Inhibitors of the signal transduction, for example (13.001) fludioxonil, (13.002) iprodione, (13.003) procymidone, (13.004) proquinazid, (13.005) quinoxyfen, (13.006) vinclozolin.
14) Compounds capable to act as an uncoupler, for example (14.001) fluazinam, (14.002) meptyldinocap.
15) Further compounds, for example (15.001) Abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) dipymetitrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) Ipflufenoquin, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) quinofumelin, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2 (1H)-one, (15.063) aminopyrifen.

Biological Pesticides as Mixing Components

The compounds of the formula (I) can be combined with biological pesticides.

Biological pesticides comprise in particular bacteria, fungi, yeasts, plant extracts and products formed by microorganisms, including proteins and secondary metabolites.

Biological pesticides comprise bacteria such as spore-forming bacteria, root-colonising bacteria and bacteria which act as biological insecticides, fungicides or nematicides.

Examples of such bacteria which are employed or can be used as biological pesticides are:

Bacillus amyloliquefaciens, strain FZB42 (DSM 231179), or Bacillus cereus, in particular B. cereus strain CNCM I-1562 or Bacillus firmus, strain I-1582 (Accession number CNCM I-1582) or Bacillus pumilus, in particular strain GB34 (Accession No. ATCC 700814) and strain QST2808 (Accession No. NRRL B-30087), or Bacillus subtilis, in particular strain GB03 (Accession No. ATCC SD-1397), or Bacillus subtilis strain QST713 (Accession No. NRRL B-21661) or Bacillus subtilis strain OST 30002 (Accession No. NRRL B-50421) Bacillus thuringiensis, in particular B. thuringiensis subspecies israelensis (serotype H-14), strain AM65-52 (Accession No. ATCC 1276), or B. thuringiensis subsp. aizawai, in particular strain ABTS-1857 (SD-1372), or B. thuringiensis subsp. kurstaki strain HD-1, or B. thuringiensis subsp. tenebrionis strain NB 176 (SD-5428), Pasteuria penetrans, Pasteuria spp. (Rotylenchulus reniformis nematode)-PR3 (Accession Number ATCC SD-5834), Streptomyces microflavus strain AQ6121 (=QRD 31.013, NRRL B-50550), Streptomyces galbus strain AQ 6047 (Accession Number NRRL 30232).

Examples of fungi and yeasts which are employed or can be used as biological pesticides are:

Beauveria bassiana, in particular strain ATCC 74040, Coniothyrium minitans, in particular strain CON/M/91-8 (Accession No. DSM-9660), Lecanicillium spp., in particular strain HRO LEC 12, Lecanicillium lecanii, (formerly known as Verticillium lecanii), in particular strain KV01, Metarhizium anisopliae, in particular strain F52 (DSM3884/ATCC 90448), Metschnikowia fructicola, in particular strain NRRL Y-30752, Paecilomyces fumosoroseus (now: Isaria fumosorosea), in particular strain IFPC 200613, or strain Apopka 97 (Accession No. ATCC 20874), Paecilomyces lilacinus, in particular P. lilacinus strain 251 (AGAL 89/030550), Talaromyces flavus, in particular strain V117b, Trichoderma atroviride, in particular strain SC1 (Accession Number CBS 122089), Trichoderma harzianum, in particular T. harzianum rifai T39. (Accession Number CNCM I-952).

Examples of viruses which are employed or can be used as biological pesticides are:

Adoxophyes orana (summer fruit tortrix) granulosis virus (GV), Cydia pomonella (codling moth) granulosis virus (GV), Helicoverpa annigera (cotton bollworm) nuclear polyhedrosis virus (NPV), Spodoptera exigua (beet armyworm) mNPV, Spodoptera frugiperda (fall armyworm) mNPV, Spodoptera littoralis (African cotton leafworm) NPV.

Also included are bacteria and fungi which are added as 'inoculant' to plants or plant parts or plant organs and which, by virtue of their particular properties, promote plant growth and plant health. Examples which may be mentioned are:

Agrobacterium spp., Azorhizobium caulinodans, Azospirillum spp., Azotobacter spp., Bradyrhizobium spp., Burkholderia spp., in particular Burkholderia cepacia (formerly known as Pseudomonas cepacia), Gigaspora spp., or Gigaspora monosporum, Glomus spp., Laccaria spp., Lactobacillus buchneri, Paraglomus spp., Pisolithus tinctorus, Pseudomonas spp., Rhizobium spp., in particular Rhizobium trifolii, Rhizopogon spp., Scleroderma spp., Suillus spp., Streptomyces spp.

Examples of plant extracts and products formed by microorganisms including proteins and secondary metabolites which are employed or can be used as biological pesticides are:

Allium sativum, Artemisia absinthium, azadirachtin, Biokeeper WP, Cassia nigricans, Celastrus angulatus, Chenopodium anthelminticum, chitin, Armour-Zen, Dryopteris filix-mas, Equisetum arvense, Fortune Aza, Fungastop, Heads Up (Chenopodium quinoa saponin extract), Pyrethrum/Pyrethrins, Quassia amara, Quercus, Quillaja, Regalia, "Requiem™ Insecticide", rotenone, ryania/ryanodine, Symphytum officinale, Tanacetum vulgare, thymol, Triact 70, TriCon, Tropaeulum majus, Urtica dioica, Veratrin, Viscum album, Brassicaceae extract, in particular oilseed rape powder or mustard powder.

Safener as Mixing Components

The compounds of the formula (I) can be combined with safeners such as, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Here, plants are to be understood to mean all plants and plant parts such as wanted and unwanted wild plants or crop plants (including naturally occurring crop plants), for example cereals (wheat, rice, triticale, barley, rye, oats), maize, soya bean, potato, sugar beet, sugar cane, tomatoes, pepper, cucumber, melon, carrot, watermelon, onion, lettuce, spinach, leek, beans, Brassica oleracea (e.g. cabbage) and other vegetable species, cotton, tobacco, oilseed rape, and also fruit plants (with the fruits apples, pears, citrus fruits and grapevines). Crop plants can be plants which can be obtained by conventional breeding and optimization methods or by biotechnological and genetic engineering methods or combinations of these methods, including the transgenic plants and including the plant varieties which can or cannot be protected by varietal property rights. Plants should be understood to mean all developmental stages, such as seeds, seedlings, young (immature) plants up to mature plants. Plant parts should be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested plants or harvested plant parts and vegetative and generative propagation material, for example seedlings, tubers, rhizomes, cuttings and seeds.

Treatment according to the invention of the plants and plant parts with the compounds of the formula (I) is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. The invention is used with particular preference to treat plants of the respective commercially customary cultivars or those that are in use. Plant cultivars are to be understood as meaning plants having new properties ("traits") and which have been obtained by conventional breeding, by mutagenesis or by recombinant DNA techniques. They can be cultivars, varieties, bio- or genotypes.

Transgenic Plant, Seed Treatment and Integration Events

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products. Further and particularly emphasized examples of such properties are increased resistance of the plants against animal and microbial pests, such as against insects, arachnids, nematodes, mites, slugs and snails owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), furthermore increased resistance of the plants against phytopathogenic fungi, bacteria and/or viruses owing, for example, to systemic acquired resistance (SAR), systemin, phytoalexins, elicitors and also resistance genes and correspondingly expressed proteins and toxins, and also increased tolerance of the plants to certain herbicidally active compounds, for example imidazolinones, sulphonylureas, glyphosate or phosphinothricin (for example the "PAT" gene). The genes which impart the desired traits in question may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. the compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This may be done, for example, by drenching, or by mixing into the soil or the nutrient solution, i.e. the locus of the plant (e.g. soil or hydroponic systems) is impregnated with a liquid form of the compounds of the formula (I), or by soil application, i.e. the compounds of the formula (I) according to the invention are introduced in solid form (e.g. in the form of granules) into the locus of the plants, or by drip application (often also referred to as "chemigation"), i.e. the liquid application of the compounds of the formula (I) according to the invention from surface or sub-surface driplines over a certain period of time together with varying amounts of water at defined locations in the vicinity of the plants. In the case of paddy rice crops, this can also be done by metering the compound of the formula (I) in a solid application form (for example as granules) into a flooded paddy field.

Treatment of Seed

The control of animal pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is furthermore desirable to optimize the amount of active compound employed in such a way as to provide optimum protection for the seed and the germinating plant from attack by animal pests, but without damaging the plant itself by the active compound employed. In particular, methods for the treatment of seed should also take into consideration the intrinsic insecticidal or nematicidal properties of pest-resistant or -tolerant transgenic plants in order to achieve optimum protection of the seed and also the germinating plant with a minimum of pesticides being employed.

The present invention therefore in particular also relates to a method for the protection of seed and germinating plants, from attack by pests, by treating the seed with one of the compounds of the formula (I). The method according to the invention for protecting seed and germinating plants against attack by pests furthermore comprises a method where the seed is treated simultaneously in one operation or sequentially with a compound of the formula (I) and a mixing component. It also comprises a method where the seed is treated at different times with a compound of the formula (I) and a mixing component.

The invention likewise relates to the use of the compounds of the formula (I) for the treatment of seed for protecting the seed and the resulting plant from animal pests.

Furthermore, the invention relates to seed which has been treated with a compound of the formula (I) according to the invention so as to afford protection from animal pests. The invention also relates to seed which has been treated simultaneously with a compound of the formula (I) and a mixing component. The invention furthermore relates to seed which has been treated at different times with a compound of the formula (I) and a mixing component. In the case of seed which has been treated at different points in time with a compound of the formula (I) and a mixing component, the individual substances may be present on the seed in different layers. Here, the layers comprising a compound of the formula (I) and mixing components may optionally be separated by an intermediate layer. The invention also relates to seed where a compound of the formula (I) and a mixing component have been applied as component of a coating or as a further layer or further layers in addition to a coating.

Furthermore, the invention relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this manner, the immediate treatment of the crop at the time of sowing or shortly thereafter can be dispensed with.

It has to be considered a further advantage that by treatment of the seed with a compound of the formula (I), germination and emergence of the treated seed may be enhanced.

It is likewise to be considered advantageous that compounds of the formula (I) can be used in particular also for transgenic seed.

Furthermore, compounds of the formula (I) can be employed in combination with compositions or compounds of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. In particular, this takes the form of seed of cereals (for example wheat, barley, rye, millet and oats), corn, cotton, soya beans, rice, potatoes, sunflowers, coffee, tobacco, canola, oilseed rape, beets (for example sugarbeets and fodder beets), peanuts, vegetables (for example tomatoes, cucumbers, bean, cruciferous vegetables, onions and lettuce), fruit plants, lawns and ornamental plants. The treatment of the seed of cereals (such as wheat, barley, rye and oats), maize, soya beans, cotton, canola, oilseed rape, vegetables and rice is of particular importance.

As already mentioned above, the treatment of transgenic seed with a compound of the formula (I) is also of particular importance. This takes the form of seed of plants which, as a rule, comprise at least one heterologous gene which governs the expression of a polypeptide with in particular insecticidal and/or nematicidal properties. The heterologous genes in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. It is particularly preferably a heterologous gene derived from *Bacillus thuringiensis*.

In the context of the present invention, the compound of the formula (I) is applied to the seed. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water to a certain stage of the rice embryo ('pigeon breast stage'), stimulating the germination and a more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This must be ensured particularly in the case of active compounds which can exhibit phytotoxic effects at certain application rates.

In general, the compounds of the formula (I) are applied to the seed in a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing the compounds of the formula (I) with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of agrochemically active compounds. Preference is given to using alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are in particular ligno-sulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Preference is given to using silicone antifoams and magnesium stearate.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions. Cellulose derivatives, acrylic acid derivatives, xanthan, modified clays and finely divided silica are preferred.

Adhesives which may be present in the seed dressing formulations usable in accordance with the invention are all customary binders usable in seed dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel", vol. 2, Springer Verlag, 1970, pp. 401-412).

The seed dressing formulations usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom by adding water, all mixing units usable customarily for the seed dressing are useful. Specifically, the procedure in the seed dressing is to place the seed into a mixer, operated batch-wise or continuously, to add the particular desired amount of seed dressing formulations, either as such or after prior dilution with water, and to mix everything until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. in the field of veterinary medicine, the compounds of the formula (I) are active against animal parasites, in particular ectoparasites or endoparasites. The term endoparasite includes in particular helminths and protozoae, such as coccidia. Ectoparasites are typically and preferably arthropods, in particular insects or acarids.

In the field of veterinary medicine the compounds of the formula (I) are suitable, with favourable toxicity in warm blooded animals, for controlling parasites which occur in animal breeding and animal husbandry in livestock, breeding, zoo, laboratory, experimental and domestic animals. They are active against all or specific stages of development of the parasites.

Agricultural livestock include, for example, mammals, such as, sheep, goats, horses, donkeys, camels, buffaloes, rabbits, reindeers, fallow deers, and in particular cattle and pigs; or poultry, such as turkeys, ducks, geese, and in particular chickens; or fish or crustaceans, e.g. in aquaculture; or, as the case may be, insects such as bees.

Domestic animals include, for example, mammals, such as hamsters, guinea pigs, rats, mice, chinchillas, ferrets or in particular dogs, cats; cage birds; reptiles; amphibians or aquarium fish.

According to a particular embodiment, the compounds of the formula (I) are administered to mammals.

According to another particular embodiment, the compounds of the formula (I) are administered to birds, namely cage birds or in particular poultry.

By using the compounds of the formula (I) to control animal parasites, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling", as used herein with regard to the animal health field, means that the compounds of the formula (I) are effective in reducing the incidence of the respective parasite in an animal infected with such parasites to innocuous levels. More specifically, "controlling", as used herein, means that the compounds of the formula (I) are effective in killing the respective parasite, inhibiting its growth, or inhibiting its proliferation.

Exemplary arthropods include, without any limitation from the order of the Anoplurida, for example, *Haematopinus* spp., *Linognathus* spp., *Pediculus* spp., *Phtirus* spp., *Solenopotes* spp.;

from the order of the Mallophagida and the suborders Amblycerina and Ischnocerina, for example *Bovicola* spp., *Damalina* spp., *Felicola* spp., *Lepikentron* spp., *Menopon* spp., *Trichodectes* spp., *Trimenopon* spp., *Trinoton* spp., *Werneckiella* spp.;

from the order of the Diptera and the suborders Nematocerina and Brachycerina, for example *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.

from the order of the Siphonapterida, for example *Ceratophyllus* spp.; *Ctenocephalides* spp., *Pulex* spp., *Tunga* spp., *Xenopsylla* spp.;

from the order of the Heteropterida, for example *Cimex* spp., *Panstrongylus* spp., *Rhodnius* spp., *Triatoma* spp.; as well as nuisance and hygiene pests from the order of the Blattarida.

Further, among the arthropods, the following acari may be mentioned by way of example, without any limitation:

from the subclass of the Acari (Acarina) and the order of the Metastigmata, for example, from the family of argasidae like *Argas* spp., *Ornithodorus* spp., *Otobius* spp., *from the family of Ixodidae like Amblyomma* spp., *Dermacentor* spp., *Haemaphysalis* spp., *Hyalomma* spp., *Ixodes* spp., *Rhipicephalus* (*Boophilus*) spp, *Rhipicephalus* spp. (the original genus of multi host ticks); from the order of mesostigmata like *Dermanyssus* spp., *Ornithonyssus* spp., *Pneumonyssus* spp., *Raillietia* spp., *Sternostoma* spp., *Tropilaelaps* spp., *Varroa* spp.; from the order of the Actinedida (Prostigmata), for example *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of the Acaridida (Astigmata), for example *Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Exemplary parasitic protozoa include, without any limitation:

Mastigophora (*Flagellata*) such as:

Metamonada: from the order Diplomonadida, for example, *Giardia* spp., *Spironucleus* spp.

Parabasala: from the order Trichomonadida, for example, *Histomonas* spp., *Pentatrichomonas* spp., *Tetratrichomonas* spp., *Trichomonas* spp., *Tritrichomonas* spp.

Euglenozoa: from the order Trypanosomatida, for example, *Leishmania* spp., *Trypanosoma* spp Sarcomastigophora (*Rhizopoda*), such as Entamoebidae, for example, *Entamoeba* spp., Centramoebidae, for example, *Acanthamoeba* sp., Euamoebidae, e.g. *Hartmanella* sp.

Alveolata such as Apicomplexa (Sporozoa): e.g. *Cryptosporidium* spp.; from the order Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order Adeleida e.g. *Hepatozoon* spp., *Klossiella* spp.; from the order Haemosporida e.g. *Leucocytozoon* spp., *Plasmodium* spp.; from the order Piroplasmida e.g. *Babesia* spp., *Ciliophora* spp., *Echinozoon* spp., *Theileria* spp.; from the order Vesibuliferida e.g. *Balantidium* spp., *Buxtonella* spp.

*Microspora* such as *Encephalitozoon* spp., *Enterocytozoon* spp., *Globidium* spp., *Nosema* spp., and furthermore, e.g. *Myxozoa* spp.

Helminths pathogenic for humans or animals include, for example, acanthocephala, nematodes, pentastoma and platyhelmintha (e.g. monogenea, cestodes and trematodes).

Exemplary helminths include, without any limitation:

Monogenea: e.g.: *Dactylogyrus* spp., *Gyrodactylus* spp., *Microbothrium* spp., *Polystoma* spp., *Troglocephalus* spp.

Cestodes: from the order of the Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

from the order of the Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of the Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp. Nematodes: from the order of the Trichinellida, for example: *Capillaria* spp., *Eucoleus* spp., *Paracapillaria* spp., *Trichinella* spp., *Trichomosoides* spp., *Trichuris* spp.

from the order of the Tylenchida, for example: *Micronema* spp., *Parastrongyloides* spp., *Strongyloides* spp.

from the order of the Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

from the order of the Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acantocephala: from the order of the Oligacanthorhynchida, for example: *Macracanthorhynchus* spp., *Prosthenorchis* spp.; from the order of the Moniliformida, for example: *Moniliformis* spp.

from the order of the Polymorphida, for example: *Filicollis* spp.; from the order of the Echinorhynchida, for example: *Acanthocephalus* spp., *Echinorhynchus* spp., *Leptorhynchoides* spp.

Pentastoma: from the order of the Porocephalida, for example: *Linguatula* spp.

In the veterinary field and in animal keeping, the administration of the compounds of the formula (I) is carried out by methods generally known in the art, such as enterally, parenterally, dermally or nasally, in the form of suitable preparations. Administration can be carried out prophylactically, methaphylactically or therapeutically.

Thus, one embodiment of the present invention refers to the compounds of the formula (I) for use as a medicament.

Another aspect refers to the compounds of the formula (I) for use as an antiendoparasitical agent.

Another particular aspect refers to the compounds of the formula (I) for use as a anthelmintic agent, more particular for use as a nematicidal agent, a platyhelminthicidal agent, an acanthocephalicidal agent, or a pentastomicidal agent.

Another particular aspect refers to the compounds of the formula (I) for use as an antiprotozoal agent.

Another aspect refers to the compounds of the formula (I) for use as an antiectoparasitical agent, in particular an arthropodicidal agent, more particular an insecticidal agent or acaricidal agent.

Further aspects of the invention are veterinary formulations, comprising an effective amount of at least one compound of the formula (I) and at least one of the following: pharmaceutically acceptable excipient (e.g. solid or liquid diluents), pharmaceutically acceptable auxiliary (e.g. surfactants), in particular a pharmaceutically acceptable excipient and/or pharmaceutically acceptable auxiliary which is normally used in veterinary formulations.

A related aspect of the invention is a method for preparing a veterinary formulation as described herein, comprising the step of mixing at least one compound of the formula (I) with pharmaceutically acceptable excipients and/or auxiliaries, in particular with pharmaceutically acceptable excipients and/or auxiliaries which are normally used in veterinary formulations.

Another particular aspect of the invention are veterinary formulations, selected from the group of ectoparasiticidal and endoparasiticidal formulations, more particular selected from the group of anthelmintic, antiprotozoal, and arthropodicidal formulations, even more particular selected from the group of nematicidal, platyhelminthicidal, acanthocephalicidal, pentastomicidal, insecticidal, and acaricidal formulations, in accordance with the mentioned aspects, as well as their methods for preparation.

Another aspect refers to a method for treatment of a parasitic infection, in particular an infection by a parasite selected from the group of ectoparasites and endoparasites mentioned herein, by applying an effective amount of a compound of the formula (I) to an animal, in particular a non-human animal, in need thereof.

Another aspect refers to a method for treatment of a parasitic infection, in particular an infection by a parasite selected from the group of ectoparasites and endoparasites mentioned herein, by applying a veterinary formulation as defined herein to an animal, in particular a non-human animal, in need thereof.

Another aspect refers to the use of the compounds of the formula (I) in the treatment of a parasitic infection, in particular an infection by a parasite selected from the group of ectoparasites and endoparasites mentioned herein, in an animal, in particular a non-human animal.

In the present context of the animal health or veterinary field, the term "treatment" includes prophylactic, metaphylactic or therapeutical treatment.

In a particular embodiment, mixtures of at least one compound of the formula (I) with other active ingredients, particularly with endo- and ectoparasiticides, for the veterinary field are provided herewith.

In the field of animal health "mixture" not only means that two (or more) different active ingredients are formulated in a joint formulation and are accordingly applied together but also refers to products which comprise separate formulations for each active compound. Accordingly, if more than two active compounds are to be applied, all active compounds may be formulated in a joint formulation or all active compounds may be formulated in separate formulations; also feasible are mixed forms where some of the active compounds are formulated jointly and some of the active compounds are formulated separately. Separate formulations allow the separate or successive application of the active compounds in question.

The active compounds specified herein by their common names are known and described, for example, in the Pesticide Manual (see above) or can be searched in the internet (e.g. http://www.alanwood.net/pesticides).

Exemplary active ingredients from the group of ectoparasiticides, as mixing partners, include, without limitation insecticides and acaricides listed in detail above. Further active ingredients which may be used are listed below following the aforementioned classification which is based on the current IRAC Mode of Action Classification Scheme: (1) Acetylcholinesterase (AChE) inhibitors; (2) GABA-gated chloride channel blockers; (3) Sodium channel modulators; (4) Nicotinic acetylcholine receptor (nAChR) competitive modulators; (5) Nicotinic acetylcholine receptor (nAChR) allosteric modulators; (6) Glutamate-gated chloride channel (GluCl) allosteric modulators; (7) Juvenile hormone mimics; (8) Miscellaneous non-specific (multi-site) inhibitors; (9) Modulators of Chordotonal Organs; (10) Mite growth inhibitors; (12) Inhibitors of mitochondrial ATP synthase, such as, ATP disruptors; (13) Uncouplers of oxidative phosphorylation via disruption of the proton gradient; (14) Nicotinic acetylcholine receptor channel blockers; (15) Inhibitors of chitin biosynthesis, type 0; (16) Inhibitors of chitin biosynthesis, type 1; (17) Moulting disruptor (in particular for Diptera, i.e. dipterans); (18) Ecdysone receptor agonists; (19) Octopamine receptor agonists; (21) Mitochondrial complex I electron transport inhibitors; (25) Mitochondrial complex II electron transport inhibitors; (20) Mitochondrial complex III electron transport inhibitors; (22) Voltage-dependent sodium channel blockers; (23) Inhibitors of acetyl CoA carboxylase; (28) Ryanodine receptor modulators;

Active compounds with unknown or non-specific mode of action, e.g., fentrifanil, fenoxacrim, cycloprene, chlorobenzilate, chlordimeform, flubenzimine, dicyclanil, amidoflumet, quinomethionate, triarathene, clothiazoben, tetrasul, potassium oleate, petroleum, metoxadiazone, gossyplure, flutenzin, bromopropylate, cryolite;

Compounds from other classes, e.g. butacarb, dimetilan, cloethocarb, phosphocarb, pirimiphos (-ethyl), parathion (-ethyl), methacrifos, isopropyl o-salicylate, trichlorfon, tigolaner, sulprofos, propaphos, sebufos, pyridathion, prothoate, dichlofenthion, demeton-S-methylsulphone, isazofos, cyanofenphos, dialifos, carbophenothion, autathiofos, aromfenvinfos (-methyl), azinphos (-ethyl), chlorpyrifos (-ethyl), fosmethilan, iodofenphos, dioxabenzofos, formothion, fonofos, flupyrazofos, fensulfothion, etrimfos; organochlorines, e.g. camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-), metofluthrin, profluthrin, flufenprox, flubrocythrinate, fubfenprox, fenfluthrin, protrifenbute, pyresmethrin, RU15525, terallethrin, cis-resmethrin, heptafluthrin-bioethanomethrin, biopermethrin, fenpyrithrin, cis-cypermethrin, cis-permethrin, clocythrin, cyhalothrin (lambda-), chlovaporthrin, or halogenated carbonhydrogen compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

Biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz Bee hive *varroa* acaricides, for example organic acids, e.g. formic acid, oxalic acid.

Exemplary active ingredients from the group of endoparasiticides, as mixing partners, include, without limitation, anthelmintically active compounds and antiprotozoal active compounds.

Anthelmintically active compounds, including, without limitation, the following nematicidally, trematicidally and/or cestocidally active compounds:

from the class of macrocyclic lactones, for example: eprinomectin, abamectin, nemadectin, moxidectin, doramectin, selamectin, lepimectin, latidectin, milbemectin, ivermectin, emamectin, milbemycin;

from the class of benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole-sulphoxide, albendazole, flubendazole;

from the class of depsipeptides, preferably cyclic depsipetides, in particular 24-membered cyclic depsipeptides, for example: emodepside, PF1022A;

from the class of tetrahydropyrimidines, for example: morantel, pyrantel, oxantel;

from the class of imidazothiazoles, for example: butamisole, levamisole, tetramisole;

from the class of aminophenylamidines, for example: amidantel, deacylated amidantel (dAMD), tribendimidine;

from the class of aminoacetonitriles, for example: monepantel;

from the class of paraherquamides, for example: paraherquamide, derquantel;

from the class of salicylanilides, for example: tribromsalan, bromoxanide, brotianide, clioxanide, closantel, niclosamide, oxyclozanide, rafoxanide;

from the class of substituted phenols, for example: nitroxynil, bithionol, disophenol, hexachlorophene, niclofolan, meniclopholan;

from the class of organophosphates, for example: trichlorfon, naphthalofos, dichlorvos/DDVP, crufomate, coumaphos, haloxon;

from the class of piperazinones/quinolines, for example: praziquantel, epsiprantel;

from the class of piperazines, for example: piperazine, hydroxyzine;

from the class of tetracyclines, for example: tetracyclin, chlorotetracycline, doxycyclin, oxytetracyclin, rolitetracyclin;

from diverse other classes, for example: bunamidine, niridazole, resorantel, omphalotin, oltipraz, nitroscanate, nitroxynile, oxamniquine, mirasan, miracil, lucanthone, hycanthone, hetolin, emetine, diethylcarbamazine, dichlorophen, diamfenetide, clonazepam, bephenium, amoscanate, clorsulon.

Antiprotozoal active compounds, including, without limitation, the following active compounds:

from the class of triazines, for example: diclazuril, ponazuril, letrazuril, toltrazuril;

from the class of polyether ionophore, for example: monensin, salinomycin, maduramicin, narasin;

from the class of macrocyclic lactones, for example: milbemycin, erythromycin;

from the class of quinolones, for example: enrofloxacin, pradofloxacin;

from the class of quinines, for example: chloroquine;

from the class of pyrimidines, for example: pyrimethamine;

from the class of sulfonamides, for example: sulfaquinoxaline, trimethoprim, sulfaclozin;

from the class of thiamines, for example: amprolium;

from the class of lincosamides, for example: clindamycin;

from the class of carbanilides, for example: imidocarb;

from the class of nitrofuranes, for example: nifurtimox;

from the class of quinazolinone alkaloids, for example: halofuginon;

from diverse other classes, for example: oxamniquin, paromomycin;

from the class of vaccines or antigenes from microorganisms, for example: *Babesia canis* rossi, *Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All named mixing partners can, if their functional groups enable this, optionally form salts with suitable bases or acids.

Vector Control

The compounds of the formula (I) can also be used in vector control. For the purpose of the present invention, a vector is an arthropod, in particular an insect or arachnid, capable of transmitting pathogens such as, for example, viruses, worms, single-cell organisms and bacteria from a reservoir (plant, animal, human, etc.) to a host. The pathogens can be transmitted either mechanically (for example trachoma by non-stinging flies) to a host, or by injection (for example malaria parasites by mosquitoes) into a host.

Examples of vectors and the diseases or pathogens they transmit are:

1) Mosquitoes

*Anopheles*: malaria, filariasis;

*Culex*: Japanese encephalitis, other viral diseases, filariasis, transmission of other worms;

Aedes: yellow fever, dengue fever, other viral diseases, filariasis;

Simuliidae: transmission of worms, in particular *Onchocerca volvulus*;

Psychodidae: transmission of leishmaniasis

2) Lice: skin infections, epidemic typhus;
3) Fleas: plague, endemic typhus, cestodes;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia burgdorferi sensu lato., Borrelia duttoni*, tick-borne encephalitis, Q fever (*Coxiella burnetii*), babesioses (*Babesia canis canis*), ehrlichiosis.

Examples of vectors in the sense of the present invention are insects, for example aphids, flies, leafhoppers or *thrips*, which are capable of transmitting plant viruses to plants. Other vectors capable of transmitting plant viruses are spider mites, lice, beetles and nematodes.

Further examples of vectors in the sense of the present invention are insects and arachnids such as mosquitoes, in particular of the genera *Aedes, Anopheles*, for example *A. gambiae, A. arabiensis, A. funestus, A. dirus* (malaria) and *Culex*, psychodids such as *Phlebotomus, Lutzomyia*, lice, fleas, flies, mites and ticks capable of transmitting pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protecting wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. Likewise, the compounds of the formula (I), alone or in combinations with other active compounds, can be used as antifouling agents.

Control of Animal Pests in the Hygiene Sector

The compounds of the formula (I) are suitable for controlling animal pests in the hygiene sector. In particular, the invention can be applied in the domestic sector, in the hygiene sector and in the protection of stored products, especially for controlling insects, arachnids, ticks and mites encountered in enclosed spaces such as dwellings, factory halls, offices, vehicle cabins, animal husbandries. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

They are used, for example, in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

ABBREVIATIONS AND SYMBOLS

AcOH: acetic acid
aq.: aqueous
BINAP 2,2'-Bis(diphenylphosphino)-1,1'-binaphthyl
br.: broad
d: doublet
dppf 1,1'-Bis(diphenylphosphino)ferrocene
DCC: N,N'-dicyclohexylcarbodiimide
DCM dichloromethane
DIPEA: diisopropylethylamine
DMF: N,N-dimethylformamide
DMSO: dimethylsulfoxide
ee: enantiomeric excess
eq.: equivalent
ES: electrospray ionization
EtOAc: ethyl acetate
HATU: 1-[bis(dimethylamino)methylene]-1H-1,2,3-triazolo[4,5-b]pyridinium-3-oxid hexafluorophosphate
HOBt: 1-hydroxybenzotriazole hydrate
HPLC: high performance liquid chromatography
iPrOH: isopropanol
J: coupling constant
LCMS: liquid chromatography-mass spectrometry
m/z: mass-to-charge ratio
M: molarity
m: multiplet
MeCN acetonitrile
MeOH: methanol
MTBE tert-butyl methyl ether
NMR: nuclear magnetic resonance
q: quartet
r. t.: room temperature
$R_t$: retention time
s: singlet
sat.: saturated
T: temperature
t: triplet
T3P®: propylphosphonic anhydride
THF: tetrahydrofuran wt.: weight
XantPHOS 4,5-Bis(diphenylphosphino)-9,9-dimethyl-xanthene (CAS RN 161265-03-8)
δ: chemical shift
λ: wavelength Description of the Processes and Intermediates Compounds of formula I may be prepared as illustrated in the following scheme 1 where $R^1$, $R^2$, $R^3$, $R^4$, $Q^1$, $Q^2$ are as previously defined, Hal stands for F, Cl, Br or I.

Secondary amine (I-a) may be converted into tertiary amines (I) using an alkylation reaction with an alkylating agent (c) where LG is a Cl, Br, I, tosylate, mesylate or triflate group. The reaction is carried out in the presence of a base, such as $K_2CO_3$ or DIPEA in a suitable solvent, such as acetonitrile or DMF at a temperature in the range of 20 to 100° C.

Azole derivatives (a) may be prepared as outlined in scheme 2. A precursor (d) carrying an appropriate leaving group LG is reacted with ammonia or with a primary amine

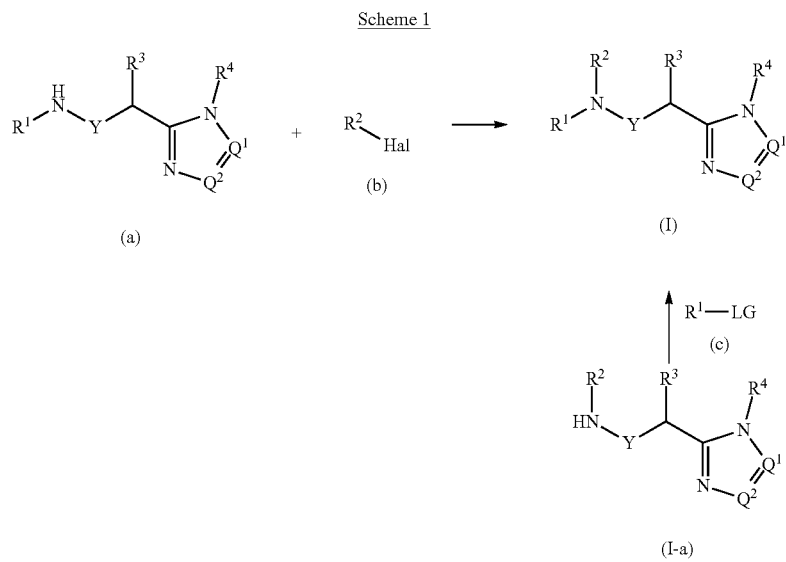

An azole compound of formula (a) is reacted with a heterocyclyl halogenide of formula (b) (Hal=F, Cl, Br, I) to form compounds of formula I. For example, a mixture of an azole of formula (a), a heterocyclyl halogenide (b) (Hal=F, Cl, Br, I), a suitable base such as triethylamine or DIPEA, in a suitable solvent, such as THF, 1,4-dioxane, pyridine, DMF are mixed at temperatures ranging from around 0 to 100° C. to provide compounds of formula I which may then be isolated and, if necessary and desired, purified using techniques well known in the art, such as chromatography. A preferred set of conditions for this transformation uses DIPEA as a base, THF as solvent and a temperature of 65° C. for 2 hours.

In cases where Hal is $C_1$, Br or I, the coupling of an azole compound of formula (a) and a heterocyclyl halogenide (b) can be carried out under the conditions of a Buchwald-Hartwig coupling using a palladium catalyst such as $PdCl_2dppf$, tetrakis triphenylphosphinepalladium(0), palladium(II) acetate, bis-dibenzylideneacetonepalladium(II), a suitable ligand such as, for instance, BINAP, XantPHOS, dppf and a suitable base such as sodium tert-butylate, potassium phosphate, potassium carbonate or cesium carbonate, in a suitable solvent, such as toluene, THF, 1,4-dioxane, are mixed and then reacted at temperatures ranging from room temperature to 200° C. to provide compounds of formula I' which may then be isolated and, if necessary and desired, purified using techniques well known in the art, such as chromatography. An extensive review on Buchwald-Hartwig reactions may be used to find appropriate conditions for every individual transformation: P. R. Castillo, S. L. Buchwald, Chem. Rev. 2016, 116, 12564-12649.

(e), respectively, to give primary amines of formula (a') or secondary amines of formula (a).

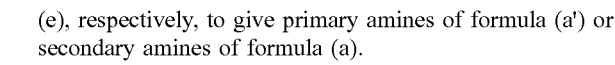

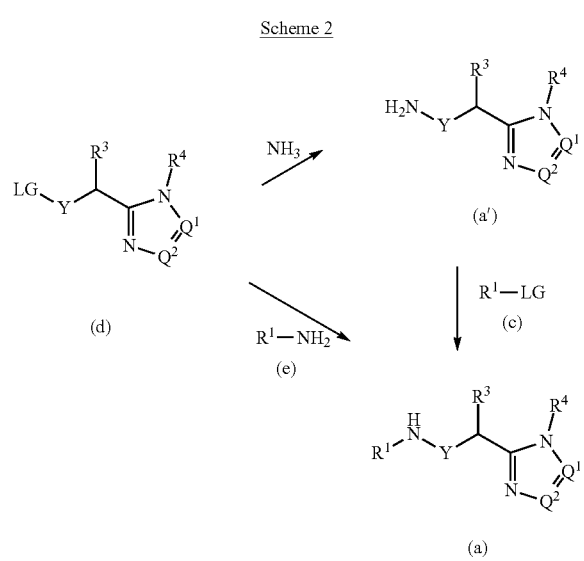

Examples of leaving groups LG are Cl, Br, I, tosylate, mesylate or triflate groups. The reaction may be carried out by mixing a compound of formula (d), an amine of formula (e) or ammonia, and optionally a suitable base, such as $K_2CO_3$ or DIPEA in a suitable solvent, such as acetonitrile or DMF and letting them react at a temperature in the range of 20 to 100° C. to provide compounds of formula (a) or (a') which may then be isolated and, if necessary and desired, purified using techniques well known in the art, such as chromatography. Alternatively, secondary amines (a) may be prepared from primary amines (a') by an alkylation reaction with an alkylating agent (c) where LG is a Cl, Br, I, tosylate, mesylate or triflate group. The reaction is carried out in the presence of a base, such as $K_2CO_3$ or DIPEA in a suitable solvent, such as acetonitrile or DMF at a temperature in the range of 20 to 100° C. Compounds (d) are commercially available or made by methods known in the art.

Heterocyclyl halogenides of formula (b-1) or (b-2) (Hal=F, Cl, Br, I) are commercially available or may be synthesized as outlined in schemes 3 or 4.

Benzoxazoles may be synthesized following scheme 3.

Scheme 3

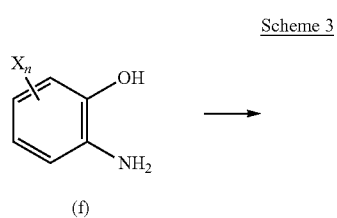

(f)

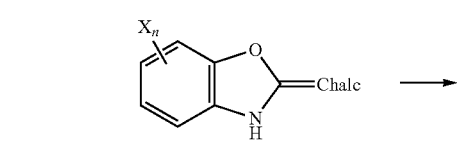

(g)

Benzothiazoles may be synthesized according to scheme 4.

Scheme 4

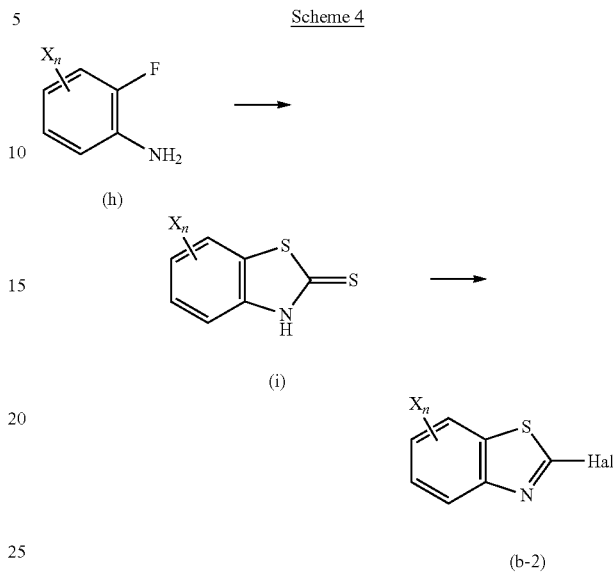

A fluoroaniline (h) is reacted with a xanthogenate, e.g. potassium O-ethyl carbonodithioate in a suitable solvent such as DMF at a temperature in the range of 50 to 180° C. giving rise to a 1,3-benzothiazole-2(3H)-thione of formula (i). This is then converted into a heterocyclyl halide according to formula (b-2) by the action of a halogenating agent such as thionyl chloride, phosphorus trichloride, phosphorus tribromide, phosphoroxychloride or iodine.

Scheme 5

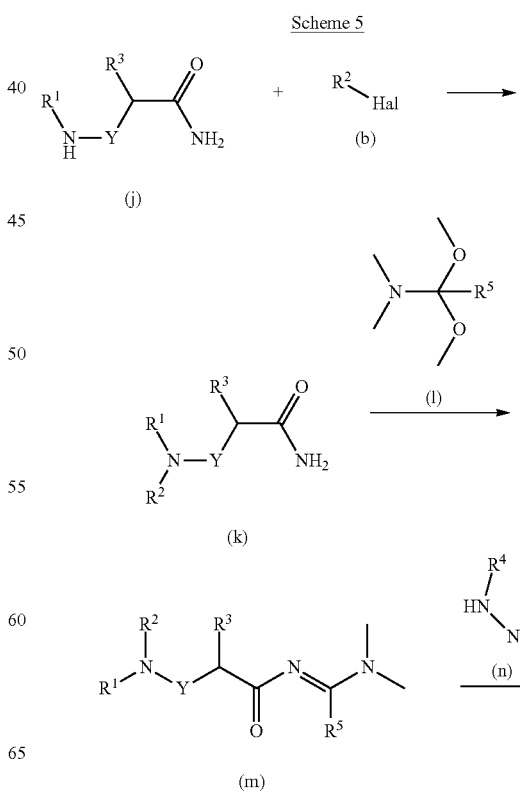

An aromatic compound of formula (f) where every X is defined as above is first converted into a chalcogen derived intermediate (g) where Chalc stands for O or S. In cases where Chalc is O, this transformation can be achieved using an agent such as, for instance, phosgene, diphosgene, triphosgene, carbonyldiimidazol (CDI), in an appropriate solvent such as dichloromethane at a temperature ranging from 0 to 120° C. When Chalc is S, the reaction may be carried out using carbon disulfide or a xanthogenate, e.g. potassium O-ethyl carbonodithioate, in an appropriate solvent such as DMF at a temperature ranging from 0 to 150° C. Compounds (g) are then converted into heteroaryl halogenides (b-1) by reacting them with a halogenating agent such as thionyl chloride, phosphoryl chloride or phosphorus tribromide either neat or in a suitable solvent such as DMF.

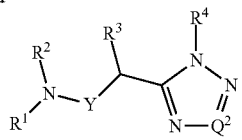

(I-b) Q² = CR⁵

Compounds of formula I-b can be synthesized according to scheme 5. In this case, a heterocyclyl halide of formula (b) (Hal=F, Cl, Br, I) is first reacted with an amide derivative (j) by mixing the two components in a suitable solvent such as THF, 2-butanol or 1,4-dioxane at a temperature ranging from 0° C.-150° C. in the presence of a base such as TEA, DIPEA or potassium carbonate. The resulting intermediates of formula (k) might be isolated or directly reacted with an N,N-dimethylamide dimethyl acetal of formula (l) in a suitable solvent, such as DCM at reflux to provide compounds of formula (m). Upon removal of the solvent, compounds of formula (m) are reacted with a substituted hydrazine (n) in a suitable solvent such as 1,4-dioxane, acetic acid or a mixture of such solvents at temperatures ranging from around 20 to 100° C. to provide compounds of formula (I-b) which may then be isolated and, if necessary and desired, purified using techniques well known in the art, such as chromatography.

Intermediates (b) are synthesized as exemplified in schemes 3 and 4.

Scheme 6 outlines the preparation of amide derivatives of formula (j). To this end, an amide of formula (o) bearing a suitable leaving group LG is reacted with an amine of formula (e).

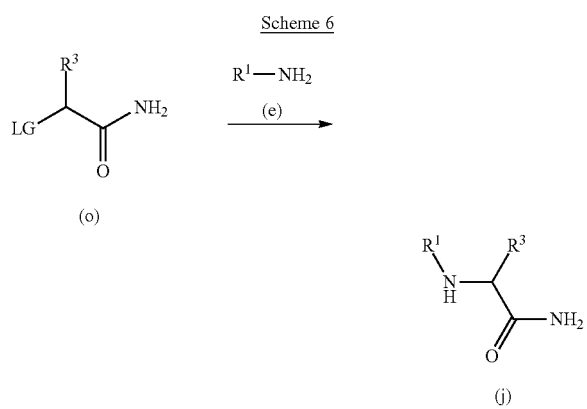

Examples of leaving groups LG are Cl, Br, I, tosylate, mesylate or triflate groups. The reaction may be carried out by mixing the reagents (o) and (e) together with a base, such as $K_2CO_3$ or DIPEA in a suitable solvent, such as acetonitrile or DMF and letting them react at a temperature in the range 20 to 100° C. Compounds of formula (j) may then be isolated and, if necessary and desired, purified using techniques well known in the art, such as chromatography. Amide derivatives (o) are commercially available or can be synthesized according to methods known in the art.

N,N-dimethylamide acetals of formula (l), and hydrazines of formula (n) are commercially available or may be synthesized by methods known to a person skilled in the state of the art.

Compounds of formula I-b may be also prepared as illustrated in the following scheme 7 where $R^1$, $R^2$, $R^3$, $R^4$, $R^5$ are as previously defined.

Scheme 7

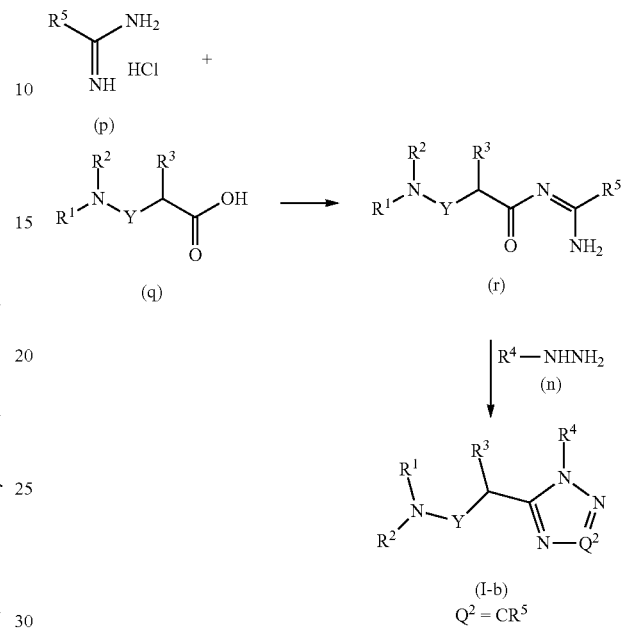

$R^5$ = H, alkyl, cycloalkyl, haloalkyl, alkoxy

An amidine hydrochloride of formula (p) or a suitable corresponding salt is reacted with an acid of formula (q) to form compounds of formula (r) which are subsequently reacted with substituted hydrazines of formula (n) under acidic conditions to form compounds of formula I-b. For example, an amidine hydrochloride of formula (p), a carboxylic acid (q), a suitable coupling reagent, such as HATU or DCC/HOBt, a suitable base such as triethylamine or DIPEA, in a suitable solvent such as acetonitrile or DMF are mixed at temperatures ranging from around 0 to 100° C., to form compounds of formula (r) which are subsequently reacted with substituted hydrazines of formula (n) or their corresponding salts, e.g. hydrochloride salts, under acidic conditions to form compounds of formula (I-b) which may then be isolated and, if necessary and desired, purified using techniques well known in the art, such as chromatography.

Amidine hydrochlorides of formula (p), carboxylic acid derivatives of formula (q) and hydrazines of formula (n) are commercially available or may be synthesized by methods known to the skilled artisan.

Scheme 8

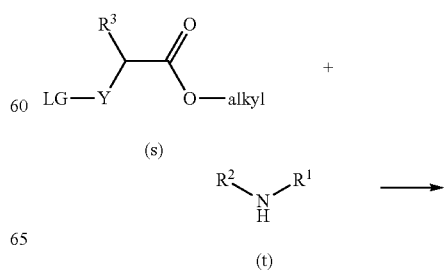

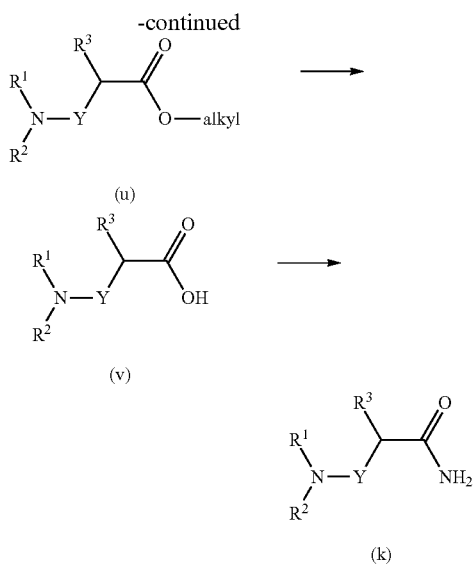

Intermediate of the general formula (k) may, in some cases, be prepared according to the strategy shown in Scheme 8. Thereby, a compound of the general formula (s) is reacted with an aminoheterobicyclic compound of the general formula (t). $R^1$, $R^2$, $R^3$ and Y are as defined above, examples of leaving groups LG are Cl, Br, I, tosylate, mesylate or triflate groups and alkyl groups are, for instance, methyl, ethyl or benzyl groups. The reaction may be carried out by mixing the reagents (s) and (t) together with a base such as $K_2CO_3$ or DIPEA in a suitable solvent, such as acetonitrile or DMF and letting them react at a temperature in the range between 20 and 120° C. to give intermediates (u). The ester moiety in (u) can be cleaved by the action of hydroxide ions, for instance with aqueous lithium hydroxide in an organic solvent such as THF, DMF, ethanol or methanol to give intermediate carboxylic acids according to formula (v). In the next synthetic transformation, compounds (k) are obtained by converting the carboxylic acid moiety of (v) into an amide by using an amine source such as ammonium chloride, a coupling agent, e.g. HATU, and a base in a dipolar, aprotic solvent such as DMF.

The processes according to the invention for the preparation of compounds of the formula (I) are preferably performed using a diluent. Useful diluents for performance of the processes according to the invention are, as well as water, all inert solvents. Examples include: halohydrocarbons (for example chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (for example methanol, ethanol, isopropanol, butanol), ethers (for example ethyl propyl ether, methyl tert-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, 1,4-dioxane, dichlorodiethyl ether and polyethers of ethylene oxide and/or propylene oxide), amines (for example trimethyl-, triethyl-, tripropyl-, tributylamine, N-methylmorpholine, pyridine and tetramethylenediamine), nitrohydrocarbons (for example nitromethane, nitroethane, nitropropane, nitrobenzene, chloronitrobenzene, o-nitrotoluene); nitriles (for example acetonitrile, propionitrile, butyronitrile, isobutyronitrile, benzonitrile, m-chlorobenzonitrile), tetrahydrothiophene dioxide, dimethyl sulphoxide, tetramethylene sulphoxide, dipropyl sulphoxide, benzyl methyl sulphoxide, diisobutyl sulphoxide, dibutyl sulphoxide, diisoamyl sulphoxide, sulphones (for example dimethyl, diethyl, dipropyl, dibutyl, diphenyl, dihexyl, methyl ethyl, ethyl propyl, ethyl isobutyl and pentamethylene sulphone), aliphatic, cycloaliphatic or aromatic hydrocarbons (for example pentane, hexane, heptane, octane, nonane and technical hydrocarbons), and also what are called "white spirits" with components having boiling points in the range from, for example, 40° C. to 250° C., cymene, petroleum fractions within a boiling range from 70° C. to 190° C., cyclohexane, methylcyclohexane, petroleum ether, ligroin, benzene, toluene, xylene, esters (for example methyl, ethyl, butyl and isobutyl acetate, dimethyl, dibutyl and ethylene carbonate); amides (for example hexamethylphosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (for example acetone, acetophenone, methyl ethyl ketone, methyl butyl ketone).

It is also possible to perform the process according to the invention in mixtures of the solvents and diluents mentioned.

When performing the process according to the invention, the reaction temperatures can be varied within a relatively wide range. In general, the temperatures employed are between −30° C. and +150° C., preferably between −10° C. and +100° C.

The process according to the invention is generally performed under atmospheric pressure. However, it is also possible to perform the process according to the invention under elevated or reduced pressure—generally at absolute pressures between 0.1 bar and 15 bar.

To perform the process according to the invention, the starting materials are generally used in approximately equimolar amounts. However, it is also possible to use one of the components in a relatively large excess. The reaction is generally carried out in a suitable diluent in the presence of a reaction auxiliary, optionally also under a protective gas atmosphere (for example under nitrogen, argon or helium) and the reaction mixture is generally stirred at the temperature required for several hours. The workup is performed by customary methods (cf. the preparation examples).

The basic reaction auxiliaries used to perform the process according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, 2-picoline, 3-picoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethylenediamine). The acidic reaction auxiliaries used to perform the process according to the invention include all mineral acids (e.g. hydrohalic acids such as hydrofluoric acid, hydrochloric acid, hydrobromic acid or hydriodic acid, and also sulphuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulphonic acid, benzoic acid, benzenesulphonic acid or para-toluenesulphonic acid).

Scheme 9 illustrates the preparation of alkoxytriazole containing amines (a″) where $R^4$ is as previously defined and alkyl is optionally substituted $C_1$-$C_6$alkyl.

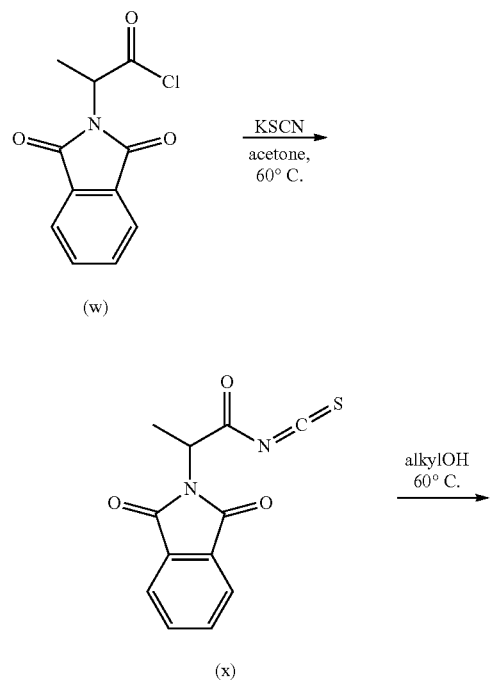

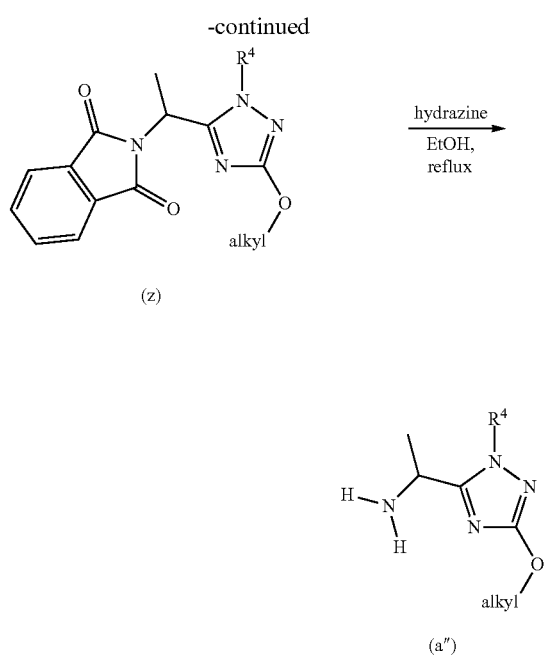

The synthesis starts with the reaction of 2-(1,3-dioxo-1,3-dihydro-2H-isoindol-2-yl)propanoyl chloride (w) (synthesis described in EP 3459941) with potassium thiocyanate (KSCN) in acetone to yield the corresponding isothiocyanate intermediate (x) which is treated in the next step with the corresponding alcohol to afford the O-alkyl [(2S)-2-(1,3-dioxo-1,3-dihydro-2H-isoindol-2-yl)propanoyl]carbamothioates (y). The reaction between intermediate (y) and a hydrazine of formula (n) in ethanol affords cyclized products of formula (z) (this sequence starting from (w) was described in Bioorganic & Medicinal Chemistry 26 (2018) 3321-3344). The deprotection of the amino group with hydrazine hydrate in a suitable solvent such as ethanol, at temperatures ranging from 20-80° C. (as described in EP 3459941) yields primary amines of formula (a″). In a final step, the obtained amine (a″) is reacted with a heterocyclyl halogenide of formula (b) (Hal=F, Cl, Br, I) to form compounds of formula I as described in scheme 1.

Scheme 10 illustrates the preparation of alkyltriazole containing amines (a‴) where $R^5$ is optionally substituted $C_3$-$C_6$cycloalkyl or $C_1$-$C_6$alkyl, wherein the $C_1$-$C_6$alkyl is substituted as previously described. $Z^{10}$ is $NH_2$ or $OC_1$-$C_6$alkyl. $R^4$ is as previously defined.

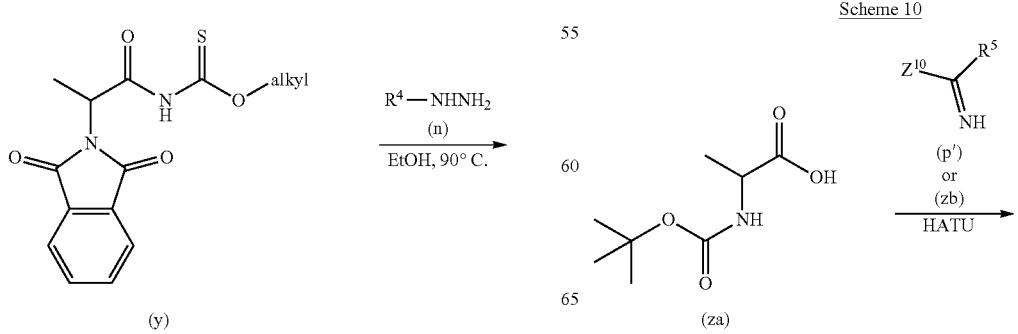

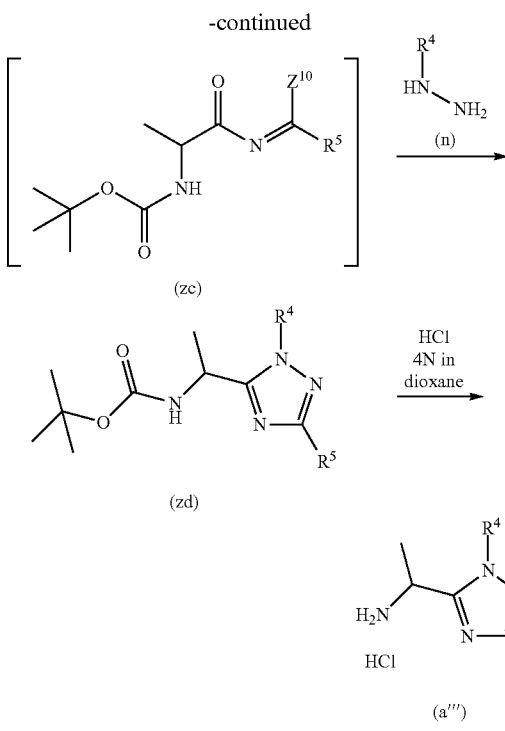

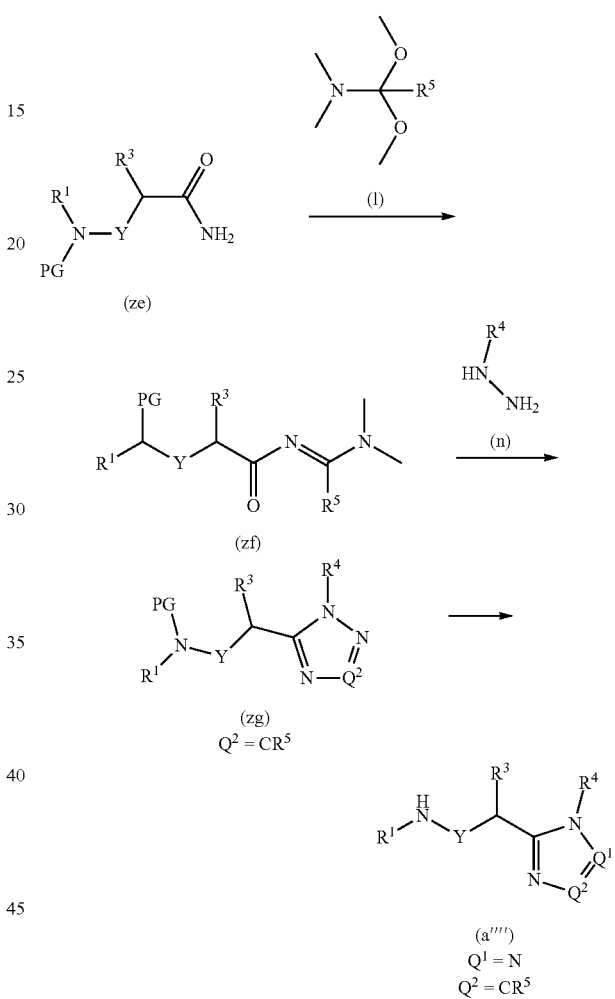

Scheme 11

N-(tert-butoxycarbonyl)-alanine (za) is reacted with a alkylamidine (p', $Z^{10}=NH_2$) or an alkylimidate (zb, $Z^{10}=OC_1-C_6$alkyl) to form intermediates of formula (zc) which are subsequently reacted with substituted hydrazines of formula (n) to form alkyltriazoles of formula (zd). For example in the case of (p', $Z^{10}=NH_2$) (compare J. Org. Chem. 2011, 76, 1177-1179) N-(tert-butoxycarbonyl)-alanine and an alkylamidine of formula (p') are reacted in the presence of a suitable coupling reagent, such as HATU, a suitable base such as triethylamine or DIPEA, in a suitable solvent, such as DMF, at temperatures ranging from 0 to 50° C. to form acylamidine intermediate of formula (zc). After removal of the solvent, the intermediates of formula (zc) are reacted with a substituted hydrazine of formula (n) in a suitable solvent such as acetic acid at temperatures ranging from around 20 to 80° C. The resulting alkyltriazoles of formula (zd) may then be isolated and, if necessary and desired, purified using techniques well known in the art, such as chromatography.

In the case of $Z^{10}=OC_1-C_6$alkyl N-(tert-butoxycarbonyl)-alanine and an alkylimidate of formula (zb) or a suitable salt thereof are reacted in the presence of a suitable coupling reagent, such as HATU, a suitable base such as triethylamine or DIPEA, in a suitable solvent, such as THF at temperatures ranging from around 0 to 25° C. to form acyl imidate intermediates of formula (zc). Upon addition of a substituted hydrazine of formula (n) the intermediate of formula (zc) reacts at temperatures ranging from around 20 to 80° C. to give alkyltriazoles of formula (zd) (compare WO 2019081302) which may then be isolated and, if necessary and desired, purified using techniques well known in the art, such as chromatography. Removal of the BOC protecting group from alkyltriazoles of formula (zd) then gives rise to intermediate amines (a''). Deprotection is preferentially carried out with 4N hydrochloric acid in dioxane or with 30% TFA in dichloromethane. The resulting intermediate (a''') can be purified by a method known in the art such as HPLC or used crude. It can be converted into a compound of the invention as shown in Scheme 1. The requisite alkylamidines (p') and alkylimidates (zb) or their suitable salts and hydrazines of formula (n) are commercially available or may be synthesized by methods described in this application or methods known to the skilled artisan (see for example WO 2011133447 for the synthesis of methyl cyclopropanecarboximidate hydrochloride).

A specific method for the preparation of certain intermediates of formula (a'''') is displayed in Scheme 11. An intermediate (ze) where Y, R1 and R3 are defined as described above and PG is a suitable protecting group, preferentially a BOC group, is reacted with an N,N-dimethylamide dimethyl acetal of formula (l) in a suitable solvent, such as DCM at reflux to provide compounds of formula (zf). Upon removal of the solvent, compounds of formula (zf) are reacted with a substituted hydrazine (n) in a suitable solvent such as 1,4-dioxane, acetic acid or a mixture of such solvents at temperatures ranging from around 20 to 100° C. to provide compounds of formula (zg) which may then be isolated and, if necessary and desired, purified using techniques well known in the art, such as chromatography. Removal of the protecting group PG then gives rise to an intermediate (a''''). In case PG is a BOC group, deprotection is preferentially carried out with 4N hydrochloric acid in dioxane or with 30% TFA in dichloromethane. The resulting intermediate (a'''') can be purified by a method known in the art such as HPLC or used crude. It can be converted into a compound of the invention as shown in Scheme 1.

The preparation and use examples which follow illustrate the invention without limiting it.

Analytical Data of the Compounds

Method 1 (Analytical HPLC-MS)

Instrument MS: Thermo Scientific FT-MS; instrument UHPLC+: Thermo Scientific UltiMate 3000; Column: Waters, HSST3, 2.1×75 mm, C18 1.8 µm; eluent A: 1 L water+0.01% formic acid; eluent B: 1 L acetonitrile+0.01% formic acid; gradient: 0.0 min 10% B→2.5 min 95% B→3.5 min 95% B; column temperature: 50° C.; flow: 0.90 mL/min; UV-detection: 210 nm/Optimum Integration Path 210-300 nm.

Method 2 (Analytical HPLC-MS)

Instrument: Waters Single Quad MS System; instrument Waters UPLC Acquity; column: Waters BEH C18 1.7µ 50×2.1 mm; eluent A: 1 l water+1.0 mL (25% aq ammonia)/L, eluent B: 1 l acetonitrile; gradient: 0.0 min 92% A→0.1 min 92% A→1.8 min 5% A→3.5 min 5% A; oven temperature: 50° C.; flow: 0.45 mL/min; UV-detection: 210 nm.

Method 3 (HPLC-MS)

Instrument: Waters ACQUITY SQD UPLC System; Column: Waters Acquity UPLC HSS T3 1.8 µm 50×1 mm; eluent A: 1l water+0.25 mL 99% formic acid, eluent B: 1 L acetonitrile+0.25 mL 99% formic acid; gradient: 0.0 min 90% A→1.2 min 5% A→2.0 min 5% A column temperature: 50° C.; flow: 0.40 mL/min; UV-detection: 210 nm.

Method 4 (HPLC-MS)

Instrument: Waters ACQUITY SQD UPLC System; Column: Waters Acquity UPLC HSS T3 1.8 µm 50×1 mm; eluent A: 1 L water+0.25 mL 99% formic acid, eluent B: 1 L acetonitrile+0.25 mL 99% formic acid; gradient: 0.0 min 95% A→6.0 min 5% A→7.5 min 5% A column temperature: 50° C.; flow: 0.35 mL/min; UV-Detection: 210 nm.

Method 5 (GC-MS)

Instrument: Waters MS SQ detector2, GC Agilent A7890; column: Restek RTX-35MS, 15 m×200 µm×0.33 µm; constant helium flow: 1.20 ml/min; oven temperature: 60° C.; inlet: 240° C.; gradient: 60° C., 30° C./min→300° C. (keep for 3.33 min).

Method 6 (GC-MS)

Instrument: Thermo Scientific DSQII, Thermo Scientific Trace GC Ultra; Column: Restek RTX-35MS, 15 m×200 µm×0.33 µm; constant flow with Helium: 1.20 ml/min; Oven: 60° C.; Inlet: 220° C.; Gradient: 60° C., 30° C./min→300° C. (3.33 min hold).

Method 7 (HPLC-MS)

Instrument: Agilent MS Quad 6150; HPLC: Agilent 1290; Column: Waters Acquity UPLC HSS T3 1.8 µm 50×2.1 mm; Eluent A: 1 l Water+0.25 ml 99% ige Formic acid, Eluent B: 1 l Acetonitrile+0.25 ml 99% ige Formic acid; Gradient: 0.0 min 90% A→0.3 min 90% A→1.7 min 5% A→3.0 min 5% A Oven: 50° C.; Flow: 1.20 ml/min; UV-Detection: 205-305 nm.

Method 8 (HPLC-MS)

System MS: Waters TOF instrument; System UPLC: Waters Acquity I-CLASS; Column: Waters Acquity UPLC HSS T3 1.8 µm 50×1 mm; Eluent A: 1 l Water+0.100 ml 99% ige Formic acid, Eluent B: 1 l Acetonitrile+0.100 ml 99% ige Formic acid; Gradient: 0.0 min 90% A —*1.2 min 5% A→2.0 min 5% A Oven: 50° C.; Flow: 0.40 ml/min; UV-Detection: 210 nm.

Method 9 (GC-MS)

Instrument: Thermo Scientific DSQII, Thermo Scientific Trace GC Ultra; Column: Restek RTX-35MS, 15 m×200 µm×0.33 µm; constant flow with Helium: 1.20 ml/min; Oven: 60° C.; Inlet: 220° C.; Gradient: 60° C., 30° C./min→300° C. (3.33 min hold).

NMR Peak Lists Procedure $^1$H-NMR data of selected examples are written in form of $^1$H-NMR peak lists. δ-Values in ppm and the signal intensity in round brackets are listed to each signal peak. Semicolons are depicted as delimiters between the δ-value-signal intensity pairs.

Therefore the peak list of an example has the form:

$\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed view of a $^1$H-NMR spectrum in cm and shows the real relations of signal intensities. Several peaks from broad signals or the middle of the signal and their relative intensity in comparison to the most intensive signal in the spectrum can be shown.

Tetramethylsilane or the chemical shift of the solvent in cases where the sample does not contain tetramethylsilane is used for a calibration of the chemical shift for $^1$H spectra. Therefore the tetramethylsilane peak can occur in $^1$H-NMR peak lists, but not necessarily.

$^1$H-NMR peak lists are equivalent to classical $^1$H-NMR prints and contain usually all peaks, which are also listed at classical $^1$H-NMR-interpretations.

In addition, they can show signals of solvents, stereoisomers of the compounds which are optionally object of the invention, and/or peaks of impurities, like classical $^1$H-NMR prints.

$^1$H-NMR solvent signals, the tetramethylsilane signal and the water signal in the corresponding solvent are excluded from the relative intensity calibration as they have very high intensity values.

On average, the peaks of stereoisomers of the compounds according to the invention and/or peaks of impurities have usually a lower intensity than the peaks of compounds according to the invention (for example with a purity >90%).

Such stereoisomers and/or impurities can be typical for the specific preparation process. Thus, the corresponding peaks can help to recognize the reproduction of the preparation process via "side-products-fingerprints".

An expert, who calculates the peaks of the target compounds with known methods (MestreC, ACD-simulation, but also with empirically evaluated expectation values), can assign the peaks of the target compounds as needed, optionally using additional intensity filters. This assignment would be similar to the usual peak picking at classical $^1$H-NMR interpretations.

The used solvent can be extracted from the JCAMP file with the parameter "solvent", the spectrometer frequency with "observe frequency" and the spectrometer type with "spectrometer/data system".

$^{13}$C-NMR data are displayed analogous to $^1$H-NMR data as peak lists from broadband decoupled $^{13}$C-NMR spectra. $^{13}$C-NMR solvent signals and tetramethylsilane are excluded from the relative intensity calibration as these signals can have very high intensities.

Further details of NMR-data description with peak lists are disclosed in the publication "Citation of NMR Peaklist Data within Patent Applications" of the Research Disclosure Database Number 564025.

The compounds according to the invention described in table 1 below are likewise preferred compounds of the formula (I) according to the invention which are obtained according to or analogously to the preparation examples described above.

PREPARATION EXAMPLES

Intermediate 1A

6-Chloro-5-(trifluoromethyl)-1,3-benzoxazole-2(3H)-thione

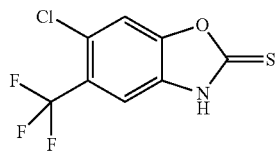 [SMILES: FC(F)(F)c1cc2[nH]c(=S)oc2cc1Cl]

2-Amino-5-chloro-4-(trifluoromethyl)phenol (1.00 g, 4.73 mmol) was dissolved in pyridine (10 mL) and potassium O-ethyl carbonodithioate (1.14 g, 7.09 mmol) was added. The mixture was heated to 120° C. for 2 h. After cooling to RT, the mixture was poured into water and acidified with 1M hydrochloric acid against universal indicator paper. The mixture was extracted with MTBE, the organic extract was washed with brine, dried over anhydrous sodium sulfate, filtered and evaporated. The crude product was purified by flash chromatography (silica gel, cyclohexane/ethyl acetate 10:1) to give 826 mg (100% purity, 69% yield) of intermediate 1A.

LC-MS (Method 1): $R_t$=1.82 min; MS (ESIneg): m/z=252 [M−H]⁻

$^1$H-NMR (600 MHz, DMSO-d⁶) δ [ppm]: 2.096 (0.64), 2.558 (14.33), 7.560 (16.00), 8.037 (13.36).

Intermediate 2A 2,6-dichloro-5-(trifluoromethyl)-1,3-benzoxazole

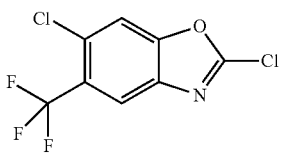 [SMILES: FC(F)(F)c1cc2nc(Cl)oc2cc1Cl]

6-chloro-5-(trifluoromethyl)-1,3-benzoxazole-2(3H)-thione (intermediate 1A, 820 mg, 3.23 mmol) was dissolved in thionyl chloride (6.0 mL, 82 mmol) and DMF (600 µL, 7.8 mmol) was added. The mixture was heated to 70° C. and stirred for 15 min until the evolution of gas ceased. The reaction mixture was poured into saturated aqueous sodium carbonate solution and extracted with three portions of MTBE. The organic extract was washed with brine, passed through a Macherey & Nagel MN 616 WA filter and evaporated. The crude product was triturated with cyclohexane and dried under vacuum. 468 mg (94% purity, 53% yield) of intermediate 2A were obtained as a light-red solid.

$^1$H-NMR (600 MHz, DMSO-d⁶) δ [ppm]: 7.452 (0.87), 7.808 (0.58), 8.336 (16.00), 8.372 (13.50).

Intermediate 3A

N²-[6-chloro-5-(trifluoromethyl)-1,3-benzoxazol-2-yl]-L-alaninamide

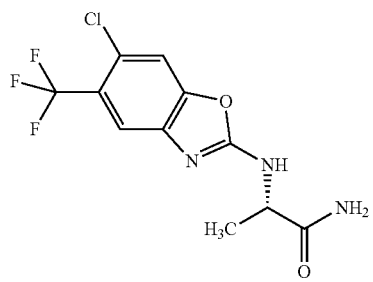 [SMILES: C[C@H](Nc1nc2cc(C(F)(F)F)c(Cl)cc2o1)C(N)=O]

2,6-Dichloro-5-(trifluoromethyl)-1,3-benzoxazole (intermediate 2A, 480 mg, 1.87 mmol), DIPEA (980 µl, 5.6 mmol) and L-alaninamide hydrochloride (1:1) (257 mg, 2.06 mmol) were dissolved in THF (5.0 mL). The mixture was heated over night to 65° C. with stirring. After cooling to RT, it was poured into water and extracted with three portions of ethyl acetate The combined organic extracts were dried over Chromabond PTL (30 mL cartridge) and evaporated. The oily residue was triturated with dichloromethane to form a precipitate that was filtered and washed with two portions of dichloromethane. The filtrate was evaporated and triturated once more with dichloromethane to yield a second crop of the product. The precipitates were combined to give 450 mg (100% purity, 78% yield) of intermediate 3A.

LC-MS (Method 1): $R_t$=1.48 min; MS (ESIpos): m/z=308 [M+H]⁺

$^1$H-NMR (600 MHz, DMSO-d6) δ [ppm]: 1.378 (16.00), 1.390 (15.94), 2.509 (10.70), 4.223 (0.64), 4.235 (2.59), 4.247 (3.82), 4.259 (2.51), 4.271 (0.61), 7.129 (4.62), 7.571 (4.60), 7.677 (12.43), 7.864 (10.42), 8.677 (3.99), 8.689 (3.84).

Example I-001

6-chloro-N-{(1S)-1-[1-(pyrimidin-2-yl)-1H-1,2,4-triazol-5-yl]ethyl}-5-(trifluoromethyl)-1,3-benzoxazol-2-amine

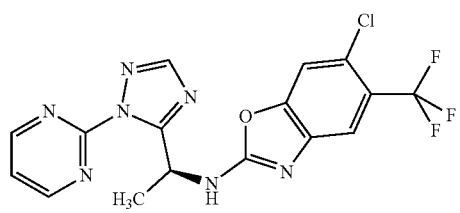 [SMILES: C[C@H](Nc1nc2cc(C(F)(F)F)c(Cl)cc2o1)c1ncnn1-c1ncccn1]

N²-[6-Chloro-5-(trifluoromethyl)-1,3-benzoxazol-2-yl]-L-alaninamide (intermediate 3A, 445 mg, 1.45 mmol) and 1,1-dimethoxy-N,N-dimethylmethanamine (480 µl, 3.6 mmol) were dissolved in dichloromethane (5.0 mL) and heated to reflux for 90 min. The solvent was distilled, the residue was taken up into a mixture of 1,4-dioxane (5.0 mL) and acetic acid (1.0 ml, 17 mmol). and 2-hydrazinylpyrimidine (319 mg, 2.89 mmol) was added. This mixture was heated to 60° C. for 3 h, then cooled, poured into saturated aqueous sodium carbonate solution and extracted with three portions of MTBE. The organic extract was washed with brine, passed through a Macherey & Nagel MN 616 WA filter and evaporated. The crude product solidified upon evaporation. It was first triturated with acetonitrile and eventually purified by preparative HPLC (RP C-18 phase with a gradient of water, acetonitrile with 0.1% ammonia) to give 364 mg (100% purity, 61% yield) of the title compound.

LC-MS (Method 1): $R_t$=1.72 min; MS (ESIpos): m/z=410 [M+H]$^+$ $^1$H-NMR (600 MHz, DMSO-d6) δ [ppm]: 1.665 (14.88), 1.677 (14.84), 5.770 (4.10), 5.899 (0.58), 5.911 (2.43), 5.923 (3.32), 5.935 (2.32), 5.946 (0.57), 7.543 (12.13), 7.656 (4.10), 7.664 (8.18), 7.672 (4.27), 7.836 (9.88), 8.192 (13.15), 8.995 (16.00), 9.003 (15.71), 9.250 (4.43), 9.263 (4.24).

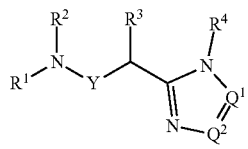
(I)

TABLE 1

| Example | Structure | NMR Peaklist[1] | LC-MS[1] |
|---|---|---|---|
| I-002 | 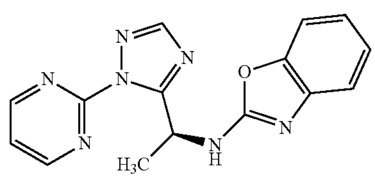 | $^1$H-NMR (600 MHz, DMSO-d$^6$) δ [ppm]: 1.653 (13.39), 1.664 (13.33), 2.089 (0.89), 5.767 (6.85), 5.864 (0.50), 5.875 (1.98), 5.887 (2.37), 5.900 (1.92), 5.912 (0.49), 6.946 (1.65), 6.952 (1.80), 6.954 (1.94), 6.960 (2.44), 6.965 (1.82), 6.967 (2.30), 6.974 (2.22), 7.045 (0.53), 7.046 (0.52), 7.058 (4.51), 7.060 (6.06), 7.066 (8.34), 7.073 (0.58), 7.291 (4.35), 7.304 (4.17), 7.666 (4.20), 7.674 (8.06), 7.682 (4.22). | LC-MS (Method 1): $R_t$ = 1.16 min; MS (ESIpos): m/z = 308 [M + H]$^+$ |
| I-003 | 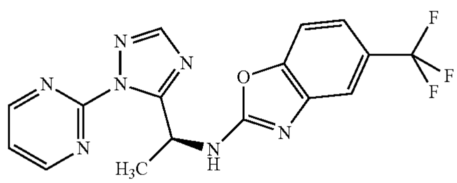 [SMILES: C[C@H](Nc1nc2cc(C(F)(F)F)ccc2o1)c1ncnn1-c1ncccn1] | $^1$H-NMR (600 MHz, DMSO-d$^6$) δ [ppm]: 1.231 (0.49), 1.667 (15.28), 1.679 (15.16), 5.901 (0.57), 5.913 (2.40), 5.925 (3.20), 5.937 (2.39), 5.949 (0.59), 7.334 (2.88), 7.348 (3.34), 7.418 (5.93), 7.420 (5.76), 7.525 (4.96), 7.538 (4.28), 7.665 (4.17), 7.673 (8.25), 7.681 (4.31), 8.182 (13.61), 9.004 (15.97), 9.012 (16.00), 9.084 (4.47), 9.097 (4.33). | LC-MS (Method 1): $R_t$ = 1.56 min; MS (ESIpos): m/z = 376 [M + H]$^+$ |
| I-004 | 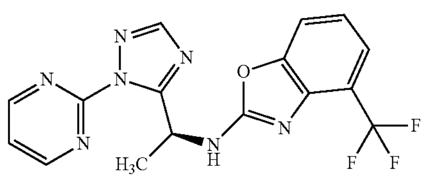 [SMILES: C[C@H](Nc1nc2c(C(F)(F)F)cccc2o1)c1ncnn1-c1ncccn1] | $^1$H-NMR (400 MHz, DMSO-d$^6$) δ [ppm]: 1.104 (1.96), 1.676 (15.79), 16.93 (16.00), 3.074 (0.62), 3.566 (0.83), 5.982 (0.76), 5.998 (2.57), 6.016 (3.75), 6.034 (2.59), 7.070 (2.56), 7.090 (5.32), 7.110 (3.21), 7.342 (5.25), 7.362 (4.62), 7.559 (4.76), 7.579 (4.46), 7.627 (3.35), 7.639 (6.38), 7.651 (3.61), 8.175 (6.31), 8.961 (10.70), 8.973 (10.73), 9.150 (4.63), 9.170 (4.60). | LC-MS (Method 1): $R_t$ = 1.56 min; MS (ESIpos): m/z = 376 [M + H]$^+$ |
| I-005 | 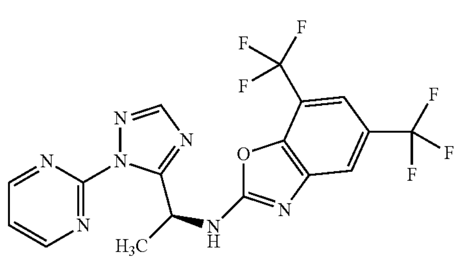 [SMILES: C[C@H](Nc1nc2cc(C(F)(F)F)cc(C(F)(F)F)c2o1)c1ncnn1-c1ncccn1] | $^1$H-NMR (600 MHz, DMSO-d$^6$) δ [ppm]: 1.672 (15.37), 1.684 (15.18), 5.935 (0.54), 5.946 (2.22), 5.959 (3.23), 5.971 (2.18), 5.982 (0.53), 7.618 (6.12), 7.668 (4.28), 7.676 (8.47), 7.684 (4.39), 7.797 (6.17), 8.186 (14.31), 9.011 (16.00), 9.019 (15.75), 9.593 (4.45), 9.606 (4.24). | LC-MS (Method 1): $R_t$ = 1.87 min; MS (ESIpos): m/z = 444 [M + H]$^+$ |
| I-006 | 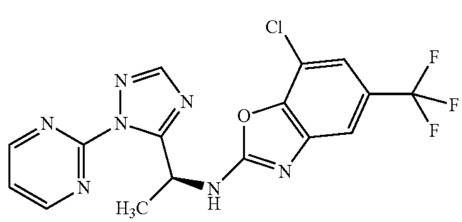 [SMILES: C[C@H](Nc1nc2cc(C(F)(F)F)cc(Cl)c2o1)c1ncnn1-c1ncccn1] | $^1$H-NMR (600 MHz, DMSO-d$^6$) δ [ppm]: 1.666 (14.80), 1.677 (14.80), 5.932 (1.56), 7.443 (6.25), 7.445 (6.33), 7.487 (6.44), 7.663 (4.32), 7.671 (8.48), 7.679 (4.37), 8.186 (13.36), 9.003 (16.00), 9.011 (16.00), 9.423 (2.11). | LC-MS (Method 1): $R_t$ = 1.79 min; MS (ESIpos): m/z = 410 [M + H]$^+$ |

TABLE 1-continued

| Example | Structure | NMR Peaklist[1] | LC-MS[1] |
|---|---|---|---|
| I-007 | 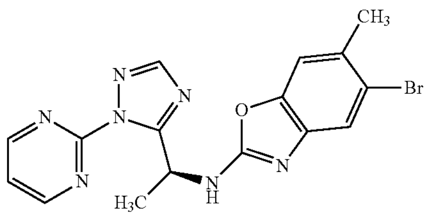 [SMILES: Cc1cc2oc(N[C@@H](C)c3ncnn3-c3ncccn3)nc2cc1Br] | ¹H-NMR (400 MHz, DMSO-d⁶) δ [ppm]: 1.635 (8.54), 1.652 (8.65), 2.322 (16.00), 5.844 (1.27), 5.862 (1.81), 5.881 (1.28), 7.270 (4.99), 7.351 (5.05), 7.646 (1.86), 7.658 (3.79), 7.670 (2.00), 8.155 (4.44), 8.779 (2.23), 8.799 (2.18), 8.983 (6.63), 8.995 (6.62). | LC-MS (Method 1): Rt = 1.62 min; MS (ESIpos): m/z = 400 [M + H]⁺ |
| I-008 | 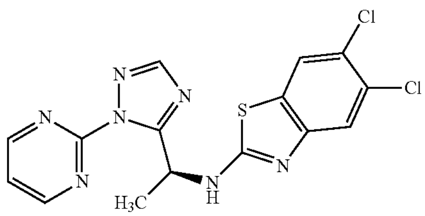 [SMILES: C[C@H](Nc1nc2cc(Cl)c(Cl)cc2s1)c1ncnn1-c1ncccn1] | ¹H-NMR (400 MHz, DMSO-d⁶) δ [ppm]: 1.652 (15.82), 1.669 (16.00), 2.075 (1.89), 5.992 (0.57), 6.009 (2.28), 6.027 (3.47), 6.044 (2.30), 6.062 (0.60), 7.206 (12.03), 7.676 (4.03), 7.689 (8.05), 7.701 (4.30), 7.953 (12.25), 8.171 (12.12), 8.970 (4.26), 8.988 (4.23), 9.014 (15.44), 9.027 (15.30). | LC-MS (Method 1): R$_t$ = 1.77 min; MS (ESIpos): m/z = 292 [M + H]⁺ |
| I-009 | 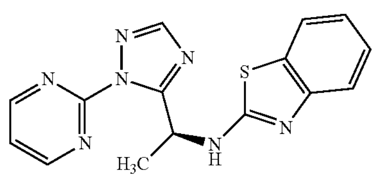 [SMILES: C[C@H](Nc1nc2ccccc2s1)c1ncnn1-c1ncccn1] | ¹H-NMR (400 MHz, DMSO-d⁶) δ [ppm]: 1.658 (15.74), 1.675 (16.00), 5.991 (0.58), 6.008 (2.44), 6.025 (3.66), 6.044 (2.48), 6.061 (0.61), 6.954 (2.55), 6.966 (4.65), 6.972 (5.63), 6.986 (6.24), 6.989 (5.21), 7.118 (3.14), 7.137 (4.67), 7.156 (2.05), 7.591 (4.89), 7.609 (3.71), 7.612 (3.96), 7.686 (3.72), 7.698 (7.55), 7.710 (3.99), 8.148 (10.36), 8.645 (4.24), 8.664 (4.17), 9.032 (13.91), 9.044 (13.94). | LC-MS (Method 3): R$_t$ = 0.65 min; MS (ESIpos): m/z = 324 [M + H]⁺ |
| I-010 | 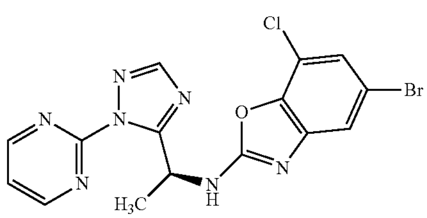 [SMILES: C[C@H](Nc1nc2cc(Br)cc(Cl)c2o1)c1ncnn1-c1ncccn1] | ¹H-NMR (600 MHz, DMSO-d⁶) δ [ppm]: 1.649 (16.00), 1.660 (15.99), 2.078 (1.52), 5.874 (0.54), 5.866 (2.23), 5.898 (3.16), 5.910 (2.20), 5.921 (0.56), 7.271 (7.04), 7.274 (9.19), 7.288 (9.51), 7.290 (6.90), 7.653 (3.97), 7.661 (7.70), 7.669 (3.96), 8.171 (13.88), 8.991 (15.73), 8.999 (15.41), 9.250 (3.90), 9.263 (3.74). | LC-MS (MCW-FT-MS-M1): R$_t$ = 1.72 min; MS (ESIpos): m/z = 420 [M + H]⁺ |
| I-011 | 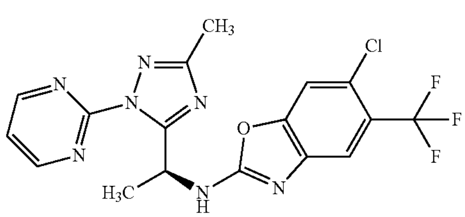 [SMILES: Cc1nc([C@H](C)Nc2nc3cc(C(F)(F)F)c(Cl)cc3o2)n(-c2ncccn2)n1] | ¹H-NMR (600 MHz, DMSO-d⁶) δ [ppm]: 1.637 (6.15), 1.649 (6.08), 2.074 (1.79), 2.321 (16.00), 5.893 (1.01), 5.906 (1.22), 5.917 (1.00), 7.544 (5.06), 7.598 (1.70), 7.606 (3.35), 7.614 (1.73), 7.823 (4.05), 8.947 (6.55), 8.955 (6.37), 9.198 (1.74), 9.211 (1.70). | LC-MS (Method 1): R$_t$ = 1.74 min; MS (ESIpos): m/z = 424 [M + H]⁺ |
| I-12 | 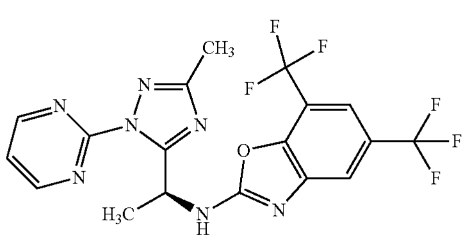 [SMILES: Cc1nc([C@H](C)Nc2nc3cc(C(F)(F)F)cc(C(F)(F)F)c3o2)n(-c2ncccn2)n1] | ¹H-NMR (500 MHz, DMSO-d⁶) δ [ppm]: −0.006 (0.82), 0.006 (0.62), 1.645 (6.01), 1.659 (6.01), 2.316 (16.00), 5.926 (0.96), 5.940 (1.32), 5.955 (0.93), 7.606 (4.17), 7.1616 (3.53), 7.625 (1.80), 7.789 (2.51), 8.960 (6.60), 8.969 (6.46), 9.531 (1.73), 9.547 (1.67). | LC-MS (Method 1): R$_t$ = 1.89 min; MS (ESIpos): m/z = 458 [M + H]⁺ |

TABLE 1-continued

| Example | Structure | NMR Peaklist[1] | LC-MS[1] |
|---|---|---|---|
| I-13 | 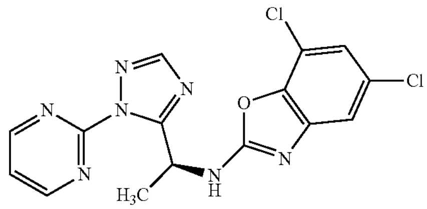 [SMILES: C[C@H](Nc1nc2cc(Cl)cc(Cl)c2o1)c1ncnn1-c1ncccn1] | ¹H-NMR (400 MHz, DMSO-d⁶) δ [ppm]: 1.106 (2.66), 1.157 (0.71), 1.175 (1.42), 1.193 (0.73), 1.643 (15.79), 1.660 (16.00), 1.989 (2.63), 3.077 (0.79), 4.021 (0.63), 4.039 (0.62), 5.755 (4.87), 5.861 (0.57), 5.878 (2.44), 5.896 (3.51), 5.914 (2.45), 5.932 (0.61), 7.152 (4.64), 7.156 (5.57), 7.181 (5.33), 7.186 (3.70), 7.647 (3.59), 7.659 (7.38), 7.671 (3.87), 8.167 (9.27), 8.987 (13.21), 8.999 (13.23), 9.240 (4.39), 9.259 (4.30). | LC-MS (Method 1): R$_t$ = 1.68 min; MS (ESIpos): m/z = 376 [M + H]⁺ |
| I-14 | 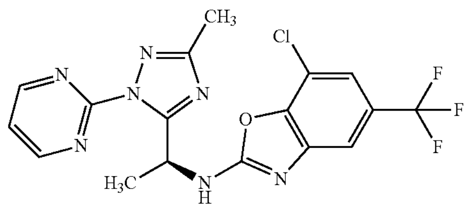 [SMILES: Cc1nc([C@H](C)Nc2nc3cc(C(F)(F)F)cc(Cl)c3o2)n(-c2ncccn2)n1] | ¹H-NMR (400 MHz, DMSO-d⁶) δ [ppm]: −0.008 (0.53), 0.008 (0.67), 1.639 (6.14), 1.656 (6.28), 2.318 (16.00), 5.898 (1.00), 5.917 (1.32), 5.935 (1.01), 7.444 (2.89), 7.474 (2.75), 7.601 (1.78), 7.613 (3.55), 7.625 (1.88), 8.954 (6.76), 8.966 (6.67), 9.363 (1.79), 9.383 (1.78). | LC-MS (Method 3): R$_t$ = 0.94 min; MS (ESIpos): m/z = 424 [M + H]⁺ |
| I-15 | 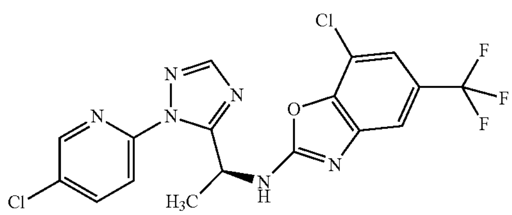 [SMILES: C[C@H](Nc1nc2cc(C(F)(F)F)cc(Cl)c2o1)c1ncnn1-c1ccc(Cl)cn1] | ¹H-NMR (400 MHz, DMSO-d6) δ [ppm]: 1.397 (4.67), 1.640 (15.80), 1.657 (16.00), 5.889 (1.42), 5.906 (2.09), 5.922 (1.44), 7.472 (9.38), 7.917 (5.87), 7.939 (6.86), 8.180 (9.52), 8.218 (4.39), 8.225 (4.57), 8.240 (3.94), 8.246 (4.08), 8.629 (4.81), 8.635 (4.67), 9.386 (2.60), 9.401 (2.23). | LC-MS (Method 1): R$_t$ = 2.36 min; MS (ESIpos): m/z = 443 [M + H]⁺ |
| I-16 | 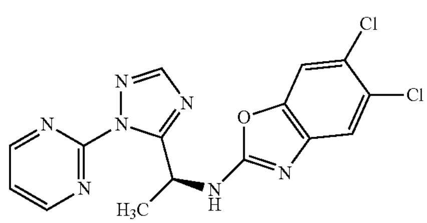 [SMILES: C[C@H](Nc1nc2cc(Cl)c(Cl)cc2o1)c1ncnn1-c1ncccn1] | ¹H-NMR (500 MHz, DMSO-d6) δ [ppm]: 1.162 (0.73), 1.177 (1.46), 1.191 (0.74), 1.362 (0.42), 1.377 (0.43), 1.397 (1.70), 1.649 (14.79), 1.663 (14.70), 1.991 (2.74), 4.025 (0.64), 4.039 (0.63), 5.863 (0.56), 5.877 (2.27), 5.891 (3.03), 5.906 (2.23), 5.92 (0.55), 7.339 (14.12), 7.645 (4.19), 7.655 (8.20), 7.664 (4.28), 7.720 (13.52), 8.173 (13.09), 8.982 (16.00), 8.992 (15.69), 9.065 (3.93), 9.081 (3.78). | LC-MS (Method 1): R$_t$ = 1.65 min; MS (ESIpos): m/z = 376 [M + H]⁺ |
| I-17 | 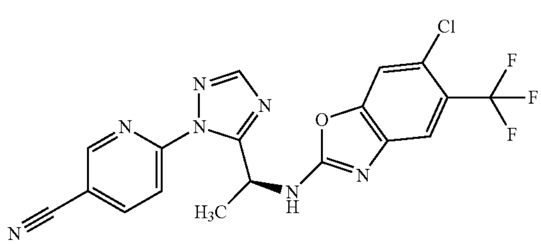 [SMILES: C[C@H](Nc1nc2cc(C(F)(F)F)c(Cl)cc2o1)c1ncnn1-c1ccc(C#N)cn1] | ¹H-NMR (600 MHz, DMSO-d6) δ [ppm]: 1.177 (0.83), 1.648 (16.00), 1.659 (15.89), 1.991 (1.56), 5.758 (3.56), 5.975 (0.44), 5.987 (1.72), 5.998 (2.58), 6.010 (1.67), 6.021 (0.42), 7.578 (13.08), 7.841 (10.72), 8.101 (6.05), 8.116 (6.42), 8.256 (13.89), 8.584 (4.27), 8.588 (4.24), 8.598 (4.04), 8.602 (4.02), 9.053 (6.27), 9.057 (5.97), 9.265 (3.02), 9.278 (2.81). | LC-MS (Method 1): R$_t$ = 2.02 min; MS (ESIpos): m/z = 434 [M + H]⁺ |
| I-18 | 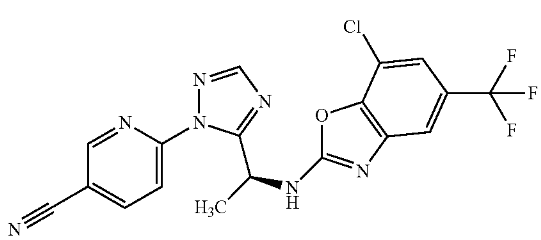 [SMILES: C[C@H](Nc1nc2cc(C(F)(F)F)cc(Cl)c2o1)c1ncnn1-c1ccc(C#N)cn1] | ¹H-NMR (600 MHz, DMSO-d6) δ [ppm]: 1.107 (1.09), 1.166 (0.72), 1.178 (1.44), 1.189 (0.72), 1.655 (14.29), 1.667 (14.24), 1.992 (2.78), 4.026 (0.66), 4.038 (0.66), 5.758 (5.11), 5.988 (0.51), 5.999 (1.98), 6.011 (2.94), 6.023 (1.95), 6.035 (0.48), 7.483 (16.00), 81.06 (5.22), 8.120 (5.55), 8.256 (11.45), 8.589 (3.64), 8.593 (3.69), 8.604 (3.47), 8.607 (3.50), 9.061 (5.51), 9.064 (5.57), 9.440 (3.65), 9.453 (3.51). | LC-MS (Method 1): R$_t$ = 2.09 min; MS (ESIpos): m/z = 434 [M + H]⁺ |

TABLE 1-continued

| Example | Structure | NMR Peaklist[1] | LC-MS[1] |
| --- | --- | --- | --- |
| I-019 | 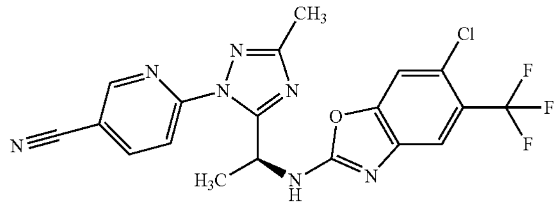 [SMILES: Cc1nc([C@H](C)Nc2nc3cc(C(F)(F)F)c(Cl)cc3o2)n(-c2ccc(C#N)cn2)n1] | 1H-NMR (600 MHz, DMSO-d6) δ [ppm]: 1.594 (0.45), 1.606 (0.48), 1.625 (6.43), 1.636 (6.42), 2.192 (0.67), 2.332 (16.00), 3.582 (2.29), 5.974 (1.07), 5.986 (1.42), 5.998 (1.06), 7.589 (5.33), 7.842 (4.47), 8.037 (2.46), 8.051 (2.60), 8.541 (1.79), 8.545 (1.79), 8.555 (1.71), 8.559 (1.72), 9.021 (2.46), 9.024 (2.49), 9.250 (1.89), 9.264 (1.85). | LC-MS (Method 4): R$_t$ = 3.47 min; MS (ESIpos): m/z = 448 [M + H]$^+$ |
| I-020 | 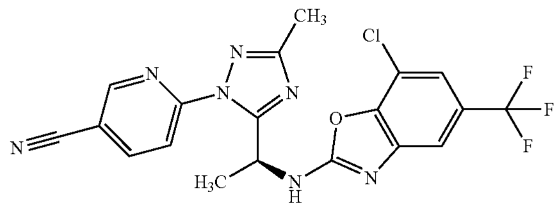 [SMILES: Cc1nc([C@H](C)Nc2nc3cc(C(F)(F)F)cc(Cl)c3o2)n(-c2ccc(C#N)cn2)n1] | 1H-NMR (600 MHz, DMSO-d6) δ [ppm]: 1.632 (6.22), 1.643 (6.20), 1.653 (0.49), 2.332 (16.00), 5.985 (0.99), 5.997 (1.38), 6.010 (1.03), 7.484 (3.42), 7.493 (3.13), 8.042 (2.33), 8.056 (2.48), 8.546 (1.76), 8.549 (1.82), 8.560 (1.67), 8.564 (1.74), 9.029 (2.28), 9.032 (2.38), 9.421 (1.84), 9.433 (1.77). | LC-MS (Method 3): R$_t$ = 1.12 min; MS (ESIpos): m/z = 448 [M + H]$^+$ |
| I-021 | 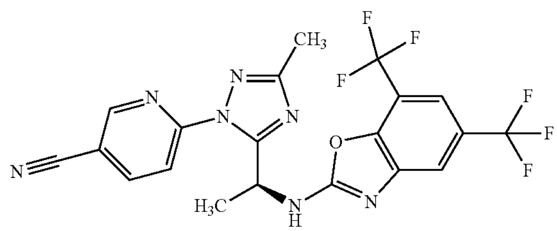 [SMILES: Cc1nc([C@H](C)Nc2nc3cc(C(F)(F)F)cc(C(F)(F)F)c3o2)n(-c2ccc(C#N)cn2)n1] | 1H-NMR (600 MHz, DMSO-d6) δ [ppm]: 1.640 (6.09), 1.651 (6.11), 1.660 (0.40), 2.079 (0.66), 2.332 (16.00), 6.012 (0.96), 6.024 (1.37), 6.036 (0.96), 7.613 (2.54), 7.841 (2.56), 8.048 (2.36), 8.063 (2.50), 8.552 (1.76), 8.556 (1.80), 8.567 (1.66), 8.570 (1.72), 9.034 (2.27), 9.037 (2.33), 9.585 (1.86), 9.599 (1.77). | LC-MS (Method 3): R$_t$ = 1.15 min; MS (ESIpos): m/z = 482 [M + H]$^+$ |
| I-022 | 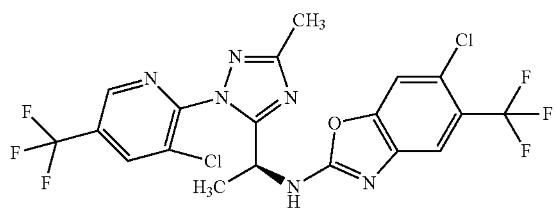 [SMILES: Cc1nc([C@H](C)Nc2nc3cc(C(F)(F)F)c(Cl)cc3o2)n(-c2ncc(C(F)(F)F)cc2Cl)n1] | 1H-NMR (600 MHz, DMSO-d6) δ [ppm]: 1.664 (6.05), 1.676 (6.08), 2.361 (16.00), 5.172 (1.01), 5.185 (1.24), 5.197 (0.99), 7.333 (4.02), 7.779 (4.00), 8.773 (2.38), 8.776 (2.44), 8.917 (2.32), 8.919 (2.29), 9.119 (1.87), 9.133 (1.79). | LC-MS (Method 1): Rt = 2.22 min; MS (ESIpos): m/z = 525 [M + H]$^+$ |
| I-023 | 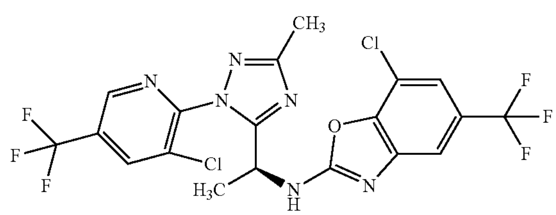 [SMILES: Cc1nc([C@H](C)Nc2nc3cc(C(F)(F)F)cc(Cl)c3o2)n(-c2ncc(C(F)(F)F)cc2Cl)n1] | 1H-NMR (600 MHz, DMSO-d6) δ [ppm]: 1.664 (5.73), 1.675 (5.72), 2.359 (16.00), 5.166 90.98), 5.179 (1.16), 5.191 (0.96), 7.259 (2.14), 7.485 (2.43), 8.789 (2.09), 8.792 (2.18), 8.907 (2.01), 8.909 (1.98), 9.269 (1.68), 9.282 (1.60). | LC-MS (Method 1): Rt = 2.32 min; MS (ESIpos): m/z = 525 [M + H]$^+$ |
| I-024 | 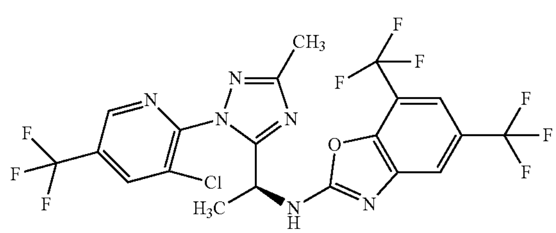 [SMILES: Cc1nc([C@H](C)Nc2nc3cc(C(F)(F)F)cc(C(F)(F)F)c3o2)n(-c2ncc(C(F)(F)F)cc2Cl)n1] | 1H-NMR (600 MHz, DMSO-d6) δ [ppm]: 1.671 (5.91), 1.682 (5.87), 2.075 (0.98), 2.357 (16.00), 5.185 (1.03), 5.198 (1.33), 5.210 (1.00), 7.624 (5.27), 8.766 (2.20), 8.769 (2.25), 8.870 (2.09), 8.872 (2.02), 9.397 (1.64), 9.410 (1.56). | LC-MS (Method 1): Rt = 2.33 min; MS (ESIpos): m/z = 559 [M + H]$^+$ |
| I-025 | 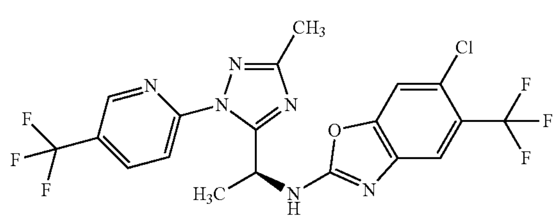 [SMILES: Cc1nc([C@H](C)Nc2nc3cc(C(F)(F)F)c(Cl)cc3o2)n(-c2ccc(C(F)(F)F)cn2)n1] | 1H-NMR (600 MHz, DMSO-d6) δ [ppm]: 1.643 (6.14), 1.655 (6.09), 2.337 (16.00), 5.992 (1.02), 6.003 (1.22), 6.016 (1.01), 7.545 (5.20), 7.832 (4.10), 8.060 (1.80), 8.074 (1.90), 8.467 (1.16), 8.471 (1.16), 8.481 (1.11), 8.485 (1.08), 8.958 (1.78), 9.247 (1.80), 9.260 (1.72). | LC-MS (Method 1): R$_t$ = 2.38 min; MS (ESIpos): m/z = 491 [M + H]$^+$ |

TABLE 1-continued

| Example | Structure | NMR Peaklist[1] | LC-MS[1] |
|---|---|---|---|
| I-026 | 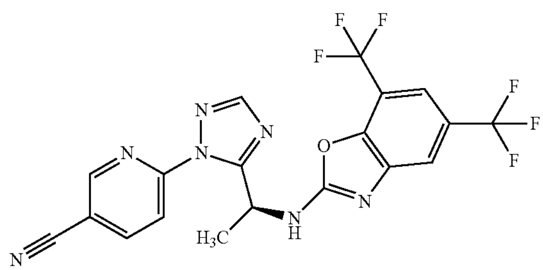 [SMILES: C[C@H](Nc1nc2cc(C(F)(F)F)cc(C(F)(F)F)c2o1)c1ncnn1-c1ccc(C#N)cn1] | $^1$H-NMR (600 MHz, DMSO-d6) δ [ppm]: −0.021 (0.91), 1.232 (1.78), 1.657 (16.00), 1.668 (15.89), 2.427 (0.46), 2.657 (0.41), 3.353 (0.50), 6.033 (2.02), 7.614 (6.83), 7.834 (7.01), 8.111 (5.75), 8.125 (6.13), 8.253 (12.11), 8.593 (4.11), 8.596 (4.08), 8.607 (3.91), 8.611 (3.89), 9.062 (6.37), 9.065 (6.16), 9.605 (3.20). | LC-MS (Method 1): R$_t$ = 2.17 min; MS (ESIpos): m/z = 468 [M + H]$^+$ |
| I-027 | 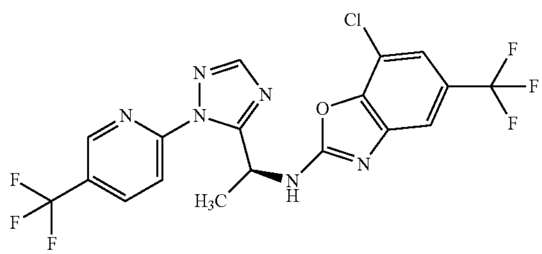 [SMILES: C[C@H](Nc1nc2cc(C(F)(F)F)cc(Cl)c2o1)c1ncnn1-c1ccc(C(F)(F)F)cn1] | $^1$H-NMR (600 MHz, DMSO-d6) δ [ppm]: −0.021 (1.84), 0.005 (1.42), 1.230 (3.69), 1.672 (16.00), 1.684 (15.95), 6.002 (0.51), 6.013 (2.00), 6.025 (2.97), 6.037 (1.98), 6.048 (0.48), 7.443 (7.19), 7.476 (6.79), 8.119 (4.71), 8.133 (5.04), 8.247 (14.16), 8.511 (3.01), 8.515 (3.09), 8.526 (2.87), 8.529 (2.91), 8.991 (4.89), 9.430 (3.76), 9.442 (3.62). | LC-MS (Method 1): R$_t$ = 2.41 min; MS (ESIpos): m/z = 477 [M + H]$^+$ |
| I-028 | 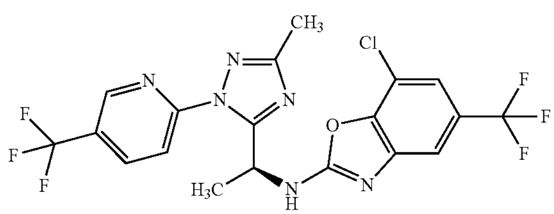 [SMILES: Cc1nc([C@H](C)Nc2nc3cc(C(F)(F)F)cc(Cl)c3o2)n(-c2ccc(C(F)(F)F)cn2)n1] | $^1$H-NMR (600 MHz, DMSO-d6) ι [ppm]: 1.649 (6.04 ), 1.661 (5.97), 2.338 (16.00), 6.005 (0.92), 6.017 (1.22), 6.029 (0.91), 7.456 (2.76), 7.478 (2.63), 8.066 (1.81), 8.080 (1.91), 8.471 (1.16), 8.475 (1.16), 8.485 (1.11), 8.489 (1.08), 8.959 (1.80), 9.413 (1.78), 9.426 (1.68). | LC-MS (Method 1): R$_t$ = 2.48 min; MS (ESIpos): m/z = 491 [M + H]$^+$ |
| I-029 | 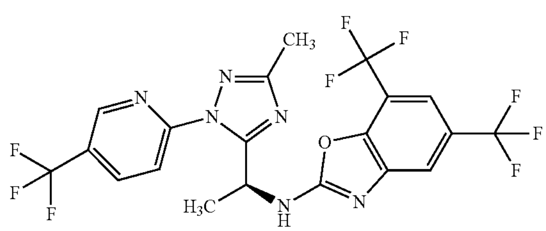 [SMILES: Cc1nc([C@H](C)Nc2nc3cc(C(F)(F)F)cc(C(F)(F)F)c3o2)n(-c2ccc(C(F)(F)F)cn2)n1] | $^1$H-NMR (600 MHz, DMSO-d6) δ [ppm]: 1.656 (5.96), 1.667 (5.97), 2.076 (1.21), 2.336 (16.00), 6.027 (0.78), 6.040 (1.11), 6.052 (0.76), 7.608 (2.30), 7.806 (2.37), 8.070 (1.78), 8.084 (1.88), 8.473 (1.16), 8.477 (1.15), 8.488 (1.08), 8.492 (1.07), 8.956 (1.73), 9.570 (1.43), 9.583 (1.37). | LC-MS (Method 1): R$_t$ = 2.52 Min; MS (ESIpos): m/z = 525 [M + H]$^+$ |
| I-30 | 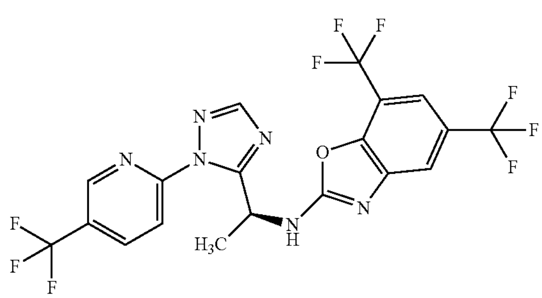 [SMILES: C[C@H](Nc1nc2cc(C(F)(F)F)cc(C(F)(F)F)c2o1)c1ncnn1-c1ccc(C(F)(F)F)cn1] | $^1$H-NMR (600 MHz, DMSO-d6) δ [ppm]: 0.005 (0.67), 1.168 (2.53), 1.180 (5.24), 1.191 (2.60), 1.397 (2.41), 1.683 (16.00), 1.695 (15.93), 1.994 (9.92), 4.016 (0.77), 4.029 (2.33), 4.040 (2.29), 4.052 (0.75), 6.028 (0.55), 6.039 (2.29), 6.051 (3.40), 6.063 (2.28), 6.074 (0.57), 7.604 (6.33), 7.795 (6.52), 8.125 (4.81), 8.140 (5.13), 8.248 (14.42), 8.514 (3.07), 8.518 (3.14), 8.528 (2.90), 8.532 (2.92), 8.983 (4.95), 9.592 (4.74), 9.604 (4.53). | LC-MS (Method 1): Rt = 2.45 min; MS (ESIpos): m/z = 511 [M + H]$^+$ |
| I-031 | 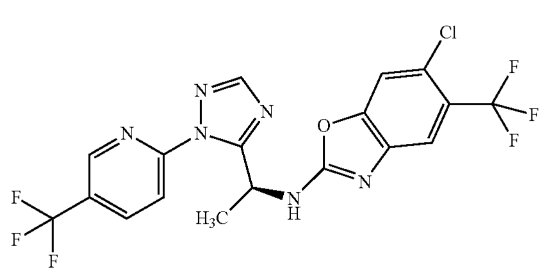 [SMILES: C[C@H](Nc1nc2cc(C(F)(F)F)c(Cl)cc2o1)c1ncnn1-c1ccc(C(F)(F)F)cn1] | $^1$H-NMR (600 MHz, DMSO-d6) δ [ppm]: 1.671 (16.00), 1.682 (15.97), 5.991 (0.66), 6.003 (2.58), 6.015 (3.73), 6.027 (2.57), 6.039 (0.67), 7.530 (12.17), 7.828 (10.25), 8.115 (4.99), 8.129 (5.31), 8.249 (12.43), 8.507 (3.37), 8.511 (3.49), 8.522 (3.24), 8.525 (3.25), 8.988 (6.01), 9.265 (4.71), 9.278 (4.58). | LC-MS (Method 1): R$_t$ = 2.34 min; MS (ESIpos): m/z = 477 [M + H]$^+$ |

TABLE 1-continued

| Example | Structure | NMR Peaklist[1] | LC-MS[1] |
|---|---|---|---|
| I-032 | 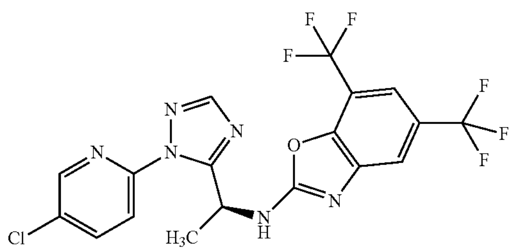 [SMILES: C[C@H](Nc1nc2cc(C(F)(F)F)cc(C(F)(F)F)c2o1)c1ncnn1-c1ccc(Cl)cn1] | ¹H-NMR (600 MHz, DMSO-d6) δ [ppm]: 1.397 (0.63), 1.649 (15.96), 1.660 (16.00), 5.907 (0.60), 5.919 (2.49), 5.930 (3.70), 5.942 (2.42), 5.954 (0.60), 7.609 (7.05), 7.820 (7.31), 7.929 (6.44), 7.943 (7.06), 8.180 (13.41), 8.228 (4.26), 8.232 (4.16), 8.242 (3.86), 8.246 (3.77), 8.632 (6.49), 8.636 (6.26), 9.558 (4.69), 9.570 (4.55). | LC-MS (Method 1): R$_t$ = 2.40 min; MS (ESIpos): m/z = 477 [M + H]⁺ |
| I-033 | 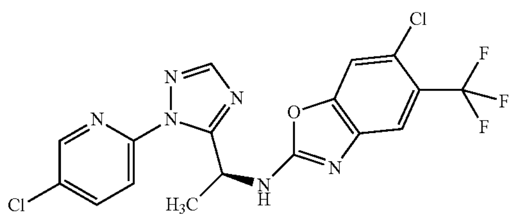 [SMILES: C[C@H](Nc1nc2cc(C(F)(F)F)c(Cl)cc2o1)c1ncnn1-c1ccc(Cl)cn1] | ¹H-NMR (600 MHz, DMSO-d6) δ [ppm]: 1.165 (1.10), 1.177 (2.22), 1.189 (1.11), 1.640 (6.09), 1.652 (6.06), 1.991 (4.19), 3.324 (16.00), 4.026 (0.99), 4.038 (0.98), 5.885 (0.95), 5.897 (1.32), 5.909 (0.95), 7.565 (4.88), 7.828 (3.73), 7.918 (2.42), 7.932 (2.67), 8.183 (5.28), 8.219 (1.67), 8.223 (1.68), 8.233 (1.50), 8.238 (1.54), 8.625 (2.36), 8.629 (2.33), 9.224 (1.75), 9.237 (1.68). | LC-MS (Method 1): R$_t$ = 2.28 min; MS (ESIpos): m/z = 443 [M + H]⁺ |
| I-034 | 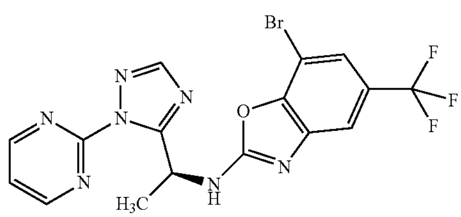 | ¹H-NMR (600 MHz, DMSO-d6) δ [ppm]: 1.666 (15.96), 1.678 (16.00), 5.907 (0.58), 5.918 (2.33), 5.930 (3.43), 5.942 (2.30), 5.954 (0.58), 7.453 (7.55), 7.556 (7.61), 7.658 (3.74), 7.666 (7.45), 7.674 (3.88), 8.176 (12.70), 9.000 (14.34), 9.008 (14.18), 9.393 (4.31), 9.406 (4.16). | LC-MS (Method 1): R$_t$ = 1.81 min; MS (ESIpos): m/z = 454 [M + H]⁺ |

TABLE 2

Intermediates according to structure (b)

| Intermediate | Structure | Analytics/NMR Peaklist[1] |
|---|---|---|
| (b)-001 | 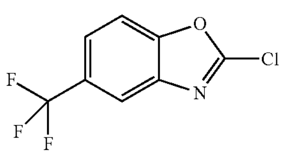 [SMILES: FC(F)(F)c1ccc2oc(Cl)nc2c1] | ¹H-NMR (400 MHz, DMSO-d6) δ [ppm]: −0.008 (0.93), 0.008 (0.93), 3.371 (16.00), 7.377 (0.67), 7.479 (0.64), 7.483 (0.67), 7.489 (0.95), 7.836 (1.33), 7.840 (1.37), 7.858 (1.74), 7.861 (1.77), 8.007 (2.58), 8.028 (2.03), 8.220 (2.53). |
| (b)-002 | 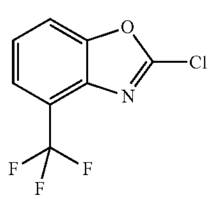 [SMILES: FC(F)(F)c1cccc2oc(Cl)nc12] | ¹H-NMR (600 MHz, DMSO-d6) δ [ppm]: 2.423 (11.11), 2.497 (11.78), 2.500 (16.00), 2.503 (12.44), 2.511 (2.22), 2.515 (2.00), 2.605 (0.89), 2.616 (0.67), 2.652 (11.33), 7.636 (4.67), 7.650 (10.00), 7.663 (6.00), 7.794 (10.00), 7.807 (8.44), 8.117 (9.78), 8.131 (9.33). |
| (b)-003 | 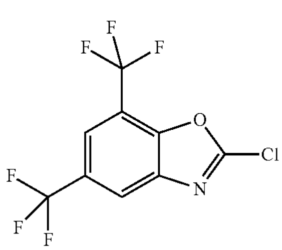 [SMILES: FC(F)(F)c1cc(C(F)(F)F)c2oc(Cl)nc2c1] | ¹H-NMR (600 MHz, DMSO-d6) δ [ppm]: 2.428 (0.64), 2.580 (0.64), 2.617 (0.45), 2.657 (0.76), 3.327 (0.52), 3.391 (0.53), 8.222 (16.00), 8.640 (15.98). |

TABLE 2-continued
Intermediates according to structure (b)
| Intermediate | Structure | Analytics/NMR Peaklist[1] |
|---|---|---|
| (b)-004 | 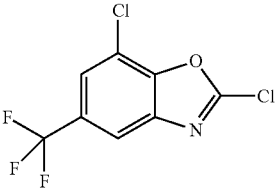 [SMILES: FC(F)(F)c1cc(Cl)c2oc(Cl)nc2c1] | $^1$H-NMR (400 MHz, DMSO-d6) δ [ppm]: −0.008 (1.11), 8.060 (15.98), 8.240 (16.00). |
| (b)-005 | 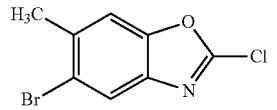 | $^1$H-NMR (500 MHz, DMSO-d6) δ [ppm]: 2.463 (16.00), 7.832 (4.23), 8.023 (5.39). |
| (b)-006 | 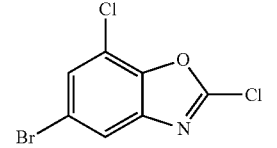 [SMILES: Clc1nc2cc(Br)cc(Cl)c2o1] | $^1$H-NMR (400 MHz, DMSO-d6) δ [ppm]: −0.008 (1.68), 0.008 (2.29), 1.231 (1.27), 1.249 (0.65), 1.266 (0.92), 1.283 (0.47), 2.525 (1.16), 3.149 (1.08), 3.154 (1.26), 3.626 (0.84), 7.872 (15.12), 7.875 (16.00), 8.045 (16.00), 8.048 (15.41). |
| (b)-007 | 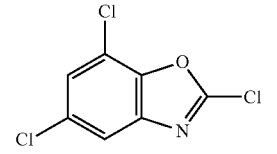 [SMILES: Clc1cc(Cl)c2oc(Cl)nc2c1] | $^1$H-NMR (400 MHz, DMSO-d6) δ [ppm]: −0.008 (1.32), 0.008 (1.33), 1.232 (0.52), 2.712 (0.43), 5.755 (3.73), 7.161 (0.61), 7.166 (0.65), 7.334 (0.45), 7.339 (0.44), 7.779 (14.75), 7.783 (16.00), 7.934 (15.74), 7.938 (15.24). |
| (b)-008 | 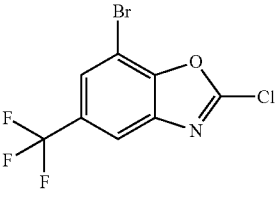 [SMILES: FC(F)(F)c1cc(Br)c2oc(Cl)nc2c1] | GC-MS (Method 5) R[1] = 4.11 min; MS (ESI) m/z = 300.9 [M+]. |
| (b)-009 | 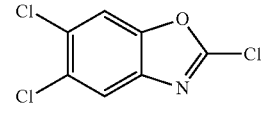 [SMILES: Clc1nc2cc(Cl)c(Cl)cc2o1] | $^1$H-NMR (600 MHz, DMSO-d6) δ [ppm]: 8.144 (16.00), 8.270 (15.79). |
| (b)-010 | 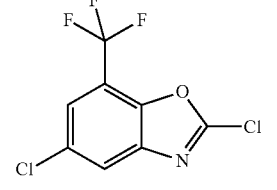 | $^1$H-NMR (400 MHz, DMSO-d6) δ [ppm]: −0.008 (0.41), 0.008 (0.49), 1.107 (16.00), 3.077 (4.56), 3.162 (0.75), 7.965 (2.95), 7.967 (3.14), 8.301 (2.00), 8.305 (2.04). |
| (b)-011 | 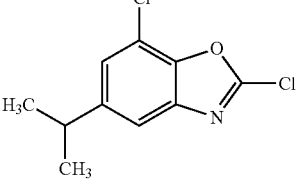 | GC-MS (method 9) Rt = 4.80 min; MS (EI) m/z = 229 [M]+. |

TABLE 2-continued
| Intermediate | Structure | Analytics/NMR Peaklist[1] |
|---|---|---|
| (b)-012 | 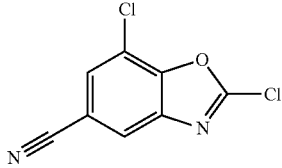 [SMILES: N#Cc1cc(Cl)c2oc(Cl)nc2c1] | ¹H-NMR (600 MHz, DMSO-d6) δ [ppm]: 4.298 (0.44), 4.371 (0.47), 4.381 (0.43), 7.595 (0.96), 7.837 (0.82), 8.227 (16.00), 8.416 (15.80). |
| (b)-013 | 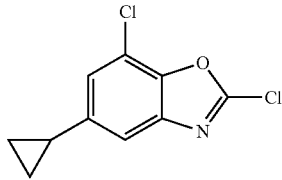 [SMILES: Clc1nc2cc(C3CC3)cc(Cl)c2o1] | GC-MS (method 9) Rt = 5.36 min; MS (EI) m/z = 227 [M]⁺. |
| (b)-014 | 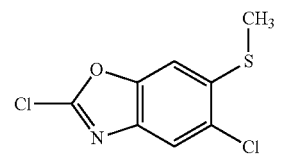 | GC-MS (method 9) Rt = 5.86 min; MS (EI) m/z = 233 [M]⁺. |
| (b)-015 | 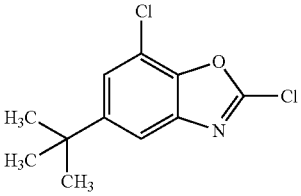 | ¹H-NMR (600 MHz, DMSO-d6) δ [ppm]: 1.331 (16.00), 7.580 (1.03), 7.583 (1.03), 7.714 (1.07), 7.717 (0.99). |
| (b)-016 | 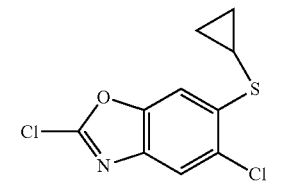 [SMILES: Clc1nc2cc(Cl)c(SC3CC3)cc2o1] | LC-MS (method 1): Rt = 2.35 min; MS (ESIpos): m/z = 260 [M + H]⁺ |
| (b)-017 | 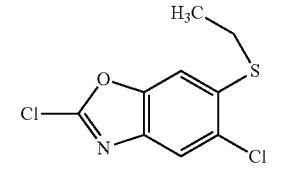 | LC-MS (method 1): Rt = 2.29 min; MS (ESIpos): m/z = 248 [M + H]⁺ |
| (b)-018 | 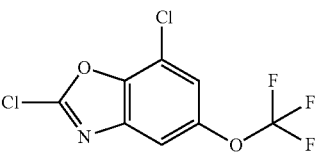 [SMILES: FC(F)(F)Oc1cc(Cl)c2oc(Cl)nc2c1] | GC-MS (method 9) Rt = 3.17 min; MS (EI) m/z = 271 [M]⁺. |

TABLE 2-continued

Intermediates according to structure (b)

| Intermediate | Structure | Analytics/NMR Peaklist[1] |
|---|---|---|
| (b)-019 | 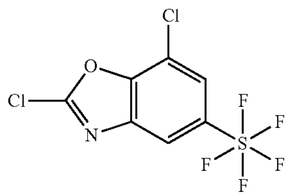 [SMILES: FS(F)(F)(F)(F)c1cc(Cl)c2oc(Cl)nc2c1] | GC-MS (method 9) Rt = 3.92 min; MS (EI) m/z = 313 [M]+. |
| (b)-020 | 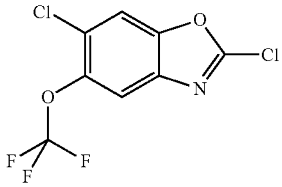 [SMILES: FC(F)(F)Oc1cc2nc(Cl)oc2cc1Cl] | $^1$H-NMR (600 MHz, DMSO-d6) δ [ppm]: 1.194 (0.45), 3.147 (2.46), 8.098 (9.29), 8.324 (16.00). |
| (b)-021 | 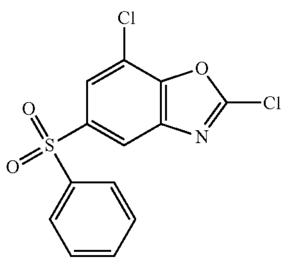 [SMILES: O=S(=O)(c1ccccc1)c1cc(Cl)c2oc(Cl)nc2c1] | $^1$H-NMR (400 MHz, DMSO-d6) δ [ppm]: −0.010 (0.91), 0.006 (1.04), 1.396 (4.42), 1.987 (0.48), 2.327 (0.50), 2.365 (0.70), 2.669 (0.51), 2.709 (0.72), 7.615 (6.00), 7.619 (2.47), 7.632 (15.79), 7.636 (8.19), 7.652 (11.27), 7.688 (3.67), 7.691 (6.53), 7.694 (3.77), 7.704 (2.59), 7.709 (7.97), 7.715 (1.76), 7.725 (1.61), 7.728 (2.45), 8.074 (11.05), 8.077 (16.00), 8.082 (3.74), 8.095 (12.80), 8.103 (1.41), 8.191 (12.89), 8.195 (12.82), 8.391 (12.99), 8.395 (12.18). |

TABLE 3

(k)

| Intermediate | Structure | LC-MS[1] |
|---|---|---|
| (k)-001 | 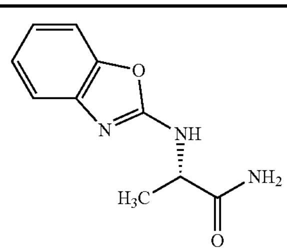 | HPLC-MS (method 2) R$_t$ = 0.94 min; MS (ESIpos): m/z = 206 [M + H]+ |
| (k)-002 | 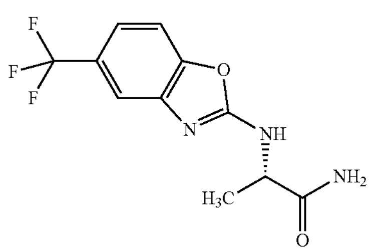 [SMILES: C[C@H](Nc1nc2cc(C(F)(F)F)ccc2o1)C(N)=O] | HPLC-MS (method 2) R$_t$ = 1.24 min; MS (ESIpos): m/z = 274 [M + H]+ |

TABLE 3-continued (k)

| Intermediate | Structure | LC-MS[1] |
|---|---|---|
| (k)-003 | 4-(trifluoromethyl)benzoxazol-2-yl amino alaninamide | HPLC-MS (method 2) $R_t$ = 1.29 min; MS (ESIpos): m/z = 274 [M + H]$^+$ |
| (k)-004 | 5,7-bis(trifluoromethyl)benzoxazol-2-yl amino alaninamide | HPLC-MS (method 1) $R_t$ = 1.64 min; MS (ESIpos): m/z = 342 [M + H]$^+$ |
| (k)-005 | 7-chloro-5-(trifluoromethyl)benzoxazol-2-yl amino alaninamide | HPLC-MS (method 1) $R_t$ = 1.55 min; MS (ESIpos): m/z = 308 [M + H]$^+$ |
| (k)-006 | 5-bromo-6-methylbenzoxazol-2-yl amino alaninamide | HPLC-MS (method 1) $R_t$ = 1.35 min; MS (ESIpos): m/z = 298 [M + H]$^+$ |

TABLE 3-continued
(k)
| Intermediate | Structure | LC-MS[1] |
|---|---|---|
| (k)-007 | 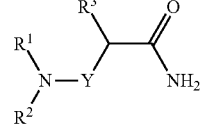 | HPLC-MS (method 1) R$_t$ = 1.50 min; MS (ESIpos): m/z = 290 [M + H]$^+$ |
| (k)-008 | 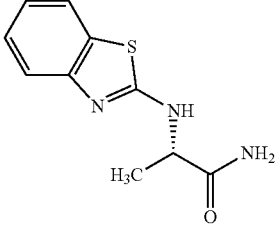 | HPLC-MS (method 1) R$_t$ = 0.98 min, MS (ESIpos): m/z = 222 [M + H]$^+$ |
| (k)-009 | 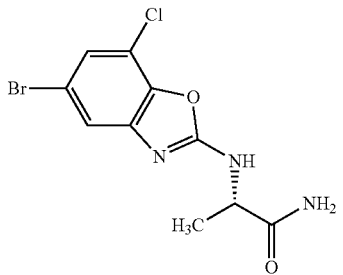 | HPLC-MS (method 2) R$_t$ = 1.36 min; MS (ESIpos): m/z = 321 [M + H]$^+$ |
| (k)-010 | 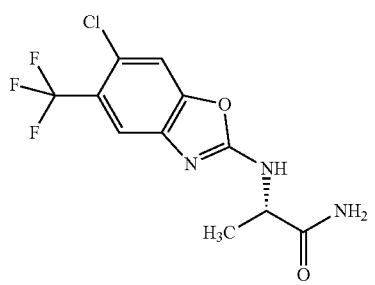 [SMILES: C[C@H](Nc1nc2cc(C(F)(F)F)c(Cl)cc2o1)C(N)=O] | HPLC-MS (method 1) R$_t$ = 1.48 min; MS (ESIpos): m/z = 308 [M + H]$^+$ |
| (k)-011 | 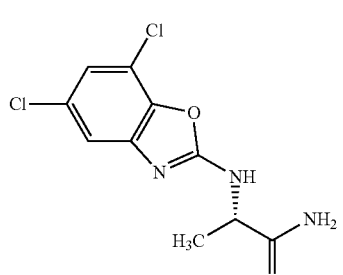 | HPLC-MS (method 1) R$_t$ = 1.40 min; MS (ESIpos): m/z = 274 [M + H]$^+$ |

TABLE 3-continued (k)

[Structure: R¹R²N-Y-CH(R³)-C(=O)NH₂]

| Intermediate | Structure | LC-MS[1] |
|---|---|---|
| (k)-012 | 5-bromo-7-chloro-benzoxazol-2-yl-NH-CH(CH₃)-C(=O)NH₂ | HPLC-MS (method 2) R$_t$ = 1.36 min; MS (ESIpos): m/z = 321 [M + H]⁺ |
| (k)-013 | 5,7-dichloro-benzoxazol-2-yl-NH-CH(CH₃)-C(=O)NH₂ | HPLC-MS (method 1) R$_t$ = 1.40 min; MS (ESIpos): m/z = 274 [M + H]⁺ |
| (k)-014 | 7-bromo-5-trifluoromethyl-benzoxazol-2-yl-NH-CH(CH₃)-C(=O)NH₂ | HPLC-MS (method 3): R$_t$ = 0.83 min; MS (ESIpos): m/z = 352 [M + H]⁺ |
| (k)-015 | 5,6-dichloro-benzoxazol-2-yl-NH-CH(CH₃)-C(=O)NH₂ | HPLC-MS (method 3): R$_t$ = 0.72 min; MS (ESIpos): m/z = 274 [M + H]⁺ |

TABLE 3-continued (k)

| Intermediate | Structure | LC-MS[1] |
|---|---|---|
| (k)-016 | 7-chloro-5-cyclopropyl-benzoxazol-2-yl with NH-CH(CH₃)-C(O)NH₂ | HPLC-MS (method 1) R$_t$ = 1.51 min; MS (ESIpos): m/z = 280 [M + H]$^+$ |
| (k)-017 | 7-chloro-5-cyano-benzoxazol-2-yl with NH-CH(CH₃)-C(O)NH₂ | HPLC-MS (method 1) R$_t$ = 1.14 min; MS (ESIpos): m/z = 265 [M + H]$^+$ |
| (k)-018 | 5-chloro-7-trifluoromethyl-benzoxazol-2-yl with NH-CH(CH₃)-C(O)NH₂ | HPLC-MS (method 1) R$_t$ = 1.54 min; MS (ESIpos): m/z = 308 [M + H]$^+$ |
| (k)-019 | 7-chloro-5-(1-methylethyl)-benzoxazol-2-yl with NH-CH(CH₃)-C(O)NH₂ | HPLC-MS (method 1) R$_t$ = 1.64 min; MS (ESIpos): m/z = 282 [M + H]$^+$ |

TABLE 3-continued
(k)
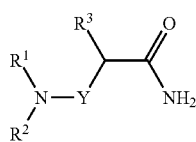
| Intermediate | Structure | LC-MS[1] |
|---|---|---|
| (k)-020 | 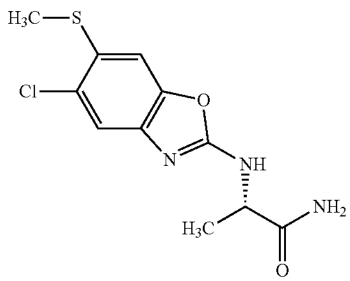 [SMILES: CSc1cc2oc(N[C@@H](C)C(N)=O)nc2cc1Cl] | HPLC-MS (method 7) $R_t$ = 0.98 min; MS (ESIneg): m/z = 284 [M − H]⁻ |
| (k)-021 | 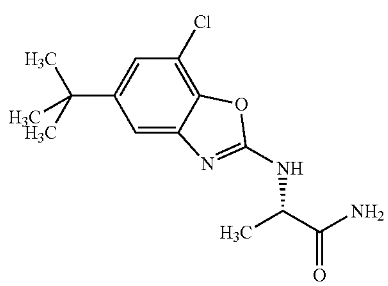 [SMILES: C[C@H](Nc1nc2cc(C(C)(C)C)cc(Cl)c2o1)C(N)=O] | HPLC-MS (method 1) $R_t$ = 1.74 min; MS (ESIpos): m/z = 296 [M + H]⁺ |
| (k)-022 | 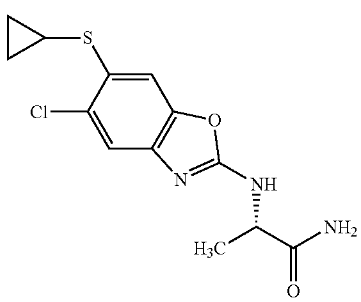 [SMILES: C[C@H](Nc1nc2cc(Cl)c(SC3CC3)cc2o1)C(N)=O] | HPLC-MS (method 1) $R_t$ = 1.56 min; MS (ESIpos): m/z = 312 [M + H]⁺ |
| (k)-023 | 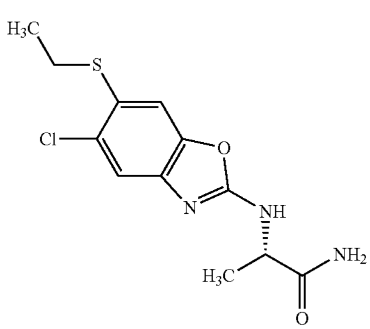 [SMILES: CCSc1cc2oc(N[C@@H](C)C(N)=O)nc2cc1Cl] | HPLC-MS (method 1) $R_t$ = 1.48 min; MS (ESIpos): m/z = 300 [M + H]⁺ |

TABLE 3-continued
(k)
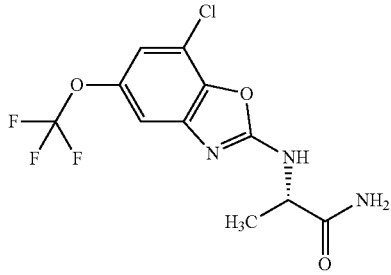 [SMILES: C[C@H](Nc1nc2cc(OC(F)(F)F)cc(Cl)c2o1)C(N)=O]
| Intermediate | Structure | LC-MS[1] |
|---|---|---|
| (k)-024 | 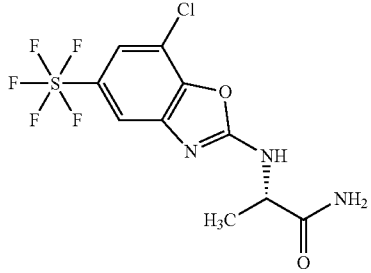 | HPLC-MS (method 1) $R_t$ = 1.59 min; MS (ESIpos): m/z = 324 [M + H]$^+$ |
| (k)-025 | 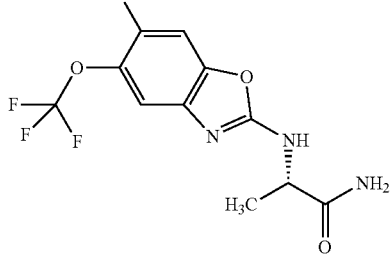 | HPLC-MS (method 1) $R_t$ = 1.66 min; MS (ESIpos): m/z = 366 [M + H]$^+$ |
| (k)-026 | 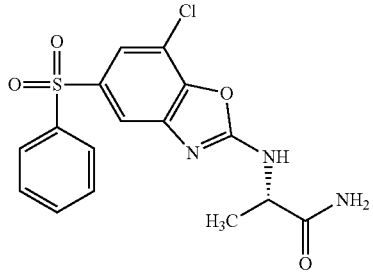 [SMILES: C[C@H](Nc1nc2cc(S(=O)(=O)c3ccccc3)cc(Cl)c2o1)C(N)=O] | HPLC-MS (method 1) $R_t$ = 1.53 min; MS (ESIpos): m/z = 324 [M + H]$^+$ |
| (k)-027 | 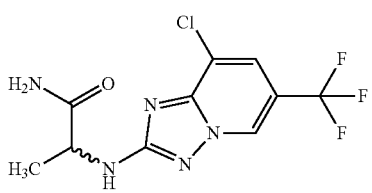 | HPLC-MS (method 1) $R_t$ = 1.41 min; MS (ESIpos): m/z = 380 [M + H]$^+$ |
| (k)-28 | 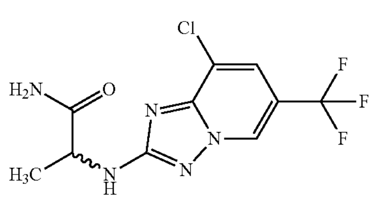 | LC-MS (method 7): $R_t$ = 0.90 min; MS (ESIneg): m/z = 306 [M − H]$^-$ |

TABLE 3-continued
(k)
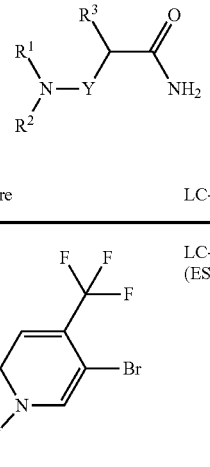
| Intermediate | Structure | LC-MS[1] |
|---|---|---|
| (k)-29 | 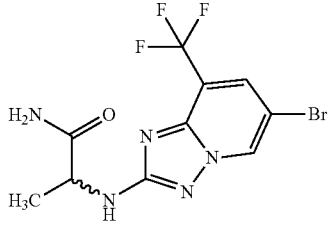 [SMILES: CC(Nc1nc2c(C(F)(F)F)cc(Br)cn2n1)C(N)=O] | LC-MS (method 1): R$_t$ = 1.24 min; MS (ESIpos): m/z = 352 [M + H]$^+$ |
| (k)-30 | 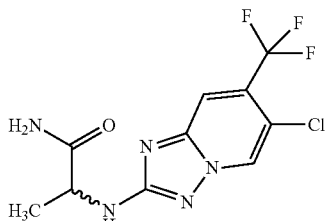 | LC-MS (method 1): R$_t$ = 1.23 min; MS (ESIpos): m/z = 352 [M + H]$^+$ |
| (k)-31 | 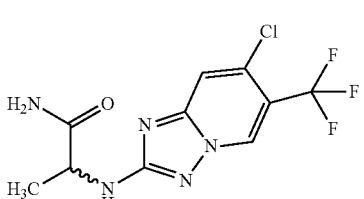 | LC-MS (method 1): R$_t$ = 1.22 min; MS (ESIpos): m/z = 308 [M + H]$^+$ |
| (k)-32 | 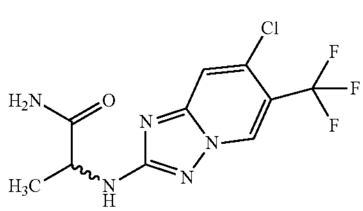 [SMILES: CC(Nc1nc2cc(Cl)c(C(F)(F)F)cn2n1)C(N)=O] | LC-MS (method 1): R$_t$ = 1.22 min; MS (ESIpos): m/z = 308 [M + H]$^+$<br>$^1$H-NMR (600 MHz, DMSO-d6) δ [ppm]: 1.350 (15.92), 1.361 (16.00), 4.150 (1.31), 4.162 (1.94), 4.174 (1.26), 6.943 (2.36), 7.059 (1.44), 7.072 (1.39), 7.293 (2.36), 7.848 (8.53), 9.272 (7.46). |

Synthesis of Intermediates According to Formulas (t), (u), (v)

Intermediate 4A

Ethyl {[4-chloro-5-(trifluoromethyl)pyridin-2-yl]carbamothioyl}carbamate

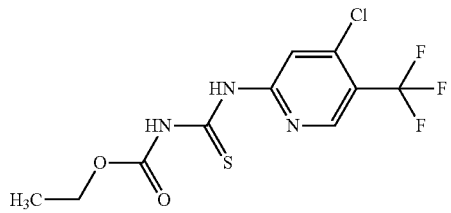 [SMILES: CCOC(=O)NC(=S)Nc1cc(Cl)c(C(F)(F)F)cn1]

4-Chloro-5-(trifluoromethyl)pyridin-2-amine (1.80 g, 9.16 mmol) was dissolved in 1,4-dioxane (20 mL), ethyl carbonisothiocyanatidate (1.3 mL, 11 mmol) was added and the mixture was stirred at 95° C. for 4 h. The solvent was removed by distillation and the residue was purified by flash chromatography on silica gel (eluent: gradient of cyclohexane with 0-60% dichloromethane). 3.00 g (98% purity, 97% yield) of the title compound were obtained.

LC-MS (method 1): $R_t$=2.22 min; MS (ESIpos): m/z=328 [M+H]$^+$ $^1$H-NMR (600 MHz, DMSO-d6) δ [ppm]: 1.261 (7.79), 1.273 (16.00), 1.285 (7.76), 1.398 (0.86), 4.229 (2.44), 4.240 (7.51), 4.252 (7.45), 4.264 (2.36), 8.828 (5.86), 9.049 (2.65), 11.941 (1.34), 12.450 (1.50).

Intermediate 5A, (t)-005

7-Chloro-6-(trifluoromethyl)[1,2,4]triazolo[1,5-a]pyridin-2-amine

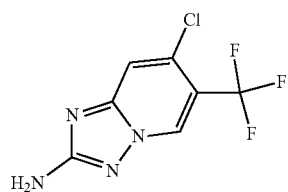 [SMILES: Nc1nc2cc(Cl)c(C(F)(F)F)cn2n1]

DIPEA (7.8 ml, 45 mmol) was added to a suspension of hydroxyl amine hydrochloride (3.13 g, 45.0 mmol) in a mixture of ethanol and methanol (1:1, 91 mL). This mixture was stirred at room temperature for 30 min, then ethyl {[4-chloro-5-(trifluoromethyl)pyridin-2-yl]carbamothioyl}carbamate (intermediate 4A, 2.95 g, 9.00 mmol) was added and the mixture was heated slowly to reflux. After 90 min at reflux, the solvents were distilled and the residue was mixed with water (100 mL). The solid precipitate was isolated by suction and dried under vacuum to give 2.11 g (94% purity, 93% yield) of the title compound.

Analytic data see table 4.

TABLE 4

Intermediates according to structure (t)

(t)

$$R^2-\underset{H}{N}-R^1$$

| Intermediate | Structure | Analytics/NMR (Peaklist[1]) |
|---|---|---|
| (t)-001 | ![structure] | LC-MS (method 1): $R_t$ = 1.21 min; MS (ESIpos): m/z = 237 [M + H]$^+$ |
| (t)-002 | ![structure] | LC-MS (method 1): $R_t$ = 1.31 min; MS (ESIpos): m/z = 281 [M + H]$^+$ |

TABLE 4-continued
Intermediates according to structure (t)
(t)
R²—N(R¹)—H
| Intermediate | Structure | Analytics/NMR (Peaklist[1]) |
|---|---|---|
| (t)-003 | 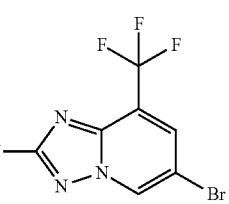 | LC-MS (method 1): R$_t$ = 1.27 min; MS (ESIpos): m/z = 281 [M + H]$^+$ |
| (t)-004 | 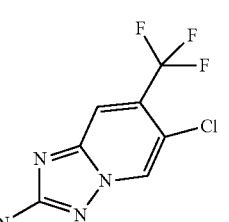 | LC-MS (method 1): R$_t$ = 1.28 min; MS (ESIpos): m/z = 237 [M + H]$^+$ |
| (t)-005 | 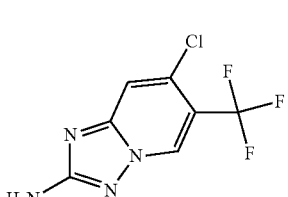 | LC-MS (method 1): R$_t$ = 1.28 min; MS (ESIpos): m/z = 237 [M + H]$^+$<br>$^1$H-NMR (500 MHz, DMSO-d6) δ [ppm]: 1.030 (0.51), 1.043 (0.46), 1.257 (0.63), 6.511 (14.27), 7.782 (16.00), 9.194 (14.47). |

147

Intermediate 6A, (u)-005

Ethyl N-[7-chloro-6-(trifluoromethyl)[1,2,4]triazolo[1,5-a]pyridin-2-yl]-DL-alaninate

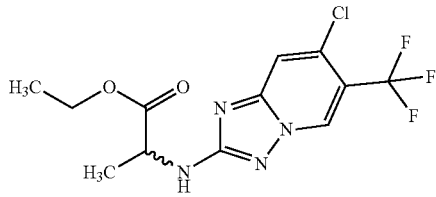 [SMILES: CCOC(=O)C(C)Nc1nc2cc(Cl)c(C(F)(F)F)cn2n1]

148

7-Chloro-6-(trifluoromethyl)[1,2,4]triazolo[1,5-a]pyridin-2-amine (intermediate 5A, 473 mg, 2.00 mmol) was dissolved in DMF (20 mL), cesium carbonate (2.61 g, 8.00 mmol) and (rac) ethyl 2-bromopropanoate were added and the mixture was heated to 60° C. for 16 h. The mixture was filtered and the filtrate was charged upon a prep HPLC device and chromatographed (RP C-18 10 µm, acetonitrile/water+0.1% TFA 10:90→95:5) 336 mg (100% purity, 50% yield) of the title compound were isolated.

Analytical data see table 5.

TABLE 5

Intermediates according to structure (u)

| Intermediate | Structure | Analytics/NMR Peaklist[1] |
|---|---|---|
| (u)-001 | [structure: ethyl alaninate linked to 8-Cl, 6-CF₃ triazolopyridine] | LC-MS (method 7): $R_t$ = 1.26 min; MS (ESIpos): m/z = 337 [M + H]⁺ |
| (u)-002 | [structure: ethyl alaninate linked to 7-CF₃, 6-Br triazolopyridine] | LC-MS (method 1): $R_t$ = 1.88 min; MS (ESIpos): m/z = 381 [M + H]⁺ |
| (u)-003 | [structure: ethyl alaninate linked to 8-CF₃, 6-Br triazolopyridine] | LC-MS (method 1): $R_t$ = 1.91 min; MS (ESIpos): m/z = 381 [M + H]⁺ |
| (u)-004 | [structure: ethyl alaninate linked to 7-CF₃, 6-Cl triazolopyridine] | LC-MS (method 1): $R_t$ = 1.85 min; MS (ESIpos): m/z = 337 [M + H]⁺ |

TABLE 5-continued

Intermediates according to structure (u)

(u)

| Intermediate | Structure | Analytics/NMR Peaklist[1] |
|---|---|---|
| (u)-005 | H3C-O, O, Cl, F, F, F, N, N, N, H3C, N, H (structure) | LC-MS (method 3): $R_t$ = 0.93 min; MS (ESIpos): m/z = 337 [M + H]+<br>1H-NMR (400 MHz, DMSO-d6) δ [ppm]:<br>1.106 (2.02), 1.148 (4.32), 1.165 (9.03), 1.183 (4.50), 1.196 (1.01), 1.204 (0.47), 1.214 (0.50), 1.370 (0.40), 1.411 (6.27), 1.430 (6.22), 1.441 (0.85), 3.077 (0.56), 3.353 (16.00), 4.038 (0.63), 4.048 (0.65), 4.056 (0.70), 4.065 (1.83), 4.070 (0.81), 4.083 (1.92), 4.088 (1.96), 4.101 (0.81), 4.105 (1.87), 4.115 (0.70), 4.123 (0.74), 4.132 (0.65), 4.275 (0.70), 4.293 (0.96), 4.312 (0.64), 7.557 (0.89), 7.577 (0.84), 7.881 (2.08), 9.309 (2.55). |

Intermediate 7A, (v)-005

N-[7-chloro-6-(trifluoromethyl)[1,2,4]triazolo[1,5-a]pyridin-2-yl]-DL-alanine

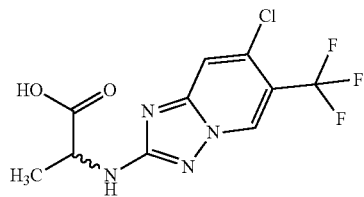 [SMILES: CC(Nc1nc2cc(Cl)c(C(F)(F)F)cn2n1)C(=O)O]

Ethyl N-[7-chloro-6-(trifluoromethyl)[1,2,4]triazolo[1,5-a]pyridin-2-yl]-DL-alaninate (336 mg, 998 μmol) was dissolved in ethanol (20 mL), an aqueous solution of lithium hydroxide (3.0 ml, 1.0 M, 3.0 mmol) was added and the mixture was stirred at room temperature for 30 min. The solution was acidified with 1 M hydrochloric acid and extracted with ethyl acetate. The organic extract was washed with water and brine, dried over anhydrous sodium sulfate, filtered and evaporated to give 324 mg (97% purity, quant) of the title compound.

Analytical data see table 6.

TABLE 6

Intermediates according to structure (v)

(v)

| Intermediate | Structure | Analytics/NMR Peaklist[1] |
|---|---|---|
| (v)-001 | HO, O, Cl, F, F, F, N, N, N, H3C, N, H (structure) | LC-MS (method 7): $R_t$ = 1.00 min; MS (ESIneg): m/z = 307 [M − H]− |

TABLE 6-continued

Intermediates according to structure (v)

(v)

R¹R²N—Y—C(R³)(H)—C(=O)OH structure shown

| Intermediate | Structure | Analytics/NMR Peaklist[1] |
|---|---|---|
| (v)-002 | [structure: 6-Br, 7-CF₃ [1,2,4]triazolo[1,5-a]pyridine with NH-CH(CH₃)-COOH] | LC-MS (method 1): R$_t$ = 1.43 min; MS (ESIpos): m/z = 353 [M + H]$^+$ |
| (v)-003 | [structure: 6-Br, 8-CF₃ [1,2,4]triazolo[1,5-a]pyridine with NH-CH(CH₃)-COOH] | LC-MS (method 1): R$_t$ = 1.42 min; MS (ESIpos): m/z = 353 [M + H]$^+$ |
| (v)-004 | [structure: 6-Cl, 7-CF₃ [1,2,4]triazolo[1,5-a]pyridine with NH-CH(CH₃)-COOH] | LC-MS (method 1): R$_t$ = 1.39 min; MS (ESIpos): m/z = 309 [M + H]$^+$ |
| (v)-005 | [structure: 8-Cl, 6-CF₃ [1,2,4]triazolo[1,5-a]pyridine with NH-CH(CH₃)-COOH] | LC-MS (method 1): R$_t$ = 1.39 min; MS (ESIpos): m/z = 309 [M + H]$^+$ $^1$H-NMR (600 MHz, DMSO-d6) δ [ppm]: 1.164 (4.03), 1.176 (8.04), 1.188 (4.16), 1.206 (0.51), 1.218 (0.66), 1.229 (2.15), 1.240 (2.09), 1.392 (0.60), 1.405 (0.99), 1.414 (15.92), 1.427 (16.00), 1.909 (0.81), 1.987 (15.42), 4.014 (1.28), 4.026 (3.86), 4.038 (4.00), 4.049 (1.46), 4.221 (1.23), 4.232 (1.71), 4.243 (1.21), 7.385 (1.22), 7.396 (1.20), 7.859 (9.46), 9.294 (8.70). |

Intermediate 8A, (k)-32

N²-[7-chloro-6-(trifluoromethyl)[1,2,4]triazolo[1,5-a]pyridin-2-yl]-DL-alaninamide

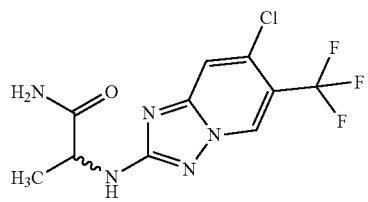 [SMILES: CC(Nc1nc2cc(Cl)c(C(F)(F)F)cn2n1)C(N)=O]

N-[7-chloro-6-(trifluoromethyl)[1,2,4]triazolo[1,5-a]pyridin-2-yl]-DL-alanine (309 mg, 1.00 mmol) was dissolved in DMF (5.5 mL). Ammonium chloride (107 mg, 2.00 mmol), HATU (570 mg, 1.50 mmol) and eventually DIPEA (520 µL, 3.0 mmol) were added and the mixture was stirred at ambient temperature. The crude mixture was directly charged upon a preparative HPLC device and chromatographed (RP C-18 10 µm acetonitrile/water+0.1% TFA 10:90→95:5) to give 230 mg (100% purity, 75% yield) of the title compound.

Analytical data see table 3.

Synthesis of Starting Materials According to Structure (f)

Most compounds according to structure (f) (see scheme 3) are commercially available or described in the literature.

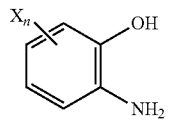

In some cases these intermediates had to be prepared. Procedures are given in the following.

Intermediate 9A

2-Chloro-6-nitro-4-(pentafluoro-lambda⁶-sulfanyl)phenol

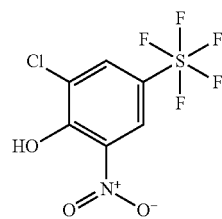

2-Chloro-4-(pentafluoro-lambda⁶-sulfanyl)phenol (910 mg, 3.57 mmol) was dissolved in glacial acetic acid (16 mL). The mixture was heated to 50° C. and sodium nitrite (493 mg, 7.15 mmol) was added. The mixture was heated to 60° C. over night. After cooling to RT, the mixture was diluted with water and extracted with ethyl acetate. The organic extract was filtered, dried and evaporated. The crude material (1.15 g, 88% purity, 94% yield) was used directly in the next step.

LC-MS (method 1): $R_t$=1.89 min; MS (ESIneg): m/z=300 [M−H]⁻

¹H NMR (600 MHz, DMSO-d6) δ [ppm]: 1.236 (0.46), 2.380 (0.64), 2.569 (1.94), 4.406 (1.58), 7.105 (0.64), 7.120 (0.68), 7.697 (0.77), 7.702 (0.65), 7.712 (0.58), 7.717 (0.61), 7.889 (1.18), 7.894 (1.14), 7.982 (1.99), 8.076 (1.59), 8.081 (1.57), 8.312 (9.48), 8.315 (10.32), 8.317 (12.80), 8.319 (11.45), 8.358 (16.00), 8.363 (13.49), 8.513 (1.36), 8.518 (1.34).

Intermediate 10A

2-Amino-6-chloro-4-(pentafluoro-lambda⁶-sulfanyl)phenol

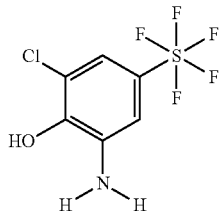 [SMILES: Nc1cc(S(F)(F)(F)(F)F)cc(Cl)c1O]

2-Chloro-6-nitro-4-(pentafluoro-lambda⁶-sulfanyl)phenol (intermediate 9A, 910 mg, 3.04 mmol) was dissolved in ethanol (10 mL) and hydrogenated for 4 h in the presence of Raney-Nickel (17.8 mg, 304 µmot) at ambient pressure and room temperature. The catalyst was then filtered off and the filtrate was evaporated. The crude product was eventually purified by preparative HPLC (RP C-18 phase with a gradient of water, acetonitrile with 0.1% ammonia) to give 655 mg (80% yield) of the title compound.

LC-MS (method 1): $R_t$=1.71 min; MS (ESIneg): m/z=268 [M−H]⁻

¹H-NMR (600 MHz, DMSO-d6) δ [ppm]: 2.140 (0.42), 3.722 (1.55), 7.013 (13.72), 7.018 (14.76), 7.091 (16.00), 7.095 (13.83).

Intermediate 11A

Cyclopropanethiol

To a solution of Cyclopropyl magnesium bromide (1.00 M, 700 mL, 1.00 eq) in THF was added sulfur (22.5 g, 700 mmol, 1.00 eq) at 0° C. in portions slowly. The mixture was stirred at 50° C. for 3 hr. Then lithium aluminium hydride (13.3 g, 350 mmol, 0.50 eq) was added at 0° C. in portions. The mixture was stirred at 65° C. for 1 hr. The mixture was quenched by addition H₂O (100 mL) slowly at 0° C. 400 mL of 5% sulfuric acid were added and the mixture was extracted with MTBE (3×150 mL) and the combined organic phase were dried over sodium sulfate, filtered and the crude product (51.9 g) was used in the next step without further purification.

Intermediate 12A

4-Chloro-5-(cyclopropylsulfanyl)-2-nitrophenol

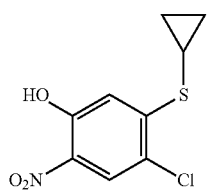

To a solution of intermediate 11A (51.9 g, 700 mmol) in MTBE (450 ml), sodium hydride (25.1 g, 626 mmol, 60% in mineral oil, 2.00 eq) was added. The mixture was stirred at 0° C. for 30 min. Then a solution of 4-chloro-5-fluoro-2-nitrophenol (60.0 g, 313 mmol) in THF (120 mL) was added drop-wise at 0° C. The mixture was stirred at 45° C. for 11.5 hr. The reaction mixture was quenched by addition of water (500 mL), then extracted with ethyl acetate (3×200 mL). The combined organic layers were washed with brine (200 mL), dried with anhydrous sodium sulfate, filtered and concentrated in vacuo. The crude product was purified by recrystallization from MTBE (100 mL) at 25° C. to give the title compound (60.0 g, 244 mmol, 78% yield) as yellow solid.

$^1$H NMR: (400 MHz, DMSO-d$_6$) δ 11.35 (br s, 1H), 7.99 (s, 1H), 7.39 (s, 1H), 2.31-2.25 (m, 1H), 1.26-1.19 (m, 2H), 0.74-0.66 (m, 2H).

Intermediate 13A

4-Chloro-5-(cyclopropylsulfonyl)-2-nitrophenol

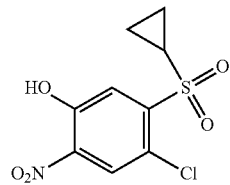 [SMILES: O=[N+]([O-])c1cc(Cl)c(S(=O)(=O)C2CC2)cc1O]

To a solution of intermediate 12A (40.0 g, 163 mmol, 1.00 eq) in methanol (300 mL) and water (100 mL), potassium peroxomonosulfate (Oxon®, 500 g, 814 mmol) was added slowly at 0° C. The mixture was stirred at 25° C. for 16 h. The reaction mixture was quenched by addition of saturated sodium sulfite solution (600 mL), then it was filtered and the filtrate was extracted with ethyl acetate (3×200 mL). The combined organic layers were washed with brine (200 mL), dried with anhydrous sodium sulfate, filtered and concentrated in vacuum. The crude product title compound (40.0 g, 144 mmol, 89% yield) was obtained as a yellow solid and used in the next step without further purification.

Intermediate 14A

2-Amino-4-chloro-5-(cyclopropylsulfonyl)phenol

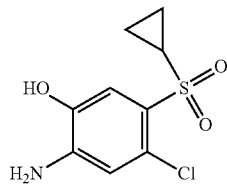

To a solution of intermediate 13A (40.0 g, 144 mmol) in ethanol (400 mL), tin(II)chloride dihydrate (97.5 g, 432 mmol) was added. The mixture was stirred at 80° C. for 1 h. The reaction mixture was cooled to room temperature, and aqueous sodium hydrogen carbonate was added to adjust the pH to 8-9. The mixture was then extracted with ethyl acetate (3×200 mL). The combined organic layers were concentrated in vacuo. The crude product was triturated with dichloromethane (100 mL) at 25° C. for 30 min, then filtered and the filter cake was obtained as product. (14.00 g, 33.7 mmol, 39% yield, 99% purity) as grey solid.

$^1$H NMR (400 MHz, DMSO-d$_6$) δ=9.93 (s, 1H), 7.17 (s, 1H), 6.74 (s, 1H), 5.77 (s, 2H), 3.03-2.80 (m, 1H), 1.01 (d, J=6.4 Hz, 4H)

Intermediate 15A 2-amino-4-chloro-5-(cyclopropylsulfanyl)phenol

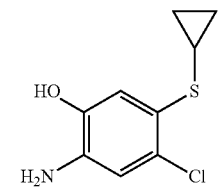 [SMILES: Nc1cc(Cl)c(SC2CC2)cc1O]

To a solution of 12A (20.0 g, 81.4 mmol, 1.00 eq) in EtOH (200 mL) tin(II)chloride dihydrate (55.1 g, 244 mmol) was added. The mixture was stirred at 80° C. for 1 h. The reaction mixture was cooled to room temperature and aqueous sodium hydrogen carbonate was added to adjust the system pH to 8-9. The mixture was extracted with ethyl acetate (3×100 mL). The combined organic layers were concentrated in vacuo. The mixture was cooled to room temperature and then filtered, and the filtrate was concentrated under reduce pressure with rotary-evaporator. The crude product was triturated with dichloromethane (100 mL) at 25° C. for 30 min, then filtered and the filter cake was obtained as product (10.0 g, 45.9 mmol, 56% yield, 99.0% purity) as grey solid.

$^1$H NMR (400 MHz, DMSO-d6) δ 9.43 (br s, 1H), 6.95-6.91 (m, 1H), 6.66 (s, 1H), 4.80 (br s, 2H), 2.12 (tt, J=4.3, 7.4 Hz, 1H), 1.00-0.94 (m, 2H), 0.59-0.53 (m, 2H)

Intermediate 16A

4-Chloro-5-(methylsulfanyl)-2-nitrophenol

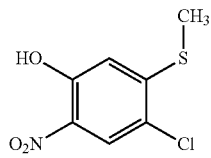

To a solution of 4-chloro-5-fluoro-2-nitrophenol (30.0 g, 157 mmol) in methanol (300 mL), sodium methylsulfide (110 g, 313 mmol, 100 mL) was slowly added at 0° C. The mixture was stirred at 80° C. for 3 h. The reaction mixture was concentrated under reduced pressure to give crude product. The crude product was purified by re-crystallization from dichloromethane (100 mL) at 25° C. to give the title compound (40.0 g, crude) as red solid which was used in the next step without further purification.

$^1$H NMR: (400 MHz, DMSO-d6) δ 7.71 (s, 1H), 6.17 (s, 1H), 2.33 (s, 3H).

Intermediate 17A

4-Chloro-5-(methylsulfonyl)-2-nitrophenol

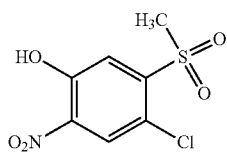

To a solution of 4-chloro-5-(methylsulfanyl)-2-nitrophenol (intermediate 16A, 20.0 g, 91.1 mmol) in methanol (300 mL) and water (100 mL), potassium peroxomonosulfate (Oxone®, 140 g, 228 mmol) was slowly added at 0° C. The mixture was stirred at 25° C. for 16 h. The reaction mixture was quenched by addition of saturated sodium sulfite solution (300 mL). Then it was filtered, and the filtrate was extracted with ethyl acetate (3×300 mL). The combined organic layers were washed with brine (200 mL), dried with anhydrous sodium sulfate, filtered and concentrated in vacuo to obtain the crude title compound (15.0 g, 59.6 mmol, 66% yield) which was used in the next step without further purification.

$^1$H NMR: δ 10.44 (s, 1H), 8.32 (s, 1H), 8.04 (s, 1H), 3.32 (s, 3H).

Intermediate 18A

2-Amino-4-chloro-5-(methylsulfonyl)phenol

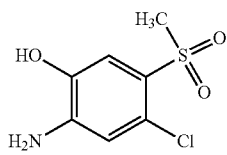

To a solution of 4-chloro-5-(methylsulfonyl)-2-nitrophenol (intermediate 17A, 15.0 g, 59.6 mmol) in ethanol (150 mL), tin(II)chloride dihydrate (40.4 g, 179 mmol) was added. The mixture was stirred at 80° C. for 1 h. The reaction mixture was cooled to room temperature, and aqueous sodium hydrogen carbonate was added to adjust the system pH to 8-9. Then it was extracted with ethyl acetate (3×50.0 mL). The combined organic layers were concentrated under vacuum. The crude product was triturated with DCM (30.0 mL) and MeOH (5.00 mL) at 25° C. for 30 min. The title compound (5.00 g, 24.4 mmol, 41% yield, 96.5% purity) was obtained as grey solid.

$^1$H NMR (400 MHz, DMSO-d$_6$) δ 9.97 (br s, 1H), 7.26 (s, 1H), 6.72 (s, 1H), 5.78 (s, 2H), 3.17 (s, 3H).

Intermediate 19A

2-Amino-4-chloro-5-(methylsulfanyl)phenol

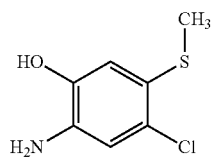

To a solution of 4-Chloro-5-(methylsulfanyl)-2-nitrophenol (20.0 g, 91.1 mmol) in ethanol (200 mL), tin(II)chloride dihydrate (61.6 g, 273 mmol) was added. The mixture was stirred at 80° C. for 1 h. The reaction mixture was cooled to room temperature, and aqueous sodium hydrogen carbonate was added to adjust the system pH to 8-9. Then it was extracted with ethyl acetate (3×100 mL). The combined organic layers were dried over anhydrous sodium sulfate and then evaporated. The crude product was triturated with ethanol (20.0 mL) at 62° C. for 30 min, then cooled to 25° C. The title compound precipitated as a white solid (5.00 g, 25.6 mmol, 28% yield, 97.0% purity).

$^1$H NMR (400 MHz, DMSO-d$_6$) δ 9.42 (br s, 1H), 6.69 (s, 1H), 6.66 (s, 1H), 4.83 (br s, 2H), 2.31 (s, 3H)

Intermediate 20A

4-Chloro-5-(ethylsulfanyl)-2-nitrophenol

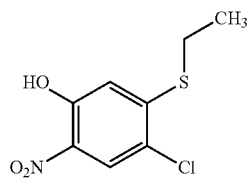

To a solution of 4-chloro-5-fluoro-2-nitrophenol (30.0 g, 157 mmol) in methanol (300 mL), sodium ethylsulfide (43.9 g, 522 mmol) was slowly added at 0° C. The mixture was stirred at 80° C. for 12 h. The reaction mixture was concentrated under reduced pressure to give the crude product. The crude product was purified by triturated with dichloromethane (100 mL) at 25° C. to give the title compound (50.0 g, crude) as red solid which was used in the next step without further purification.

¹H NMR: (400 MHz, DMSO-d₆) δ 7.71 (s, 1H), 6.24 (s, 1H), 3.44 (q, J=6.9 Hz, 2H), 1.27 (t, J=7.3 Hz, 3H).

Intermediate 21A

4-Chloro-5-(ethylsulfonyl)-2-nitrophenol

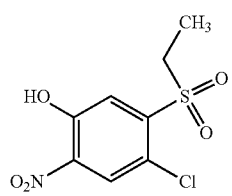 [SMILES: CCS(=O)(=O)c1cc(O)c([N+](=O)[O-])cc1Cl]

To a solution of 4-chloro-5-(ethylsulfanyl)-2-nitrophenol (intermediate 20A, 30.0 g, 129 mmol) in methanol (300 mL) and water (100 mL), potassium peroxomonosulfate (Oxone®, 197 g, 321 mmol) was slowly added at 0° C. The mixture was stirred at 25° C. for 16 h. The reaction mixture was quenched by addition of saturated sodium sulfite solution (300 mL). Then it was filtered, and the filtrate was extracted with ethyl acetate (3×300 mL). The combined organic layers were washed with brine (200 mL), dried with anhydrous sodium sulfate, filtered and concentrated in vacuo to obtain the title compound (30 g, crude) which was used in the next step without further purification.

¹H NMR: δ 8.17 (s, 1H), 7.67 (s, 1H), 3.51 (q, J=7.4 Hz, 2H), 1.15 (t, J=7.4 Hz, 3H).

Intermediate 22A

2-Amino-4-chloro-5-(ethylsulfonyl)phenol

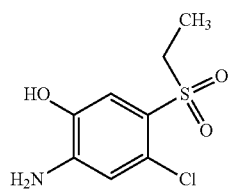

To a solution of 4-chloro-5-(ethylsulfonyl)-2-nitrophenol (intermediate 21A, 30.0 g, 113 mmol) in ethanol (300 mL), tin(II)chloride dihydrate (76.4 g, 339 mmol) was added. The mixture was stirred at 80° C. for 1 h. The reaction mixture was cooled to room temperature, and aqueous sodium hydrogen carbonate was added to adjust the system pH to 8-9. Then it was extracted with ethyl acetate (3×50.0 mL). The combined organic layers were concentrated under vacuum. The crude product was purified by preparative HPLC (RP-18 column, water-acetonitrile gradient with 0.1% conc hydrochloric acid) to obtain the title compound (5.00 g, 24.4 mmol, 41% yield, 97% purity) as grey solid.

¹H NMR (400 MHz, DMSO-d6) δ 9.94 (br s, 1H), 7.23 (s, 1H), 6.73 (s, 1H), 5.78 (s, 2H), 3.28 (q, J=7.4 Hz, 2H), 1.07 (t, J=7.4 Hz, 3H).

Intermediate 23A

2-Amino-4-chloro-5-(ethylsulfanyl)phenol

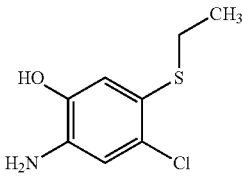

To a solution of 4-Chloro-5-(ethylsulfanyl)-2-nitrophenol (intermediate 20A, 20.0 g, 85.6 mmol) in ethanol (200 mL), tin(II)chloride dihydrate (57.9 g, 257 mmol) was added. The mixture was stirred at 80° C. for 1 h. The reaction mixture was cooled to room temperature, and aqueous sodium hydrogen carbonate was added to adjust the system pH to 8-9. Then it was extracted with ethyl acetate (3×100 mL). The combined organic layers were dried over anhydrous sodium sulfate and then evaporated. The crude product was triturated with dichloromethane (50.0 mL) at 25° C. for 30 min, then cooled to 25° C. and eventually filtered. The filter cake contained the title compound (7.00 g, 33.7 mmol, 39% yield, 98.0% purity) as a grey solid.

¹H NMR (400 MHz, DMSO-d₆) δ 9.41 (br s, 1H), 6.78 (s, 1H), 6.67 (s, 1H), 4.93 (br s, 2H), 2.73 (q, J=7.3 Hz, 2H), 1.14 (t, J=7.3 Hz, 3H).

Intermediate 24A

2-Chloro-4-cyclopropyl-6-nitrophenol

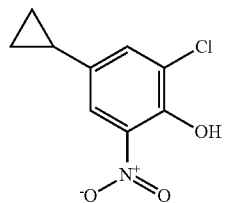

2-Chloro-4-cyclopropylphenol (1.53 g, 9.07 mmol) was dissolved in glacial acetic acid (23 mL) at RT, sodium nitrite (1.25 g, 18.1 mmol) was added in small portions over 2 h. The reaction was concentrated under vacuum, the residue was diluted with ethyl acetate, washed with water (50 mL) and brine (50 mL), dried over sodium sulfate filtered and evaporated. The crude material was purified over silica gel (cyclohexane-ethyl acetate gradient) to provide 794 mg (88% purity, 36% yield) of the title compound.

LC-MS (method 1): $R_t$=1.99 min; MS (ESIneg): m/z=212 [M−H]⁻

¹H-NMR (600 MHz, DMSO-d6) δ [ppm]: 0.700 (4.18), 0.708 (14.97), 0.711 (12.32), 0.716 (13.12), 0.719 (13.99), 0.727 (4.89), 0.743 (0.42), 0.841 (1.05), 0.844 (1.23), 0.849 (1.21), 0.859 (0.79), 0.903 (0.44), 0.917 (0.56), 0.928 (4.68), 0.936 (11.66), 0.939 (11.92), 0.942 (5.63), 0.950 (11.90), 0.953 (11.42), 0.961 (3.88), 1.003 (0.77), 1.007 (0.74), 1.017 (0.80), 1.021 (0.71), 1.959 (1.83), 1.967 (3.63), 1.973 (3.86), 1.981 (6.84), 1.990 (3.73), 1.995 (3.30), 2.004 (1.54), 2.039 (0.44), 6.032 (0.49), 7.282 (0.97), 7.285 (1.12), 7.322 (1.06), 7.326 (0.92), 7.371 (0.58), 7.374 (0.55), 7.525 (15.03), 7.529 (16.00), 7.622 (15.85), 7.626 (14.44), 10.735 (2.00).

Intermediate 25A

2-Amino-6-chloro-4-cyclopropylphenol

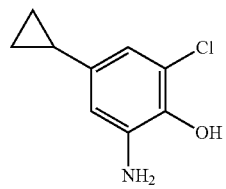 [SMILES: Nc1cc(C2CC2)cc(Cl)c1O]

2-Chloro-4-cyclopropyl-6-nitrophenol (intermediate 24A, 1.43 g, 6.71 mmol) was dissolved in ethanol (130 mL) and hydrogenated at room temperature and ambient pressure in the presence of Raney-nickel (17.8 mg, 304 µmol) for 2.5 h. The catalyst was removed by filtration over a pad of celite and the crude product was chromatographed over silica gel (cyclohexane-ethyl acetate gradient) to give 1.07 g (100% purity, 87% yield) of the title compound.

LC-MS (method 1): $R_t$=1.39 min; MS (ESIpos): m/z=184 [M+H]$^+$ $^1$H-NMR (400 MHz, DMSO-d6) δ [ppm]: 0.467 (3.75), 0.478 (11.44), 0.483 (10.51), 0.490 (11.45), 0.495 (11.06), 0.506 (4.42), 0.782 (4.19), 0.792 (9.75), 0.797 (10.71), 0.803 (5.13), 0.808 (4.54), 0.813 (10.60), 0.818 (10.28), 0.829 (3.92), 1.157 (1.64), 1.175 (3.36), 1.192 (1.70), 1.655 (1.40), 1.668 (2.78), 1.677 (2.86), 1.681 (1.76), 1.689 (5.21), 1.698 (1.74), 1.702 (2.71), 1.710 (2.56), 1.723 (1.21), 1.988 (5.79), 4.002 (0.44), 4.021 (1.33), 4.038 (1.34), 4.056 (0.44), 4.798 (0.65), 6.251 (9.22), 6.257 (14.40), 6.274 (16.00), 6.279 (10.34).

In analogy to intermediates 32A and 33A, the following intermediates were synthesized:

Intermediate 26A 4-(Benzenesulfonyl)-2-chloro-6-nitrophenol

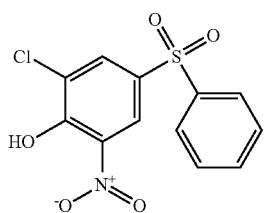

LC-MS (method 1): $R_t$=1.48 min; MS (ESIneg): m/z=312 [M−H]$^-$ $^1$H-NMR (600 MHz, DMSO-d6) δ [ppm]: 2.384 (0.53), 2.423 (0.75), 2.612 (0.56), 2.652 (0.68), 7.561 (5.26), 7.573 (15.32), 7.577 (16.00), 7.582 (13.79), 7.586 (11.90), 7.608 (5.96), 7.620 (7.49), 7.632 (2.11), 7.864 (14.21), 7.877 (13.41), 8.129 (11.27), 8.133 (10.96).

Intermediate 27A

2-Amino-4-(benzenesulfonyl)-6-chlorophenol

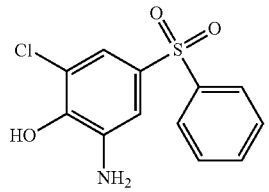 [SMILES: Nc1cc(S(=O)(=O)c2ccccc2)cc(Cl)c1O]

LC-MS method 1): $R_t$=1.38 min; MS (ESIpos): m/z=284 [M+H]$^+$ $^1$H-NMR (500 MHz, DMSO-d6) δ [ppm]: 1.042 (3.54), 1.056 (7.00), 1.070 (3.52), 3.420 (2.62), 3.434 (5.21), 3.448 (5.19), 3.462 (2.69), 3.851 (0.43), 6.663 (8.68), 6.668 (8.73), 6.969 (7.71), 6.975 (7.28), 7.310 (0.42), 7.462 (0.47), 7.491 (1.40), 7.498 (2.13), 7.508 (8.37), 7.523 (16.00), 7.533 (3.25), 7.546 (0.87), 7.574 (0.56), 7.587 (0.67), 7.728 (8.01), 7.732 (7.15), 7.744 (7.36), 7.747 (6.13).

Synthesis of Carboxylic Acid Derivatives

Example I-120 tert-Butyl 6-{5-[(1S)-1-{[6-chloro-5-(trifluoromethyl)-1,3-benzoxazol-2-yl]amino}ethyl]-1H-1,2,4-triazol-1-yl}pyridine-3-carboxylate

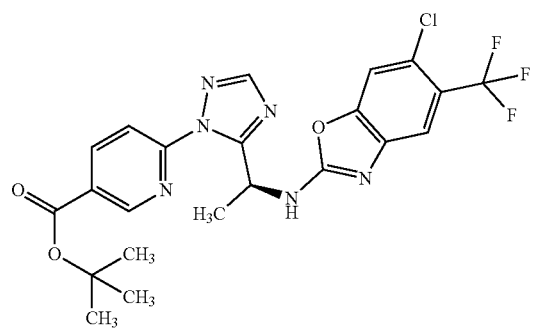 [SMILES: C[C@H](Nc1nc2cc(C(F)(F)F)c(Cl)cc2o1)c1ncnn1-c1ccc(C(=O)OC(C)(C)C)cn1]

N$^2$-[6-Chloro-5-(trifluoromethyl)-1,3-benzoxazol-2-yl]-L-alaninamide (intermediate 3A, 500 mg, 1.63 mmol) and 1,1-dimethoxy-N,N-dimethylmethanamine (540 µl, 4.1 mmol) were dissolved in dichloromethane (10.0 mL) and heated to reflux for 30 min. The solvent was distilled, the residue was taken up into a mixture of 1,4-dioxane (10.0 mL) and acetic acid (2.0 ml, 34 mmol) and tert-butyl 6-hydrazinylpyridine-3-carboxylate (CAS RN 163213-19-2, 680 mg, 3.25 mmol) was added. This mixture was heated to 60° C. for 1 h, then cooled, poured into saturated aqueous sodium carbonate solution and basified with 1M sodium hydroxide and extracted three times with ethyl acetate. The combined organic extracts were washed with brine, dried over anhydrous sodium sulfate, evaporated and eventually purified by preparative HPLC (RP C-18 phase with a gradient of water, acetonitrile with 0.1% ammonia) to give 760 mg (100% purity, 92% yield) of the title compound. Analytical data see table 7.

Example I-121

6-{5-[(1S)-1-{[6-chloro-5-(trifluoromethyl)-1,3-benzoxazol-2-yl]amino}ethyl]-1H-1,2,4-triazol-1-yl}pyridine-3-carboxylic acid

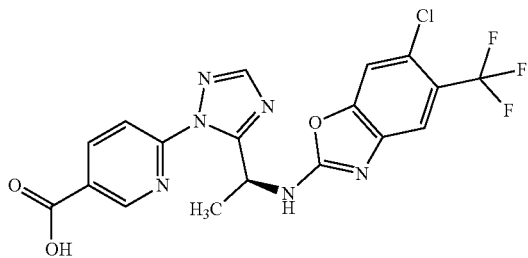 [SMILES: C[C@H](Nc1nc2cc(C(F)(F)F)c(Cl)cc2o1)c1ncnn1-c1ccc(C(=O)O)cn1]

tert-Butyl 6-{5-[(1S)-1-{[6-chloro-5-(trifluoromethyl)-1,3-benzoxazol-2-yl]amino}ethyl]-1H-1,2,4-triazol-1-yl}pyridine-3-carboxylate (intermediate 16A, 760 mg, 100% purity, 1.49 mmol) was dissolved in 1,4-dioxane (1.0 mL) and cooled to 0° C., 4 M hydrochloric acid in 1,4-dioxane (7.4 mL, 30 mmol) and 1 M aqueous hydrochloric acid (1.5 mL, 1.5 mmol) were added slowly and stirring was maintained over night. Then the mixture was poured into water. The precipitate was filtered and dried under vacuum to give 542 mg (98% purity, 78% yield) of the title compound. For analytical data, see table 7.

Example I-110

6-{5-[(1S)-1-{[6-chloro-5-(trifluoromethyl)-1,3-benzoxazol-2-yl]amino}ethyl]-1H-1,2,4-triazol-1-yl}-N-ethylpyridine-3-carboxamide

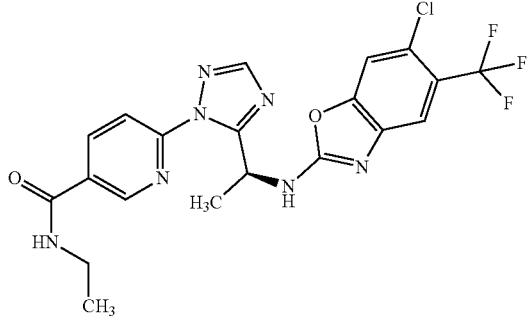 [SMILES: CCNC(=O)c1ccc(-n2ncnc2[C@H](C)Nc2nc3cc(C(F)(F)F)c(Cl)cc3o2)nc1]

6-{5-[(1S)-1-{[6-chloro-5-(trifluoromethyl)-1,3-benzoxazol-2-yl]amino}ethyl]-1H-1,2,4-triazol-1-yl}pyridine-3-carboxylic acid (intermediate 17A, 120 mg, 265 µmot) was dissolved in DMF (2.4 mL). The mixture was cooled to 0° C. on an ice bath, then HATU (151 mg, 398 µmot) and ethanamine (2 M in THF, 400 µl, 800 µmot) were added. The mixture was stirred at ambient temperature over night. Then another portion of HATU (151 mg, 398 µmot) and ethanamine (2 M in THF, 400 µl, 800 µmot) were added, the mixture was heated to 60° C. on a heating block for 5 h. The mixture was poured into water and extracted with ethyl acetate. The organic extract was dried over a Chromabond PTL cartridge, evaporated and the crude product was purified by preparative HPLC (RP C-18 phase with a gradient of water, acetonitrile with 0.1% ammonia) to give 49.0 mg (100% purity, 39% yield) of the title compound. For analytical data, see table 7.

Example I-56

6-Chloro-N-[(1S)-1-{1-[5-(oxetan-3-yl)pyrimidin-2-yl]-1H-1,2,4-triazol-5-yl}ethyl]-5-(trifluoromethyl)-1,3-benzoxazol-2-amine

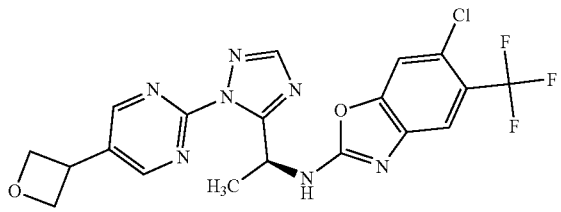

N-{(1S)-1-[1-(5-bromopyrimidin-2-yl)-1H-1,2,4-triazol-5-yl]ethyl}-6-chloro-5-(trifluoromethyl)-1,3-benzoxazol-2-amine (example I-62, 50.0 mg, 102 µmot) and) Ir(4',6'-dF5-CF3-ppy)2(4,4'-dtbbpy)PF6) (CAS RN 870987-63-6, 2.30 mg, 2.1 µmot) were put into a 5 mL microwave vial which was then sealed (vial A). In another 5 mL vial, werden nickel(II)chloride dimethoxyethane complex (1.1 mg, 5.1 µmot) and 4,4'-di-tert-butyl-2,2'-bipyridine (1.4 mg, 5.1 µmot) were dissolved in 1,2-dimethoxyethane (2.0 mL) and stirred for 5 min. The solution was transferred to vial A, tris-trimethylsilane (25 mg, 102 µmot), 2,6-dimethylpyridine (36 µl, 310 µmot and 3-bromooxetane (63 mg, 460 µmot) were added. The vial was placed in a Blue Box with one 34 W Kessil light and the mixture was irradiated over night. Then, the vial was opened and the reaction mixture was diluted with a 1:1 mixture of water and conc. Sodium hydrogen carbonate. It was extracted with 3 portions of ethyl acetate, the combined extracts were washed with brine, dried over anhydrous sodium sulfate and evaporated. The crude product was purified by preparative HPLC (RP-C18, water acetonitrile gradient) to give the title compound (11.0 mg, 22% yield). For analytics, see table 7.

TABLE 7

Structure
IUPAC-Name
LC-MS (method): Retention time; Mass found
Example ¹H-NMR

I-035

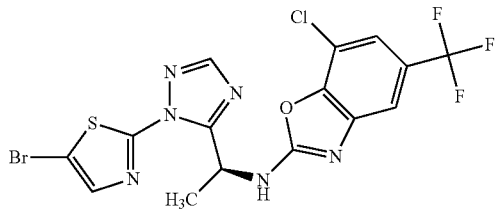 [SMILES: C[C@H](Nc1nc2cc(C(F)(F)F)cc(Cl)c2o1)c1ncnn1-c1ncc(Br)s1]

N-{(1S)-1-[1-(5-bromo-1,3-thiazol-2-yl)-1H-1,2,4-triazol-5-yl]ethyl}-7-chloro-
5-(trifluoromethyl)-1,3-benzoxazol-2-amine
LC-MS (method 3): $R_t$ = 1.18 min; MS (ESIpos): m/z = 492.9 [M + H]⁺
¹H-NMR (600 MHz, DMSO-d6) δ [ppm]: 1.656 (6.16), 1.668 (6.31), 1.681
(16.00), 1.692 (15.90), 2.072 (15.27), 5.941 (0.91), 5.953 (1.39), 5.965 (0.89),
5.981 (0.58), 5.993 (2.24), 6.004 (3.42), 6.016 (2.24), 6.027 (0.53), 7.554 (11.03),
7.653 (4.88), 7.761 (6.00), 7.766 (9.21), 7.788 (11.22), 7.794 (7.50), 8.210 (4.59),
8.226 (11.92), 9.584 (1.50), 9.596 (1.44), 9.685 (4.00), 9.697 (3.85).

I-036

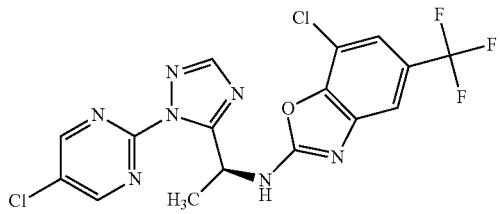 [SMILES: C[C@H](Nc1nc2cc(C(F)(F)F)cc(Cl)c2o1)c1ncnn1-c1ncc(Cl)cn1]

7-chloro-N-{(1S)-1-[1-(5-chloropyrimidin-2-yl)-1H-1,2,4-triazol-5-yl]ethyl}-5-
(trifluoromethyl)-1,3-benzoxazol-2-amine
LC-MS (method 1): $R_t$ = 1.99 min; MS (ESIpos): m/z = 444 [M + H]⁺
¹H-NMR (600 MHz, DMSO-d6) δ [ppm]: 1.661 (9.02), 1.672 (9.03), 5.873 (1.44),
5.885 (2.10), 5.897 (1.42), 7.424 (4.21), 7.484 (4.22), 8.204 (7.29), 9.140 (16.00),
9.406 (2.69), 9.419 (2.60).

I-037

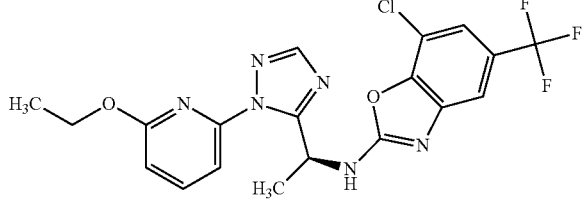 [SMILES: CCOc1cccc(-n2ncnc2[C@H](C)Nc2nc3cc(C(F)(F)F)cc(Cl)c3o2)n1]

7-chloro-N-{(1S)-1-[1-(4-ethoxypyrimidin-2-yl)-1H-1,2,4-triazol-5-yl]ethyl}-5-
(trifluoromethyl)-1,3-benzoxazol-2-amine
LC-MS (method 1): $R_t$ = 2.10 min; MS (ESIpos): m/z = 454 [M + H]⁺
¹H-NMR (600 MHz, DMSO-d6) δ [ppm]: 1.338 (7.74), 1.350 (16.00), 1.362
(7.88), 1.679 (12.18), 1.690 (12.15), 3.645 (1.83), 4.426 (1.08), 4.432 (1.03),
4.439 (1.18), 4.444 (3.09), 4.449 (1.48), 4.456 (3.17), 4.461 (3.21), 4.467 (1.44),
4.473 (3.09), 4.478 (1.19), 4.485 (1.01), 4.490 (1.05), 5.930 (0.44), 5.942 (1.85),
5.954 (2.75), 5.966 (1.86), 5.977 (0.45), 7.038 (5.58), 7.047 (5.70), 7.438 (6.00),
7.481 (5.97), 8.147 (9.93), 8.653 (5.47), 8.662 (5.40), 9.407 (3.60), 9.420 (3.49).

I-038

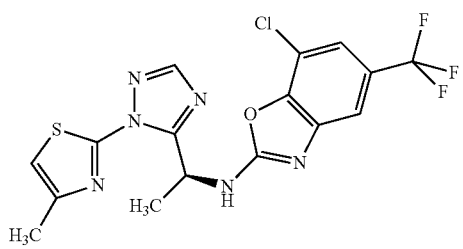 [SMILES: Cc1csc(-n2ncnc2[C@H](C)Nc2nc3cc(C(F)(F)F)cc(Cl)c3o2)n1]

TABLE 7-continued

Structure
IUPAC-Name
LC-MS (method): Retention time; Mass found
Example ¹H-NMR 7-chloro-N-{(1S)-1-[1-(4-methyl-1,3-thiazol-2-yl)-1H-1,2,4-triazol-5-yl]ethyl}-
5-(trifluoromethyl)-1,3-benzoxazol-2-amine
LC-MS (method 3): $R_t$ = 1.21 min; MS (ESIpos): m/z = 429 [M + H]⁺
¹H-NMR (600 MHz, DMSO-d6) δ [ppm]: 1.230 (0.67), 1.665 (8.84), 1.677 (8.85),
2.078 (0.71), 2.258 (16.00), 5.875 (1.43), 5.887 (2.13), 5.899 (1.41), 7.290 (4.81),
7.499 (4.47), 7.552 (4.62), 8.192 (6.60), 9.424 (2.49), 9.437 (2.42).

I-039

7-chloro-N-{(1S)-1-[1-(pyrazin-2-yl)-1H-1,2,4-triazol-5-yl]ethyl}-5-
(trifluoromethyl)-1,3-benzoxazol-2-amine
LC-MS (method 1): $R_t$ = 1.96 min; MS (ESIpos): m/z = 410 [M + H]⁺
¹H-NMR (600 MHz, DMSO-d6) δ [ppm]: 1.683 (16.00), 1.694 (15.99), 2.091
(2.57), 2.559 (8.53), 3.693 (0.41), 5.860 (0.64), 5.871 (2.56), 5.883 (3.84), 5.895
(2.53), 5.906 (0.63), 7.441 (8.69), 7.471 (8.58), 8.276 (12.15), 8.660 (6.67), 8.796
(7.29), 8.800 (6.64), 9.213 (9.66), 9.432 (4.85), 9.444 (4.70).

I-040

7-Chlor-N-{(1S)-1-[1-(5-methylpyrimidin-2-yl)-1H-1,2,4-triazol-5-yl]ethyl}-5-
(trifluormethyl)-1,3-benzoxazol-2-amin
LC-MS (method 1): $R_t$ = 1.90 min; MS (ESIpos): m/z = 424 [M + H]⁺
¹H-NMR (600 MHz, DMSO-d6) δ [ppm]: 1.652 (8.67), 1.664 (8.62), 2.354 (16.00),
5.856 (1.31), 5.868 (1.82), 5.880 (1.27), 7.431 (3.68), 7.465 (3.63), 8.138 (6.99),
8.827 (10.12), 9.338 (2.22), 9.351 (2.14).

I-041

5-{5-[(1S)-1-{[7-Chlor-5-(trifluormethyl)-1,3-benzoxazol-2-yl]amino}ethyl]-1H-
1,2,4-triazol-1-yl}pyrazin-2-carbonitril
LC-MS (method 1): $R_t$ = 2.07 min; MS (ESIpos): m/z = 435 [M + H]⁺
¹H-NMR (600 MHz, DMSO-d6) δ [ppm]: 1.653 (15.59), 1.665 (16.00), 2.069 (0.48),
5.743 (0.64), 5.911 (0.57), 5.923 (2.41), 5.935 (3.63), 5.947 (2.54), 5.958 (0.71),
7.459 (7.28), 7.477 (7.01), 8.357 (12.52), 9.228 (7.65), 9.230 (8.21), 9.376 (7.72),
9.378 (7.97), 9.425 (4.27), 9.437 (4.21).

TABLE 7-continued

Structure
IUPAC-Name
LC-MS (method): Retention time; Mass found
Example ¹H-NMR

I-042

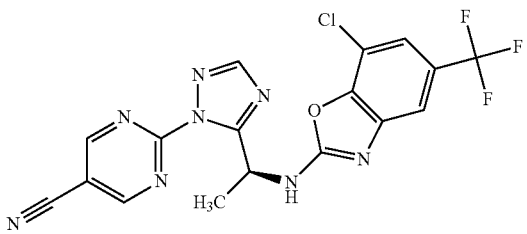 [SMILES: C[C@H](Nc1nc2cc(C(F)(F)F)cc(Cl)c2o1)c1ncnn1-c1ncc(C#N)cn1]

2-{5-[(1S)-1-{[7-Chlor-5-(trifluormethyl)-1,3-benzoxazol-2-yl]amino}ethyl]-1H-
1,2,4-triazol-1-yl}pyrimidin-5-carbonitril
LC-MS (method 3): $R_t$ = 0.94 min; MS (ESIpos): m/z = 435 [M + H]⁺
¹H-NMR (400 MHz, DMSO-d6) δ [ppm]: −0.008 (1.61), 0.008 (1.71), 1.656 (8.00),
1.673 (8.06), 2.524 (0.55), 5.961 (1.27), 5.979 (1.81), 5.997 (1.27), 7.469 (3.62),
7.489 (3.42), 8.267 (6.50), 9.432 (2.33), 9.451 (2.23), 9.490 (16.00).

I-043

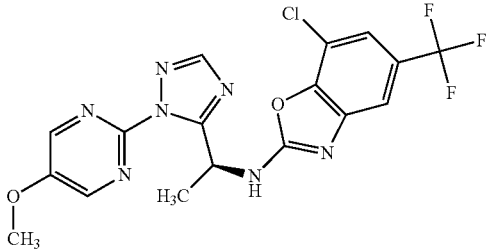 [SMILES: COc1cnc(-n2ncnc2[C@H](C)Nc2nc3cc(C(F)(F)F)cc(Cl)c3o2)nc1]

7-Chlor-N-{(1S)-1-[1-(5-methoxypyrimidin-2-yl)-1H-1,2,4-triazol-5-yl]ethyl}-5-
(trifluormethyl)-1,3-benzoxazol-2-amin
LC-MS (method 1): $R_t$ = 1.88 min; MS (ESIpos): m/z = 440 [M + H]⁺
¹H-NMR (600 MHz, DMSO-d6) δ [ppm]: 1.646 (5.36), 1.658 (5.38), 3.961 (16.00),
5.747 (0.83), 5.759 (1.14), 5.772 (0.81), 7.406 (2.22), 7.407 (2.27), 7.460 (2.27),
8.116 (4.53 ), 8.701 (10.56), 9.309 (1.46), 9.322 (1.41).

I-044

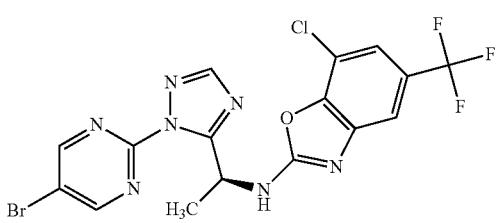

N-{(1S)-1-[1-(5-Brompyrimidin-2-yl)-1H-1,2,4-triazol-5-yl]ethyl}-7-chlor-5-
(trifluormethyl)-1,3-benzoxazol-2-amin
LC-MS (method 1): $R_t$ = 2.03 min; MS (ESIpos): m/z = 488 [M + H]⁺
¹H-NMR (600 MHz, DMSO-d6) δ [ppm]: 1.665 (10.62), 1.677 (10.54), 5.859 (0.44),
5.871 (1.70), 5.883 (2.52), 5.895 (1.67), 5.906 (0.42), 7.410 (5.29), 7.469 (5.28),
8.196 (7.72), 9.188 (16.00), 9.370 (3.09), 9.383 (2.98).

I-045

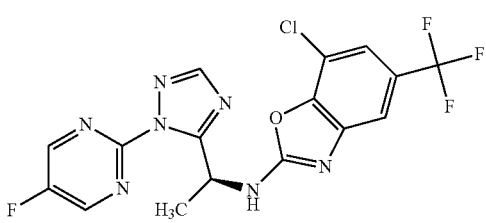 [SMILES: C[C@H](Nc1nc2cc(C(F)(F)F)cc(Cl)c2o1)c1ncnn1-c1ncc(F)cn1]

TABLE 7-continued

Structure
IUPAC-Name
LC-MS (method): Retention time; Mass found
Example $^1$H-NMR 7-Chlor-N-{(1S)-1-[1-(5-fluorpyrimidin-2-yl)-1H-1,2,4-triazol-5-yl]ethyl}-5-(trifluormethyl)-1,3-benzoxazol-2-amin
LC-MS (method 1): R$_t$ = 1.89 min; MS (ESIpos): m/z = 428 [M + H]$^+$
$^1$H-NMR (600 MHz, DMSO-d6) δ [ppm]: 1.658 (9.04), 1.670 (9.11), 5.830 (1.40), 5.842 (2.01), 5.855 (1.39), 7.433 (3.86), 7.482 (3.78), 8.184 (8.02), 9.116 (16.00), 9.393 (2.53), 9.406 (2.42).

I-046

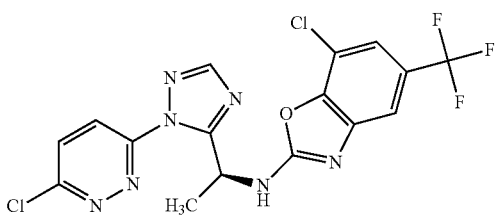 [SMILES: C[C@H](Nc1nc2cc(C(F)(F)F)cc(Cl)c2o1)c1ncnn1-c1ccc(Cl)nn1]

7-Chlor-N-{(1S)-1-[1-(6-chlorpyridazin-3-yl)-1H-1,2,4-triazol-5-yl]ethyl}-5-(trifluormethyl)-1,3-benzoxazol-2-amin
LC-MS (method 1): R$_t$ = 2.10 min; MS (ESIpos): m/z = 444 [M + H]$^+$
$^1$H-NMR (600 MHz, DMSO-d6) δ [ppm]: 1.690 (16.00), 1.701 (15.83), 5.838 (0.80), 5.849 (2.74), 5.861 (4.04), 5.872 (2.69), 5.883 (0.72), 7.437 (9.14), 7.482 (8.94), 8.247 (3.97), 8.262 (8.45), 8.288 (8.31), 8.303 (4.17), 8.320 (10.92), 9.459 (4.95), 9.472 (4.79).

I-047

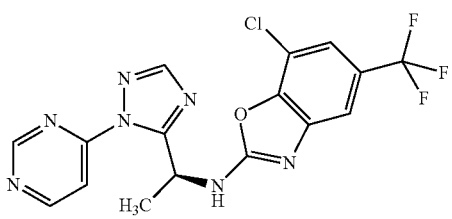 [SMILES: C[C@H](Nc1nc2cc(C(F)(F)F)cc(Cl)c2o1)c1ncnn1-c1ccncn1]

7-Chlor-N-{(1S)-1-[1-(pyrimidin-4-yl)-1H-1,2,4-triazol-5-yl]ethyl}-5-(trifluormethyl)-1,3-benzoxazol-2-amin
LC-MS (method 1): R$_t$ = 1.96 min; MS (ESIpos): m/z = 410 [M + H]$^+$
$^1$H-NMR (600 MHz, DMSO -d6) δ [ppm]: −0.006 (3.89), 1.671 (16.00), 1.682 (15.99), 6.104 (0.59), 6.116 (2.42), 6.128 (3.53), 6.140 (2.40), 6.151 (0.61), 7.479 (7.59), 7.491 (8.01), 8.012 (4.84), 8.013 (4.80), 8.021 (5.04), 8.023 (4.92), 8.272 (13.19), 9.042 (7.29), 9.051 (7.12), 9.210 (8.55), 9.464 (4.56), 9.476 (4.38).

I-048

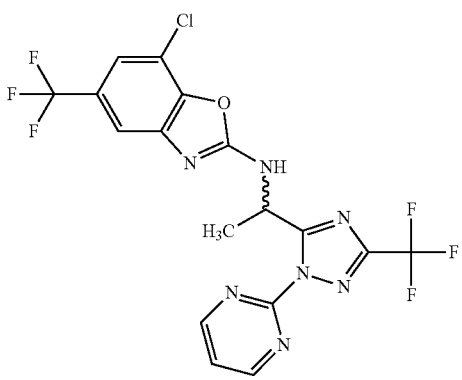 [SMILES: CC(Nc1nc2cc(C(F)(F)F)cc(Cl)c2o1)c1nc(C(F)(F)F)nn1-c1ncccn1]

7-Chlor-N-{(rac)-1-[1-(pyrimidin-2-yl)-3-(trifluormethyl)-1H-1,2,4-triazol-5-yl]ethyl}-5-(trifluormethyl)-1,3-benzoxazol-2-amin
LC-MS (method 1): R$_t$ = 2.18 min; MS (ESIpos): m/z = 478 [M + H]$^+$
$^1$H-NMR (600 MHz, DMSO-d6) δ [ppm]: 1.724 (16.00), 1.735 (15.74), 1.875 (0.68), 1.887 (0.67), 2.074 (7.35), 5.960 (0.66), 5.973 (2.70), 5.984 (3.95), 5.996 (2.47), 6.007 (0.59), 7.415 (7.87), 7.480 (7.82), 7.757 (3.81), 7.765 (7.46), 7.774 (3.82), 8.728 (0.55), 8.736 (0.54), 9.049 (14.30), 9.057 (14.12), 9.469 (4.61), 9.482 (4.45).

TABLE 7-continued

Structure
IUPAC-Name
LC-MS (method): Retention time; Mass found
Example ¹H-NMR

I-049

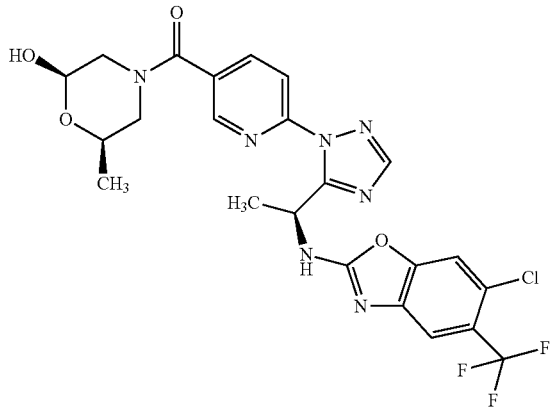 [SMILES: C[C@@H]1CN(C(=O)c2ccc(-n3ncnc3[C@H](C)Nc3nc4cc(C(F)(F)F)c(Cl)cc4o3)nc2)C[C@H](O)O1]

(6-{5-[(1S)-1-{[6-chloro-5-(trifluoromethyl)-1,3-benzoxazol-2-yl]amino}ethyl]-
1H-1,2,4-triazol-1-yl}pyridin-3-yl)[(2R,6S)-2,6-dimethylmorpholin-4-
yl]methanone
LC-MS (method 7): $R_t$ = 1.35 min; MS (ESIpos): m/z = 550 [M + H]⁺
¹H-NMR (600 MHz, DMSO-d6) δ [ppm]: 0.985 (1.95), 1.164 (5.98), 1.176 (9.65),
1.188 (4.89), 1.238 (0.56), 1.288 (0.43), 1.298 (0.45), 1.399 (3.50), 1.665 (15.36),
1.676 (15.09), 1.908 (0.67), 1.986 (16.00), 2.039 (0.86), 2.069 (2.41), 2.422 (0.71),
2.571 (0.44), 2.652 (0.56), 2.869 (0.44), 3.324 (0.98), 3.441 (0.58), 3.573 (2.05),
4.014 (1.21), 4.025 (3.78), 4.037 (3.75), 4.049 (1.23), 4.387 (0.60), 5.987 (0.54),
5.998 (2.12), 6.010 (2.94), 6.022 (2.10), 6.033 (0.53), 7.6563 (12.88), 7.577 (0.42),
7.810 (10.30), 7.959 (4.71), 7.973 (5.51), 8.133 (4.33), 8.136 (4.36), 8.147 (3.59),
8.150 (3.78), 8.188 (14.26), 8.572 (5.96), 8.575 (5.93), 9.190 (3.55), 9.204 (3.49).

I-050

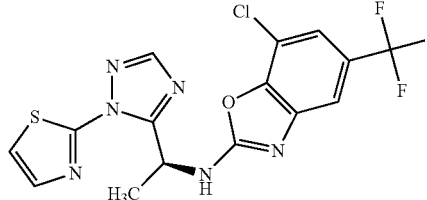

7-Chlor-N-{(1S)-1-[1-(1,3-thiazol-2-yl)-1H-1,2,4-triazol-5-yl]ethyl}-5-
(trifluormethyl)-1,3-benzoxazol-2-amin
LC-MS (method 3): $R_t$ = 1.12 min; MS (ESIpos): m/z = 415 [M + H]⁺
¹H-NMR (600 MHz, DMSO-d6) δ [ppm]: 1.602 (4.89), 1.643 (15.89), 1.655 (16.00),
3.570 (3.29), 5.911 (1.19), 5.922 (3.53), 5.933 (3.54), 5.944 (1.21), 7.456 (5.19),
7.485 (4.99), 7.770 (5.85), 7.776 (8.81), 7.797 (8.72), 7.803 (5.97), 8.203 (11.40).

I-051

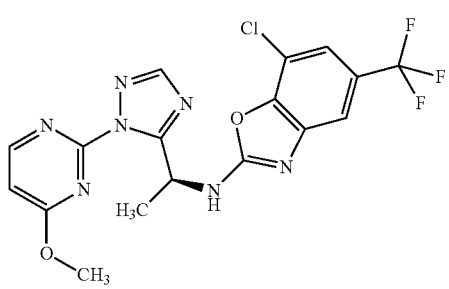 [SMILES: COc1ccnc(-n2ncnc2[C@H](C)Nc2nc3cc(C(F)(F)F)cc(Cl)c3o2)n1]

7-Chlor-N-{(1S)-1-[1-(4-methoxypyrimidin-2-yl)-1H-1,2,4-triazol-5-yl]ethyl}-5-
(trifluormethyl)-1,3-benzoxaozl-2-amin
LC-MS (method 1): $R_t$ = 1.96 min; MS (ESIpos): m/z = 440 [M + H]⁺
¹H-NMR (400 MHz, DMSO-d6) δ [ppm]: 1.677 (6.13), 1.694 (6.20), 1.989 (0.45),
4.030 (16.00), 5.967 (0.98), 5.985 (1.44), 6.003 (0.99), 7.064 (2.71), 7.079 (2.82),
7.453 (2.86), 7.480 (2.74), 8.148 (4.04), 8.657 (2.80), 8.671 (2.78), 9.401 (1.90),
9.421 (1.85).

TABLE 7-continued

Structure
IUPAC-Name
LC-MS (method): Retention time; Mass found
Example ¹H-NMR

I-052

2-{5-[(1S)-1-{[7-Chlor-5-(trifluormethyl)-1,3-benzoxazol-2-yl]amino}ethyl]-1H-1,2,4-triazol-1-yl}isonicotinonitril
LC-MS (method 1): R$_t$ = 2.11 min; MS (ESIpos): m/z = 434 [M + H]⁺
¹H-NMR (400 MHz, DMSO-d6) δ [ppm]: 1.651 (15.86), 1.668 (16.00), 1.906 (0.63), 1.920 (0.61), 1.934 (1.04), 1.977 (0.99), 2.075 (5.61), 5.919 (1.65), 5.936 (2.52), 5.954 (1.67), 5.970 (0.42), 7.469 (8.25), 7.480 (7.66), 7.979 (4.81), 7.982 (5.03), 7.992 (5.10), 7.995 (5.33), 8.240 (13.85), 8.350 (7.83), 8.785 (6.13), 8.787 (5.92), 9.798 (6.06), 8.800 (5.85), 9.401 (2.97), 9.419 (2.92).

I-053

7-Bromo-N-{(1S)-1-[3-methyl-1-(pyrimidin-2-yl)-1H-1,2,4-triazol-5-yl]ethyl}-5-(trifluormethyl)-1,3-benzoxazol-2-amin
LC-MS (method 1): R$_t$ = 1.85 min; MS (ESIpos): m/z = 468 [M + H]⁺
¹H-NMR (600 MHz, DMSO-d6) δ [ppm]: 1.644 (8.41), 1.655 (8.54), 2.321 (16.00), 5.906 (1.50), 5.918 (2.14), 5.929 (1.52), 7.460 (4.62), 7.554 (4.67), 7.617 (3.40), 7.625 (2.16), 8.962 (6.38), 8.970 (6.52), 9.376 (2.55), 9.388 (2.54).

I-054

7-Brom-N-{(1S)-1-[1-(5-chlorpyridin-2-yl)-1H-1,2,4-triazol-5-yl]ethyl}-5-(trifluormethyl)-1,3-benzoxazol-2-amin
LC-MS (method 1): R$_t$ = 2.34 min; MS (ESIpos): m/z = 487 [M + H]⁺
¹H-NMR (400 MHz, DMSO-d6) δ [ppm]: 1.638 (15.77), 1.655 (16.00), 5.883 (1.40), 5.900 (2.10), 5.916 (1.41), 7.488 (6.21), 7.555 (6.02), 7.919 (5.87), 7.941 (6.88), 8.177 (9.82), 8.217 (4.20), 8.223 (4.32), 8.239 (3.72), 8.245 (3.88), 8.630 (4.55), 8.636 (4.61), 9.387 (2.58), 9.402 (2.56).

I-055

TABLE 7-continued

Structure
IUPAC-Name
LC-MS (method): Retention time; Mass found
Example ¹H-NMR

6-[5-[(1S)-1-{[7-Brom-5-(trifluormethyl)-1,3-benzoxazol-2-yl]amino}ethyl]-1H-1,2,4-triazol-1-yl]nicotinonitril
LC-MS (Method 1): R$_t$ = 2.09 min; MS (ESIpos): m/z = 478 [M + H]$^+$
¹H-NMR (400 MHz, DMSO-d6) δ [ppm]: 1.646 (15.70), 1.663 (16..00), 5.986 (1.77), 6.003 (2.61), 6.018 (1.78), 7.499 (7.20), 7.560 (7.20), 8.101 (5.70), 8.123 (6.34), 8.249 (9.12), 8.581 (4.00), 8.586 (4.06), 8.603 (3.78), 8.608 (3.79), 9.059 (5.16), 9.063 (5.10), 9.431 (3.26), 9.446 (3.19).

I-056

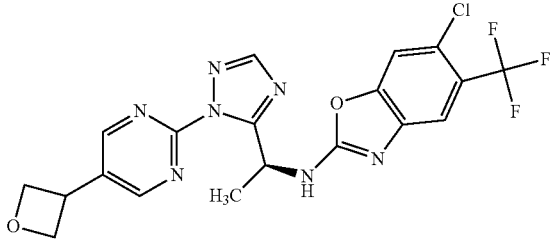 [SMILES: C[C@H](Nc1nc2cc(C(F)(F)F)c(Cl)cc2o1)c1ncnn1-c1ncc(C2COC2)cn1]

6-Chlor-N-[(1S)-1-{1-[5-(oxetan-3-yl)pyrimidin-2-yl]-1H-1,2,4-triazol-5-yl}ethyl]-5-(trifluormethyl)-1,3-benzoxazol-2-amin
LC-MS (method 1): R$_t$ = 1.68 min; MS (ESIpos): m/z = 466 [M + H]$^+$
¹H-NMR (600 MHz, DMSO-d6) δ [ppm]: 1.660 (9.60), 1.671 (9.78), 1.679 (1.97), 1.691 (1.62), 1.699 (1.01), 1.710 (0.86), 4.381 (0.41), 4.393 (1.19), 4.406 (2.00), 4.419 (1.37), 4.432 (0.55), 4.681 (2.14), 4.692 (4.12), 4.697 (2.45), 4.702 (2.52), 4.707 (4.09), 4.718 (2.17), 4.939 (4.16), 4.949 (4.41), 4.953 (4.29), 4.963 (3.56), 5.880 (1.03), 5.891 (1.52), 5.903 (1.03), 7.415 (0.63), 7.516 (8.03), 7.637 (0.69), 7.821 (7.55), 8.171 (8.21), 8.178 (0.93), 8.186 (1.26), 8.955 (1.33), 8.962 (1.30, 9.043 (16.00), 9.215 (1.55), 9.227 (1.53).

I-057

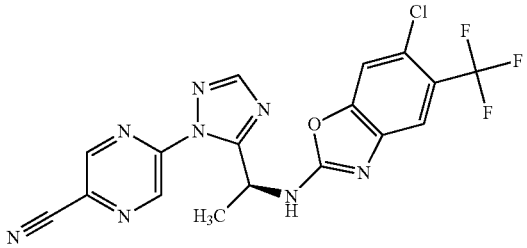 [SMILES: C[C@H](Nc1nc2cc(C(F)(F)F)c(Cl)cc2o1)c1ncnn1-c1cnc(C#N)cn1]

5-{5-[(1S)-1-{[6-Chlor-5-(trifluormethyl)-1,3-benzoxazol-2-yl]amino}ethyl]-1H-1,2,4-triazol-1-yl}pyrazin-2-carbonitril
LC-MS (method 3): R$_t$ = 1.02 min; MS (ESIpos): m/z = 435 [M + H]$^+$
¹H-NMR (600 MHz, DMSO-d6) δ [ppm]: 1.178 (0.64), 1.398 (0.88), 1.654 (16.00), 1.666 (15.98), 1.990 (1.16), 2.074 (1.17), 5.902 (0.63), 5.914 (2.57), 5.925 (3.69), 5.937 (2.53), 5.949 (0.61), 7.552 (12.67), 7.834 (10.41), 8.360 (13.38), 9.227 (8.54), 9.229 (8.27), 9.258 (4.59), 9.271 (4.37), 9.377 (8.84), 9.379 (8.29).

I-058

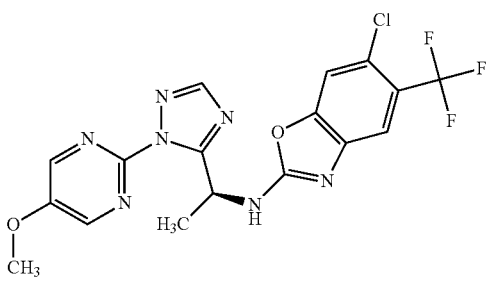 [SMILES: COc1cnc(-n2ncnc2[C@H](C)Nc2nc3cc(C(F)(F)F)c(Cl)cc3o2)nc1]

6-Chlor-N-{(1S)-1-[1-(5-methoxypyrimidin-2-yl)-1H-1,2,4-triazol-5-yl]ethyl}-5-(trifluormethyl)-1,3-benzoxazol-2-amin
LC-MS (method 1): R$_t$ = 1.82 min; MS (ESIpos): m/z = 440 [M + H]$^+$
¹H-NMR (400 MHz, DMSO-d6) δ [ppm]: 1.638 (5.30), 1.655 (5.36), 3.959 (16.00), 5.731 (0.84), 5.750 (1.13), 5.768 (0.82), 7.507 (4.15), 7.814 (2.67), 8.126 (3.79), 8.705 (9.91), 9.168 (1.56), 9.187 (1.51).

TABLE 7-continued

Structure
IUPAC-Name
LC-MS (method): Retention time; Mass found
Example ¹H-NMR

I-0159

6-Chlor-N-{(1)S-1-[1-(5-chlorpyrimidin-2-yl)-1H-1,2,4-triazol-5-yl]ethyl}-5-(trifluormethyl)-1,3-benzoxazol-2-amin
LC-MS (method 1): R$_t$ = 1.94 min; MS (ESIpos): m/z = 444 [M + H]⁺
¹H-NMR (600 MHz, DMSO-d6) δ [ppm]: 1.659 (9.44), 1.671 (9.45), 5.857 (1.48), 5.869 (2.11), 5.881 (1.46), 7.507 (7.29), 7.815 (6.04), 8.195 (7.39), 9.124 (16.00), 9.196 (2.59), 9.209 (2.50).

I-060

6-Chlor-N-{(1S)-1-[1-(5-methylpyrimidin-2-yl)-1H-1,2,4-triazol-5-yl]ethyl}-5-(trifluormethyl)-1,3-benzoxazol-2-amin
LC-MS (method 1): R$_t$ = 1.84 min; MS (ESIpos): m/z = 424 [M + H]⁺
¹H-NMR (600 MHz, DMSO-d6) δ [ppm]: 1.651 (8.39), 1.662 (8.45), 2.352 (16.00), 5.847 (1.35), 5.859 (1.94), 5.871 (1.33), 7.524 (6.16), 7.804 (5.15), 8.141 (6.04), 8.824 (10.43), 9.166 (2.42), 9.179 (2.35).

I-061

6-Chlor-N-{(1S)-1-[1-(5-fluorpyrimidin-2-yl)-1H-1,2,4-triazol-5-yl]ethyl}-5-(trifluormethyl)-1,3-benzoxazol-2-amin
LC-MS (method 1): R$_t$ = 1.81 min; MS (ESIpos): m/z = 428 [M + H]⁺
¹H-NMR (600 MHz, DMSO-d6) δ [ppm]: 1.656 (9.85), 1.668 (9.84), 3.635 (1.39), 5.816 (1.49), 5.828 (2.08), 5.840 (1.46), 7.516 (7.58), 7.812 (6.17), 8.175 (7.89), 9.098 (16.00), 9.181 (2.48), 9.194 (2.38).

I-062

N-{(1S)-1-[1-(5-Brompyrimidin-2-yl)-1H-1,2,4-triazol-5-yl]ethyl}-6-chlor-5-(trifluormethyl)-1,3-benzoxazol-2-amin
LC-MS (method 3): R$_t$ = 1.02 min; MS (ESIpos): m/z = 488 [M + H]⁺
¹H-NMR (600 MHz, DMSO-d6) δ [ppm]: 1.165 (1.92), 1.177 (3.95), 1.189 (1.97), 1.657 (8.22), 1.669 (8.22), 1.991 (7.45), 4.014 (0.60), 4.026 (1.79), 4.038 (1.76), TABLE 7-continued Structure
IUPAC-Name
LC-MS (method): Retention time; Mass found
Example ¹H-NMR 4.049 (0.59), 5.857 (1.31), 5.869 (1.84), 5.881 (1.29), 7.508 (6.50), 7.829 (5.52), 8.205 (7.05), 9.194 (16.00), 9.234 (2.44), 9.247 (2.32).

I-063

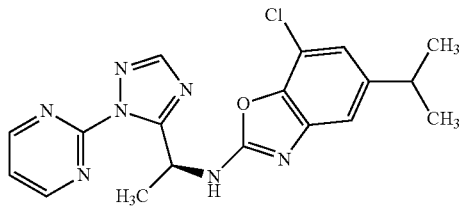 [SMILES: CC(C)c1cc(Cl)c2oc(N[C@@H](C)c3ncnn3-c3ncccn3)nc2c1]

7-Chlor-5-isopropyl-N-{(1S)-1-[1-(pyrimidin-2-yl)-1H-1,2,4-triazol-5-yl]ethyl}-1,3-benzoxazol-2-amin
LC-MS (method 3): $R_t$ = 0.97 min; MS (ESIpos): m/z = 384 [M + H]⁺
¹H-NMR (600 MHz, DMSO-d6) δ [ppm]: 1.152 (15.94), 1.154 (15.70), 1.163 (16.00), 1.165 (15.54), 1.646 (10.66), 1.657 (10.63), 2.077 (0.75), 2.841 (0.64), 2.852 (1.58), 2.864 (2.09), 2.876 (1.52), 2.887 (0.60), 3.959 (0.48), 5.857 (1.57), 5.870 (2.22), 5.882 (1.55), 6.909 (5.87), 6.924 (5.90), 7.667 (2.77), 7.676 (5.43), 7.683 (2.83), 8.150 (9.01), 8.954 (2.78), 8.967 (2.66), 9.009 (10.57), 9.017 (10.30).

I-064

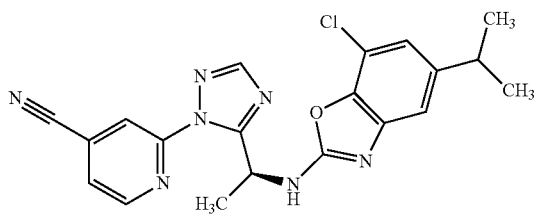 [SMILES: CC(C)c1cc(Cl)c2oc(N[C@@H](C)c3ncnn3-c3cc(C#N)ccn3)nc2c1]

2-(5-{(1S)-1-[(7-Chlor-5-isopropyl-1,3-benzoxazol-2-yl)amino]ethyl}-1H-1,2,4-triazol-1-yl)isonicotinonitril
LC-MS (method 7): $R_t$ = 1.45 min; MS (ESIpos): m/z = 408 [M + H]⁺
¹H-NMR (400 MHz, DMSO-d6) δ [ppm]: 1.153 (15.66), 1.169 (16.00), 1.628 (9.28), 1.645 (9.33), 2.074 (0.83), 2.831 (0.57), 2.848 (1.43), 2.865 (1.89), 2.882 (1.37), 2.899 (0.53), 5.860 (1.43), 5.878 (2.03), 5.896 (1.43), 6.911 (4.44), 6.914 (5.12), 6.946 (5.22), 6.949 (4.35), 7.991 (2.76 ), 7.995 (2.83), 8.004 (2.91), 8.007 (2.96), 8.216 (6.81), 8.341 (3.94), 8.810 (3.43), 8.811 (3.43), 8.822 (3.38), 8.824 (3.36), 8.969 (2.61), 8.989 (2.52).

I-065

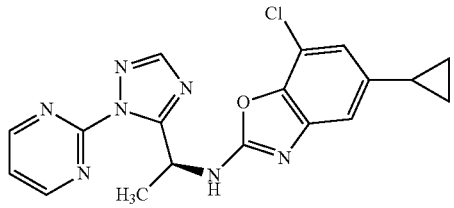 [SMILES: C[C@H](Nc1nc2cc(C3CC3)cc(Cl)c2o1)c1ncnn1-c1ncccn1]

7-Chlor-5-cyclopropyl-N-{(1S)-1-[1-(pyrimidin-2-yl)-1H-1,2,4-triazol-5-yl]ethyl}-1,3-benzoxazol-2-amin
LC-MS (method 3): $R_t$ = 0.90 min; MS (ESIpos): m/z = 382 [M + H]⁺
¹H-NMR (400 MHz, DMSO-d6) δ [ppm]: 0.612 (1.76), 0.623 (5.50), 0.628 (5.47), 0.636 (5.83), 0.640 (5.56), 0.651 (2.30), 8.62 (2.02), 0.872 (5.16), 0.877 (5.16), 0.883 (2.75), 0.893 (5.45), 0.898 (5.16), 0.909 (1.81), 1.633 (15.83), 1.650 (16.00), 1.868 (0.81), 1.880 (1.62), 1.889 (1.77), 1.901 (3.06), 1.914 (1.65), 1.922 (1.54), 1.935 (0.73), 5.754 (6.17), 5.826 (0.55), 5.844 (2.37), 5.862 (3.35), 5.880 (2.36), 5.898 (0.57), 6.728 (7.71), 6.732 (8.25), 6.789 (8.34), 6.792 (7.43), 7.651 (4.00), 7.663 (8.12), 7.675 (4.26), 8.147 (10.78), 8.937 (4.26), 8.957 (4.16), 8.993 (14.60), 9.005 (14.60).

TABLE 7-continued

Structure
IUPAC-Name
LC-MS (method): Retention time; Mass found
Example ¹H-NMR

I-066

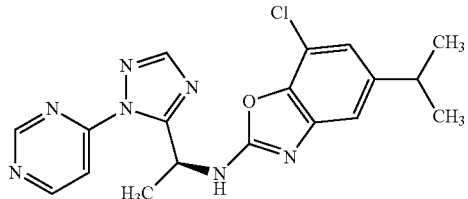

7-Chlor-5-isopropyl-N-{(1S)-1-[1-(pyrimidin-4-yl)-1H-1,2,4-triazol-5-yl]ethyl}-1,3-benzoxazol-2-amin
LC-MS (method 1): $R_t$ = 2.04 min; MS (ESIpos): m/z = 384 [M + H]⁺
¹H-NMR (600 MHz, DMSO-d6) δ [ppm]: −0.007 (0.69), 1.140 (16.00), 1.151 (15.99), 1.646 (7.38), 1.657 (7.30), 2.071 (4.65), 2.830 (0.43), 2.842 (1.07), 2.854 (1.42), 2.865 (1.03), 6.071 (1.08), 6.083 (1.53), 6.095 (1.05), 6.911 (3.53), 6.913 (3.64), 6.978 (3.77), 6.980 (3.44), 8.010 (2.16), 8.011 (2.11), 8.019 (2.20), 8.021 (2.15), 8.246 (6.44), 9.037 (1.96), 9.043 (3.79), 9.052 (4.30), 9.223 (3.72), 9.224 (3.67).

I-067

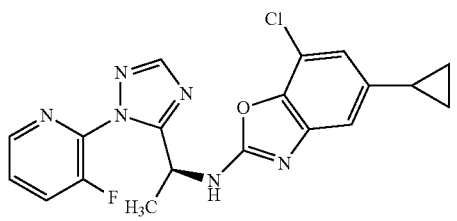 [SMILES: C[C@H](Nc1nc2cc(C3CC3)cc(Cl)c2o1)c1ncnn1-c1ncccc1F]

7-Chlor-5-cyclopropyl-N-{(1S)-1-[1-(3-fluorpyridin-2-yl)-1H-1,2,4-triazol-5-yl]ethyl}-1,3-benzoxazol-2-amin
LC-MS (method 1): $R_t$ = 1.90 min; MS (EISpos): m/z = 399 [M + H]⁺
¹H-NMR (600 MHz, DMSO-d6) δ [ppm]: 0.644 (6.94), 0.651 (7.32), 9.901 (6.04), 0.904 (6.21), 0.915 (6.56), 0.918 (6.23), 1.627 (15.82), 1.638 (16.00), 1.904 (0.88), 1.913 (1.75), 1.918 (2.05), 1.927 (3.15), 1.935 (2.05), 1.941 (1.72), 1.949 (0.87), 2.075 (1.24), 5.188 (0.69), 5.200 (2.57), 5.212 (3.89), 5.224 (2.66), 5.236 (0.77), 6.710 (9.16), 6.766 (9.02), 6.768 (9.15), 7.698 (1.61), 7.705 (2.71), 7.711 (3.48), 7.719 (3.02), 7.725 (1.90), 8.094 (2.44), 8.108 (4.32), 8.124 (2.33), 8.194 (11.59), 8.417 (4.92), 8.425 (4.86), 8.860 (4.52), 8.872 (4.49).

I-068

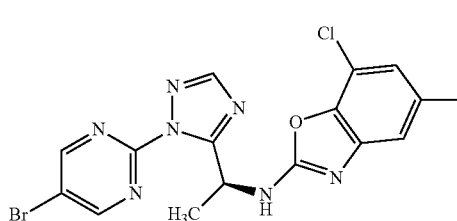

N-{(1S)-1-[1-(5-Brompyrimidin-2-yl)-1H-1,2,4-triazol-5-yl]ethyl}-7-chlor-5-isopropyl-1,3-benzoxazol-2-amin
LC-MS (method 3): $R_t$ = 1.12 min; MS (ESIneg): m/z = 460 [M − H]⁻
¹H-NMR (600 MHz, DMSO-d6) δ [ppm]: 1.162 (13.45), 1.166 (13.74), 1.174 (13.81), 1.178 (13.13), 1.204 (0.40), 1.646 (10.40), 1.657 (10.33), 2.850 (0.70), 2.861 (1.66), 2.872 (2.17), 2.884 (1.58), 2.895 (0.64), 3.665 (0.44), 5.797 (0.43), 5.809 (1.63), 5.821 (2.40), 5.833 (1.60), 5.844 (0.40), 6.890 (6.11), 6.908 (6.02), 8.170 (7.68), 8.930 (2.87), 8.943 (2.77), 9.197 (16.00).

I-069

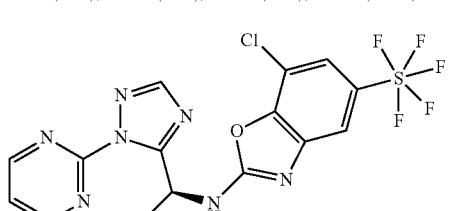

TABLE 7-continued

Structure
IUPAC-Name
LC-MS (method): Retention time; Mass found
Example ¹H-NMR

7-Chlor-5-(pentafluor-lambda⁶-sulfanyl)-N-{(1S)-1-[1-(pyrimidin-2-yl)-1H-1,2,4-triazol-5-yl]ethyl}-1,3-benzoxazol-2-amin
LC-MS (method 1): $R_t$ = 1.90 min; MS (ESIpos): m/z = 468 [M + H]⁺
¹H-NMR (400 MHz, DMSO-d6) δ [ppm]: −0.008 (1.22), 0.008 (1.17), 1.660 (14.13), 1.677 (14.13), 2.525 (0.86), 5.891 (0.48), 5.909 (2.13), 5.927 (2.97), 5.945 (2.13), 5.962 (0.49), 7.50 (10.93), 7.55 (8.82), 7.661 (9.45), 7.674 (4.95), 7.685 (8.22), 7.690 (6.16), 8.176 (9.15), 8.991 (16.00), 9.003 (15.76), 9.464 (3.89), 9.484 (3.77).

I-070

7-Chlor-N-{(1S)-1-[1-(pyrimidin-2-yl)-1H-1,2,4-triazol-5-yl]ethyl}-5-(triflourmethoxy)-1,3-benzoxazol-2-amin
LC-MS (method 1): $R_t$ = 1.83 min; MS (ESIpos): m/z = 426 [M + H]⁺
¹H-NMR (600 MHz, DMSO-d6) δ [ppm]: 1.655 (16.00), 1.667 (15.93), 2.852 (0.41), 2.916 (0.70), 3.091 (0.50), 5.885 (0.57), 5.896 (2.42), 5.908 (3.43), 5.920 (2.36), 5.932 (0.60), 7.124 (5.06), 7.158 (5.37), 7.649 (3.82), 7.657 (7.57), 7.665 (3.95), 8.161 (12.54), 8.989 (14.51), 8.998 (14.28), 9.285 (4.18), 9.298 (4.06).

I-071

N-{(1S)-1-[1-(5-Brompyrimidin-2-yl)-1H-1,2,4-triazol-5-yl]ethyl}-7-chlor-5-(difluormethoxy)-1,3-benzoxazol-2-amin
LC-MS (method 1): $R_t$ = 1.86 min; MS (ESIpos): m/z = 486 [M + H]⁺
¹H-NMR (600 MHz, DMSO-d6) δ [ppm]: 1.647 (9.52), 1.658 (9.57), 2.071 (1.55), 5.837 (1.49), 5.849 (2.22), 5.860 (1.49), 6.899 (3.65), 6.903 (4.31), 6.943 (4.46), 6.947 (3.93), 7.024 (1.91), 7.147 (3.82), 7.271 (1.84), 8.182 (7.75), 9.185 (16.00), 9.196 (2.85), 9.209 (2.63).

I-072

5-Chlor-6-(cyclopropylsulfanyl)-N-{(1S)-1-[1-(pyrimidin-2-yl)-1H-1,2,4-triazol-5-yl]ethyl}-1,3-benzoxazol-2-amin
LC-MS (method 1): $R_t$ = 1.76 min; MS (ESIpos): m/z = 414 [M + H]⁺
¹H-NMR (600 MHz, DMSO-d6) δ [ppm]: 0.588 (1.86), 0.595 (5.86), 0.605 (6.13), 0.612 (3.15), 0.622 (1.88), 1.114 (1.57), 1.121 (5.47), 1.125 (5.94), 1.133 (6.58), 1.136 (5.78), 1.143 (2.02), 1.166 (0.86), 1.179 (0.80), 1.363 (1.26), 1.375 (1.27), 1.420 (0.45), 1.438 (0.42), 1.466 (0.92), 1.478 (0.91), 1.503 (0.72), 1.514 (1.04), 1.522 (1.15), 1.653 (16.00), 1.664 (15.89), 2.261 (0.92), 2.268 (1.74), 2.273 (2.08), 2.281 (3.40), 2.288 (2.06), 2.293 (2.01), 2.300 (1.21), 2.311 (0.56), 3.131 (0.58), 3.310 (0.89), 3.464 (0.97), 3.907 (2.04), 4.162 (0.56), 4.172 (0.52), 4.211 (0.50), 4.223 (0.56), 4.236 (0.48), 5.212 (0.44), 5.861 (0.58), 5.872 (2.30), 5.885 (3.16), 5.897 (2.23), 5.909 (0.54), 6.759 (0.42), 7.184 (13.79), 7.209 (0.41), 7.282 (0.87), TABLE 7-continued Structure
IUPAC-Name
LC-MS (method): Retention time; Mass found
Example ¹H-NMR 7.335 (1.04), 7.353 (0.76), 7.542 (13.43), 7.574 (0.86), 7.595 (1.16), 7.603 (0.96), 7.653 (4.29), 7.661 (7.89), 7.669 (4.07), 8.170 (13.66), 8.348 (0.76), 8.356 (0.72), 8.884 (4.02), 8.897 (3.85), 8.989 (15.08), 8.998 (14.91), 10.010 (0.47).

I-073

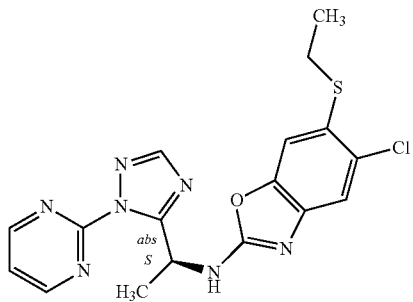

5-Chor-6-(ethylsulfanoyl)-N-{(1S)-1-[1-(pyrimidin-2-yl)-1H-1,2,4-triazol-5-yl]ethyl}-1,3-benzoxazol-2-amin
LC-MS (method 1): $R_t$ = 1.70 min; MS (ESIpos): m/z = 402 [M + H]⁺
¹H-NMR (600 MHz, DMSO-d6) δ [ppm]: 1.196 (7.65), 1.208 (16.00), 1.221 (8.07), 1.646 (11.71), 1.658 (11.63), 2.939 (2.50), 2.951 (7.57), 2.963 (7.54), 2.975 (2.51), 5.858 (0.44), 5.870 (1.77), 5.882 (2.42), 5.894 (1.71), 5.905 (0.40), 7.203 (9.76), 7.438 (9.90), 7.650 (2.77), 7.658 (5.51), 7.666 (2.84), 8.166 (9.82), 8.928 (3.16), 8.941 (3.01), 8.988 (10.59), 8.996 (10.46).

I-074

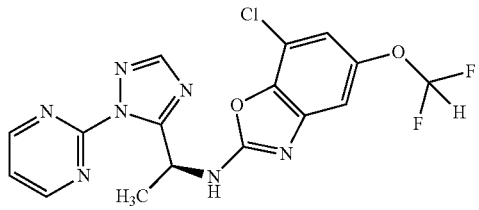 [SMILES: C[C@H](Nc1nc2cc(OC(F)(F)F)cc(Cl)c2o1)c1ncnn1-c1ncccn1]

7-Chlor-5-(difluormethoxy)-N-{(1S)-1-[1-(pyrimidin-2-yl)-1H-1,2,4-triazol-5-yl]ethyl}-1,3-benzoxazol-2-amin
LC-MS (method 1): $R_t$ = 1.62 min; MS (ESIpos): m/z = 408 [M + H]⁺
¹H-NMR (600 MHz, DMSO-d6) δ [ppm]: 1.517 (0.45), 1.655 (16.00), 1.666 (15.98), 5.873 (0.60), 5.885 (2.38), 5.897 (3.56), 5.908 (2.39), 5.920 (0.58), 6.918 (7.55), 6.934 (7.60), 7.022 (2.53), 7.145 (5.12), 7.269 (2.49), 7.650 (3.45), 7.658 (6.88), 7.666 (3.56), 8.156 (11.38), 8.991 (13.34), 8.992 (9.58), 8.999 (13.15), 9.179 (4.11), 9.192 (3.98).

I-075

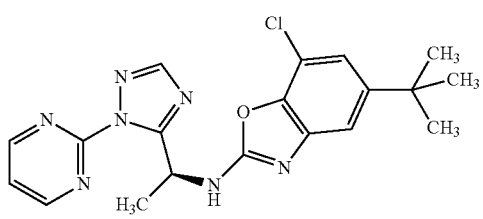 [SMILES: C[C@H](Nc1nc2cc(C(C)(C)C)cc(Cl)c2o1)c1ncnn1-c1ncccn1]

5-tert-Butyl-7-chlor-N-{(1S)-1-[1-(pyrimidin-2-yl)-1H-1,2,4-triazol-5-yl]ethyl}-1,3-benzoxazol-2-amin
LC-MS (method 1): $R_t$ = 1.97 min; MS (ESIpos): m/z = 398 [M + H]⁺
¹H-NMR (600 MHz, DMSO-d6) δ [ppm]: 1.246 (16.00), 1.645 (2.09), 1.656 (2.06), 5.870 (0.43), 7.012 (1.07), 7.015 (1.12), 7.064 (1.15), 7.067 (1.03), 7.669 (0.51), 7.677 (1.00), 7.685 (0.52), 8.149 (1.77), 8.958 (0.52), 8.971 (0.50), 9.011 (1.94), 9.019 (1.91).

TABLE 7-continued

Structure
IUPAC-Name
LC-MS (method): Retention time; Mass found
Example ¹H-NMR

I-076

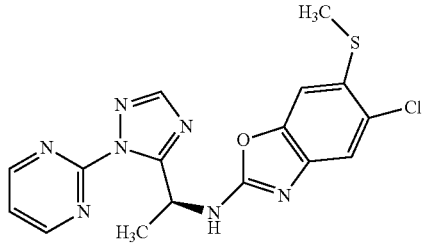 [SMILES: CSc1cc2oc(N[C@@H](C)c3ncnn3-c3ncccn3)nc2cc1Cl]

5-Chlor-6-(methylsulfanyl)-N-{(1S)-1-[1-(pyrimidin-2-yl)-1H-1,2,4-triazol-5-yl]ethyl}-1,3-benzoxazol-2-amin
LC-MS (method 1): $R_t$ = 1.58 min; MS (ESIpos): m/z = 388 [M + H]⁺
¹H-NMR (600 MHz, DMSO-d6) δ [ppm]: 1.646 (6.19), 1.657 (6.13), 2.466 (16.00), 2.492 (0.62), 3.831 (0.71), 5.863 (0.91), 5.875 (1.20), 5.887 (0.87), 7.191 (5.59), 7.339 (5.14), 7.649 (1.62), 7.657 (3.22), 7.665 (1.67), 8.165 (5.36), 8.887 (1.58), 8.901 (1.52), 8.986 (6.21), 8.994 (6.11).

I-077

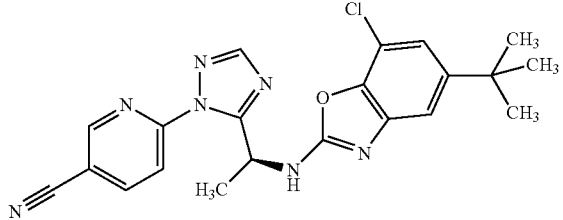 [SMILES: C[C@H](Nc1nc2cc(C(C)(C)C)cc(Cl)c2o1)c1ncnn1-c1ccc(C#N)cn1]

6-(5-[(1S)-1-[(5-tert-Butyl-7-chlor-1,3-benzoxazol-2-yl)amino]ethyl}-1H-1,2,4-triazol-1-yl)nicotinonitril
LC-MS (method 1): $R_t$ = 2.25 min; MS (ESIpos): m/z = 422 [M + H]⁺
¹H-NMR (600 MHz, DMSO-d6) δ [ppm]: 1.243 (16.00), 1.629 (2.14), 1.641 (2.13), 5.968 (0.49), 7.020 (1.08), 7.022 (1.11), 7.102 (1.14), 7.104 (1.06), 8.105 (0.85), 8.119 (0.90), 8.231 (1.80), 8.591 (0.54), 8.595 (0.54), 8.606 (0.51), 8.609 (0.52), 9.014 (0.66), 9.027 (0.63), 9.079 (0.85), 9.083 (0.82).

I-078

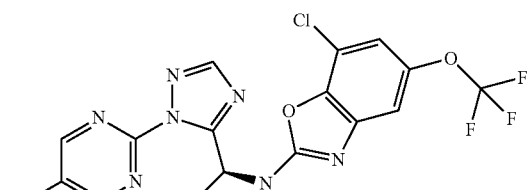

N-{(1S)-1-[1-(5-Brompyrimidin-2-yl)-1H-1,2,4-triazol-5-yl]ethyl}-7-chlor-5-(trifluormethoxy)-1,3-benzoxazol-2-amin
LC-MS (method 1): $R_t$ = 2.08 min; MS (ESIpos): m/z = 504 [M + H]⁺
¹H-NMR (600 MHz, DMSO-d6) δ [ppm]: 1.649 (9.48), 1.660 (9.37), 3.676 (1.43), 5.849 (1.49), 5.861 (2.16), 5.873 (1.43), 7.104 (3.24), 7.167 (3.43), 8.187 (7.48), 9.183 (16.00), 9.299 (2.62), 9.312 (2.52).

I-079

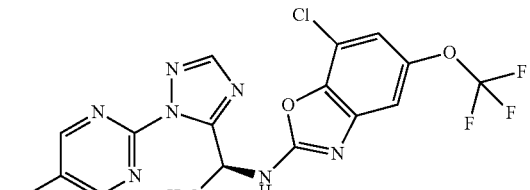

7-Chlor-N-{(1S)-1-[1-(5-chlorpyrimidin-2-yl)-1H-1,2,4-triazol-5-yl]ethyl}-5-(trifluormethoxy)-1,3-benzoxazol-2-amin
LC-MS (method 1): $R_t$ = 2.05 min; MS (ESIpos): m/z = 460 [M + H]⁺
¹H-NMR (600 MHz, DMSO-d6) δ [ppm]: 1.650 (8.12), 1.662 (8.05), 3.649 (1.62), TABLE 7-continued Structure
IUPAC-Name
LC-MS (method): Retention time; Mass found
Example ¹H-NMR 3.676 (1.45), 3.716 (0.67), 5.851 (1.22), 5.863 (1.71), 5.875 (1.18), 7.109 (2.41), 7.111 (2.46), 7.169 (2.55), 7.171 (2.32), 8.189 (6.78 ), 9.126 (16.00), 9.301 (2.08), 9.314 (1.99).

I-080

7-Chlor-5-(phenylsulfonyl)-N-{(1S)-1-[1-(pyrimidin-2-yl)-1H-1,2,4-triazol-5-yl]ethyl}-1,3-benzoxazol-2-amin
LC-MS (method 1): $R_t$ = 1.62 min; MS (ESIpos): m/z = 482 [M + H]⁺
¹H-NMR (600 MHz, DMSO-d6) δ [ppm]: 1.648 (15.36), 1.660 (15.14), 2.074 (0.48), 5.884 (0.55), 5.896 (2.34), 5.908 (3.36), 5.920 (2.29), 5.931 (0.53), 7.587 (4.18), 7.592 (8.36), 7.594 (8.85), 7.599 (8.85), 7.613 (5.83), 7.652 (4.82), 7.656 (9.39), 7.659 (11.10), 7.665 (3.60), 7.668 (4.86), 7.677 (4.52), 7.690 (1.61), 7.980 (6.60), 7.982 (8.33), 7.995 (7.52), 8.148 (13.27), 8.988 (16.00), 8.996 (15.59), 9.441 (4.36), 9.454 (4.15).

I-081

6-Chlor-N-{(1S)-1-[1-(5-fluorpyrimidin-2-yl)-1H-1,2,4-triazol-5-yl]ethyl}-5-(trifluormethoxy)-1,3-benzoxazol-2-amin
LC-MS (method 1): $R_t$ = 1.86 min; MS (ESIpos): m/z = 444 [M + H]⁺
¹H-NMR (600 MHz, DMSO-d6) δ [ppm]: 1.644 (9.63), 1.656 (9.58), 5.796 (1.48), 5.808 (2.06), 5.820 (1.44), 7.266 (3.82), 7.762 (7.96), 8.168 (7.85), 9.094 (16.00), 9.114 (2.55), 9.127 (2.44).

I-082

6-Chlor-N-{(1S)-1-[1-(pyrimidin-2-yl)-1H-1,2,4-triazol-5-yl]ethyl}-5-(trifluormethoxy)-1,3-benzoxazol-2-amin
LC-MS (method 1): $R_t$ = 1.77 min; MS (ESIpos): m/z = 426 [M + H]⁺
¹H-NMR (600 MHz, DMSO-d6) δ [ppm]: 1.652 (16.00), 1.663 (15.95), 2.069 (1.50), 5.874 (0.63), 5.886 (2.51), 5.898 (3.53), 5.910 (2.45), 5.922 (0.61), 7.275 (6.87), 7.641 (3.87), 7.649 (7.57), 7.657 (3.91), 7.753 (12.48), 8.161 (12.33), 8.980 (14.62), 8.988 (14.41), 9.110 (4.40), 9.123 (4.24).

I-083

TABLE 7-continued

Structure
IUPAC-Name
LC-MS (method): Retention time; Mass found
Example ¹H-NMR

N-{(1S)-1-[1-(5-Brompyrimidin-2-yl)-1H-1,2,4-triazol-5-yl]ethyl}-7-chlor-5-
(pentafluor-lambda⁶-sulfanyl)-1,3-benzoxazol-2-amin
LC-MS (method 1): $R_t$ = 2.13 min; MS (ESIpos): m/z = 546 [M + H]⁺
¹H-NMR (600 MHz, DMSO-d6) δ [ppm]: 1.663 (9.93), 1.675 (9.93), 5.855 (0.41),
5.867 (1.60), 5.879 (2.35), 5.891 (1.58), 5.902 (0.40), 7.611 (4.56), 7.614 (4.77),
7.679 (4.93), 7.682 (4.55), 8.197 (7.48), 9.187 (16.00), 9.451 (2.90), 9.464 (2.81).

I-084

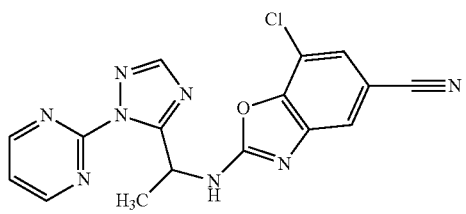 [SMILES: CC(Nc1nc2cc(C#N)cc(Cl)c2o1)c1ncnn1-c1ncccn1]

7-Chlor-2-({1-[1-(pyrimidin-2-yl)-1H-1,2,4-triazol-5-yl]ethyl}amino)-1,3-
benzoxazol-5-carbonitril
LC-MS (method 1): $R_t$ = 1.42 min; MS (ESIpos): m/z = 367 [M + H]⁺
¹H-NMR (600 MHz, DMSO-d6) δ [ppm]: 1.452 (0.47), 1.464 (0.48), 1.661 (15.38),
1.673 (15.29), 5.900 (0.56), 5.912 (2.30), 5.924 (3.23), 5.936 (2.26), 5.947 (0.55),
7.586 (7.64), 7.588 (7.93), 7.656 (4.18), 7.664 (8.32), 7.672 (4.50), 7.678 (7.98),
7.680 (7.83), 8.180 (13.72), 8.995 (16.00), 9.003 (15.76), 9.452 (4.24), 9.465 (4.07).

I-085

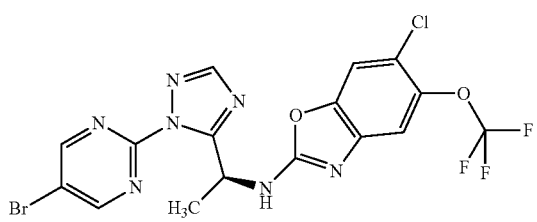 [SMILES: C[C@H](Nc1nc2cc(OC(F)(F)F)c(Cl)cc2o1)c1ncnn1-c1ncc(Br)cn1]

N-{(1S)-1-[1-(5-Brompyrimidin-2-yl)-1H-1,2,4-triazol-5-yl]ethyl}-6-chlor-5
(trifluormethoxy)-1,3-benzoxazol-2-amin
LC-MS (method 1): $R_t$ = 2.02 min; MS (ESIpos): m/z = 504 [M + H]⁺
¹H-NMR (600 MHz, DMSO-d6) δ [ppm]: 1.646 (8.16), 1.658 (8.10), 3.264 (0.48),
5.838 (1.27), 5.850 (1.71), 5.862 (1.27), 7.247 (3.02), 7.248 (2.92), 7.765 (6.58),
8.187 (6.80), 9.129 (2.20), 9.142 (2.15), 9.179 (16.00).

I-086

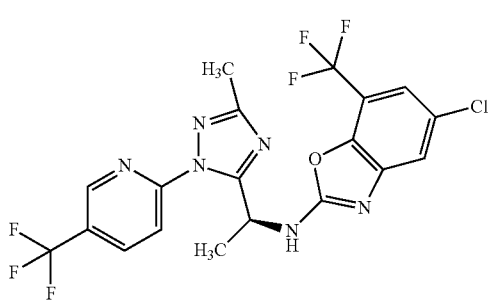 [SMILES: Cc1nc([C@H](C)Nc2nc3cc(Cl)cc(C(F)(F)F)c3o2)n(-c2ccc(C(F)(F)F)cn2)n1]

5-Chlor-N-[(1S)-1-{3-methyl-1-[5-(trifluormethyl)pyridin-2-yl]-1H-1,2,4-
triazol-5-yl}ethyl]-7-(trifluormethyl)-1,3-benzoxazol-2-amin
LC-MS (method 3): $R_t$ = 1.28 min; MS (ESIpoz): m/z = 491 [M + H]⁺
¹H-NMR (500 MHz, DMSO-d6) δ [ppm]: 1.636 (5.76), 1.650 (5.72), 2.336 (16.00),
5.997 (0.86), 6.011 (1.16), 6.026 (0.83), 7.336 (2.16), 7.338 (2.20), 7.519 (2.16),
7.522 (2.05), 8.063 (1.75), 8.080 (1.88), 8.468 (1.14), 8.472 (1.13), 8.485 (1.06),
8.490 (1.03), 8.946 (1.75), 8.947 (1.74), 8.949 (1.72), 8.950 (1.71), 9.425 (1.59),
9.441 (1.52).

TABLE 7-continued

Structure
IUPAC-Name
LC-MS (method): Retention time; Mass found
Example ¹H-NMR

I-087

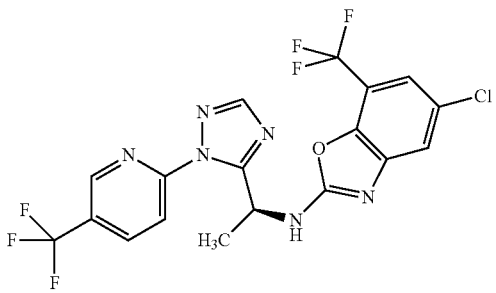 [SMILES: C[C@H](Nc1nc2cc(Cl)cc(C(F)(F)F)c2o1)c1ncnn1-c1ccc(C(F)(F)F)cn1]

5-Chlor-7-(trifluormethyl)-N-[(1S)-1-{1-[5-(trifluormethyl)pyridin-2-yl]-1H-
1,2,4-triazol-5-yl}ethyl]-1,3-benzoxazol-2-amin
LC-MS (method 3): $R_t$ = 1.24 min; MS (ESIpos): m/z = 477 [M + H]⁺
¹H-NMR (600 MHz, DMSO-d6) δ [ppm]: 1.657 (16.00), 1.669 (15.81), 6.010 (1.91),
6.021 (1.91), 7.338 (5.79), 7.340 (5.95), 7.512 (5.76), 7.515 (5.60), 8.117 (4.75),
8.131 (5.04), 8.239 (14.00), 8.511 (3.12), 8.515 (3.14), 8.525 (2.93), 8.529 (2.91),
8.978 (4.99), 9.454 (3.53).

I-088

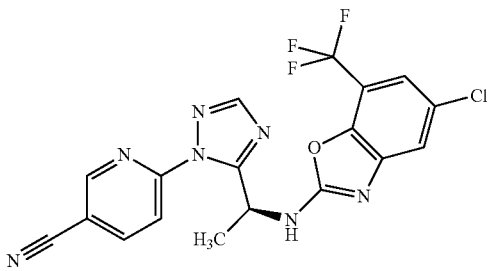 [SMILES: C[C@H](Nc1nc2cc(Cl)cc(C(F)(F)F)c2o1)c1ncnn1-c1ccc(C#N)cn1]

6-{5-[(1S)-1-{[5-Chlor-7-(trifluormethyl)-1,3-benzoxazol-2-yl]amino}ethyl]-1H-
1,2,4-triazol-1-yl}nicotinonitril
LC-MS (method 3): $R_t$ = 1.09 min; MS (ESIpos): m/z = 434 [M + H]⁺
¹H-NMR (600 MHz, DMSO-d6) δ [ppm]: 1.640 (16.00), 1.651 (15.98), 1.920 (0.40),
5.988 (1.49), 5.999 (2.19), 6.010 (1.48), 7.344 (5.99), 7.346 (6.31), 7.538 (5.93),
7.541 (5.92), 8.100 (6.02), 8.114 (6.40), 8.247 (13.65), 8.589 (4.26), 8.593 (4.37),
8.603 (4.04), 8.607 (4.17), 9.056 (6.02), 9.059 (6.07), 9.462 (2.70), 9.472 (2.47).

I-089

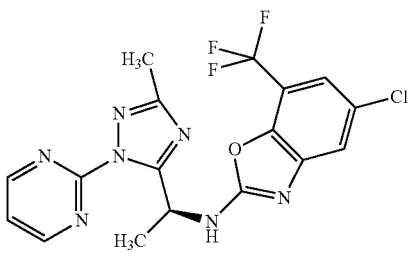 [SMILES: Cc1nc([C@H](C)Nc2nc3cc(Cl)cc(C(F)(F)F)c3o2)n(-c2ncccn2)n1]

5-Chlor-N-{(1S)-1-[3-methyl-1-(pyrimidin-2-yl)-1H-1,2,4-triazol-5-yl]ethyl}-7-
(trifluormethyl)-1,3-benzoxazol-2-amin
LC-MS (method 3): $R_t$ = 0.95 min; MS (ESIpos): m/z = 424 [M + H]⁺
¹H-NMR (400 MHz, DMSO-d6) δ [ppm]: −0.008 (0.58), 0.008 (0.69), 1.175 (0.56),
1.625 (5.83), 1.643 (5.88), 1.989 (1.04), 2.075 (0.41), 2.315 (16.00), 5.890 (0.94),
5.908 (1.22), 5.926 (0.94), 7.336 (2.14), 7.339 (2.25), 7.493 (2.08), 7.497 (1.97),
7.602 (1.87), 7.614 (3.74), 7.626 (1.98), 8.955 (7.27), 8.967 (7.07), 9.386 (1.67),
9.406 (1.62).

TABLE 7-continued

Structure
IUPAC-Name
LC-MS (method): Retention time; Mass found
Example ¹H-NMR

I-090

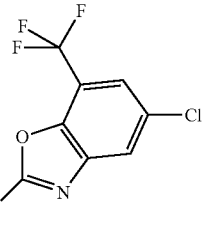

5-Chlor-N-{(1S)-1-[1-(pyrimidin-2-yl)-1H-1,2,4-triazol-5-yl]ethyl}-7-(trifluormethyl)-1,3-benzoxazol-2-amin
LC-MS (method 3): R$_t$ = 0.93 min; MS (ESIpos): m/z = 410 [M + H]$^+$
¹H-NMR (600 MHz, DMSO-d6) δ [ppm]: 1.652 (16.00), 1.664 (15.90), 2.078 (0.63), 5.758 (2.50), 5.898 (0.62), 5.910 (2.45), 5.922 (3.54), 5.934 (2.40), 5.945 (0.61), 7.338 (6.26), 7.340 (6.43), 7.489 (6.05), 7.491 (5.86), 7.656 (4.04), 7.664 (7.81), 7.672 (4.13), 8.169 (12.75), 8.996 (14.79), 9.004 (14.70), 9.414 (4.50), 9.426 (4.30).

I-091

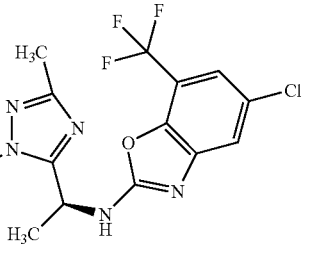

6-{5-[(1S)-1-{[5-Chlor-7-(trifluormethyl)-1,3-benzoxazol-2-yl]amino}ethyl]-3-methyl-1H-1,2,4-triazol-1-yl)nicotinonitril
LC-MS (method 3): R$_t$ = 1.12 min; MS (ESIpos): m/z = 448 [M + H]$^+$
¹H-NMR (600 MHz, DMSO-d6) δ [ppm]: 1.618 (6.24), 1.630 (6.20), 1.919 (0.45), 1.928 (0.48), 2.329 (16.00), 2.657 (0.63), 5.977 (0.89), 5.898 (1.29), 6.001 (0.89), 7.344 (2.33), 7.347 (2.41), 7.545 (2.36), 7.548 (2.29), 8.037 (2.35), 8.051 (2.51), 8.546 (1.76), 8.550 (1.78), 8.561 (1.66), 8.565 (1.73), 9.026 (2.30), 9.029 (2.34), 9.443 (1.55), 9.456 (1.51).

I-092

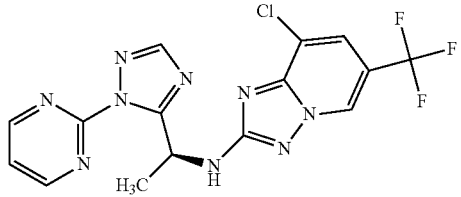 [SMILES: C[C@H](Nc1nc2c(Cl)cc(C(F)(F)F)cn2n1)c1ncnn1-c1ncccn1]

8-chloro-N-{(1S)-1-[1-(pyrimidin-2-yl)-1H-1,2,4-triazol-5-yl]ethyl}-6-(trifluoromethyl)[1,2,4]triazolo[1,5-a]pyridin-2-amine
LC-MS (method 7): R$_t$ = 1.05 min; MS (ESIpos): m/z = 410 [M + H]$^+$
¹H-NMR (500 MHz, DMSO-d6) δ [ppm]: 1.033 (0.49), 1.045 (0.44), 1.630 (12.36), 1.643 (12.26), 2.519 (0.62), 3.568 (1.23), 5.754 (0.71), 5.854 (1.02), 5.868 (1.50), 5.882 (0.98), 7.628 (4.15), 7.638 (8.01), 7.647 (4.20), 7.854 (1.22), 7.870 (1.19), 7.979 (5.40), 7.981 (5.25 ), 8.111 (11.37), 8.985 (16.00), 8.995 (15.39), 9.101 (4.66).

I-093

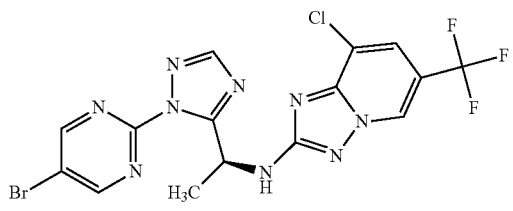 [SMILES: C[C@H](Nc1nc2c(Cl)cc(C(F)(F)F)cn2n1)c1ncnn1-c1ncc(Br)cn1]

TABLE 7-continued

| Structure |
| --- |
| IUPAC-Name |
| LC-MS (method): Retention time; Mass found |
| Example ¹H-NMR |

N-{(1S)-1-[1-(5-bromopyrimidin-2-yl)-1H-1,2,4-triazol-5-yl]ethyl}-8-chloro-6-(trifluoromethyl)[1,2,4]triazolo[1,5-a]pyridin-2-amine
LC-MS (method 1): R$_t$ = 1.75 min; MS (ESIpos): m/z = 488 [M + H]$^+$
¹H-NMR (500 MHz, DMSO-d6) δ [ppm]: −0.120 (0.80), −0.007 (8.39), 0.007 (6.71), 0.117 (0.82), 1.422 (0.55), 1.436 (0.57), 1.631 (6.12), 1.645 (6.06), 2.731 (0.67), 2.891 (0.84), 3.634 (1.35), 3.935 (1.93), 5.817 (0.46), 5.831 (0.69), 5.844 (0.48), 7.880 (0.53), 7.897 (0.50), 7.986 (2.88), 7.989 (2.80), 8.141 (6.18), 9.104 (2.44), 9.183 (16.00).

I-094

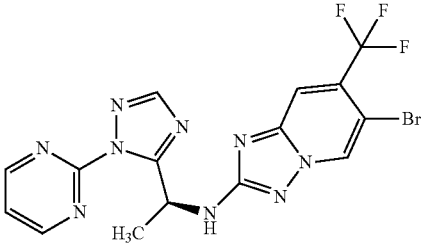 [SMILES: C[C@H](Nc1nc2cc(C(F)(F)F)c(Br)cn2n1)c1ncnn1-c1ncccn1]

6-bromo-N-{(1S)-1-[1-(pyrimidin-2-yl)-1H-1,2,4-triazol-5-yl]ethyl}-7-(trifluoromethyl)[1,2,4]triazolo[1,5-a]pyridin-2-amine
LC-MS (method 8): R$_t$ = 0.83 min; MS (ESIpos): m/z = 456 [M + H]$^+$
¹H-NMR (500 MHz, DMSO-d6) δ [ppm]: 1.106 (16.00), 1.616 (4.42), 1.630 (4.41), 3.077 (5.23), 3.169 (0.43), 5.753 (0.85), 5.852 (0.53), 7.625 (1.29), 7.634 (2.50), 7.644 (1.28), 7.857 (2.68), 8.098 (4.03), 8.980 (4.90), 8.990 (4.75), 9.122 (2.72).

I-095

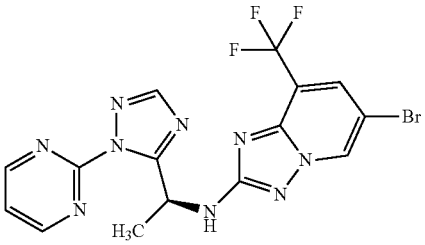

6-bromo-N-{(1S)-1-[1-(pyrimidin-2-yl)-1H-1,2,4-triazol-5-yl]ethyl}-8-(trifluoromethyl)[1,2,4]triazolo[1,5-a]pyridin-2-amine
LC-MS (method 1): R$_t$ = 1.50 min; MS (ESIpos): m/z = 454 [M + H]$^+$
¹H-NMR (600 MHz, DMSO-d6) δ [ppm]: 1.619 (15.53), 1.631 (15.40), 3.933 (2.57), 5.744 (2.14), 5.848 (1.44), 5.860 (1.44), 7.620 (4.18), 7.628 (8.33), 7.636 (4.30), 7.821 (0.66), 7.985 (5.57), 8.088 (12.93), 8.975 (16.00), 8.983 (15.87), 9.095 (5.31).

I-096

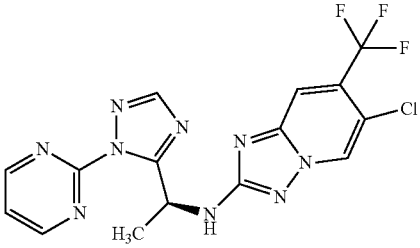 [SMILES: C[C@H](Nc1nc2cc(C(F)(F)F)c(Cl)cn2n1)c1ncnn1-c1ncccn1]

6-chloro-N-{(1S)-1-[1-(pyrimidin-2-yl)-1H-1,2,4-triazol-5-yl]ethyl}-7-(trifluoromethyl)[1,2,4]triazolo[1,5-a]pyridin-2-amine
LC-MS (method 1): R$_t$ = 1.48 min; MS (ESIpos): m/z = 410 [M + H]$^+$
¹H-NMR (600 MHz, DMSO-d6) δ [ppm]: 1.624 (15.09), 1.635 (14.98), 5.848 (1.06), 5.859 (1.56), 5.870 (1.04), 7.624 (4.12), 7.632 (8.27), 7.640 (4.30), 7.680 (1.07), 7.692 (1.05), 7.859 (8.27), 8.096 (12.33), 8.980 (16.00), 8.988 (15.64), 9.073 (8.18).

TABLE 7-continued

Structure
IUPAC-Name
LC-MS (method): Retention time; Mass found
Example ¹H-NMR

I-097

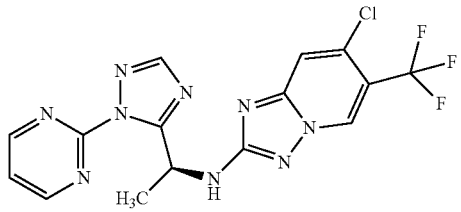 [SMILES: C[C@H](Nc1nc2cc(Cl)c(C(F)(F)F)cn2n1)c1ncnn1-c1ncccn1]

7-chloro-N-{(1S)-1-[1-(pyrimdin-2-yl)-1H-1,2,4-triazol-5-yl]ethyl}-6-
(trifluoromethyl)[1,2,4]triazolo[1,5-a]pyridin-2-amine
LC-MS (method 7): $R_t$ = 1.07 min; MS (ESIpos): m/z = 410 [M + H]$^+$
¹H-NMR (400 MHz, DMSO-d6) δ [ppm]: 1.413 (0.79), 1.431 (0.80), 1.613 (13.67),
1.630 (13.35), 2.368 (0.56), 2.711 (0.51), 5.827 (1.40), 5.844 (1.90), 5.863 (1.28),
7.623 (4.40), 7.635 (8.50), 7.647 (4.45), 7.731 (7.60), 7.761 (1.70), 7.895 (0.43),
8.105 (10.20), 8.980 (16.00), 8.992 (15.36), 9.104 (6.91), 9.299 (0.41).

I-098

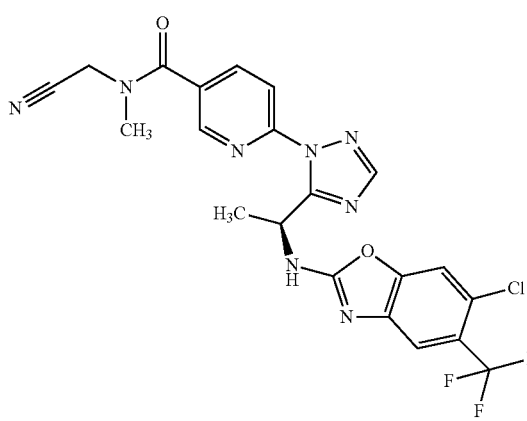

6-{5-[(1S)-1-{[6-chloro-4-(trifluoromethyl)-1,3-benzoxazol-2-yl]amino}ethyl]-
1H-1,2,4-triazol-1-yl}-N-(cyanomethyl)-N-methylpyridine-3-carboxamide
LC-MS (method 7): $R_t$ = 1.25 min; MS (ESIpos): m/z = 505 [M + H]$^+$
¹H-NMR (600 MHz, DMSO-d6) δ [ppm]: 1.164 (1.40), 1.175 (2.78), 1.187 (1.44),
1.663 (10.79), 1.674 (10.72), 1.986 (5.41), 2.691 (0.60), 3.071 (16.00), 3.252 (0.46),
3.256 (0.51), 3.263 (0.50), 4.013 (0.44), 4.025 (1.24), 4.037 (1.26), 4.049 (0.42),
4.585 (5.93), 5.744 (9.41), 5.980 (0.43), 5.991 (1.73), 6.003 (2.53), 6.016 (1.80),
6.027 (0.46), 7.570 (7.90), 7.811 (6.35), 7.985 (2.59), 7.999 (2.92), 8.198 (8.63),
8.228 (1.00), 8.669 (1.74), 9.197 (2.19), 9.211 (2.20).

I-099

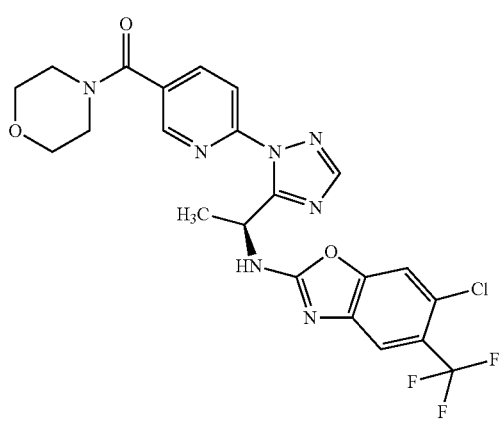 [SMILES: C[C@H](Nc1nc2cc(C(F)(F)F)c(Cl)cc2o1)c1ncnn1-c1ccc(C(=O)N2CCOCC2)cn1]

(6-{5-[(1S)-1-{[6-chloro-5-(trifluoromethyl)-1,3-benzoxazol-2-yl]amino}ethyl]-
1H-1,2,4-triazol-1-yl}pyridin-3-yl)(morpholin-4-yl)methanone
LC-MS (method 7): $R_t$ = 1.23 min; MS (ESIpos): m/z = 522 [M + H]$^+$
¹H-NMR (600 MHz, DMSO-d6) δ [ppm]: 1.107 (1.86), 1.664 (16.00), 1.675 (15.91), TABLE 7-continued Structure
IUPAC-Name
LC-MS (method): Retention time; Mass found
Example ¹H-NMR 2.070 (2.61), 2.424 (0.40), 3.078 (0.64), 3.371 (1.13), 5.970 (0.65), 5.981 (2.63),
5.994 (3.82), 6.005 (2.60), 6.017 (0.64), 7.574 (12.56), 7.814 (9.68), 7.957 (5.94),
7.971 (6.82), 8.147 (4.14), 8.150 (4.11), 8.161 (3.61), 8.165 (3.58), 8.188 (12.45),
8.582 (6.87), 8.585 (6.68), 9.188 (3.22), 9.201 (3.08).

I-100

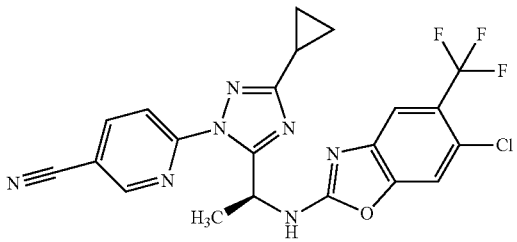 [SMILES: C[C@H](Nc1nc2cc(C(F)(F)F)c(Cl)cc2o1)c1nc(C2CC2)nn1-c1ccc(C#N)cn1]

6-{5-[(1S)-1-{[6-chloro-5-(trifluoromethyl)-1,3-benzoxazol-2-yl]amino}ethyl]-3-
cyclopropyl-1H-1,2,4-triazol-1-yl}pyridine-3-carbonitrile
LC-MS (method 1): R$_t$ = 2.31 min; MS (ESIpos): m/z = 474 [M + H]$^+$
¹H-NMR (600 MHz, DMSO-d6) δ [ppm]: 0.804 (0.73), 0.814 (1.39), 0.819 (1.59),
0.823 (2.06), 0.831 (2.73), 0.838 (1.57), 0.875 (1.65), 0.882 (2.78), 0.890 (2.07),
0.896 (1.52), 0.900 (1.57), 0.908 (0.96), 0.941 (0.76), 0.946 (0.69), 0.956 (2.09),
0.961 (2.30), 0.970 (4.70), 0.975 (3.24), 0.982 (4.62), 0.989 (1.88), 0.994 (1.71),
1.004 (0.47), 1.009 (0.48), 1.614 (16.00), 1.626 (15.88), 2.020 (0.96), 2.028 (1.85),
2.034 (2.10), 2.042 (3.42), 2.050 (1.98), 2.056 (1.68), 2.064 (0.81), 5.939 (0.71),
5.951 (2.72), 5.963 (3.78), 5.975 (2.74), 5.986 (0.66), 7.577 (12.58), 7.822 (9.48),
8.020 (6.10), 8.034 (6.44), 8.524 (4.16), 8.527 (4.29), 8.538 (3.98), 8.542 (4.06),
8.992 (6.09), 8.995 (6.02), 9.177 (3.47), 9.190 (3.31).

I-101

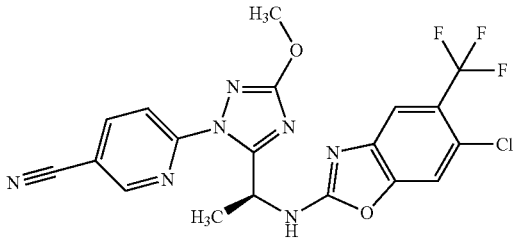 [SMILES: COc1nc([C@H](C)Nc2nc3cc(C(F)(F)F)c(Cl)cc3o2)n(-c2ccc(C#N)cn2)n1]

6-{5-[(1S)-1-{[6-chloro-5-(trifluoromethyl)-1,3-benzoxazol-2-yl]amino}ethyl]-3-
methoxy-1H-1,2,4-triazol-1-yl}pyridine-3-carbonitrile
LC-MS (method 1): R$_t$ = 2.17 min; MS (ESIpos): m/z = 464 [M + H]$^+$
¹H-NMR (600 MHz, DMSO-d6) δ [ppm]: 1.627 (6.47), 1.639 (6.43), 3.953 (16.00),
5.959 (1.07), 5.971 (1.59), 5.983 (1.08), 7.592 (5.06), 7.839 (3.81), 7.982 (2.61),
7.996 (2.72), 8.533 (1.56), 8.536 (1.66), 8.547 (1.50), 8.5551 (1.62), 8.999 (2.41),
9.002 (2.47), 9.232 (1.33), 9.245 (1.27).

I-102

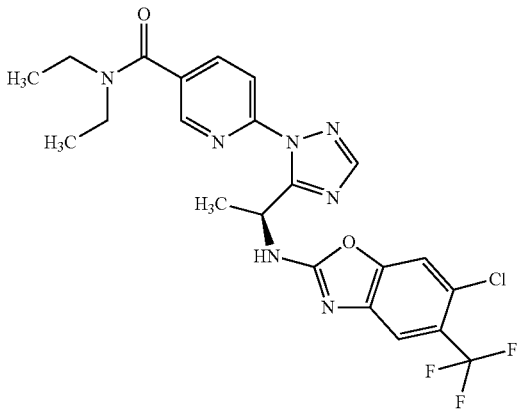 [SMILES: CCN(CC)C(=O)c1ccc(-n2ncnc2[C@H](C)Nc2nc3cc(C(F)(F)F)c(Cl)cc3o2)nc1]

6-{5-[(1S)-1-{[6-chloro-5-(trifluoromethyl)-1,3-benzoxazol-2-yl]amino}ethyl]-
1H-1,2,4-triazol-1-yl}-N,N-diethylpyridine-3-carboxamide
LC-MS (method 7): R$_t$ = 1.35 min; MS (ESIpos): m/z = 508 [M + H]$^+$ TABLE 7-continued Structure
IUPAC-Name
LC-MS (method): Retention time; Mass found
Example ¹H-NMR ¹H-NMR (600 MHz, DMSO-d6) δ [ppm]: 1.039 (3.33), 1.155 (3.36), 1.235 (0.44), 1.249 (0.71), 1.261 (0.77), 1.274 (0.50), 1.665 (16.00), 1.676 (15.96), 2.423 (0.49), 2.652 (0.45), 3.187 (2.01), 3.462 (1.92), 5.969 (0.69), 5.980 (2.70), 5.993 (3.78), 6.004 (2.57), 6.016 (0.65), 7.575 (12.54), 7.808 (10.22), 7.930 (5.94), 7.944 (6.85), 8.093 (4.24), 8.097 (4.20), 8.107 (3.53), 8.111 (3.47), 8.184 (12.55), 8.501 (6.96), 8.504 (6.43), 9.163 (3.86), 9.176 (3.68).

I-103

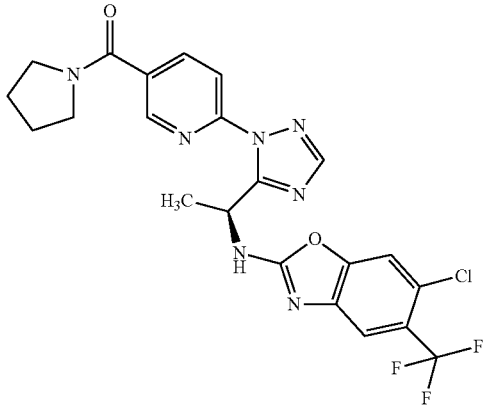 [SMILES: C[C@H](Nc1nc2cc(C(F)(F)F)c(Cl)cc2o1)c1ncnn1-c1ccc(C(=O)N2CCCC2)cn1]

(6-{5-[(1S)-1-{[6-chloro-5-(trifluroomethyl)-1,3-benzoxazol-2-yl]amino}ethyl]-1H-1,2,4-triazol-1-yl}pyridin-3-yl)(pyrrolidin-1-yl)methanone
LC-MS (method 7): $R_t$ = 1.29 min; MS (ESIpos): m/z = 506 [M + H]⁺
¹H-NMR (500 MHz, DMSO-d6) δ [ppm]: 1.232 (1.16), 1.247 (5.63), 1.261 (6.41), 1.275 (3.52), 1.642 (0.69), 1.662 (13.21), 1.676 (13.07), 1.776 (1.70), 1.789 (2.74), 1.797 (2.96), 1.810 (2.32), 1.833 (0.78), 1.856 (2.40), 1.862 (2.36), 1.868 (2.88), 1.876 (2.72), 1.890 (1.58), 2.560 (1.47), 2.690 (0.60), 3.130 (0.54), 3.139 (0.54), 3.145 (0.54), 3.154 (0.52), 3.324 (2.00), 3.337 (4.50), 3.350 (4.50), 3.63 (2.25), 3.369 (1.56), 3.383 (1.19), 3.488 (16.00), 3.502 (7.71), 3.604 (0.64), 3.617 (0.68), 3.624 (0.67), 3.630 (0.60), 3.638 (0.52), 5.976 (0.51), 5.990 (2.20), 6.005 (2.93), 6.020 (2.11), 6.033 (0.50), 7.592 (11.72), 7.820 (9.92), 7.930 (5.24), 7.947 (5.80), 8.198 (12.98), 8.219 (4.06), 8.223 (4.03), 8.235 (3.47), 8.240 (3.54), 8.638 (5.76), 8.642 (5.51), 9.183 (4.04), 9.199 (3.86).

I-104

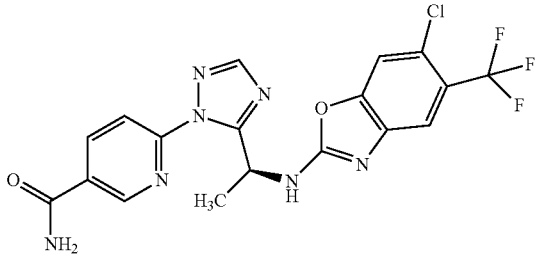 [SMILES: C[C@H](Nc1nc2cc(C(F)(F)F)c(Cl)cc2o1)c1ncnn1-c1ccc(C(N)=O)cn1]

6-{5-[(1S)-1-{[6-chloro-5-(trifluoromethyl)-1,3-benzoxazol-2-yl]amino}ethyl]-1H-1,2,4-triazol-1-yl}pyridine-3-carboxamide
LC-MS (method 1): $R_t$ = 1.62 min; MS (ESIpos): m/z = 452 [M + H]⁺
¹H-NMR (600 MHz, DMSO-d6) δ [ppm]: 1.234 (0.58), 1.664 (16.00), 1.675 (15.92), 5.988 (0.67), 5.999 (2.62), 6.012 (3.74), 6.023 (2.60), 6.035 (0.67), 7.570 (12.64), 7.683 (2.80), 7.814 (9.38), 7.997 (6.03), 8.011 (6.35 ), 8.195 (12.47), 8.237 (2.89), 8.486 (4.06), 8.490 (4.07), 8.500 (3.78), 8.504 (3.84), 8.983 (6.66), 8.986 (6.55), 9.215 (3.44), 9.227 (3.21).

I-105

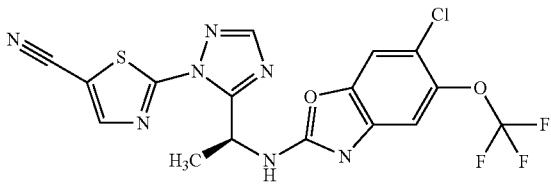

TABLE 7-continued

Structure
IUPAC-Name
LC-MS (method): Retention time; Mass found
Example ¹H-NMR

2-{5-[(1S)-1-{[6-chloro-5-(trifluoromethoxy)-1,3-benzoxazol-2-yl]amino}ethyl]-
1H-1,2,4-triazol-1-yl}-1,3-thiazole-5-carbonitrile
LC-MS (method 1): R$_t$ = 2.16 min; MS (ESIpos): m/z = 456 [M + H]$^+$
¹H-NMR (600 MHz, DMSO-d6) δ [ppm]: 1.645 (16.00), 1.656 (15.99), 5.881 (0.62),
5.892 (2.62), 5.904 (3.95), 5.916 (2.61), 5.927 (0.61), 7.387 (6.77), 7.810 (12.61),
8.317 (13.15), 8.664 (13.86), 9.261 (3.61), 9.274 (3.49).

I-106

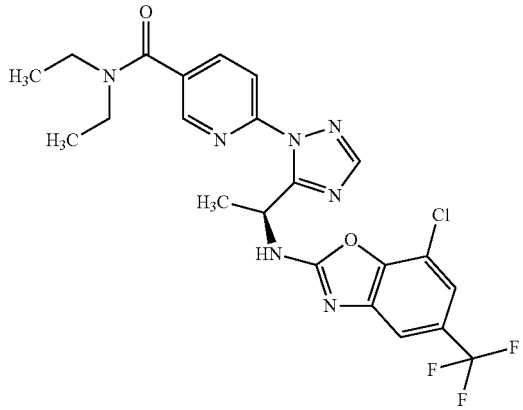 [SMILES: CCN(CC)C(=O)c1ccc(-n2ncnc2[C@H](C)Nc2nc3cc(C(F)(F)F)cc(Cl)c3o2)nc1]

6-{5-[(1S)-1-{[7-chloro-5-(trifluoromethyl)-1,3-benzoxazol-2-yl]amino}ethyl]-
1H-1,2,4-triazol-1-yl}-N,N-diethylpyridine-3-carboxamide
LC-MS (method 7): R$_t$ = 1.39 min; MS (ESIpos): mz = 508 [M + H]$^+$
¹H-NMR (600 MHz, DMSO-d6) δ [ppm]: 1.039 (3.70), 1.155 (3.92), 1.637 (0.65),
1.648 (0.80), 1.671 (15.77), 1.683 (16.00), 2.345 (1.30), 2.424 (0.46), 2.652 (0.76),
3.192 (2.24), 3.457 (2.74), 5.984 (0.64), 5.996 (2.59), 6.008 (3.79), 6.020 (2.61),
6.032 (0.82), 7.462 (7.77), 7.481 (8.20), 7.940 (5.67), 7.954 (6.72), 8.100 (4.31),
8.104 (4.41), 8.114 (3.74), 8.117 (3.83), 8.186 (12.12), 8.448 (0.53), 8.509 (6.58),
8.512 (6.50), 9.341 (3.38), 9.353 (3.42).

I-107

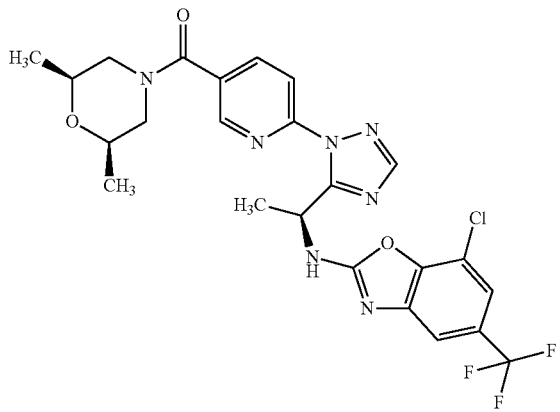 [SMILES: C[C@@H]1CN(C(=O)c2ccc(-n3ncnc3[C@H](C)Nc3nc4cc(C(F)(F)F)cc(Cl)c4o3)nc2)C[C@H](C)O1]

(6-{5-[(1S)-1-{[7-chloro-5-(trifluoromethyl)-1,3-benzoxazol-2-yl]amino}ethyl]-
1H-1,2,4-triazol-1-yl}pyridin-3-yl)[(2R,6S)-2,6-dimethylmorpholin-4-
yl]methanone
LC-MS (method 7): R$_t$ = 1.39 min; MS (ESIpos): m/z = 550 [M + H]$^+$
¹H-NMR (600 MHz, DMSO-d6) δ [ppm]: 0.984 (2.38), 1.165 (4.70), 1.177 (6.58),
1.188 (3.31), 1.235 (0.47), 1.250 (0.53), 1.262 (0.53), 1.640 (0.65), 1.651 (0.83),
1.672 (16.00), 1.684 (15.70), 1.988 (10.15), 2.344 (1.20), 2.424 (0.47), 2.734 (9.19),
2.892 (10.76), 3.46 (0.66), 3.567 (2.49), 3.578 (2.64), 4.014 (1.54), 4.026 (3.23),
4.038 (3.28), 4.050 (1.78), 4.165 (2.08), 4.380 (0.98), 6.004 (0.55), 6.016 (2.11),
6.028 (3.10), 6.040 (2.09), 6.051 (0.53), 7.466 (11.69), 7.954 (1.54), 7.968 (5.28),
7.983 (6.12), 8.140 (4.31), 8.143 (4.41), 8.154 (3.71), 8.158 (3.80), 8.189 (13.33),
8.586 (6.47), 8.590 (6.50), 9.37 (3.04), 9.386 (2.93).

TABLE 7-continued

Structure
IUPAC-Name
LC-MS (method): Retention time; Mass found
Example ¹H-NMR

I-108

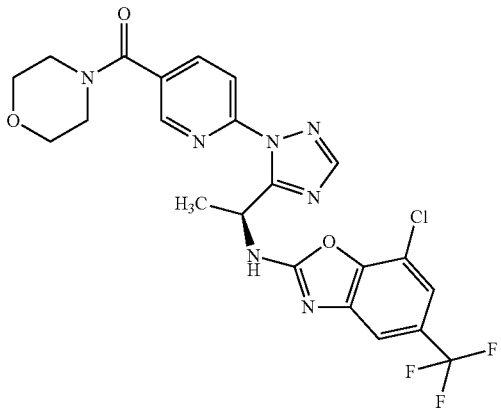 [SMILES: C[C@H](Nc1nc2cc(C(F)(F)F)cc(Cl)c2o1)c1ncnn1-c1ccc(C(=O)N2CCOCC2)cn1]

(6-{5-[(1S)-1-{[7-chloro-5-(trifluoromethyl)-1,3-benzoxazol-2-yl]amino}ethyl]-
1H-1,2,4-triazol-1-yl}pyridin-3-yl)(morpholin-4-yl)methanone
LC-MS (method 7): $R_t$ = 1.26 min; MS (ESIpos): m/z = 522 [M + H]⁺
¹H-NMR (600 MHz, DMSO-d6) δ [ppm]: 1.638 (0.65), 1.648 (0.86), 1.668 (16.00),
1.679 (15.78), 2.340 (1.23), 2.691 (2.85), 2.732 (3.51), 2.890 (3.96), 3.392 (1.31),
5.982 (0.61), 5.994 (2.54), 6.006 (3.69), 6.018 (2.50), 6.029 (0.58), 7.466 (8.16),
7.475 (8.34), 7.964 (5.62), 7.978 (6.45), 8.152 (4.18), 8.155 (4.32), 8.166 (3.66),
8.169 (3.76), 8.185 (12.55), 8.464 (0.50), 8.593 (6.42), 8.597 (6.53), 9.362 (3.62),
9.375 (3.50).

I-109

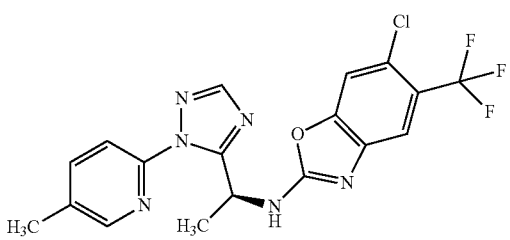 [SMILES: Cc1ccc(-n2ncnc2[C@H](C)Nc2nc3cc(C(F)(F)F)c(Cl)cc3o2)nc1]

N-{(1S)-1-[1-(5-amnopyridin-2-yl)-1H-1,2,4-triazol-5-yl]ethyl}-6-chloro-5-
(trifluoromethyl)-1,3-benzoxazol-2-amine
LC-MS (method 10: $R_t$ = 1.73 min; MS (ESIpos): m/z = 424 [M + H]⁺
¹H-NMR (600 MHz, DMSO-d6) δ [ppm]: 1.165 (2.67), 1.177 (5.39), 1.189 (2.74),
1.398 (1.68), 1.591 (16.00), 1.603 (15.91), 1.989 (10.26), 2.087 (0.81), 4.015 (0.82),
4.027 (2.45), 4.039 (2.43), 4.051 (0.81), 5.666 (13.07), 5.682 (1.77), 5.693 (2.28),
5.705 (1.53), 5.747 (0.52), 6.743 (0.50), 6.757 (0.65), 7.143 (3.95), 7.148 (3.86),
7.158 (4.27), 7.162 (4.14), 7.454 (6.66), 7.468 (6.04), 7.602 (13.11), 7.788 (6.84),
7.795 (10.87), 8.004 (13.30), 9.083 (2.63), 9.094 (2.06), 9.277 (0.76).

I-110

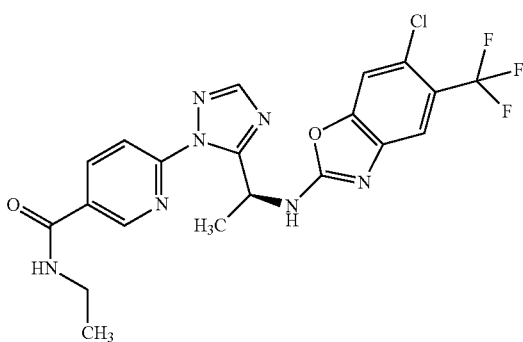 [SMILES: CCNC(=O)c1ccc(-n2ncnc2[C@H](C)Nc2nc3cc(C(F)(F)F)c(Cl)cc3o2)nc1]

6-{5-[(1S)-1-{[6-chloro-5-(trifluromethyl)-1,3-benzoxazol-2-yl]amino}ethyl]-
1H-1,2,4-triazol-1-yl}-N-ethylpyridine-3-carboxamide
LC-MS (method 1): $R_1$ = 1.86 min; MS (ESIpos): m/z = 480 [M + H]⁺
¹H-NMR (600 MHz, DMSO-d6) δ [ppm]: 1.141 (4.59), 1.153 (9.47), 1.165 (4.63),

TABLE 7-continued

Structure
IUPAC-Name
LC-MS (method): Retention time; Mass found
Example $^1$H-NMR 1.664 (7.27), 1.675 (7.24), 3.307 (1.15), 3.319 (4.46), 3.328 (16.00), 3.340 (3.40), 3.352 (0.97), 5.988 (1.12), 6.000 (1.58), 6.012 (1.14), 7.564 (5.78), 7.180 (4.59), 7.990 (2.63), 8.005 (2.78), 8.193 (5.88), 8.455 (1.80), 8.458 (1.85), 8.469 (1.69), 8.472 (1.73), 8.727 (0.83), 8.736 (1.55), 8.745 (0.81), 8.941 (2.86), 8.945 (2.87), 9.204 (2.15), 9.217 (2.05).

I-111

6-chloro-N-{(1S)-1-[1-(3-fluoropyridin-2-yl)-1H-1,2,4-triazol-5-yl]ethyl}-5-(trifluoromethyl)-1,3-benzoxazol-2-amine
LC-MS (method 1): R$_t$ = 1.88 min; MS (ESIpos): m/z = 427 [M + H]$^+$
$^1$H-NMR (600 MHz, DMSO-d6) δ [ppm]: 1.654 (16.00), 1.665 (15.84), 2.072 (2.49), 5.248 (0.71), 5.260 (2.66), 5.272 (3.90), 5.283 (2.60), 5.295 (0.67), 7.448 (11.05), 7.679 (1.69), 7.686 (2.80), 7.693 (3.44), 7.700 (3.02), 7.707 (1.85), 7.777 (9.04), 8.082 (2.34), 8.096 (4.07), 8.112 (2.15), 8.211 (10.80), 8.406 (4.74), 8.413 (4.66), 9.113 (4.47), 9.126 (4.34).

I-112

6-{5-[(1S)-1-{[7-chloro-5-(trifluoromethyl)-1,3-benzoxazol-2-yl]amino}ethyl]-1H-1,2,4-triazol-1-yl}pyridine-3-sulfonamide
LC-MS (method 1): R$_t$ = 1.79 min; MS (ESIpos): m/z = 488 [M + H]$^+$
$^1$H-NMR (600 MHz, DMSO-d6) δ [ppm]: 1.676 (16.00), 1.687 (15.85), 2.072 (0.60), 3.570 (3.35), 3.643 (3.24), 5.982 (0.64), 5.994 (2.53), 6.006 (3.73), 6.018 (2.47), 6.029 (0.62), 7.466 (8.05), 7.482 (8.58), 7.731 (15.43), 8.126 (6.00), 8.140 (6.55), 8.226 (12.27), 8.457 (4.06), 8.461 (3.95), 8.471 (3.71), 8.475 (3.62), 8.906 (6.63), 8.910 (6.56), 9.401 (4.72), 9.414 (4.54).

I-113

6-{5-[(1S)-1-{[6-chloro-5-(trifluoromethyl)-1,3-benzoxazol-2-yl]amino}ethyl]-1H-1,2,4-triazol-1-yl}-N-(cyclopropylmethyl)-N-methyylpyridine-3-carboxamide
LC-MS (method 7): R$_t$ = 1.38 min; MS (ESIpos): m/z = 520 [M + H]$^+$
$^1$H-NMR (600 MHz, DMSO-d6) δ [ppm]: 0.045 (1.18), 0.297 (1.34), 0.441 (1.23), 0.512 (1.34), 0.935 (0.53), 1.070 (0.52), 1.665 (16.00), 1.677 (15.83), 2.967 (2.55), TABLE 7-continued Structure
IUPAC-Name
LC-MS (method): Retention time; Mass found
Example ¹H-NMR 3.081 (3.18), 3.369 (1.61), 5.990 (1.64), 6.002 (2.37), 6.014 (1.62), 7.575 (9.47),
7.809 (10.73), 7.840 (0.42), 7.940 (5.56), 7.954 (6.42), 8.131 (1.58), 8.18 (13.70),
8.549 (2.74), 9.179 (4.30), 9.193 (4.11).

I-114

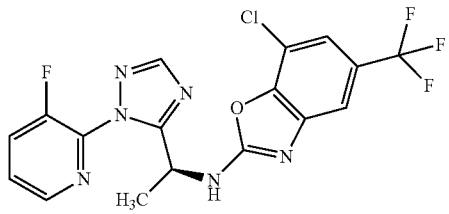 [SMILES: C[C@H](Nc1nc2cc(C(F)(F)F)cc(Cl)c2o1)c1ncnn1-c1ncccc1F]

7-chloro-N-{(1S)-1-[1-(3-fluoropyridin-2-yl)-1H-1,2,4-triazol-5-yl]ethyl}-5-
(trifluoromethyl)-1,3-benzoxazol-2-amine
LC-MS (method 7): R$_t$ = 1.32 min; MS (ESIpos): m/z = 427 [M + H]$^+$
¹H-NMR (600 MHz, DMSO-d6) δ [ppm]: 1.654 (16.00), 1.666 (15.90), 3.261 (0.43),
3.270 (0.95), 3.333 (0.41), 3.338 (0.52), 5.246 (0.62), 5.258 (2.54), 5.269 (3.77),
5.281 (2.47), 5.293 (0.56), 7.348 (6.78), 7.469 (6.91), 7.684 (1.59), 7.691 (2.58),
7.698 (3.32), 7.705 (2.80), 7.712 (1.73), 7.838 (0.58), 8.089 (2.08), 8.104 (3.61),
8.119 (1.88), 8.207 (12.31), 8.406 (4.25), 8.414 (4.16), 9.284 (4.21), 9.296 (4.02).

I-115

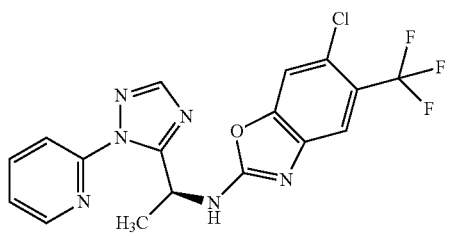 [SMILES: C[C@H](Nc1nc2cc(C(F)(F)F)c(Cl)cc2o1)c1ncnn1-c1ccccn1]

6-chloro-N-{(1S)-1-[1-(pyridin-2-yl)-1H-1,2,4-triazol-5-yl]ethyl}-5-
(trifluoromethyl)-1,3-benzoxazol-2-amine
LC-MS (method 1): R$_t$ = 2.07 min; MS (ESIpos): m/z = 409 [M + H]$^+$
¹H-NMR (600 MHz, DMSO-d6) δ [ppm]: 1.651 (8.43), 1.663 (8.35), 3.571 (16.00),
5.959 (1.24), 5.971 (1.75), 5.983 (1.26), 7.493 (1.35), 7.502 (1.49), 7.506 (1.47),
7.514 (1.45), 7.574 (6.51), 7.807 (5.03), 7.897 (2.43), 7.910 (2.83), 8.090 (1.14),
8.093 (1.21), 8.103 (1.74), 8.106 (1.82), 8.116 (0.99), 8.119 (1.01), 8.147 (6.52),
8.531 (1.66), 8.533 (1.73), 8.539 (1.71), 8.541 (1.68), 9.175 (2.11), 9.188 (2.05).

I-116

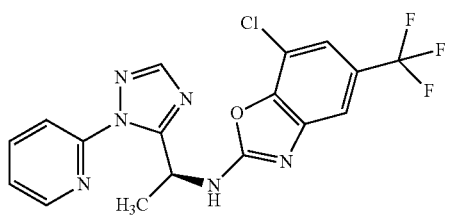 [SMILES: C[C@H](Nc1nc2cc(C(F)(F)F)cc(Cl)c2o1)c1ncnn1-c1ccccn1]

7-chloro-N-{(1S)-1-[1-(pyridin-2-yl)-1H-1,2,4-triazol-5-yl]ethyl}-5-
(trifluoromethyl)-1,3-benzoxazol-2-amine
LC-MS (method 1): R$_t$ = 2.15 min; MS (ESIpos): m/z = 409 [M + H]$^+$
¹H-NMR (600 MHz, DMSO-d6) δ [ppm]: 1.656 (16.00), 1.668 (15.82), 3.328 (0.41),
3.570 (13.84), 5.982 (1.95), 7.459 (7.58), 7.474 (7.92), 7.498 (2.85), 7.506 (3.17),
7.510 (3.15), 7.518 (2.98), 7.902 (4.70), 7.916 (5.46), 8.094 (2.18), 8.097 (2.15),
8.108 (3.60), 8.120 (1.90), 8.123 (1.79), 8.146 (11.47), 8.542 (3.72), 8.550 (3.65),
9.352 (2.75).

TABLE 7-continued

Structure
IUPAC-Name
LC-MS (method): Retention time; Mass found
Example $^1$H-NMR

I-117

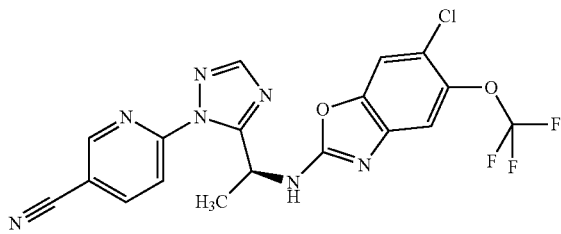 [SMILES: C[C@H](Nc1nc2cc(OC(F)(F)F)c(Cl)cc2o1)c1ncnn1-c1ccc(C#N)cn1]

6-{5-[(1S)-1-{[6-chloro-5-(trifluoromethoxy)-1,3-benzoxazol-2-yl]amino}ethyl]-
1H-1,2,4-triazol-1-yl}pyridine-3-carbonitrile
LC-MS (method 1): R$_t$ = 2.08 min; MS (ESIpos): m/z = 450 [M + H]$^+$
$^1$H-NMR (600 MHz, DMSO-d6) δ [ppm]: 1.643 (16.00), 1.655 (15.78), 5.967 (0.65),
5.978 (2.59), 5.990 (3.71), 6.002 (2.51), 6.014 (0.63), 7.328 (7.42), 7.778 (11.53),
8.097 (5.78), 8.111 (6.16), 8.243 (11.94), 8.577 (4.02), 8.580 (3.79), 8.591 (3.85),
8.594 (3.61), 9.046 (6.50), 9.049 (5.84), 9.170 (4.68), 9.183 (4.49).

I-118

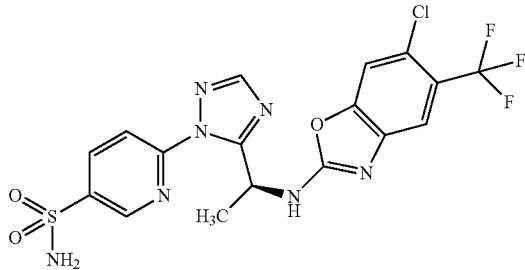 [SMILES: C[C@H](Nc1nc2cc(C(F)(F)F)c(Cl)cc2o1)c1ncnn1-c1ccc(S(N)(=O)=O)cn1]

6-{5-[(1S)-1-{[6-chloro-5-(trifluoromethyl)-1,3-benzoxazol-2-yl]amino}ethyl]-
1H-1,2,4-triazol-1-yl}pyridine-3-sulfonamide
LC-MS (method 1): R$_t$ = 1.73 min; MS (ESIpos): m/z = 488 [M + H]$^+$
$^1$H-NMR (600 MHz, DMSO-d6) δ [ppm]: 1.671 (16.00), 1.683 (15.88), 5.966 (0.61),
5.978 (2.55), 5.990 (3.68), 6.002 (2.52), 6.013 (0.62), 7.580 (12.86), 7.731 (14.69),
7.819 (10.31), 8.120 (6.08), 8.134 (6.61), 8.226 (13.21), 8.452 (4.13), 8.456 (4.17),
8.467 (3.77), 8.471 (3.84), 8.894 (6.40), 8.898 (6.35), 9.226 (4.62), 9.239 (4.44).

I-119

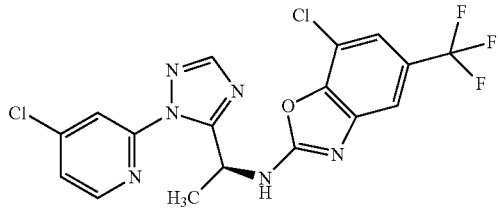 [SMILES: C[C@H](Nc1nc2cc(C(F)(F)F)cc(Cl)c2o1)c1ncnn1-c1cc(Cl)ccn1]

7-chloro-N-{(1S)-1-[1-(4-chloropyridin-2-yl)-1H-1,2,4-triazol-5-yl]ethyl}-5-
(trifluoromethyl)-1,3-benzoxazol-2-amine
LC-MS (method 1): R$_t$ = 2.09 min; MS (ESIpos): m/z = 443 [M + H]$^+$
$^1$H-NMR (600 MHz, DMSO-d6) δ [ppm]: 1.663 (16.00), 1.674 (15.82), 1.911 (4.05),
1.915 (0.95), 1.933 (0.85), 1.977 (0.70), 2.565 (0.48), 2.735 (8.57), 2.893 (9.75),
3.600 (1.73), 5.364 (0.61), 5.375 (2.48), 5.387 (3.63), 5.399 (2.44), 5.410 (0.59),
7.485 (8.16), 7.493 (7.58), 7.764 (4.17), 7.767 (4.52), 7.773 (4.33), 7.776 (4.55),
7.903 (7.64), 7.906 (7.52), 7.955 (1.42), 8.251 (12.92), 8.578 (7.17), 8.587 (6.87),
9.323 (4.05), 9.336 (3.93).

TABLE 7-continued

Structure
IUPAC-Name
LC-MS (method): Retention time; Mass found
Example ¹H-NMR

I-120

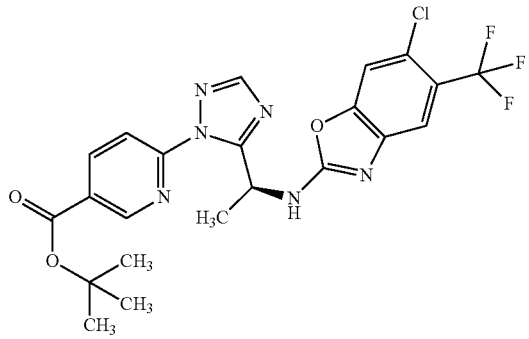 [SMILES: C[C@H](Nc1nc2cc(C(F)(F)F)c(Cl)cc2o1)c1ncnn1-c1ccc(C(=O)OC(C)(C)C)cn1]

tert-Butyl 6-{5-[(1S)-1-{[6-chloro-5-(trifluoromethyl)-1,3-benzoxazol-2-yl]amino}ethyl]-1H-1,2,4-triazol-1-yl}pyridine-3-carboxylate
LC-MS (method 1): $R_t$ = 2.52 min; MS (ESIpos): m/z = 509 [M + H]⁺
¹H-NMR (600 MHz, DMSO-d6) δ [ppm]: 1.398 (1.04), 1.527 (1.76), 1.552 (16.00), 1.665 (2.26), 1.676 (2.24), 1.908 (1.81), 1.944 (0.53), 1.975 (0.52), 1.986 (0.73), 5.745 (1.05), 6.013 (0.52), 7.568 (1.76), 7.816 (1.33), 8.006 (0.88), 8.020 (0.92), 8.218 (1.70), 8.469 (0.57), 8.473 (0.57), 8.483 (0.53), 8.487 (0.53), 8.878 (0.91), 8.882 (0.88), 9.157 (0.45), 9.170 (0.44).

I-121

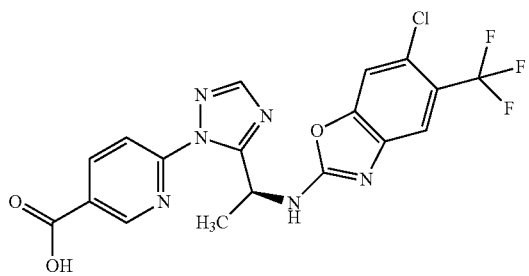 [SMILES: C[C@H](Nc1nc2cc(C(F)(F)F)c(Cl)cc2o1)c1ncnn1-c1ccc(C(=O)O)cn1]

6-{5-[(1S)-1-{[6-chloro-5-(trifluoromethyl)-1,3-benzoxazol-2-yl]amino}ethyl]-1H-1,2,4-triazol-1-yl}pyridine-3-carboxylic acid
LC-MS (method 8): $R_t$ = 0.96 min; MS (ESIpos): m/z = 453 [M + H]⁺
¹H-NMR (600 MHz, DMSO-d6) δ [ppm]: 1.166 (0.94), 1.178 (1.88), 1.190 (0.96), 1.232 (0.41), 1.499 (0.54), 1.511 (0.56), 1.665 (16.00), 1.677 (15.81), 1.990 (3.60), 4.028 (0.90), 4.039 (0.87), 6.002 (0.70), 6.014 (2.61), 6.026 (3.78), 6.038 (2.55), 6.049 (0.68), 7.65 (11.86), 7.814 (9.25), 8.027 (6.07), 8.041 (6.23), 8.213 (11.67), 8.520 (4.18), 8.524 (4.02), 8.535 (3.99), 8.538 (3.79), 8.984 (6.80), 8.987 (6.67), 9.204 (3.43), 9.217 (3.25), 13.572 (1.15).

Biological Examples

*Boophilus microplus*—Injection Test (BOOPMI Injection)

Solvent: dimethyl sulfoxide

To produce a suitable preparation of active compound, 10 mg of active compound are dissolved in 0.5 mL solvent, and the concentrate is diluted with solvent to the desired concentration.

Five adult engorged female ticks (*Boophilus microplus*) are injected with 1 μL compound solution into the abdomen. The ticks are transferred into replica plates and incubated in a climate chamber.

After 7 days egg deposition of fertile eggs is monitored. Eggs where fertility is not visible are stored in a climate chamber till hatching after about 42 days. An efficacy of 100% means all eggs are infertile; 0% means all eggs are fertile.

In this test, for example, the following compounds from the preparation examples showed good activity of 100% at an application rate of 20 μg/animal: I-001, I-005, I-006, I-010, I-011, I-012, I-014, I-015, I-016, I-017, I-018, I-019, I-021, I-026, I-027, I-030, I-032, I-034, I-036, I-039, I-045, I-047, I-051, I-052, I-053, I-054, I-055, I-056, I-062, I-063, I-065, I-066, I-067, I-068, I-073, I-075, I-076, I-077, I-084, I-089, I-090, I-091, I-092, I-094.

In this test, for example, the following compounds from the preparation examples showed good activity of 80% at an application rate of 20 μg/animal I-008, I-050, I-064.

In this test, for example, the following compounds from the preparation examples showed good activity of 100% at an application rate of 4 μg/animal: I-001, I-005, I-006, I-011, I-012, I-014, I-017, I-018, I-021, I-026, I-027, I-034, I-036, I-039, I-040, I-044, I-045, I-047, I-052, I-053, I-062, I-065, I-066, I-067, I-068, I-069, I-075, I-076, I-077, I-084, I-089, I-094.

In this test, for example, the following compounds from the preparation examples showed good activity of 80% at an application rate of 4 μg/animal I-015, I-030, I-035, I-038, I-050, I-055, I-056, I-057, I-063, I-074, I-079, I-090.

*Rhipicephalus microplus*—in-Vitro Contact Tests Larval Cattle Tick (Strain Parkhurst, Resistant Against Synthetic Pyrethroids) (BOOPMI Contact)

9 mg compound is solved in 1 ml acetone and diluted with acetone to the desired concentration. 250 µL of the test solution is filled in 25 ml glass test tubes and homogeneously distributed on the inner walls by rotation and tilting on a shaking device (2 h at 30 rpm). With a compound concentration of 900 ppm, an inner surface of 44.7 cm$^2$ and a homogeneous distribution, a dose of 5 µg/cm$^2$ is achieved.

After the solvent has evaporated, each test tube is filled with 20-50 cattle tick larvae (*Rhipicephalus microplus*), closed with a perforated lid and incubated in a horizontal position at 85% relative humidity and 27° C. in an incubator. After 48 hours efficacy is determined. The larvae are patted on the ground of the tubes and negative geotactic behaviour is recorded. Larvae that climb back to the top of the vial in a manner comparable to untreated control larvae are marked as alive, larvae not climbing back up comparable to untreated control larvae but are moving uncoordinatedly or only twitching their legs are marked as moribund, tick larvae remaining on the bottom and not moving at all are counted as dead.

A compound shows a good efficacy against *Rhipicephalus microplus*, if at a compound concentration of 5 µg/cm$^2$ an efficacy of at least 80% is monitored. An efficacy of 100% means all larvae are dead or moribund; 0% means no larvae are dead or moribund.

In this test, for example, the following compounds from the preparation examples showed good activity of 100% at an application rate of 5 µg/cm$^2$ (=500 g/ha): I-001, I-005, I-006, I-007, I-013, I-014, I-015, I-016, I-017, I-019, I-020, I-026, I-027, I-029, I-033, I-036, I-044, I-047, I-049, I-054, I-055, I-057, I-058, I-059, I-060, I-061, I-062, I-073, I-080, I-082, I-083, I-085, I-087, I-088, I-090, I-092, I-093, I-097.

In this test, for example, the following compounds from the preparation examples showed good activity of 90% at an application rate of 5 µg/cm$^2$ (=500 g/ha): I-034, I-039, I-040, I-042, I-066, I-072, I-076, I-081, I-086, I-091, I-096.

In this test, for example, the following compounds from the preparation examples showed good activity of 80% at an application rate of 5 µg/cm$^2$ (=500 g/ha): I-008, I-011, I-018, I-021, I-037, I-041, I-045, I-046, I-051, I-056, I-068, I-069, I-084, I-095.

*Ctenocephalides felis*—in-Vitro Contact Tests Adult Cat Flea 9 mg compound is solved in 1 ml acetone and diluted with acetone to the desired concentration. 250 of the test solution is filled in 25 ml glass test tubes and homogeneously distributed on the inner walls by rotation and tilting on a shaking device (2 h at 30 rpm). With a compound concentration of 900 ppm, an inner surface of 44.7 cm$^2$ and a homogeneous distribution, a dose of 5 µg/cm$^2$ is achieved.

After the solvent has evaporated, each test tube is filled with 5-10 adult cat fleas (*Ctenocephalides felis*), closed with a perforated lid and incubated in a lying position at room temperature and relative humidity. After 48 hours efficacy is determined. The fleas are patted on the ground of the tubes and are incubated on a heating plate at 45-50° C. for at most 5 minutes Immotile or uncoordinated moving fleas, which are not able to escape the heat by climbing upwards, are marked as dead or moribund.

A compound shows a good efficacy against *Ctenocephalides felis*, if at a compound concentration of 5 µg/cm$^2$ an efficacy of at least 80% is monitored. An efficacy of 100% means all fleas are dead or moribund; 0% means no fleas are dead or moribund.

In this test, for example, the following compounds from the preparation examples showed good activity of 100% at an application rate of 5 µg/cm$^2$ (=500 g/ha): I-001, I-005, I-006, I-017, I-019, I-040, I-045, I-052, I-057, I-058, I-059, I-060, I-061, I-062, I-065, I-074, I-079, I-081, I-082, I-084, I-085, I-093, I-094, I-096, I-097, I-098.

In this test, for example, the following compounds from the preparation examples showed good activity of 90% at an application rate of 5 µg/cm$^2$ (=500 g/ha): I-042, I-049, I-070, I-071, I-092.

In this test, for example, the following compounds from the preparation examples showed good activity of 80% at an application rate of 5 µg/cm$^2$ (=500 g/ha): I-014, I-036, I-083.

*Ctenocephalides felis*—Oral Test (CTECFE)

Solvent: dimethyl sulfoxide

To produce a suitable preparation of active compound, 10 mg of active compound are dissolved in 0.5 ml solvent, and the concentrate is diluted with cattle blood to the desired concentration.

Approximately 20 adult unfed cat fleas (*Ctenocephalides felis*) are placed in flea chambers. The blood chamber, sealed with parafilm on the bottom, are filled with cattle blood supplied with compound solution and placed on the gauze covered top of the flea chamber, so that the fleas are able to suck the blood. The blood chamber is heated to 37° C. whereas the flea chamber is kept at room temperature.

After 2 days mortality in % is determined. 100% means all the fleas have been killed; 0% means none of the fleas have been killed.

In this test, for example, the following compounds from the preparation examples showed good activity of 100% at an application rate of 100 ppm: I-001, I-005, I-006, I-007, I-010, I-011, I-012, I-014, I-026, I-034, I-035, I-036, I-039, I-040, I-044, I-045, I-048, I-053, I-056, I-057, I-065, I-069, I-070, I-071, I-072, I-074, I-076, I-078, I-079, I-092, I-093, I-094, I-095, I-096.

In this test, for example, the following compounds from the preparation examples showed good activity of 90% at an application rate of 100 ppm: I-013, I-033, I-041, I-050, I-073.

In this test, for example, the following compounds from the preparation examples showed good activity of 80% at an application rate of 100 ppm: I-067, I-075.

*Rhipicephalus sanguineus*—in-Vitro Contact Tests with Adult Brown Dog Ticks (RHIPSA Contact)

9 mg compound is solved in 1 ml acetone and diluted with acetone to the desired concentration. 250 µL, of the test solution is filled in 25 ml glass test tubes and homogeneously distributed on the inner walls by rotation and tilting on a shaking device (2 h at 30 rpm). With a compound concentration of 900 ppm, an inner surface of 44.7 cm$^2$ and a homogeneous distribution, a dose of 5 µg/cm$^2$ is achieved.

After the solvent has evaporated, each test tube is filled with 5-10 adult brown dog ticks (*Rhipicephalus sanguineus*), closed with a perforated lid and incubated in a lying position at room temperature and relative humidity. After 48 hours efficacy is determined. The ticks are patted on the ground of the tubes and are incubated on a heating plate at 45-50° C. for at most 5 minutes Immotile or uncoordinated moving ticks, which are not able to escape the heat by climbing upwards, are marked as dead or moribund.

A compound shows a good efficacy against *Rhipicephalus sanguineus*, if at a compound concentration of 5 µg/cm$^2$ an efficacy of at least 80% is monitored. An efficacy of 100% means all ticks are dead or moribund; 0% means no ticks are dead or moribund.

In this test, for example, the following compounds from the preparation examples showed good activity of 100% at an application rate of 5 µg/cm$^2$ (=500 g/ha): I-001, I-034, I-036, I-039, I-040, I-045, I-047, I-049, I-055, I-059, I-062, I-065, I-081, I-082, I-083, I-085, I-090, I-096.

In this test, for example, the following compounds from the preparation examples showed good activity of 80% at an application rate of 5 µg/cm$^2$ (=500 g/ha): I-011, I-031, I-060, I-061, I-066, I-067, I-084, I-097.

*Diabrotica balteata*—Spray Test

Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvent, and the concentrate is diluted with water, containing an emulsifier concentration of 1000 ppm, to the desired concentration. Further test concentrations are prepared by dilution with emulsifier containing water.

Soaked wheat seeds (*Triticum aestivum*) are placed in a multiple well plate filled with agar and some water and are incubated for 1 day to germinate (5 seeds per well). The germinated wheat seeds are sprayed with a test solution containing the desired concentration of the active ingredient. Afterwards each unit is infected with 10-20 larvae of the banded cucumber beetle (*Diabrotica balteata*).

After 7 days efficacy in % is determined. 100% means all the seedlings have grown up like in the untreated, uninfected control; 0% means none of the seedlings have grown.

In this test, for example, the following compounds from the preparation examples showed good activity of 100% at an application rate of 500 g/ha (=160 µg/well): I-001, I-005, I-006, I-010, I-011, I-013, I-014, I-015, I-016, I-017, I-018, I-019, I-021, I-026, I-039, I-045, I-047, I-052, I-053, I-055, I-062, I-064, I-065, I-066, I-084, I-088, I-090.

In this test, for example, the following compounds from the preparation examples showed good activity of 80% at an application rate of 500 g/ha (=160 µg/well): I-003, I-009, I-034, I-063, I-067.

In this test, for example, the following compounds from the preparation examples showed good activity of 100% at an application rate of 100 g/ha: I-011, I-014, I-016, I-017, I-018, I-019, I-021, I-034, I-035, I-036, I-039, I-040, I-041, I-044, I-045, I-047, I-055, I-058, I-059, I-060, I-061, I-062, I-063, I-064, I-065, I-069, I-070, I-071, I-078, I-079, I-081, I-082, I-085, I-094, I-098, I-100, I-101, I-102, I-103.

In this test, for example, the following compounds from the preparation examples showed good activity of 80% at an application rate of 100 g/ha: I-010, I-049, I-083.

*Meloidogyne incognita*—Test

Solvent: 125.0 parts by weight of acetone

To produce a suitable preparation of active compound, 1 part by weight of active compound is mixed with the stated amount of solvent, and the concentrate is diluted with water to the desired concentration.

Vessels are filled with sand, a solution of the active ingredient, a suspension containing eggs and larvae of the southern root-knot nematode (*Meloidogyne incognita*) and salad seeds. The salad seeds germinate, and the seedlings grow. Galls develop in the roots.

After 14 days the nematicidal activity is determined based on the percentage of gall formation. 100% means no galls were found and 0% means the number of galls found on the roots of the treated plants was equal to that in untreated control plants.

In this test, for example, the following compounds from the preparation examples showed good activity of 90% at an application rate of 20 ppm: I-046, I-087, I-088, I-091.

*Myzus persicae*—Oral Test

Solvent: 100 parts by weight acetone

To produce a suitable preparation of active compound, 1 part by weight of active compound is mixed with the stated amount of solvent, and the concentrate is diluted with water to the desired concentration.

50 µl compound solution is filled in microtiter plates and 150 µl IPL41 insect medium (33%+15% sugar) is added to obtain a total volume of 200 µl per well. Afterwards the plates are sealed with parafilm through which a mixed population of the green peach aphid (*Myzus persicae*) can suck on the compound preparation.

After 5 days mortality in % is determined. 100% means all aphids have been killed and 0% means none of the aphids have been killed.

In this test, for example, the following compounds from the preparation examples showed good activity of 100% at an application rate of 4 ppm: I-001, I-061, I-082.

In this test, for example, the following compounds from the preparation examples showed good activity of 90% at an application rate of 4 ppm: I-005, I-006, I-011, I-017, I-037, I-059, I-060, I-081, I-086, I-100.

*Myzus persicae*—Spray Test

Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Chinese cabbage (*Brassica pekinensis*) leaf disks infected with all instars of the green peach aphid (*Myzus persicae*), are sprayed with a preparation of the active ingredient of the desired concentration.

After 5 days mortality in % is determined. 100% means all aphids have been killed and 0% means none of the aphids have been killed.

In this test, for example, the following compounds from the preparation examples showed good activity of 100% at an application rate of 500 g/ha: I-013.

In this test, for example, the following compounds from the preparation examples showed good activity of 90% at an application rate of 500 g/ha: I-091.

In this test, for example, the following compounds from the preparation examples showed good activity of 90% at an application rate of 100 g/ha: I-081, I-085, I-092, I-093.

*Nezara viridula*—Spray Test

Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvent, and the concentrate is diluted with water, containing an emulsifier concentration of 1000 ppm, to the desired concentration. Further test concentrations are prepared by dilution with emulsifier containing water.

Barley plants (*Hordeum vulgare*) are sprayed with a test solution containing the desired concentration of the active ingredient and are infested with larvae of the southern green stink bug (*Nezara viridula*).

After 4 days, mortality in % is determined. 100% means all the stink bugs have been killed; 0% means none of the stink bugs have been killed.

In this test, for example, the following compounds from the preparation examples showed good activity of 100% at an application rate of 500 g/ha: I-017.

In this test, for example, the following compounds from the preparation examples showed good activity of 100% at an application rate of 100 g/ha: I-085.

*Nilaparvata lugens*—Spray Test

Solvent: 78.0 parts by weight of acetone
1.5 parts by weight of dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Rice plants (*Oryza sativa*) are sprayed with a preparation of the active ingredient of the desired concentration and the plants are infested with the brown planthopper (*Nilaparvata lugens*).

After 4 days mortality in % is determined. 100% means all planthoppers have been killed and 0% means none of the planthoppers have been killed.

In this test, for example, the following compounds from the preparation examples showed good activity of 100% at an application rate of 500 g/ha: I-007, I-009.

*Spodoptera frugiperda*—Spray Test

Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

Maize (*Zea mays*) leaf sections are sprayed with a preparation of the active ingredient of the desired concentration. Once dry, the leaf sections are infested with fall armyworm larvae (*Spodoptera frugiperda*).

After 7 days mortality in % is determined. 100% means all caterpillars have been killed and 0% means none of the caterpillars have been killed.

In this test, for example, the following compounds from the preparation examples showed good activity of 100% at an application rate of 500 g/ha: I-001, I-005, I-006, I-010, I-011, I-012, I-014, I-015, I-016, I-017, I-018, I-019, I-026, I-027, I-032, I-033, I-034, I-039, I-045, I-047, I-052, I-054, I-055, I-062, I-090.

In this test, for example, the following compounds from the preparation examples showed good activity of 83% at an application rate of 500 g/ha: I-088.

In this test, for example, the following compounds from the preparation examples showed good activity of 100% at an application rate of 100 g/ha: I-001, I-005, I-006, I-017, I-018, I-026, I-034, I-036, I-043, I-044, I-045, I-047, I-049, I-055, I-057, I-059, I-061, I-062, I-069, I-070, I-081, I-082, I-083, I-085, I-098, I-100, I-102.

In this test, for example, the following compounds from the preparation examples showed good activity of 83% at an application rate of 100 g/ha: I-058, I-060.

*Tetranychus urticae*—Spray Test OP-Resistant

Solvent: 78.0 parts by weight acetone
1.5 parts by weight dimethylformamide
Emulsifier: alkylarylpolyglycol ether To produce a suitable preparation of active compound, 1 part by weight of active compound is mixed with the stated amount of solvents and is diluted with water, containing an emulsifier concentration of 1000 ppm, to the desired concentration. Further test concentrations are prepared by dilution with emulsifier containing water.

French bean (*Phaseolus vulgaris*) leaf disks infected with all instars of the two spotted spidermite (*Tetranychus urticae*) are sprayed with a preparation of the active ingredient of the desired concentration.

After 6 days mortality in % is determined. 100% means all spider mites have been killed and 0% means none of the spider mites have been killed.

In this test, for example, the following compounds from the preparation examples showed good activity of 90% at an application rate of 500 g/ha: I-016, I-067.

In this test, for example, the following compounds from the preparation examples showed good activity of 90% at an application rate of 100 g/ha: I-085.

*Aedes aegypti* Test (AEDSAE Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/mL/RME 2000 ppm). This solution is pipetted onto a glazed tile and after evaporation of the acetone, adult mosquitoes of the species *Aedes aegypti* strain MONHEIM are placed onto the dried surface. The exposure time is 30 minutes.

Mortality in percent (%) is determined 24 hours after contact of the insects to the treated surface. 100% mortality means that all tested insects are dead, whereas 0% means that no insect died.

The following examples showed in this test efficacy of 90-100% at a surface concentration of 20 mg/m$^2$: I-001, I-005, I-017, I-059, I-061, I-081.

The following examples showed in this test efficacy of 85-100% at a surface concentration of 4 mg/m$^2$: I-001, I-006, I-017, I-059, I-061, I-081.

*Culex quinquefasciatus* Test (CULXFA Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/mL/RME 2 000 ppm). This solution is pipetted onto a glazed tile and after evaporation of the acetone, adult mosquitoes of the species *Culex quinquefasciatus* strain P00 are placed onto the dried surface. The exposure time is 30 minutes.

Mortality in percent (%) is determined 24 hours after contact of the insects to the treated surface. 100% mortality means that all tested insects are dead, whereas 0% means that no insect died.

The following examples showed in this test efficacy of 90-100% at a surface concentration of 20 mg/m$^2$: I-001, I-005.

The following examples showed in this test efficacy of 90-100% at a surface concentration of 4 mg/m$^2$: I-001.

*Anopheles funestus* Test (ANPHFU Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/mL/RME 2000 ppm). This solution is pipetted onto a glazed tile and after evaporation of the acetone, adult mosquitoes of the species *Anopheles funestus* strain FUMOZ-R (Hunt et al., Med. Vet. Entomol. 2005 September; 19(3): 271-275) are placed onto the dried surface. The exposure time is 30 minutes.

Mortality in percent (%) is determined 24 hours after contact of the insects to the treated surface. 100% mortality means that all tested insects are dead, whereas 0% means that no insect died.

The following examples showed in this test efficacy of 90-100% at a surface concentration of 20 mg/m$^2$: I-005, I-017, I-059, I-081.

The following examples showed in this test efficacy of 85-100% at a surface concentration of 4 mg/m$^2$: I-017, I-059, I-061, I-081.

*Musca domestica* Test (MUSCDO Surface Treatment & Contact Assay)

Solvent: Aceton+2000 ppm rapeseed oil methyl ester (RME)

In order to produce a sufficient, active ingredient containing solution it is necessary to solve the test compound in the solvent-mix (acetone at 2 mg/mL/RME 2000 ppm). This solution is pipetted onto a glazed tile and after evaporation of the acetone, adult flies of the species *Musca domestica* strain WHO—N are placed onto the dried surface. The exposure time is 30 minutes.

Mortality in percent (%) is determined 24 hours after contact of the insects to the treated surface. 100% mortality means that all tested insects are dead, whereas 0% means that no insect died.

The following examples showed in this test efficacy of 90-100% at a surface concentration of 20 mg/m$^2$: I-001, I-017, I-081.

The following examples showed in this test efficacy of 90-100% at a surface concentration of 4 mg/m$^2$: I-017, I-059, I-061, I-081.

The invention claimed is:

1. A compound of formula (I)

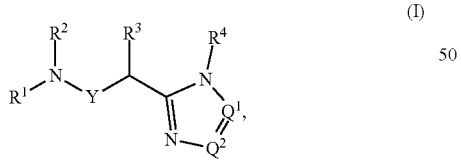

wherein
- $Q^1$ and $Q^2$ are independently $CR^5$ or N, provided at least one of $Q^1$ and $Q^2$ is N;
- Y is a direct bond;
- $R^1$ is hydrogen; $C_1$-$C_6$alkyl, $C_3$-$C_6$cycloalkyl$C_1$-$C_6$alkyl, $C_2$-$C_6$alkenyl, $C_2$-$C_6$alkynyl, wherein $C_1$-$C_6$alkyl, 03-$C_6$cycloalkyl$C_1$-$C_6$alkyl, $C_2$-$C_6$alkenyl, $C_2$-$C_6$ alkynyl are optionally substituted;
  - or phenyl-$C_1$-$C_6$alkyl, wherein phenyl is optionally substituted with one to five substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, and in each case optionally substituted $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl;
- $R^2$ is a heteroaromatic bicyclic system containing 9-10 ring members including 1-4 heteroatoms selected from the group consisting of N, O, and S and optionally substituted with 0-4 substituents X, and 0-2 substituents Z and 0-1 substituents $Z^1$;
- X is selected from the group consisting of hydrogen, halogen, hydroxy, —CN, —COOH, —CONH$_2$, —NO$_2$, —NH$_2$, —SF$_5$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_3$-$C_6$cyloalkoxy, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, phenylsulfanyl, phenylsulfinyl, phenylsulfonyl, heterocyclylsulfanyl, heterocyclylsulfinyl, heterocyclylsulfonyl, heteroarylsulfanyl, heteroarylsulfinyl, heteroarylsulfonyl, S—$C_1$-$C_6$alkylsulfinimidoyl, S—$C_3$-$C_6$cycloalkylsulfinimidoyl, S-phenylsulfinimidoyl, S—heterocyclylsulfinimidoyl, S-heteroarylsulfinimidoyl, S—$C_1$-$C_6$alkylsulfonimidoyl, S—$C_3$-$C_6$cycloalkylsulfonimidoyl, S-phenylsulfonimidoyl, S-heterocyclylsulfonimidoyl, S-heteroarylsulfonimidoyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)SO$_2$$C_1$-$C_4$alkyl, —N(SO$_2$$C_1$-$C_4$alkyl)$_2$, —CO$_2$$C_1$-$C_4$alkyl, —CONH($C_1$-$C_4$alkyl), —CONH($C_3$-$C_6$cycloalkyl), —CONH-phenyl, —CON($C_1$-$C_4$alkyl)$_2$, —CON($C_1$-$C_4$alkyl)($C_3$-$C_6$cycloalkyl), —CON($C_1$-$C_4$alkyl)-phenyl, —SO$_2$NH($C_1$-$C_6$alkyl), —SO$_2$N($C_1$-$C_6$alkyl)$_2$, —SO$_2$N($C_1$-$C_6$alkyl)($C_3$-$C_6$cycloalkyl), —SO$_2$NH($C_3$-$C_6$cycloalkyl), —SO$_2$N($C_3$-$C_6$cycloalkyl)$_2$, —SO$_2$NH(heterocyclyl), —SO$_2$N($C_1$-$C_4$alkyl)(heterocyclyl), —SO$_2$N($C_3$-$C_6$cycloalkyl)(heterocyclyl), —C(=NO$C_1$-$C_4$alkyl)H, —C(=NO$C_1$-$C_4$alkyl)-$C_1$-$C_4$alkyl, tri($C_1$-$C_4$alkyl)silyl;
- and 3-6 membered heterocyclyl containing 1-2 heteroatoms selected from the group consisting of N, O, and S and optionally substituted with up to 4 substituents selected independently from the group consisting of fluorine, chlorine, bromine and $C_1$-$C_3$ alkyl;
- Z is selected from the group consisting of hydrogen, halogen, hydroxy, —CN, —COOH, —CONH$_2$, —NO$_2$, —NH$_2$, —SF$_5$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, phenylsulfanyl, phenylsulfinyl, phenylsulfonyl, $C_1$-$C_3$haloalkylthio, $C_1$-$C_3$haloalkylsulfinyl, $C_1$-$C_3$haloalkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)SO$_2$$C_1$-$C_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CON(C$_1$-C$_4$alkyl)$_2$, —CON(C$_1$-C$_4$alkyl)(C$_3$-C$_6$cycloalkyl), —CON(C$_1$-C$_4$alkyl)-phenyl, —C(=NOC$_1$-C$_4$alkyl)H, —C(=NOC$_1$-C$_4$alkyl)-C$_1$-C$_4$alkyl, tri(C$_1$-C$_4$alkyl)silyl;

and 3-6 membered heterocyclyl containing 1-2 heteroatoms selected from the group consisting of N, O, and S and optionally substituted with up to 4 substituents selected independently from the group consisting of fluorine, chlorine, bromine and C$_1$-C$_3$alkyl;

Z$^1$ is hydrogen, C$_1$-C$_6$alkyl, C$_3$-C$_6$cycloalkyl, C$_2$-C$_3$haloalkyl, or C$_1$-C$_4$ alkoxy, wherein C$_1$-C$_6$alkyl, C$_3$-C$_6$cycloalkyl, C$_2$-C$_3$haloalkyl, or C$_1$-C$_4$alkoxy are optionally substituted;

R$^3$ is hydrogen or optionally substituted C$_1$-C$_6$ alkyl;

R$^4$ is pyridine, pyrimidine, pyrazine, pyridazine or 5-membered heteroaryl wherein the pyridine, pyrimidine, pyrazine, pyridazine or 5-membered heteroaryl is optionally substituted with one to three substituents selected from the group consisting of halogen, hydroxy, —CN, —COOH, —CO$_2$—C$_1$-C$_6$alkyl, —SO$_2$NH$_2$, —CONH$_2$, —CSNH$_2$, —NO$_2$, —NH$_2$, —SF$_5$;

and in each case optionally substituted C$_1$-C$_6$alkyl, C$_3$-C$_6$cycloalkyl, C$_1$-C$_6$haloalkyl, C$_3$-C$_6$halocycloalkyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_1$-C$_6$haloalkylthio, C$_1$-C$_6$haloalkylsulfinyl, C$_1$-C$_6$haloalkylsulfonyl, C$_3$-C$_6$cycloalkylsulfanyl, C$_3$-C$_6$cycloalkylsulfinyl, C$_3$-C$_6$cycloalkylsulfonyl, C$_2$-C$_4$alkenylsulfanyl, C$_2$-C$_4$alkenylsulfinyl, C$_2$-C$_4$alkenylsulfonyl, C$_2$-C$_4$alkinylsulfanyl, C$_2$-C$_4$alkinylsulfinyl, C$_2$-C$_4$alkinylsulfonyl, phenylsulfanyl, phenylsulfinyl, phenylsulfonyl, S—C$_1$-C$_6$alkylsulfinimidoyl, S—C$_3$-C$_6$cycloalkylsulfinimidoyl, S—C$_2$-C$_6$alkenylsulfinimidoyl, S—C$_2$-C$_6$alkinylsulfinimidoyl, S-phenylsulfinimidoyl, S—C$_1$-C$_6$alkylsulfonimidoyl, S—C$_3$-C$_6$cycloalkylsulfonimidoyl, S—C$_2$-C$_6$alkenylsulfonimidoyl, S—C$_2$-C$_6$alkinylsulfonimidoyl, S-phenylsulfonimidoyl, —NH(C$_1$-C$_6$alkyl), —N(C$_1$-C$_6$alkyl)$_2$, —NHCO—C$_1$-C$_6$alkyl, —N(C$_1$-C$_6$alkyl)CO—C$_1$-C$_6$alkyl, —N(C$_3$-C$_6$cycloalkyl)CO—C$_1$-C$_6$alkyl, —NHCO—C$_3$-C$_6$cycloalkyl, —N(C$_1$-C$_6$alkyl)CO—(C$_3$-C$_6$cycloalkyl), —N(C$_3$-C$_6$cycloalkyl)CO—(C$_3$-C$_6$cycloalkyl), —N(C$_1$-C$_6$alkyl)CO-phenyl, —N(C$_3$-C$_6$cycloalkyl)CO-phenyl, —NHCO-phenyl, —N(CO—C$_1$-C$_6$alkyl)$_2$, —N(CO—C$_3$-C$_6$cyclo-alkyl)$_2$, —N(CO-phenyl)$_2$, —N(CO—C$_3$-C$_6$cycloalkyl)(CO—C$_1$-C$_6$alkyl), —N(CO—C$_3$-C$_6$cycloalkyl)(CO-phenyl), —N(CO—C$_1$-C$_6$alkyl)(CO-phenyl), —CONH(C$_1$-C$_6$alkyl), —CON(C$_1$-C$_6$alkyl)$_2$, —CONH(C$_3$-C$_6$cycloalkyl), —CON(C$_1$-C$_6$alkyl)(C$_3$-C$_6$cycloalkyl), —CONH(C$_3$-C$_6$cycloalkylalkyl), CON(C$_1$-C$_6$alkyl)(C$_3$-C$_6$cycloalkylalkyl), —CON(C$_3$-C$_6$cycloalkyl)$_2$, —CONH—SO$_2$—C$_1$-C$_6$alkyl, —CONH—SO$_2$-phenyl, —CONH—SO$_2$—(C$_3$-C$_6$cycloalkyl), —CON(C$_1$-C$_6$alkyl)-SO$_2$—C$_1$-C$_6$alkyl, —CON(C$_1$-C$_6$alkyl)-SO$_2$-phenyl, —CON(C$_1$-C$_6$alkyl)-SO$_2$—(C$_3$-C$_6$cycloalkyl), —CONH— phenyl, —CON(C$_1$-C$_6$alkyl)phenyl, —CON(C$_3$-C$_6$cycloalkyl)phenyl, —N(SO$_2$C$_1$-C$_6$alkyl)$_2$, —N(SO$_2$C$_1$-C$_6$haloalkyl)$_2$, —N(SO$_2$C$_3$-C$_6$cycloalkyl)$_2$, —N(SO$_2$C$_1$-C$_6$alkyl)SO$_2$-phenyl, —N(SO$_2$C$_3$-C$_6$cycloalkyl)SO$_2$-phenyl, —NHSO$_2$—C$_1$-C$_6$alkyl, —NHSO$_2$—C$_1$-C$_6$haloalkyl, —N(C$_1$-C$_6$alkyl)SO$_2$—C$_1$-C$_6$alkyl, —N(C$_3$-C$_6$cycloalkyl)SO$_2$—C$_1$-C$_6$alkyl, —NHSO$_2$-phenyl, —N(C$_1$-C$_6$alkyl)SO$_2$-phenyl, —N(C$_3$-C$_6$cycloalkyl)SO$_2$-phenyl, —NHSO$_2$C$_3$-C$_6$cycloalkyl, —N(C$_1$-C$_6$alkyl)SO$_2$—(C$_3$-C$_6$cycloalkyl), —N(C$_3$-C$_6$cycloalkyl)SO$_2$—(C$_3$-C$_6$cycloalkyl), —SO$_2$NH(C$_1$-C$_6$alkyl), —SO$_2$N(C$_1$-C$_6$alkyl)$_2$, —SO$_2$N(C$_1$-C$_6$alkyl)(C$_3$-C$_6$cycloalkyl), —SO$_2$NH(C$_3$-C$_6$cycloalkyl), —SO$_2$N(C$_3$-C$_6$cycloalkyl)$_2$, —SO$_2$NH(phenyl), —SO$_2$N(C$_1$-C$_6$alkyl)(phenyl), —SO$_2$N(C$_1$-C$_4$cycloalkyl)(phenyl), —C(=NOC$_1$-C$_6$alkyl)H and —C(=NOC$_1$-C$_6$alkyl)-C$_1$-C$_6$alkyl;

and 3-6 membered heterocyclyl containing 1-2 heteroatoms selected from the group consisting of N, O, and S and optionally substituted with up to 4 substituents selected independently from the group consisting of fluorine, chlorine, bromine and C$_1$-C$_3$alkyl, or one of the substituents may optionally be selected from the following substructures S1-S24, in which the bond to the pyridine, pyrimidine, pyrazine, pyridazine or 5-membered heteroaryl is marked with a # and Z$^4$ is CO or SO$_2$ and Y$^4$ is independently selected from CO or SO$_2$:

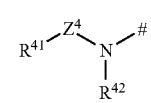

S1

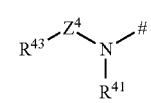

S2

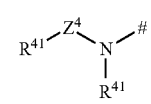

S3

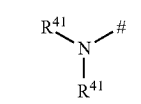

S4

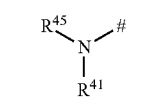

S5

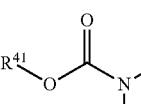

S6

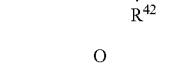

S7

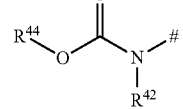

S8

R[41] is a heterocyclic ring which is selected from the group consisting of 3- to 10-membered saturated or partially unsaturated heterocyclyl, 5-membered heteroaryl, 6-membered heteroaryl, 9-membered heteroaryl and 10-membered heteroaryl, each of which is optionally substituted by one to three substituents independently selected from the group consisting of halogen, =O (oxo), =S (thiono), hydroxy, —CN, —COOH, —SO$_2$NH$_2$, —CONH$_2$, —CSNH$_2$, —NO$_2$, —SF$_5$, —NH$_2$;

and in each case optionally substituted —CO$_2$—C$_1$-C$_6$alkyl, C$_1$-C$_6$alkyl, C$_3$-C$_6$cycloalkyl, C$_3$-C$_6$cycloalkyl-C$_1$-C$_6$alkyl, C$_1$-C$_6$haloalkyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_3$-C$_6$cycloalkylsulfanyl, C$_3$-C$_6$cycloalkylsulfinyl, C$_3$-C$_6$cycloalkylsulfonyl, C$_1$-C$_6$haloalkylthio, C$_1$-C$_6$haloalkylsulfinyl, C$_1$-C$_6$haloalkylsulfonyl, C$_2$-C$_4$alkenylsulfanyl, C$_2$-C$_4$alkenylsulfinyl, C$_2$-C$_4$alkenylsulfonyl, C$_2$-C$_4$alkinylsulfanyl, C$_2$-C$_4$alkinylsulfinyl, C$_2$-C$_4$alkinylsulfonyl, phenylsulfanyl, phenylsulfinyl, phenylsulfonyl, S—C$_1$-C$_6$alkylsulfinimidoyl, S—C$_3$-C$_6$cycloalkylsulfinimidoyl, S—C$_2$-C$_6$alkenylsulfinimidoyl, S—C$_2$-C$_6$alkinylsulfinimidoyl, S-phenylsulfinimidoyl, S—C$_1$-C$_6$alkylsulfonimidoyl, S—C$_3$-C$_6$cycloalkylsulfonimidoyl, S—C$_2$-C$_6$alkenylsulfonimidoyl, S—C$_2$-C$_6$alkinylsulfonimidoyl, S-phenylsulfonimidoyl, —NH(C$_1$-C$_6$alkyl), —N(C$_1$-C$_6$alkyl)$_2$, —NHCO—C$_1$-C$_6$alkyl, —N(C$_1$-C$_6$alkyl)CO—C$_1$-C$_6$alkyl, —N(C$_3$-C$_6$cycloalkyl)CO—C$_1$-C$_6$alkyl, —NHCO—C$_3$-C$_6$cycloalkyl, —N(C$_1$-C$_6$alkyl)CO—(C$_3$-C$_6$cycloalkyl), —N(C$_3$-C$_6$cycloalkyl)CO—(C$_3$-C$_6$cycloalkyl), —N(C$_1$-C$_6$alkyl)CO-phenyl, —N(C$_3$-C$_6$cycloalkyl)CO-phenyl, —NHCO-phenyl, —N(CO—C$_1$-C$_6$alkyl)$_2$, —N(CO—C$_3$-C$_6$cycloalkyl)$_2$, —N(CO-phenyl)$_2$, —N(CO—C$_3$-C$_6$cycloalkyl)(CO—C$_1$-C$_6$alkyl), —N(CO—C$_3$-C$_6$cycloalkyl)(CO-phenyl), —N(CO—C$_1$-C$_6$alkyl)(CO-phenyl), —CONH(C$_1$-C$_6$alkyl), —CON(C$_1$-C$_6$alkyl)$_2$, —CONH(C$_3$-C$_6$cycloalkyl), —CON(C$_1$-C$_6$alkyl)(C$_3$-C$_6$cycloalkyl), —CON(C$_3$-C$_6$cycloalkyl)$_2$, —CONH—SO$_2$—C$_1$-C$_6$alkyl, —CONH—SO$_2$-phenyl, —CONH—SO$_2$—(C$_3$-C$_6$cycloalkyl), —CON(C$_1$-C$_6$alkyl)-SO$_2$—C$_1$-C$_6$alkyl, —CON(C$_1$-C$_6$alkyl)-SO$_2$-phenyl, —CON(C$_1$-C$_6$alkyl)-SO$_2$—(C$_3$-C$_6$cycloalkyl), —CONH-phenyl, —CON(C$_1$-C$_6$alkyl)phenyl, —CON(C$_3$-C$_6$cycloalkyl)phenyl, —N(SO$_2$C$_1$-C$_6$alkyl)$_2$, —N(SO$_2$C$_1$-C$_6$haloalkyl)$_2$, —N(SO$_2$C$_3$-C$_6$cycloalkyl)$_2$, —N(SO$_2$C$_1$-C$_6$alkyl)SO$_2$-phenyl, —N(SO$_2$C$_3$-C$_6$cycloalkyl)SO$_2$-phenyl, —NHSO$_2$—C$_1$-C$_6$alkyl, —NHSO$_2$—C$_1$-C$_6$haloalkyl, —N(C$_1$-C$_6$alkyl)SO$_2$—C$_1$-C$_6$alkyl, —N(C$_3$-C$_6$cycloalkyl)

SO$_2$—C$_1$-C$_6$alkyl, —NHSO$_2$-phenyl, —N(C$_1$-C$_6$alkyl)SO$_2$-phenyl, —N(C$_3$-C$_6$cycloalkyl)SO$_2$-phenyl, —NHSO$_2$—C$_3$-C$_6$cycloalkyl, —N(C$_1$-C$_6$alkyl)SO$_2$—(C$_3$-C$_6$cycloalkyl), —N(C$_3$-C$_6$cycloalkyl)SO$_2$—(C$_3$-C$_6$cycloalkyl), —SO$_2$NH(C$_1$-C$_6$alkyl), —SO$_2$N(C$_1$-C$_6$alkyl)$_2$, —SO$_2$N(C$_1$-C$_6$alkyl)(C$_3$-C$_6$cycloalkyl), —SO$_2$NH(C$_3$-C$_6$cycloalkyl), —SO$_2$N(C$_3$-C$_6$cycloalkyl)$_2$, —SO$_2$NH(phenyl), —SO$_2$N(C$_1$-C$_6$alkyl)(phenyl), —SO$_2$N(C$_1$-C$_4$cycloalkyl)(phenyl), —NHCS—C$_1$-C$_6$alkyl, —N(C$_1$-C$_6$alkyl)CS—C$_1$-C$_6$alkyl, —N(C$_3$-C$_6$cycloalkyl)CS—C$_1$-C$_6$alkyl, —NHCS—C$_3$-C$_6$cycloalkyl, —N(C$_1$-C$_6$alkyl)CS—(C$_3$-C$_6$cycloalkyl), —N(C$_3$-C$_6$cycloalkyl)CS—(C$_3$-C$_6$cycloalkyl), —N(C$_1$-C$_6$alkyl)CS-phenyl, —N(C$_3$-C$_6$cycloalkyl)CS-phenyl, —NHCS-phenyl, —CSNH(C$_1$-C$_6$alkyl), —CSN(C$_1$-C$_6$alkyl)$_2$, —CSNH(C$_3$-C$_6$cycloalkyl), —CSN(C$_1$-C$_6$alkyl)(C$_3$-C$_6$cycloalkyl), —CSN(C$_3$-C$_6$cycloalkyl)$_2$, —CSNH-phenyl, —CSN(C$_1$-C$_6$alkyl)phenyl, —CSN(C$_3$-C$_6$cycloalkyl)phenyl, —C(=NOC$_1$-C$_6$alkyl)H, —C(=NOC$_1$-C$_6$alkyl)-C$_1$-C$_6$alkyl, phenyl and 5- to 6-membered heteroaryl;

$R^{42}$ is hydrogen, hydroxy;
  or in each case optionally substituted C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_6$alkyl, phenyl-C$_1$-C$_6$alkyl, naphthyl-C$_1$-C$_6$alkyl, C$_1$-C$_6$alkoxy-, C$_1$-C$_6$haloalkoxy;
  or phenyl, wherein the phenyl is optionally substituted by one to three substituents independently selected from the group consisting of halogen, —CN, and in each case optionally substituted C$_1$-C$_6$alkyl, C$_3$-C$_6$cycloalkyl, C$_1$-C$_6$haloalkyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_3$-C$_6$cycloalkylthio, C$_3$-C$_6$cycloalkylsulfinyl, C$_3$-C$_6$cycloalkylsulfonyl, C$_1$-C$_6$haloalkylthio, C$_1$-C$_6$haloalkylsulfinyl, and C$_1$-C$_6$ haloalkylsulfonyl;

$R^{43}$ is in each case optionally substituted C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_6$alkyl, phenyl-C$_1$-C$_6$alkyl, naphthyl-C$_1$-C$_6$alkyl, C$_1$-C$_6$alkoxy-, C$_1$-C$_6$ haloalkoxy;
  or phenyl, wherein the phenyl is optionally substituted by one to three substituents independently selected from the group consisting of halogen, —CN, and in each case optionally substituted C$_1$-C$_6$alkyl, C$_3$-C$_6$cycloalkyl, C$_1$-C$_6$haloalkyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_3$-C$_6$cycloalkylthio, C$_3$-C$_6$cycloalkylsulfinyl, C$_3$-C$_6$cycloalkylsulfonyl, C$_1$-C$_6$haloalkylthio, C$_1$-C$_6$haloalkylsulfinyl, and C$_1$-C$_6$ haloalkylsulfonyl;

$R^{44}$ is in each case optionally substituted C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_6$alkyl, phenyl-C$_1$-C$_6$alkyl, naphthyl-C$_1$-C$_6$alkyl;

$R^{45}$ is hydrogen or in each case optionally substituted C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_6$alkyl, phenyl-C$_1$-C$_6$alkyl, naphthyl-C$_1$-C$_6$ alkyl;

or
$R^{41}$ and $R^{42}$ together with the nitrogen atom to which they are attached, represent a monocyclic or polycyclic optionally substituted 3- to 12-membered saturated or partially unsaturated heterocyclyl which may contain further heteroatoms;

$R^5$ is —NH$_2$, hydrogen, halogen, —CN, or in each case optionally substituted C$_1$-C$_3$alkyl, C$_1$-C$_3$haloalkyl, C$_3$-C$_4$cycloalkyl, C$_3$-C$_4$halocycloalkyl, C$_1$-C$_3$alkoxy, C$_1$-C$_3$haloalkoxy, —CH—(C$_1$-C$_3$alkoxy)$_2$, —CO$_2$C$_1$-C$_4$alkyl, —CONH(C$_1$-C$_4$alkyl), —CON(C$_1$-C$_4$alkyl)$_2$, —NHCO—C$_1$-C$_4$alkyl, —N(C$_1$-C$_4$alkyl)CO—C$_1$-C$_4$alkyl, —NHCO—C$_3$-C$_6$cycloalkyl, —N(C$_1$-C$_4$alkyl)CO—C$_3$-C$_6$cycloalkyl, —N(C$_3$-C$_6$cycloalkyl)CO—C$_3$-C$_6$cycloalkyl, —C(=NOC$_1$-C$_4$alkyl)H, or —C(=NOC$_1$-C$_4$alkyl)-C$_1$-C$_4$alkyl.

2. The compound of claim 1, wherein,
$Q^1$ and $Q^2$ are independently CR$^5$ or N, provided at least one of $Q^1$ and $Q^2$ is N;
Y is a direct bond;
$R^1$ is hydrogen; C$_1$-C$_6$alkyl, C$_3$-C$_6$cycloalkylC$_1$-C$_6$alkyl, C$_2$-C$_6$alkenyl, C$_2$-C$_6$alkynyl, wherein C$_1$-C$_6$alkyl, C$_3$-C$_6$cycloalkylC$_1$-C$_6$alkyl, C$_2$-C$_6$alkenyl, C$_2$-C$_6$ alkynyl are optionally substituted;
  or phenyl-C$_1$-C$_6$alkyl, wherein phenyl is optionally substituted with one to five substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, and in each case optionally substituted C$_1$-C$_6$alkyl, C$_3$-C$_6$cycloalkyl, C$_3$-C$_6$cycloalkyl-C$_1$-C$_6$alkyl, C$_1$-C$_3$haloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl;

$R^2$ is selected from one of the following bicyclic heterocycles T1-T70, wherein the bond to the N atom is marked with a #;

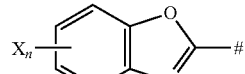

T1

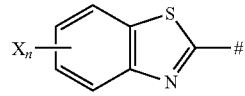

T2

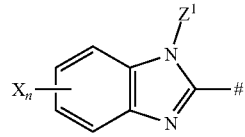

T3

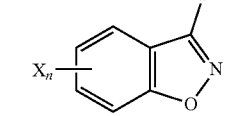

T4

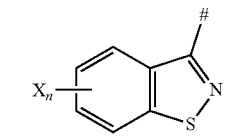

T5

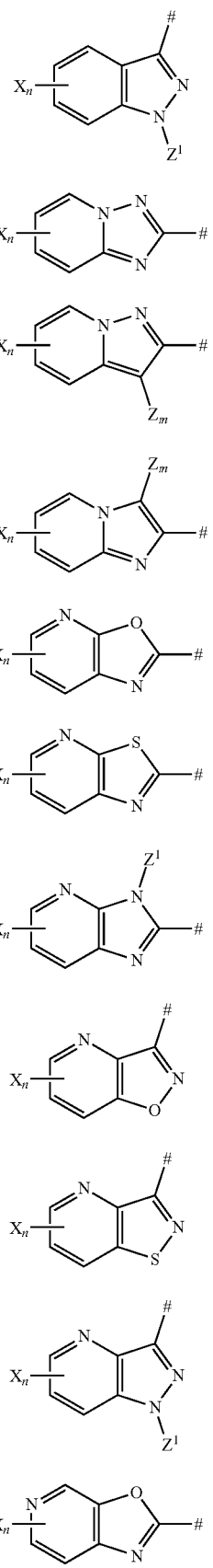
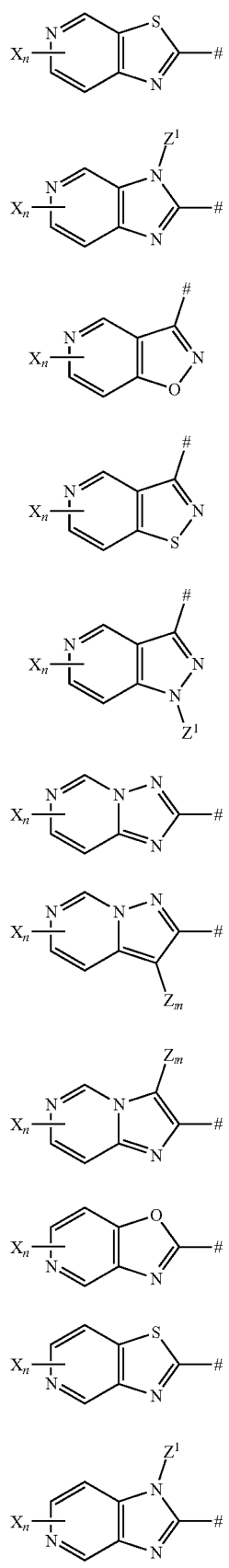

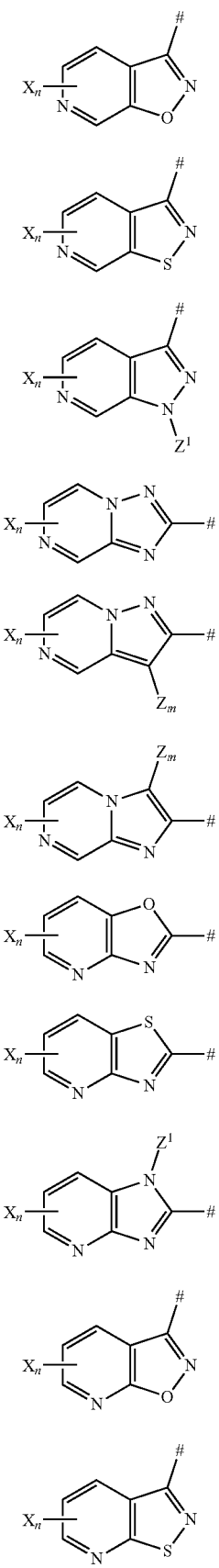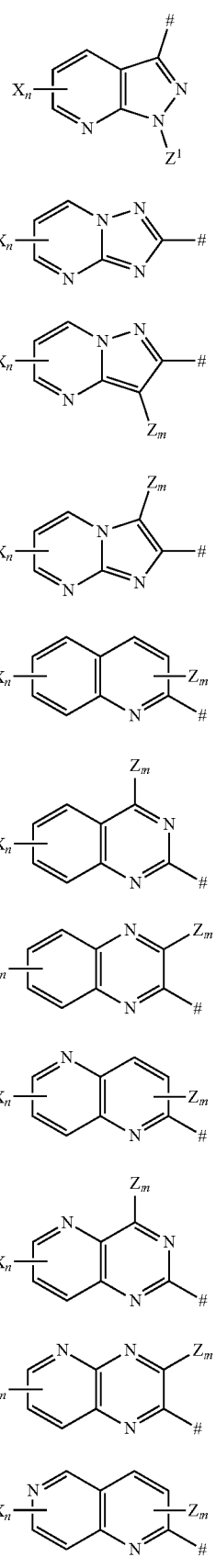

-continued

T50 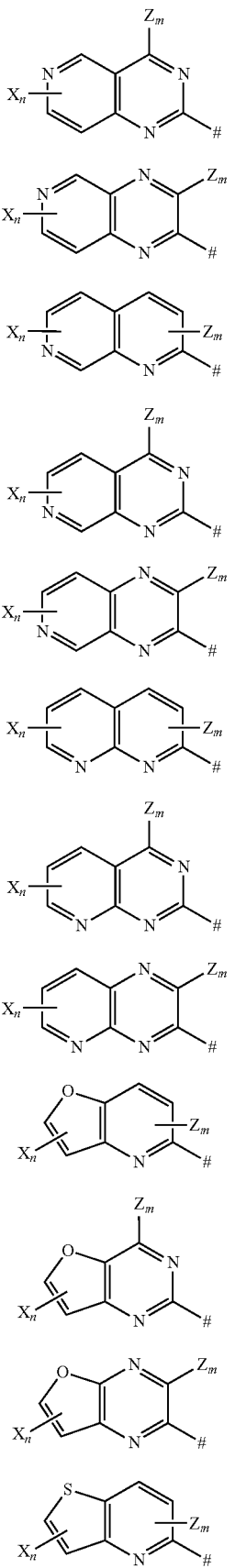

T51

T52

T53

T54

T55

T56

T57

T58

T59

T60

T61

-continued

T62 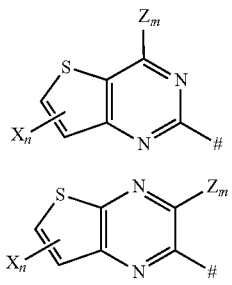

T63

T64

T65

T66

T67

T68

T69

T70 wherein
n is an integer from 0 to 4;
m is an integer from 0 to 2;
X is selected from the group consisting of hydrogen, halogen, hydroxy, —CN, —COOH, —CONH$_2$, —NO$_2$, —NH$_2$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, phenylsulfanyl, phenylsulfinyl, phenylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —NHSO$_2$($C_1$-$C_4$alkyl), —N($C_1$-$C_4$alkyl)CO—$C_1$-$C_4$alkyl, —N($C_1$-$C_4$alkyl)

CO—$C_3$-$C_6$cyclolkyl, —N($C_1$-$C_4$alkyl)$SO_2C_1$-$C_4$alkyl, —N($SO_2C_1$-$C_4$alkyl)$_2$, —$CO_2C_1$-$C_4$alkyl, —CONH($C_1$-$C_4$alkyl), —CONH($C_3$-$C_6$cycloalkyl), —CONH-phenyl, —$CONHSO_2$($C_1$-$C_4$alkyl), —CON($C_1$-$C_4$alkyl)$_2$, —CON($C_1$-$C_4$alkyl)($C_3$-$C_6$cycloalkyl), —CON($C_1$-$C_4$alkyl)-phenyl, —CON($C_1$-$C_4$alkyl)$SO_2$($C_1$-$C_4$alkyl), —C(=$NOC_1$-$C_4$alkyl)H, —C(=$NOC_1$-$C_4$alkyl)-$C_1$-$C_4$alkyl;

and 4-6 membered heterocyclyl containing 1-2 heteroatoms selected from the group consisting of N and O and optionally substituted with 1-2 substituents selected from the group consisting of methyl and ethyl;

Z is selected from the group consisting of hydrogen, halogen, hydroxy, —CN, —COOH, —$CONH_2$, —$NO_2$, —$NH_2$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —$NHSO_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)$SO_2C_1$-$C_4$alkyl, —N($SO_2C_1$-$C_4$alkyl)$_2$, —$CO_2C_1$-$C_4$alkyl, —CONH($C_1$-$C_4$alkyl), —CONH($C_3$-$C_6$cycloalkyl), —CONH-phenyl, —$CONHSO_2$($C_1$-$C_4$alkyl), —CON($C_1$-$C_4$alkyl)$_2$, —CON($C_1$-$C_4$alkyl)($C_3$-$C_6$cycloalkyl), —CON($C_1$-$C_4$alkyl)-phenyl, —CON($C_1$-$C_4$alkyl)$SO_2$($C_1$-$C_4$alkyl), —C(=$NOC_1$-$C_4$alkyl)H, —C(=$NOC_1$-$C_4$alkyl)-$C_1$-$C_4$alkyl;

$Z^1$ is hydrogen, $C_1$-$C_6$alkyl, $C_3$-$C_6$cycloalkyl, or $C_2$-$C_3$haloalkyl, wherein $C_1$-$C_6$alkyl, $C_3$-$C_6$cycloalkyl, or $C_2$-$C_3$haloalkyl are optionally substituted;

$R^3$ is hydrogen or optionally substituted $C_1$-$C_6$ alkyl;

$R^4$ is pyridine, pyrimidine, pyrazine, pyridazine or 5-membered heteroaryl, wherein the pyridine, pyrimidine, pyrazine, pyridazine or 5-membered heteroaryl is optionally substituted with one to three substituents selected from the group consisting of halogen, hydroxy, —CN, —COOH, —$CONH_2$, —$SO_2NH_2$, —$NO_2$, —$NH_2$, —$SF_5$, and in each case optionally substituted $C_1$-$C_6$alkyl, $C_3$-$C_6$cycloalkyl, $C_1$-$C_3$haloalkyl, $C_3$-$C_6$halocycloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —$NHSO_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)$SO_2C_1$-$C_4$alkyl, —N($SO_2C_1$-$C_4$alkyl)$_2$, —$CO_2C_1$-$C_4$alkyl, —CONH($C_1$-$C_4$alkyl), —CONH($C_3$-$C_6$cycloalkyl), —CONH-phenyl, —$CONHSO_2$($C_1$-$C_4$alkyl), —CON($C_1$-$C_4$alkyl)$_2$, —CON($C_1$-$C_4$alkyl)($C_3$-$C_6$cycloalkyl), —CONH($C_3$-$C_6$cycloalkylalkyl), —CON($C_1$-$C_6$alkyl)($C_3$-$C_6$cycloalkylalkyl), —CON($C_1$-$C_4$alkyl)-phenyl, —CON($C_1$-$C_4$alkyl)$SO_2$($C_1$-$C_4$alkyl), —C(=$NOC_1$-$C_4$alkyl)H, —C(=$NOC_1$-$C_4$alkyl)-$C_1$-$C_4$alkyl;

and 3-6 membered heterocyclyl containing 1-2 heteroatoms selected from the group consisting of N, O and S and optionally substituted with up to 4 substituents selected independently from the group consisting of fluorine, chlorine, bromine and $C_1$-$C_3$alkyl;

or one of the substituents may optionally be selected from the following substructures S1-S24, wherein the bond to the pyridine, pyrimidine, pyrazine, pyridazine or 5-membered heteroaryl is marked with a # and $Z^4$ is CO or $SO_2$ and $Y^4$ is independently selected from CO or $SO_2$:

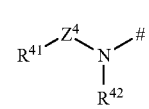

S1

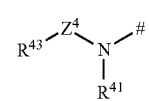

S2

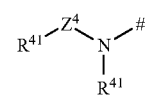

S3

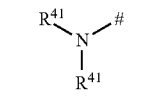

S4

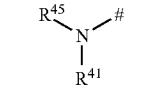

S5

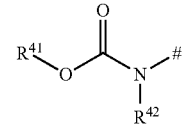

S6

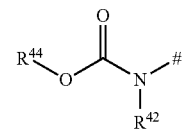

S7

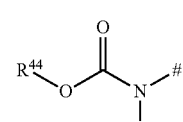

S8

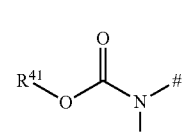

S9

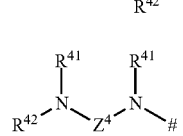

S10

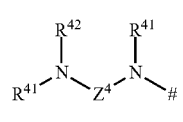

S11

-continued

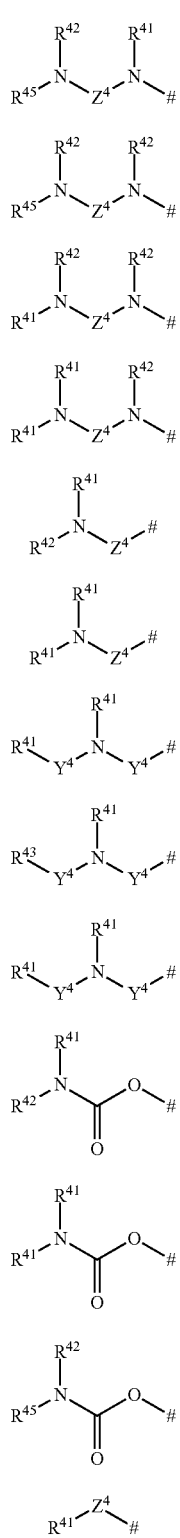

S12

S13

S14

S15

S16

S17

S18

S19

S20

S21

S22

S23

S24

$R^{41}$ is a heterocyclic ring which is selected from the group consisting of 4- to 10-membered saturated or partially unsaturated heterocyclyl, 5-membered heteroaryl and 6-membered heteroaryl, each of which is optionally substituted by one to three substituents independently selected from the group consisting of halogen, =O (oxo), =S (thiono), hydroxy, —CN, —COOH, —SO$_2$NH$_2$, —CONH$_2$, —CSNH$_2$, —NO$_2$, —SF$_5$, —NH$_2$;
and —CO$_2$—C$_1$-C$_4$alkyl, C$_1$-C$_4$alkyl, C$_3$-C$_6$cycloalkyl, C$_3$-C$_6$cycloalkyl-C$_1$-C$_4$alkyl, C$_1$-C$_4$haloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_3$-C$_6$cycloalkylsulfanyl, C$_3$-C$_6$cycloalkylsulfinyl, C$_3$-C$_6$cycloalkylsulfonyl, C$_1$-C$_4$haloalkylthio, C$_1$-C$_4$haloalkylsulfinyl, C$_1$-C$_4$haloalkylsulfonyl, —NH(C$_1$-C$_4$alkyl), —N(C$_1$-C$_4$alkyl)$_2$, —NHCO—C$_1$-C$_4$alkyl, —N(C$_1$-C$_4$alkyl)CO—C$_1$-C$_4$alkyl, —N(C$_3$-C$_6$cycloalkyl)CO—C$_1$-C$_4$alkyl, —NHCO—C$_3$-C$_6$cycloalkyl, —N(C$_1$-C$_4$alkyl)CO—(C$_3$-C$_6$cycloalkyl), —N(C$_3$-C$_6$cycloalkyl)CO—(C$_3$-C$_6$cycloalkyl), —N(CO—C$_1$-C$_4$alkyl)$_2$, —N(CO—C$_3$-C$_6$cycloalkyl)$_2$, —N(CO—C$_3$-C$_6$cycloalkyl)(CO—C$_1$-C$_4$alkyl), —CONH(C$_1$-C$_4$alkyl), —CON(C$_1$-C$_4$alkyl)$_2$, —CONH(C$_3$-C$_6$cycloalkyl), —CON(C$_1$-C$_4$alkyl)(C$_3$-C$_6$cycloalkyl), —CON(C$_3$-C$_6$cycloalkyl)$_2$, —CONH—SO$_2$—C$_1$-C$_4$alkyl, —CONH—SO$_2$—(C$_3$-C$_6$cycloalkyl), —CON(C$_1$-C$_4$alkyl)-SO$_2$—C$_1$-C$_4$alkyl, —CON(C$_1$-C$_4$alkyl)-SO$_2$—(C$_3$-C$_6$cycloalkyl), —N(SO$_2$C$_1$-C$_4$alkyl)$_2$, —N(SO$_2$C$_1$-C$_4$haloalkyl)$_2$, —N(SO$_2$C$_3$-C$_6$cycloalkyl)$_2$, —NHSO$_2$—C$_1$-C$_4$alkyl, —NHSO$_2$—C$_1$-C$_4$haloalkyl, —N(C$_1$-C$_4$alkyl)SO$_2$—C$_1$-C$_4$alkyl, —N(C$_3$-C$_6$cycloalkyl)SO$_2$—C$_1$-C$_4$alkyl, —NHSO$_2$—C$_3$-C$_6$cycloalkyl, —N(C$_1$-C$_4$alkyl)SO$_2$—(C$_3$-C$_6$cycloalkyl), —N(C$_3$-C$_6$cycloalkyl)SO$_2$—(C$_3$-C$_6$cycloalkyl), —SO$_2$NH(C$_1$-C$_4$alkyl), —SO$_2$N(C$_1$-C$_4$alkyl)$_2$, —SO$_2$N(C$_1$-C$_4$alkyl)(C$_3$-C$_6$cycloalkyl), —SO$_2$NH(C$_3$-C$_6$cycloalkyl), —SO$_2$N(C$_3$-C$_6$cycloalkyl)$_2$, —C(=NOC$_1$-C$_4$alkyl)H, —C(=NOC$_1$-C$_4$alkyl)-C$_1$-C$_4$alkyl;

$R^{42}$ is hydrogen, hydroxy;
and C$_1$-C$_4$alkyl, C$_1$-C$_4$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_4$alkyl, phenyl-C$_1$-C$_4$alkyl, naphthyl-C$_1$-C$_4$alkyl, C$_1$-C$_4$alkoxy-, C$_1$-C$_4$haloalkoxy;

$R^{43}$ is C$_1$-C$_4$alkyl, C$_1$-C$_4$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_4$alkyl, phenyl-C$_1$-C$_4$alkyl, naphthyl-C$_1$-C$_4$alkyl, C$_1$-C$_4$alkoxy-, C$_1$-C$_4$ haloalkoxy;

$R^{44}$ is C$_1$-C$_4$alkyl, C$_1$-C$_4$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_4$alkyl, phenyl-C$_1$-C$_4$alkyl, naphthyl-C$_1$-C$_4$alkyl;

$R^{45}$ is hydrogen and C$_1$-C$_4$alkyl, C$_1$-C$_4$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_4$alkyl, phenyl-C$_1$-C$_4$alkyl, naphthyl-C$_1$-C$_4$alkyl;
or $R^{41}$ and $R^{42}$ together with the nitrogen atom to which they are attached, represent a monocyclic, spirocyclic or bridged polycyclic 4- to 12-membered saturated or partially unsaturated heterocyclyl which may contain up to two further heteroatoms selected from the group of oxygen, nitrogen and sulfur and which is optionally substituted with one to three substituents selected from the group consisting of halogen, =O (oxo), =S (thiono), hydroxy, —CN, —COOH, —SO$_2$NH$_2$, —CONH$_2$, —CSNH$_2$, —NO$_2$, —SF$_5$, and —NH$_2$;

and in each case optionally substituted —CO$_2$—C$_1$-C$_4$alkyl, C$_1$-C$_4$alkyl, C$_3$-C$_6$cycloalkyl, C$_1$-C$_4$haloalkyl, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_3$-C$_6$cycloalkylsulfanyl, C$_3$-C$_6$cycloalkylsulfinyl, C$_3$-C$_6$cycloalkylsulfonyl, C$_1$-C$_4$haloalkylthio, C$_1$-C$_4$haloalkylsulfinyl, C$_1$-C$_4$haloalkylsulfonyl, —NHSO$_2$—C$_1$-C$_4$alkyl, —NHCO$_2$—C$_1$-C$_4$alkyl, —OCONH—C$_1$-C$_4$alkyl, —NH(C$_1$-C$_4$alkyl), —N(C$_1$-C$_4$alkyl)$_2$, —NHCO—C$_1$-C$_4$alkyl, —N(C$_1$-C$_4$alkyl)CO—C$_1$-C$_4$alkyl, —NHCO—C$_1$-C$_4$cycloalkyl, —N(C$_1$-C$_4$alkyl)CO—C$_3$-C$_6$cycloalkyl, —CO$_2$C$_1$-C$_4$alkyl, —CONH(C$_1$-C$_4$alkyl), —CONH(C$_3$-C$_6$cycloalkyl), —CON(C$_1$-C$_4$alkyl)$_2$, —SO$_2$NH(C$_1$-C$_4$alkyl);

R$^5$ is hydrogen, halogen, CN, or in each case optionally substituted C$_1$-C$_3$alkyl, C$_1$-C$_3$haloalkyl, C$_3$-C$_4$cycloalkyl, C$_3$-C$_4$halocycloalkyl, C$_1$-C$_3$alkoxy, C$_1$-C$_3$haloalkoxy, —CH—(C$_1$-C$_3$alkoxy)$_2$, —CO$_2$C$_1$-C$_4$alkyl, —CONH(C$_1$-C$_4$alkyl), —CON(C$_1$-C$_4$alkyl)$_2$, —NHCO—C$_1$-C$_4$alkyl, —N(C$_1$-C$_4$alkyl)CO—C$_1$-C$_4$alkyl, —C(=NOC$_1$-C$_4$alkyl)H, or —C(=NOC$_1$-C$_4$alkyl)-C$_1$-C$_4$alkyl.

3. The compound of claim 1, wherein,
Q$^1$ is N;
Q$^2$ is CR$^5$;
Y is a direct bond;
R$^1$ is hydrogen; C$_1$-C$_6$alkyl, optionally substituted with a substituent selected from the group of —CN, methoxy, ethoxy, methylthio and methylsulfonyl; or C$_1$-C$_6$haloalkyl; C$_3$-C$_6$cycloalkylC$_1$-C$_6$alkyl; C$_2$-C$_6$alkenyl; C$_2$-C$_6$alkynyl; or C$_2$-C$_6$ haloalkenyl;
R$^2$ is selected from one of the following bicyclic heterocycles T1-T21, T23-T30, T32-T39, T41, T42, T68-T70, wherein the bond to the N atom is marked with a #;

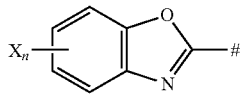
T1

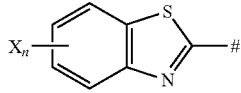
T2

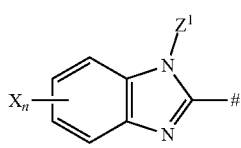
T3

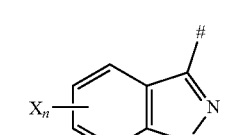
T4

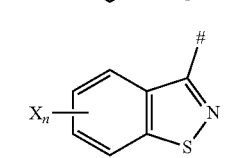
T5

-continued

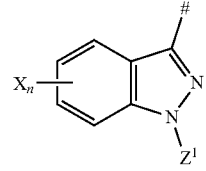
T6

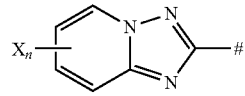
T7

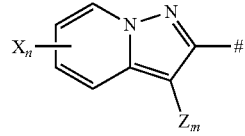
T8

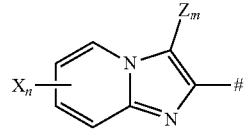
T9

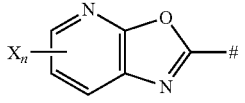
T10

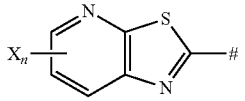
T11

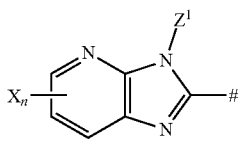
T12

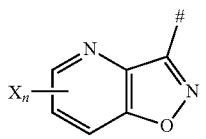
T13

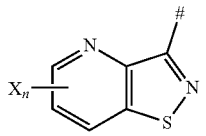
T14

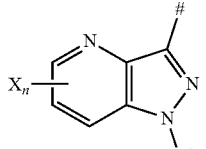
T15

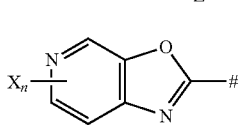
T16

-continued
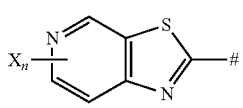 T17
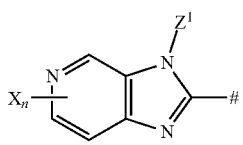 T18
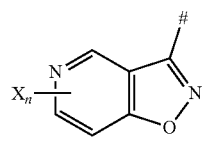 T19
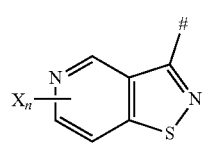 T20
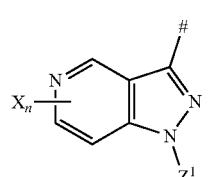 T21
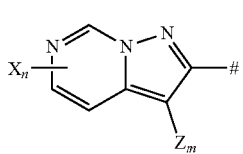 T23
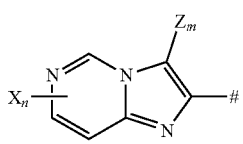 T24
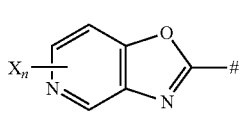 T25
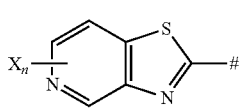 T26
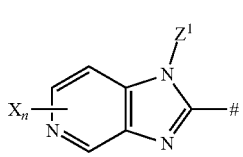 T27
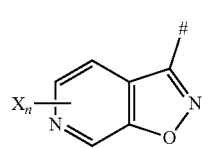 T28
-continued
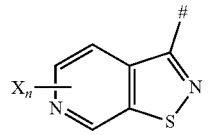 T29
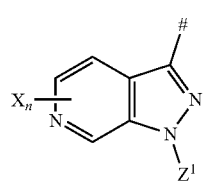 T30
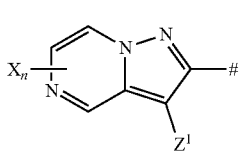 T32
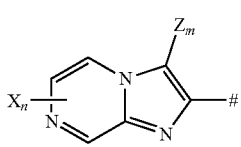 T33
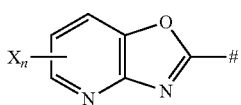 T34
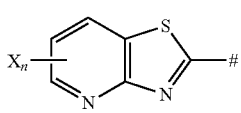 T35
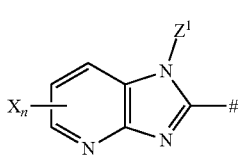 T36
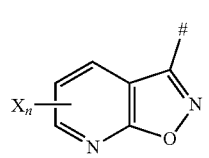 T37
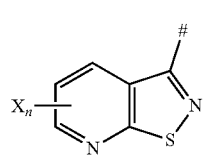 T38
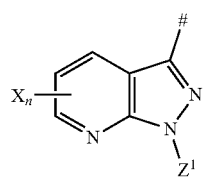 T39

-continued

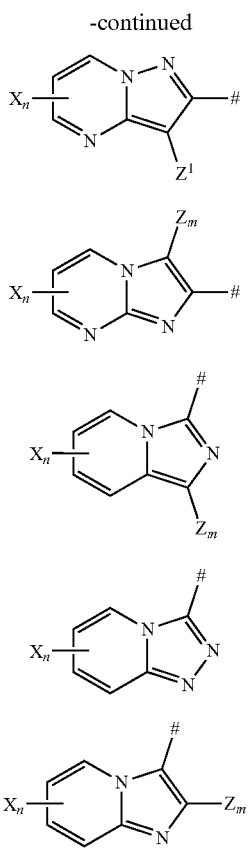

T41

T42

T68

T69

T70 wherein
n is an integer from 0 to 4;
m is an integer from 0 to 2;
X is selected from the group consisting of hydrogen, halogen, hydroxy, —CN, —COOH, —CONH$_2$, —NO$_2$, —NH$_2$, SF$_5$ and in each case optionally substituted C$_1$-C$_6$alkyl, C$_3$-C$_6$cycloalkyl, C$_1$-C$_3$haloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, cycloalkylthio, cycloalkylsulfinyl, cycloalkylsulfonyl, C$_1$-C$_3$haloalkylthio, C$_1$-C$_3$haloalkylsulfinyl, C$_1$-C$_3$haloalkylsulfonyl, phenylsulfonyl, —NH(C$_1$-C$_4$alkyl), —N(C$_1$-C$_4$alkyl)$_2$, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)CO—C$_3$-C$_6$cyclolkyl, —N(C$_1$-C$_4$alkyl)SO$_2$C$_1$-C$_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CONHSO$_2$(C$_1$-C$_4$alkyl), —CON(C$_1$-C$_4$alkyl)$_2$, —CON(C$_1$-C$_4$alkyl)(C$_3$-C$_6$cycloalkyl), —CON(C$_1$-C$_4$alkyl)-phenyl, —CON(C$_1$-C$_4$alkyl)SO$_2$(C$_1$-C$_4$alkyl), —C(=NOC$_1$-C$_4$alkyl)H, —C(=NOC$_1$-C$_4$alkyl)-C$_1$-C$_4$alkyl;

and 4-6 membered heterocyclyl containing 1-2 oxygen atoms and optionally substituted with 1-2 substituents selected from the group consisting of methyl and ethyl;

Z is selected from the group consisting of hydrogen, halogen, hydroxy, —CN, —COOH, —CONH$_2$, —NO$_2$, —NH$_2$, and in each case optionally substituted C$_1$-C$_6$alkyl, C$_3$-C$_6$cycloalkyl, C$_1$-C$_3$haloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, —NH(C$_1$-C$_4$alkyl), —N(C$_1$-C$_4$alkyl)$_2$, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)CO—C$_3$-C$_6$cyclolkyl, —N(C$_1$-C$_4$alkyl)SO$_2$C$_1$-C$_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CONHSO$_2$(C$_1$-C$_4$alkyl), —CON(C$_1$-C$_4$alkyl)$_2$, —CON(C$_1$-C$_4$alkyl)(C$_3$-C$_6$cycloalkyl), —CON(C$_1$-C$_4$alkyl)-phenyl, —CON(C$_1$-C$_4$alkyl)SO$_2$(C$_1$-C$_4$alkyl), —C(=NOC$_1$-C$_4$alkyl)H, —C(=NOC$_1$-C$_4$alkyl)-C$_1$-C$_4$alkyl;

Z$^1$ is selected from the group consisting of hydrogen and C$_1$-C$_6$ alkyl;

R$^3$ is hydrogen or C$_1$-C$_6$ alkyl;

R$^4$ is pyridine, pyrimidine, pyrazine, pyridazine or 5-membered heteroaryl, wherein the pyridine, pyrimidine, pyrazine, pyridazine or 5-membered heteroaryl is optionally substituted with one to three substituents selected from the group consisting of halogen, hydroxy, —CN, —COOH, —CONH$_2$, —SO$_2$NH$_2$, —NO$_2$, —NH$_2$, —SF$_5$, and in each case optionally substituted C$_1$-C$_6$alkyl, C$_3$-C$_6$cycloalkyl, C$_1$-C$_3$haloalkyl, C$_3$-C$_6$halocycloalkyl, C$_1$-C$_4$alkoxy, C$_1$-C$_3$haloalkoxy, C$_1$-C$_3$alkylthio, C$_1$-C$_3$alkylsulfinyl, C$_1$-C$_3$alkylsulfonyl, C$_1$-C$_3$haloalkylthio, C$_1$-C$_3$haloalkylsulfinyl, C$_1$-C$_3$haloalkylsulfonyl, —NHCO—C$_1$-C$_4$alkyl, NHCO—C$_3$-C$_6$cycloalkyl, —NHSO$_2$(C$_1$-C$_4$alkyl), —N(C$_1$-C$_4$alkyl)CO—C$_1$-C$_4$alkyl, —N(C$_1$-C$_4$alkyl)CO—C$_3$-C$_6$cyclolkyl, —N(C$_1$-C$_4$alkyl)SO$_2$C$_1$-C$_4$alkyl, —N(SO$_2$C$_1$-C$_4$alkyl)$_2$, —CO$_2$C$_1$-C$_4$alkyl, —CONH(C$_1$-C$_4$alkyl), —CONH(C$_3$-C$_6$cycloalkyl), —CONH-phenyl, —CONHSO$_2$(C$_1$-C$_4$alkyl), —CON(C$_1$-C$_4$alkyl)$_2$, —CONH(C$_3$-C$_6$cycloalkylalkyl), —CON(C$_1$-C$_4$alkyl)(C$_3$-C$_6$cycloalkyl), —CON(C$_1$-C$_6$alkyl)(C$_3$-C$_6$cycloalkylalkyl), —CON(C$_1$-C$_4$alkyl)-phenyl, —CON(C$_1$-C$_4$alkyl)SO$_2$(C$_1$-C$_4$alkyl);

and 3-6 membered heterocyclyl containing 1-2 heteroatoms selected from the group consisting of N, O, and S and optionally substituted with up to 4 substituents selected independently from the group consisting of fluorine, chlorine, bromine, methyl and ethyl;

or one of the substituents may optionally be selected from the following substructures S1, S2, S3, S4, S5, S16 and S17, in which the bond to the pyridine, pyrimidine, pyrazine, pyridazine or 5-membered heteroaryl is marked with a # and Z$^4$ is CO:

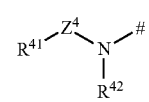

S1

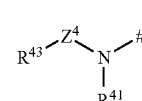

S2

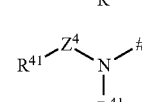

S3

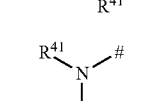

S4

-continued

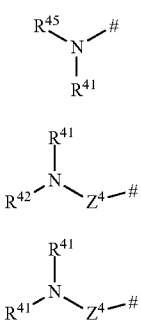

S5

S16

S17

$R^{41}$ is a heterocyclic ring which is selected from the group consisting of 4- to 8-membered saturated or partially unsaturated heterocyclyl, 5-membered heteroaryl and 6-membered heteroaryl, each of which is optionally substituted by one to two substituents independently selected from the group consisting of halogen, =O (oxo), =S (thiono), hydroxy, —CN, —COOH, —SO$_2$NH$_2$, —CONH$_2$, —CSNH$_2$, —NO$_2$, —SF$_5$, —NH$_2$;

and —CO$_2$—C$_1$-C$_3$alkyl, C$_1$-C$_3$alkyl, C$_3$-C$_4$cycloalkyl, C$_1$-C$_3$haloalkyl, C$_1$-C$_3$alkoxy, C$_1$-C$_3$haloalkoxy, C$_1$-C$_3$alkylthio, C$_1$-C$_3$alkylsulfinyl, C$_1$-C$_3$alkylsulfonyl, C$_3$-C$_4$cycloalkylsulfanyl, C$_3$-C$_4$cycloalkylsulfinyl, C$_3$-C$_4$cycloalkylsulfonyl, C$_1$-C$_3$haloalkylthio, C$_1$-C$_3$haloalkylsulfinyl, C$_1$-C$_3$haloalkylsulfonyl, —NH(C$_1$-C$_3$alkyl), —N(C$_1$-C$_3$alkyl)$_2$, —NHCO—C$_1$-C$_3$alkyl, —N(C$_1$-C$_3$alkyl)CO—C$_1$-C$_3$alkyl, —N(C$_3$-C$_4$cycloalkyl)CO—C$_1$-C$_3$alkyl, —NHCO—C$_3$-C$_4$cycloalkyl, —N(C$_1$-C$_3$alkyl)CO—(C$_3$-C$_4$cycloalkyl), —N(C$_3$-C$_4$cycloalkyl)CO—(C$_3$-C$_4$cycloalkyl), —CONH(C$_1$-C$_3$alkyl), —CON(C$_1$-C$_3$alkyl)$_2$, —CONH(C$_3$-C$_4$cycloalkyl), —CON(C$_1$-C$_3$alkyl)(C$_3$-C$_4$cycloalkyl), —CON(C$_3$-C$_4$cycloalkyl)$_2$, —NHSO$_2$—C$_1$-C$_3$alkyl, —NHSO$_2$—C$_1$-C$_3$haloalkyl, —N(C$_1$-C$_3$alkyl)SO$_2$—C$_1$-C$_3$alkyl, —N(C$_3$-C$_4$cycloalkyl)SO$_2$—C$_1$-C$_3$alkyl, —NHSO$_2$—C$_3$-C$_4$cycloalkyl, —N(C$_1$-C$_3$alkyl)SO$_2$—(C$_3$-C$_4$cycloalkyl), —N(C$_3$-C$_4$cycloalkyl)SO$_2$—(C$_3$-C$_4$cycloalkyl), —SO$_2$NH(C$_1$-C$_3$alkyl), —SO$_2$N(C$_1$-C$_3$alkyl)$_2$, —SO$_2$N(C$_1$-C$_3$alkyl)(C$_3$-C$_4$cycloalkyl), —SO$_2$NH(C$_3$-C$_4$cycloalkyl), —SO$_2$N(C$_3$-C$_4$cycloalkyl)$_2$;

$R^{42}$ is hydrogen, hydroxy;

and C$_1$-C$_3$alkyl, C$_1$-C$_3$haloalkyl, C$_2$-C$_4$alkenyl, C$_2$-C$_4$haloalkenyl, C$_2$-C$_4$alkynyl, C$_3$-C$_4$cycloalkyl, C$_3$-C$_4$cycloalkyl-C$_1$-C$_2$alkyl, phenyl-C$_1$-C$_2$alky, C$_1$-C$_3$alkoxy;

$R^{43}$ is C$_1$-C$_3$alkyl, C$_1$-C$_3$haloalkyl, C$_2$-C$_4$alkenyl, C$_2$-C$_4$haloalkenyl, C$_2$-C$_4$alkynyl, C$_3$-C$_4$cycloalkyl, C$_3$-C$_4$cycloalkyl-C$_1$-C$_2$alkyl, phenyl-C$_1$-C$_2$alkyl, C$_1$-C$_3$alkoxy;

$R^{44}$ is C$_1$-C$_3$alkyl, C$_1$-C$_3$haloalkyl, C$_2$-C$_4$alkenyl, C$_2$-C$_4$haloalkenyl, C$_2$-C$_4$alkynyl, C$_3$-C$_4$cycloalkyl, C$_3$-C$_4$cycloalkyl-C$_1$-C$_2$alkyl, phenyl-C$_1$-C$_2$alkyl;

$R^{45}$ is hydrogen and C$_1$-C$_3$alkyl, C$_1$-C$_3$haloalkyl, C$_2$-C$_4$alkenyl, C$_2$-C$_4$haloalkenyl, C$_2$-C$_4$alkynyl, C$_3$-C$_4$cycloalkyl, C$_3$-C$_4$cycloalkyl-C$_1$-C$_2$alkyl, phenyl-C$_1$-C$_2$alkyl;

or $R^{41}$ and $R^{42}$ together with the nitrogen atom to which they are attached, represent a monocyclic, spirocyclic or bridged polycyclic 4- to 8-membered saturated heterocyclyl which may contain up to one further heteroatom selected from the group of oxygen, nitrogen and sulfur and which is optionally substituted with one to three substituents selected from the group consisting of halogen, =O (oxo), =S (thiono), hydroxy, and —CN;

and —CO$_2$—C$_1$-C$_3$alkyl, C$_1$-C$_3$alkyl, C$_3$-C$_4$cycloalkyl, C$_1$-C$_3$haloalkyl, C$_1$-C$_3$alkoxy, C$_1$-C$_3$haloalkoxy, C$_1$-C$_3$alkylthio, C$_1$-C$_3$alkylsulfinyl, C$_1$-C$_3$alkylsulfonyl, C$_3$-C$_4$cycloalkylsulfanyl, C$_3$-C$_4$cycloalkylsulfinyl, C$_3$-C$_4$cycloalkylsulfonyl, C$_1$-C$_3$haloalkylthio, C$_1$-C$_3$haloalkylsulfinyl, C$_1$-C$_3$haloalkylsulfonyl, —NHCO—C$_1$-C$_3$alkyl, —N(C$_1$-C$_3$alkyl)CO—C$_1$-C$_3$alkyl, —NHCO—C$_1$-C$_3$cycloalkyl, —N(C$_1$-C$_3$alkyl)CO—C$_3$-C$_4$cycloalkyl, —CO$_2$C$_1$-C$_3$alkyl, —CONH(C$_1$-C$_3$alkyl), —CONH(C$_3$-C$_4$cycloalkyl), and —CON(C$_1$-C$_3$alkyl)$_2$;

$R^5$ is hydrogen, halogen, CN, or in each case optionally substituted C$_1$-C$_3$alkyl, C$_1$-C$_3$haloalkyl, C$_3$-C$_4$cycloalkyl, C$_3$-C$_4$halocycloalkyl, C$_1$-C$_3$alkoxy, or C$_1$-C$_3$haloalkoxy.

4. The compound of claim 1, wherein, $Q^1$ is N;

$Q^2$ is CR$^5$;

Y is a direct bond;

$R^1$ is hydrogen, methyl, ethyl, n-propyl, isopropyl, cyanomethyl, methoxymethyl, ethoxymethyl, methoxyethyl, ethoxyethyl, methylthioethyl, methylsulfonylethyl, 2,2-difluoroethyl, 2,2,2-trifluoroethyl, cyclopropylmethyl, cyclobutylmethyl, 2-propen-1-yl, 3-methyl-but-2-en-1-yl, 3,3-difluoro-prop-2-en-1-yl, 3,3-dichloro-prop-2-en-1-yl or 2-propyn-1-yl;

$R^2$ is selected from one of the following bicyclic heterocycles T1, T2, T3, T7 or T8, wherein the bond to the N atom is marked with a #;

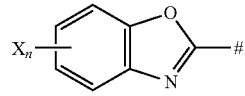

T1

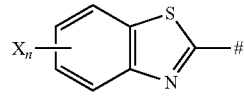

T2

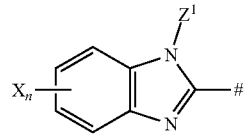

T3

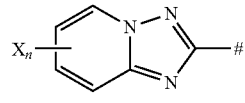

T7

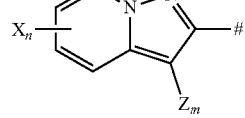

T8 wherein n is an integer from 0 to 2; and m is an integer from 0 to 1; and

X is selected from the group consisting of hydrogen, fluorine, chlorine, bromine, iodine, —CN, —NO$_2$, —SF$_5$, methyl, ethyl, isopropyl, tert-butyl, difluoromethyl, trifluoromethyl, pentafluoroethyl, cyclopropyl, cyclobutyl, oxacyclobutyl, cyclopentyl, oxacyclopent-2-yl, methoxy, difluoromethoxy, trifluoromethoxy, methylthio, methylsulfinyl, methylsulfonyl, ethylthio, ethylsulfinyl, ethylsulfonyl, difluoromethylthio, difluoromethylsulfinyl, difluoromethylsulfonyl, trifluoromethylthio, trifluoromethylsulfinyl, and trifluoromethylsulfonyl; cyclopropylthio, cyclopropylsulfinyl, cylopropylsulfonyl, phenylsulfanyl, phenylsulfinyl, phenylsulfonyl, and Z is selected from the group consisting of hydrogen, fluorine, chlorine, bromine; methyl, ethyl and cyclopropyl;

$Z^1$ is selected from the group consisting of hydrogen and methyl;

$R^3$ is hydrogen or methyl;

$R^4$ is thiazol, pyridine, pyrazine, pyridazine or pyrimidine, wherein the thiazol, pyridine, pyrazine, pyridazine or pyrimidine is optionally substituted with one to three substituents selected from the group consisting of fluorine, chlorine, bromine, iodine, —CN, —NO$_2$, —CONH$_2$, —SO$_2$NH$_2$, methyl, ethyl, difluoromethyl, trifluoromethyl, pentafluoroethyl, cyclopropyl, methoxy, difluoromethoxy, trifluoromethoxy, methylthio, methylsulfinyl, methylsulfonyl, difluoromethylthio, difluoromethylsulfinyl, difluoromethylsulfonyl, trifluoromethylthio, trifluoromethylsulfinyl, trifluoromethylsulfonyl morpholinylcarbonyl, dimethylmorpholinylcarbonyl, piperidinylcarbonyl, pyrrolidinylcarbonyl, azetidinylcarbonyl, azepanylcarbonyl, oxazepanylcarbonyl, N-methylcarbamoyl, N-ethylcarbamoyl, N,N-dimethylcarbamoyl, N,N-diethylcarbamoyl, N-cyclopropylmethyl, N-methylcarbamoyl, morpholinylsulfonyl, dimethylmorpholinylsulfonyl, piperidinylsulfonyl, pyrrolidinylsulfonyl, azetidinylsulfonyl, azepanylsulfonyl, and oxazepanylsulfonyl; oxetanyl, tetrahydrofuranyl, pyranyl $R^5$ is hydrogen, methyl, ethyl, n-propyl, isopropyl, cyclopropyl, trifluoromethyl, methoxy, ethoxy, n-propoxy, isopropoxy or difluoromethyl.

5. The compound of claim 1, wherein, $Q^1$ is N;

$Q^2$ is $CR^5$;

Y is a direct bond;

$R^1$ is hydrogen;

$R^2$ is selected from one of the following bicyclic heterocycles T1,T2 and T7 wherein the bond to the N atom is marked with a #

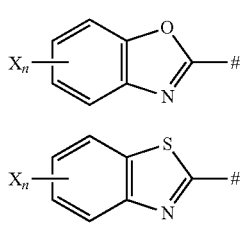

T1

T2

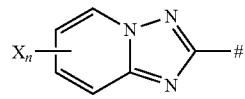

T7 wherein n is an integer of 0-2; and

X is independently selected from the group consisting of hydrogen, chlorine, bromine, —CN, —SF$_5$, trifluoromethyl, trifluormethoxy, difluormethoxy, methyl, isopropyl, tert-butyl, cyclopropyl, methylthio, ethylthio, cyclopropylthio and phenylsulfonyl;

$R^3$ is methyl;

$R^4$ is thiazol, pyridine, pyrazine, pyridazine or pyrimidine, wherein the thiazol, pyridine, pyrazine, pyridazine or pyrimidine is unsubstituted or is substituted with one substituent selected from the group consisting of fluorine, chlorine, bromine, —CN, —NH$_2$, —CONH$_2$, —SO$_2$NH$_2$, methyl, trifluoromethyl, methoxy, ethoxy, morpholin-4-ylcarbonyl, dimethylmorpholin-4-ylcarbonyl, pyrrolidine-1-ylcarbonyl, N-ethylcarbamoyl, N,N-diethylcarbamoyl, (N-cyclopropylmethyl,N-methyl)carbamoyl and oxetanyl or said thiazol, pyridine, pyrazine, pyridazine or pyrimidine optionally carries a second substituent selected from fluorine, chlorine and bromine;

$R^5$ is hydrogen, methyl, methoxy or cyclopropyl.

6. The compound of claim 1, comprising a structure according to formula (I')

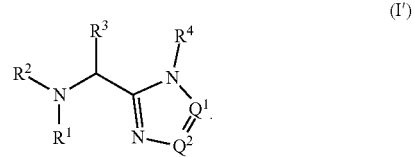

(I')

7. The compound of claim 1, comprising a structure according to formula (I")

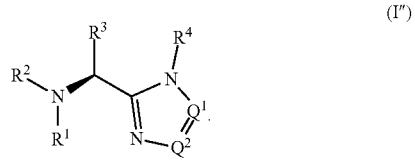

(I")

8. The compound of claim 1, wherein $Q^1$ represents N or $CR^5$ and $Q^2$ represents N.

9. The compound of claim 1, wherein $Q^1$ represents N and $Q^2$ represents $CR^5$.

10. A formulation, comprising at least one compound of formula (I)

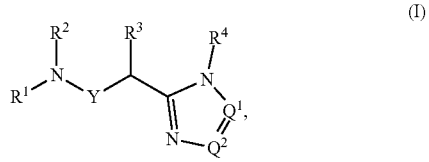

(I)

wherein, $Q^1$ and $Q^2$ are independently $CR^5$ or N, provided at least one of $Q^1$ and $Q^2$ is N;

Y is a direct bond;

$R^1$ is hydrogen;
- $C_1$-$C_6$alkyl, $C_3$-$C_6$cycloalkyl$C_1$-$C_6$alkyl, $C_2$-$C_6$alkenyl, $C_2$-$C_6$ alkynyl, wherein $C_1$-$C_6$alkyl, $C_3$-$C_6$cycloalkyl$C_1$-$C_6$alkyl, $C_2$-$C_6$alkenyl, $C_2$-$C_6$ alkynyl are optionally substituted;
- or phenyl-$C_1$-$C_6$alkyl, wherein phenyl is optionally substituted with one to five substituents, each independently selected from the group consisting of halogen, hydroxy, —CN, —COOH, —CONH$_2$, —CSNH$_2$, —NO$_2$, —Si(CH$_3$)$_3$, —SF$_5$, —NH$_2$, and in each case optionally substituted $C_1$-$C_6$alkyl, $C_3$-$C_6$cycloalkyl, $C_3$-$C_6$cycloalkyl-$C_1$-$C_6$alkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_1$-$C_3$haloalkylthio, $C_1$-$C_3$haloalkylsulfinyl, $C_1$-$C_3$haloalkylsulfonyl;

$R^2$ is a heteroaromatic bicyclic system containing 9-10 rind members including 1-4 heteroatoms selected from the group consisting of N, O, and S and optionally substituted with 0-4 substituents X, and 0-2 substituents Z and 0-1 substituents $Z^1$;

X is selected from the group consisting of hydrogen, halogen, hydroxy, —CN, —COOH, —CONH$_2$, —NO$_2$, —NH$_2$, —SF$_5$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_3$-$C_6$cyloalkoxy, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, $C_1$-$C_3$haloalkylthio, $C_1$-$C_3$haloalkylsulfinyl, $C_1$-$C_3$haloalkylsulfonyl, phenylsulfanyl, phenylsulfinyl, phenylsulfonyl, heterocyclylsulfanyl, heterocyclylsulfinyl, heterocyclylsulfonyl, heteroarylsulfanyl, heteroarylsulfinyl, heteroarylsulfonyl, S—$C_1$-$C_6$alkylsulfinimidoyl, S—$C_3$-$C_6$cycloalkylsulfinimidoyl, S-phenylsulfinimidoyl, S-heterocyclylsulfinimidoyl, S-heteroarylsulfinimidoyl, S—$C_1$-$C_6$alkylsulfonimidoyl, S—$C_3$-$C_6$cycloalkylsulfonimidoyl, S-phenylsulfonimidoyl, S-heterocyclylsulfonimidoyl, S-heteroarylsulfonimidoyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)SO$_2$$C_1$-$C_4$alkyl, —N(SO$_2$$C_1$-$C_4$alkyl)$_2$, —CO$_2$$C_1$-$C_4$alkyl, —CONH($C_1$-$C_4$alkyl), —CONH($C_3$-$C_6$cycloalkyl), —CONH-phenyl, —CON($C_1$-$C_4$alkyl)$_2$, —CON($C_1$-$C_4$alkyl)($C_3$-$C_6$cycloalkyl), —CON($C_1$-$C_4$alkyl)-phenyl, —SO$_2$NH($C_1$-$C_6$alkyl), —SO$_2$N($C_1$-$C_6$alkyl)$_2$, —SO$_2$N($C_1$-$C_6$alkyl)($C_3$-$C_6$cycloalkyl), —SO$_2$NH($C_3$-$C_6$cycloalkyl), —SO$_2$N($C_3$-$C_6$cycloalkyl)$_2$, —SO$_2$NH(heterocycyl), —SO$_2$N($C_1$-$C_4$alkyl)(heterocyclyl), —SO$_2$N($C_3$-$C_6$cycloalkyl)(heterocyclyl), —C(=NO$C_1$-$C_4$alkyl)H, —C(=NO$C_1$-$C_4$alkyl)-$C_1$-$C_4$alkyl, tri($C_1$-$C_4$alkyl)silyl;

and 3-6 membered heterocyclyl containing 1-2 heteroatoms selected from the group consisting of N, O, and S and optionally substituted with up to 4 substituents selected independently from the group consisting of fluorine, chlorine, bromine and $C_1$-$C_3$ alkyl;

Z is selected from the group consisting of hydrogen, halogen, hydroxy, —CN, —COOH, —CONH$_2$, —NO$_2$, —NH$_2$, —SF$_5$, and in each case optionally substituted $C_1$-$C_6$alkyl, $C_3$-$C_6$cycloalkyl, $C_1$-$C_3$haloalkyl, $C_1$-$C_4$alkoxy, $C_1$-$C_3$haloalkoxy, $C_1$-$C_3$alkylthio, $C_1$-$C_3$alkylsulfinyl, $C_1$-$C_3$alkylsulfonyl, $C_3$-$C_6$cycloalkylthio, $C_3$-$C_6$cycloalkylsulfinyl, $C_3$-$C_6$cycloalkylsulfonyl, phenylsulfanyl, phenylsulfinyl, phenylsulfonyl, $C_1$-$C_3$haloalkylthio, $C_1$-$C_3$haloalkylsulfinyl, $C_1$-$C_3$haloalkylsulfonyl, —NH($C_1$-$C_4$alkyl), —N($C_1$-$C_4$alkyl)$_2$, —NHCO—$C_1$-$C_4$alkyl, NHCO—$C_3$-$C_6$cycloalkyl, —NHSO$_2$($C_1$-$C_4$alkyl), —N($C_1$-$C_4$alkyl)CO—$C_1$-$C_4$alkyl, —N($C_1$-$C_4$alkyl)CO—$C_3$-$C_6$cyclolkyl, —N($C_1$-$C_4$alkyl)SO$_2$$C_1$-$C_4$alkyl, —N(SO$_2$$C_1$-$C_4$alkyl)$_2$, —CO$_2$$C_1$-$C_4$alkyl, —CONH($C_1$-$C_4$alkyl), —CONH($C_3$-$C_6$cycloalkyl), —CONH-phenyl, —CON($C_1$-$C_4$alkyl)$_2$, —CON($C_1$-$C_4$alkyl)($C_3$-$C_6$cycloalkyl), —CON($C_1$-$C_4$alkyl)-phenyl, —C(=NO$C_1$-$C_4$alkyl)H, —C(=NO$C_1$-$C_4$alkyl)-$C_1$-$C_4$alkyl, tri($C_1$-$C_4$alkyl)silyl;

and 3-6 membered heterocyclyl containing 1-2 heteroatoms selected from the group consisting of N, O, and S and optionally substituted with up to 4 substituents selected independently from the group consisting of fluorine, chlorine, bromine and $C_1$-$C_3$alkyl;

$Z^1$ is hydrogen, $C_1$-$C_6$alkyl, $C_3$-$C_6$cycloalkyl, $C_2$-$C_3$haloalkyl, or $C_1$-$C_4$ alkoxy, wherein $C_1$-$C_6$alkyl, $C_3$-$C_6$cycloalkyl, $C_2$-$C_3$haloalkyl, or $C_1$-$C_4$ alkoxy are optionally substituted;

$R^3$ is hydrogen or optionally substituted $C_1$-$C_6$ alkyl;

$R^4$ is pyridine, pyrimidine, pyrazine, pyridazine or 5-membered heteroaryl wherein the pyridine, pyrimidine, pyrazine, pyridazine or 5-membered heteroaryl is optionally substituted with one to three substituents selected from the group consisting of
- halogen, hydroxy, —CN, —COOH, —CO$_2$—$C_1$-$C_6$alkyl, —SO$_2$NH$_2$, —CONH$_2$, —CSNH$_2$, —NO$_2$, —NH$_2$, —SF$_5$;

and in each case optionally substituted $C_1$-$C_6$alkyl, $C_3$-$C_6$cycloalkyl, $C_1$-$C_6$haloalkyl, $C_3$-$C_6$halocycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_3$-$C_6$cycloalkylsulfanyl, $C_3$-$C_6$cycloalkylsulfinyl, $C_3$-$C_6$cycloalkylsulfonyl, $C_2$-$C_4$alkenylsulfanyl, $C_2$-$C_4$alkenylsulfinyl, $C_2$-$C_4$alkenylsulfonyl, $C_2$-$C_4$alkinylsulfanyl, $C_2$-$C_4$alkinylsulfinyl, $C_2$-$C_4$alkinylsulfonyl, phenylsulfanyl, phenylsulfinyl, phenylsulfonyl, S—$C_1$-$C_6$alkylsulfinimidoyl, S—$C_3$-$C_6$cycloalkylsulfinimidoyl, S—$C_2$-$C_6$alkenylsulfinimidoyl, S—$C_2$-$C_6$alkinylsulfinimidoyl, S-phenylsulfinimidoyl, S—$C_1$-$C_6$alkylsulfonimidoyl, S—$C_3$-$C_6$cycloalkylsulfonimidoyl, S—$C_2$-$C_6$alkenylsulfonimidoyl, S—$C_2$-$C_6$alkinylsulfonimidoyl, S-phenylsulfonimidoyl, —NH($C_1$-$C_6$alkyl), —N($C_1$-$C_6$alkyl)$_2$, —NHCO—$C_1$-$C_6$alkyl, —N($C_1$-$C_6$alkyl)CO—$C_1$-$C_6$alkyl, —N($C_3$-$C_6$cycloalkyl)CO—$C_1$-$C_6$alkyl, —NHCO—$C_3$-$C_6$cycloalkyl, —N($C_1$-$C_6$alkyl)CO—($C_3$-$C_6$cycloalkyl), —N($C_3$-$C_6$cycloalkyl)CO—($C_3$-$C_6$cycloalkyl), —N($C_1$-$C_6$alkyl)CO-phenyl, —N($C_3$-$C_6$cycloalkyl)CO-phenyl, —NHCO-phenyl, —N(CO—$C_1$-$C_6$alkyl)$_2$, —N(CO—$C_3$-$C_6$cyclo-alkyl)$_2$, —N(CO-phenyl)$_2$, —N(CO—$C_3$-$C_6$cycloalkyl)(CO—$C_1$-$C_6$alkyl), —N(CO—$C_3$-

$C_6$cycloalkyl)(CO-phenyl), —N(CO—$C_1$-$C_6$alkyl) (CO-phenyl), —CONH($C_1$-$C_6$alkyl), —CON($C_1$-$C_6$alkyl)$_2$, —CONH($C_3$-$C_6$cycloalkyl), —CON($C_1$-$C_6$alkyl)($C_3$-$C_6$cycloalkyl), —CONH($C_3$-$C_6$cycloalkylalkyl), CON($C_1$-$C_6$alkyl)($C_3$-$C_6$cycloalkylalkyl), —CON($C_3$-$C_6$cycloalkyl)$_2$, —CONH—SO$_2$—$C_1$-$C_6$alkyl, —CONH—SO$_2$-phenyl, —CONH—SO$_2$—($C_3$-$C_6$cycloalkyl), —CON($C_1$-$C_6$alkyl)-SO$_2$—$C_1$-$C_6$alkyl, —CON($C_1$-$C_6$alkyl)-SO$_2$-phenyl, —CON($C_1$-$C_6$alkyl)-SO$_2$—($C_3$-$C_6$cycloalkyl), —CONH-phenyl, —CON($C_1$-$C_6$alkyl)phenyl, —CON($C_3$-$C_6$cycloalkyl)phenyl, —N(SO$_2$$C_1$-$C_6$alkyl)$_2$, —N(SO$_2$$C_1$-$C_6$haloalkyl)$_2$, —N(SO$_2$$C_3$-$C_6$cycloalkyl)$_2$, —N(SO$_2$$C_1$-$C_6$alkyl)SO$_2$-phenyl, —N(SO$_2$$C_3$-$C_6$cycloalkyl)SO$_2$-phenyl, —NHSO$_2$—$C_1$-$C_6$alkyl, —NHSO$_2$—$C_1$-$C_6$haloalkyl, —N($C_1$-$C_6$alkyl)SO$_2$—$C_1$-$C_6$alkyl, —N($C_3$-$C_6$cycloalkyl)SO$_2$—$C_1$-$C_6$alkyl, —NHSO$_2$-phenyl, —N($C_1$-$C_6$alkyl)SO$_2$-phenyl, —N($C_3$-$C_6$cycloalkyl)SO$_2$-phenyl, —NHSO$_2$—$C_3$-$C_6$cycloalkyl, —N($C_1$-$C_6$alkyl)SO$_2$—($C_3$-$C_6$cycloalkyl), —N($C_3$-$C_6$cycloalkyl)SO$_2$—($C_3$-$C_6$cycloalkyl), —SO$_2$NH($C_1$-$C_6$alkyl), —SO$_2$N($C_1$-$C_6$alkyl)$_2$, —SO$_2$N($C_1$-$C_6$alkyl)($C_3$-$C_6$cycloalkyl), —SO$_2$NH($C_3$-$C_6$cycloalkyl), —SO$_2$N($C_3$-$C_6$cycloalkyl)$_2$, —SO$_2$NH(phenyl), —SO$_2$N($C_1$-$C_6$alkyl)(phenyl), —SO$_2$N($C_1$-$C_4$cycloalkyl)(phenyl), —C(=NO$C_1$-$C_6$alkyl)H and —C(=NO$C_1$-$C_6$alkyl)-$C_1$-$C_6$alkyl;

and 3-6 membered heterocyclyl containing 1-2 heteroatoms selected from the group consisting of N, O, and S and optionally substituted with up to 4 substituents selected independently from the group consisting of fluorine, chlorine, bromine and $C_1$-$C_3$alkyl, or one of the substituents may optionally be selected from the following substructures S1-S24, wherein the bond to the pyridine, pyrimidine, pyrazine, pyridazine or 5-membered heteroaryl is marked with a # and $Z^4$ is CO or SO$_2$ and $Y^4$ is independently selected from CO or SO$_2$:

-continued

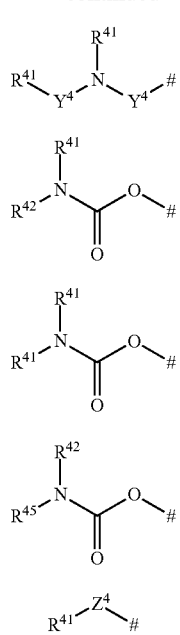

S20

S21

S22

S23

S24

$R^{41}$ is a heterocyclic ring which is selected from the group consisting of 3- to 10-membered saturated or partially unsaturated heterocyclyl, 5-membered heteroaryl, 6-membered heteroaryl, 9-membered heteroaryl and 10-membered heteroaryl, each of which is optionally substituted by one to three substituents independently selected from the group consisting of
halogen, =O (oxo), =S (thiono), hydroxy, —CN, —COOH, —SO$_2$NH$_2$, —CONH$_2$, —CSNH$_2$, —NO$_2$, —SF$_5$, —NH$_2$;
and in each case optionally substituted —CO$_2$—C$_1$-C$_6$alkyl, C$_1$-C$_6$alkyl, C$_3$-C$_6$cycloalkyl, C$_3$-C$_6$cycloalkyl-C$_1$-C$_6$alkyl, C$_1$-C$_6$haloalkyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_3$-C$_6$cycloalkylsulfanyl, C$_3$-C$_6$cycloalkylsulfinyl, C$_3$-C$_6$cycloalkylsulfonyl, C$_1$-C$_6$haloalkylthio, C$_1$-C$_6$haloalkylsulfinyl, C$_1$-C$_6$haloalkylsulfonyl, C$_2$-C$_4$alkenylsulfanyl, C$_2$-C$_4$alkenylsulfinyl, C$_2$-C$_4$alkenylsulfonyl, C$_2$-C$_4$alkinylsulfanyl, C$_2$-C$_4$alkinylsulfinyl, C$_2$-C$_4$alkinylsulfonyl, phenylsulfanyl, phenylsulfinyl, phenylsulfonyl, S—C$_1$-C$_6$alkylsulfinimidoyl, S—C$_3$-C$_6$cycloalkylsulfinimidoyl, S—C$_2$-C$_6$alkenylsulfinimidoyl, S—C$_2$-C$_6$alkinylsulfinimidoyl, S-phenylsulfinimidoyl, S—C$_1$-C$_6$alkylsulfonimidoyl, S—C$_3$-C$_6$cycloalkylsulfonimidoyl, S—C$_2$-C$_6$alkenylsulfonimidoyl, S—C$_2$-C$_6$alkinylsulfonimidoyl, S-phenylsulfonimidoyl, —NH(C$_1$-C$_6$alkyl), —N(C$_1$-C$_6$alkyl)$_2$, —NHCO—C$_1$-C$_6$alkyl, —N(C$_1$-C$_6$alkyl)CO—C$_1$-C$_6$alkyl, —N(C$_3$-C$_6$cycloalkyl)CO—C$_1$-C$_6$alkyl, —NHCO—C$_3$-C$_6$cycloalkyl, —N(C$_1$-C$_6$alkyl)CO—(C$_3$-C$_6$cycloalkyl), —N(C$_3$-C$_6$cycloalkyl)CO—(C$_3$-C$_6$cycloalkyl), —N(C$_1$-C$_6$alkyl)CO-phenyl, —N(C$_3$-C$_6$cycloalkyl)CO-phenyl, —NHCO-phenyl, —N(CO—C$_1$-C$_6$alkyl)$_2$, —N(CO—C$_3$-C$_6$cycloalkyl)$_2$, —N(CO-phenyl)$_2$, —N(CO—C$_3$-C$_6$cycloalkyl)(CO—C$_1$-C$_6$alkyl), —N(CO—C$_3$-C$_6$cycloalkyl)(CO-phenyl), —N(CO—C$_1$-C$_6$alkyl)(CO-phenyl), —CONH(C$_1$-C$_6$alkyl), —CON(C$_1$-C$_6$alkyl)$_2$, —CONH(C$_3$-C$_6$cycloalkyl), —CON(C$_1$-C$_6$alkyl)(C$_3$-C$_6$cycloalkyl), —CON(C$_3$-C$_6$cycloalkyl)$_2$, —CONH—SO$_2$—C$_1$-C$_6$alkyl, —CONH—SO$_2$-phenyl, —CONH—SO$_2$—(C$_3$-C$_6$cycloalkyl), —CON(C$_1$-C$_6$alkyl)-SO$_2$—C$_1$-C$_6$alkyl, —CON(C$_1$-C$_6$alkyl)-SO$_2$-phenyl, —CON(C$_1$-C$_6$alkyl)-SO$_2$—(C$_3$-C$_6$cycloalkyl), —CONH-phenyl, —CON(C$_1$-C$_6$alkyl)phenyl, —CON(C$_3$-C$_6$cycloalkyl)phenyl, —N(SO$_2$C$_1$-C$_6$alkyl)$_2$, —N(SO$_2$C$_1$-C$_6$haloalkyl)$_2$, —N(SO$_2$C$_3$-C$_6$cycloalkyl)$_2$, —N(SO$_2$C$_1$-C$_6$alkyl)SO$_2$-phenyl, —N(SO$_2$C$_3$-C$_6$cycloalkyl)SO$_2$-phenyl, —NHSO$_2$—C$_1$-C$_6$alkyl, —NHSO$_2$—C$_1$-C$_6$haloalkyl, —N(C$_1$-C$_6$alkyl)SO$_2$—C$_1$-C$_6$alkyl, —N(C$_3$-C$_6$cycloalkyl)SO$_2$—C$_1$-C$_6$alkyl, —NHSO$_2$-phenyl, —N(C$_1$-C$_6$alkyl)SO$_2$-phenyl, —N(C$_3$-C$_6$cycloalkyl)SO$_2$-phenyl, —NHSO$_2$—C$_3$-C$_6$cycloalkyl, —N(C$_1$-C$_6$alkyl)SO$_2$—(C$_3$-C$_6$cycloalkyl), —N(C$_3$-C$_6$cycloalkyl)SO$_2$—(C$_3$-C$_6$cycloalkyl), —SO$_2$NH(C$_1$-C$_6$alkyl), —SO$_2$N(C$_1$-C$_6$alkyl)$_2$, —SO$_2$N(C$_1$-C$_6$alkyl)(C$_3$-C$_6$cycloalkyl), —SO$_2$NH(C$_3$-C$_6$cycloalkyl), —SO$_2$N(C$_3$-C$_6$cycloalkyl)$_2$, —SO$_2$NH(phenyl), —SO$_2$N(C$_1$-C$_6$alkyl)(phenyl), —SO$_2$N(C$_1$-C$_4$cycloalkyl)(phenyl), —NHCS—C$_1$-C$_6$alkyl, —N(C$_1$-C$_6$alkyl)CS—C$_1$-C$_6$alkyl, —N(C$_3$-C$_6$cycloalkyl)CS—C$_1$-C$_6$alkyl, —NHCS—C$_3$-C$_6$cycloalkyl, —N(C$_1$-C$_6$alkyl)CS—(C$_3$-C$_6$cycloalkyl), —N(C$_3$-C$_6$cycloalkyl)CS—(C$_3$-C$_6$cycloalkyl), —N(C$_1$-C$_6$alkyl)CS-phenyl, —N(C$_3$-C$_6$cycloalkyl)CS-phenyl, —NHCS-phenyl, —CSNH(C$_1$-C$_6$alkyl), —CSN(C$_1$-C$_6$alkyl)$_2$, —CSNH(C$_3$-C$_6$cycloalkyl), —CSN(C$_1$-C$_6$alkyl)(C$_3$-C$_6$cycloalkyl), —CSN(C$_3$-C$_6$cycloalkyl)$_2$, —CSNH-phenyl, —CSN(C$_1$-C$_6$alkyl)phenyl, —CSN(C$_3$-C$_6$cycloalkyl)phenyl, —C(=NOC$_1$-C$_6$alkyl)H, —C(=NOC$_1$-C$_6$alkyl)-C$_1$-C$_6$alkyl, phenyl and 5- to 6-membered heteroaryl;

$R^{42}$ is hydrogen, hydroxy;
or in each case optionally substituted C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_6$alkyl, phenyl-C$_1$-C$_6$alkyl, naphthyl-C$_1$-C$_6$alkyl, C$_1$-C$_6$alkoxy-, C$_1$-C$_6$ haloalkoxy;
or phenyl, wherein the phenyl is optionally substituted by one to three substituents independently selected from the group consisting of halogen, —CN, and in each case optionally substituted C$_1$-C$_6$alkyl, C$_3$-C$_6$cycloalkyl, C$_1$-C$_6$haloalkyl, C$_1$-C$_6$alkoxy, C$_1$-C$_6$haloalkoxy, C$_1$-C$_6$alkylthio, C$_1$-C$_6$alkylsulfinyl, C$_1$-C$_6$alkylsulfonyl, C$_3$-C$_6$cycloalkylthio, C$_3$-C$_6$cycloalkylsulfinyl, C$_3$-C$_6$cycloalkylsulfonyl, C$_1$-C$_6$haloalkylthio, C$_1$-C$_6$haloalkylsulfinyl, and C$_1$-C$_6$ haloalkylsulfonyl;

$R^{43}$ is in each case optionally substituted C$_1$-C$_6$alkyl, C$_1$-C$_6$haloalkyl, C$_2$-C$_6$alkenyl, C$_2$-C$_6$haloalkenyl, C$_2$-C$_6$alkynyl, C$_2$-C$_6$haloalkynyl, C$_3$-C$_6$cycloalkyl, C$_3$-C$_6$cycloalkyl-C$_1$-C$_6$alkyl, phenyl-C$_1$-C$_6$alkyl, naphthyl-C$_1$-C$_6$alkyl, C$_1$-C$_6$alkoxy-, C$_1$-C$_6$ haloalkoxy;
or phenyl, wherein the phenyl is optionally substituted by one to three substituents independently selected from the group consisting of halogen, —CN, and in each case optionally substituted C$_1$-C$_6$alkyl, C$_3$-C$_6$cycloalkyl, C$_1$-C$_6$haloalkyl, C$_1$-C$_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_3$-$C_6$cycloalkylthio, $C_3$-$C_6$cycloalkylsulfinyl, $C_3$-$C_6$cycloalkylsulfonyl, $C_1$-$C_6$haloalkylthio, $C_1$-$C_6$haloalkylsulfinyl, and $C_1$-$C_6$ haloalkylsulfonyl;

$R^{44}$ is in each case optionally substituted $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_3$-$C_6$cycloalkyl-$C_1$-$C_6$alkyl, phenyl-$C_1$-$C_6$alkyl, naphthyl-$C_1$-$C_6$alkyl;

$R^{45}$ is hydrogen or in each case optionally substituted $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_3$-$C_6$cycloalkyl-$C_1$-$C_6$alkyl, phenyl-$C_1$-$C_6$alkyl, naphthyl-$C_1$-$C_6$ alkyl;

or $R^{41}$ and $R^{42}$ together with the nitrogen atom to which they are attached, represent a monocyclic or polycyclic optionally substituted 3- to 12-membered saturated or partially unsaturated heterocyclyl which may contain further heteroatoms;

$R^5$ is —$NH_2$, hydrogen, halogen, —CN, or in each case optionally substituted $C_1$-$C_3$alkyl, $C_1$-$C_3$haloalkyl, $C_3$-$C_4$cycloalkyl, $C_3$-$C_4$halocycloalkyl, $C_1$-$C_3$alkoxy, $C_1$-$C_3$haloalkoxy, —CH—($C_1$-$C_3$alkoxy)$_2$, —$CO_2C_1$-$C_4$alkyl, —CONH($C_1$-$C_4$alkyl), —CON($C_1$-$C_4$alkyl)$_2$, —NHCO—$C_1$-$C_4$alkyl, —N($C_1$-$C_4$alkyl)CO—$C_1$-$C_4$alkyl, —NHCO—$C_3$-$C_6$cycloalkyl, —N($C_1$-$C_4$alkyl)CO—$C_3$-$C_6$cycloalkyl, —N($C_3$-$C_6$cycloalkyl)CO—$C_3$-$C_6$cycloalkyl, —C(=NO$C_1$-$C_4$alkyl)H, or —C(=NO$C_1$-$C_4$alkyl)-$C_1$-$C_4$alkyl.

11. The formulation of claim 10, wherein the compound of formula (I) is in a mixture with at least one further active compound.

12. A method for controlling a pest, comprising allowing a compound of formula (I) of claim 1 or a formulation thereof to act on the pest and/or a habitat thereof, wherein methods for treatment of an animal body by surgery or therapy and methods practised on an animal body are excluded.

13. A method for protecting seed and/or a germinating plant from a pest, comprising contacting said seed with a compound of formula (I) of claim 1 or with a formulation thereof.

14. Seed A seed obtained by a method of claim 13.

15. The method of claim 12, wherein the pest is an animal pest.

16. The method of claim 13, wherein the pest is an animal pest.

* * * * *